US011267892B2

(12) United States Patent
Wong et al.

(10) Patent No.: US 11,267,892 B2
(45) Date of Patent: *Mar. 8, 2022

(54) CHIMERIC ANTIGEN RECEPTORS TARGETING EPIDERMAL GROWTH FACTOR RECEPTOR VARIANT III

(71) Applicant: Pfizer Inc., New York, NY (US)

(72) Inventors: Oi Kwan Wong, Belmont, CA (US); Joyce Ching Chou, Sunnyvale, CA (US); Mathilde Brunnhilde Dusseaux, Creteil (FR); Julianne Smith, New York, NY (US); Barbra Johnson Sasu, San Francisco, CA (US)

(73) Assignee: Pfizer Inc., New York, NY (US)

( * ) Notice: Subject to any disclaimer, the term of this patent is extended or adjusted under 35 U.S.C. 154(b) by 337 days.

This patent is subject to a terminal disclaimer.

(21) Appl. No.: 16/255,348

(22) Filed: Jan. 23, 2019

(65) Prior Publication Data

US 2019/0144550 A1  May 16, 2019

Related U.S. Application Data

(62) Division of application No. 15/402,760, filed on Jan. 10, 2017, now Pat. No. 10,259,876.

(60) Provisional application No. 62/431,758, filed on Dec. 8, 2016, provisional application No. 62/281,533, filed on Jan. 21, 2016.

(51) Int. Cl.

| | | |
|---|---|---|
| *A61K 35/17* | (2015.01) | |
| *C12N 9/64* | (2006.01) | |
| *A61K 31/436* | (2006.01) | |
| *C07K 16/28* | (2006.01) | |
| *C07K 14/47* | (2006.01) | |
| *C07K 14/725* | (2006.01) | |
| *A61K 38/00* | (2006.01) | |
| *A61K 39/00* | (2006.01) | |

(52) U.S. Cl.
CPC ...... *C07K 16/2863* (2013.01); *C07K 14/4748* (2013.01); *C07K 14/7051* (2013.01); *A61K 38/00* (2013.01); *A61K 2039/505* (2013.01); *C07K 2317/21* (2013.01); *C07K 2317/24* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/92* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 8,906,682 B2* | 12/2014 | June | A61K 35/17 |
| | | | 435/372.3 |
| 10,221,242 B2* | 3/2019 | Wong | A61P 35/02 |
| 10,259,876 B2 | 4/2019 | Wong et al. | |
| 2012/0189630 A1 | 7/2012 | Bigner | |
| 2014/0037628 A1 | 2/2014 | Morgan et al. | |
| 2014/0322275 A1 | 10/2014 | Brogdon et al. | |
| 2017/0275366 A1* | 9/2017 | Schiffer-Mannioui | |
| | | | A61K 35/17 |
| 2019/0194335 A1 | 6/2019 | Wong et al. | |

FOREIGN PATENT DOCUMENTS

| | | | |
|---|---|---|---|
| JP | 2015-524255 A | | 8/2015 |
| KR | 10-2013-0124521 A | | 11/2013 |
| WO | WO 94/02610 | * | 2/1994 |
| WO | WO-94/002610 A1 | | 2/1994 |
| WO | WO-2008/045437 A2 | | 4/2008 |
| WO | WO-2008/045437 A3 | | 4/2008 |
| WO | WO-2012/079000 A1 | | 6/2012 |
| WO | WO-2012/138475 A1 | | 10/2012 |
| WO | WO-2013/185010 A1 | | 12/2013 |
| WO | WO-2014/011988 A2 | | 1/2014 |
| WO | WO-2014/011988 A3 | | 1/2014 |
| WO | WO-2014/039523 A1 | | 3/2014 |
| WO | WO-2014/130657 A1 | | 8/2014 |
| WO | WO-2014/153002 A1 | | 9/2014 |
| WO | WO-2015/006482 A1 | | 1/2015 |
| WO | WO-2015/018527 A1 | | 2/2015 |
| WO | WO-2015/092024 A2 | | 6/2015 |
| WO | WO-2015/092024 A3 | | 6/2015 |
| WO | WO-2016/016341 A1 | | 2/2016 |
| WO | WO-2017/021370 A1 | | 2/2017 |

OTHER PUBLICATIONS

Philip et al., A highly compact epitope-based marker/suicide gene for easier and safer T-cell therapy; 2014 Blood; pp. 1277-1287.*
Chen, X. et al. (2013). Fusion protein linkers: Property, design and functionality, Advanced Drug Delivery Reviews 65:1357-1369.
Frankel, A.E. et al. (2000). Characterization of diphtheria fusion proteins targeted to the human interleukin-3 receptor, Protein Engineering 13:575-581.

(Continued)

*Primary Examiner* — Maria G Leavitt
(74) *Attorney, Agent, or Firm* — Proskauer Rose LLP

(57) ABSTRACT

The invention provides Chimeric Antigen Receptors (CARs) that specifically bind to EGFRvIII (Epidermal Growth Factor Receptor Variant III). The invention further relates to engineered immune cells comprising such CARs, CAR-encoding nucleic acids, and methods of making thereof, engineered immune cells, and nucleic acids. The invention further relates to therapeutic methods for using these CARs and engineered immune cells for the treatment of EGFRvIII-mediated pathologies, including cancers such as glioblastoma.

48 Claims, 6 Drawing Sheets

Specification includes a Sequence Listing.

(56) References Cited

OTHER PUBLICATIONS

Irving, B.A. et al. (1991). The cytoplasmic domain of the T cell receptor ζ chain is sufficient to couple to receptor-associated signal transduction pathways, Cell 64:891-901.

Kipriyanov, S.M. et al. (1997). Two amino acid mutations in an anti-human CD3 single chain Fv antibody fragment that affect the yield on bacterial secretion but not the affinity, Protein Engineering 10:445-453.

Kozak, M. (1984). Compilation and analysis of sequences upstream from the translational start site in eukaryotic mRNAs, Nucleic Acids Research 12:857-872.

Maeda, Y. et al. (1997). Engineering of functional chimeric protein G-Vargulaluciferase, Analytical Biochemistry 249:147-152.

Non-Final Office Action dated Oct. 1, 2019, for U.S. Appl. No. 15/526,649, filed May 12, 2017, 13 pages.

Pakula, A.A. et al. (1989). Genetic analysis of protein stability and function, Annual Review of Genetics 23:289-310.

Sampson, J.H. et al. (2014). EGFRvIII mCAR-modified T-cell therapy cures mice with established intracerebral glioma and generates host immunity against tumor-antigen loss, Clinical Cancer Research 20:972-984.

Teplyakov, A. et al. (2014). Antibody modeling assessment II. Structures and models, Proteins: Structure, Function, and Bioinformatics 82:1563-1582.

Wikstrand, C.J. et al. (1995). Monoclonal antibodies against EGFRvIII are tumor specific and react with breast and lung carcinomas and malignant gliomas, Cancer Research 55:3140-3148.

Foote, J. et al (1992). Antibody Framework Residues Affecting the Conformation of the Hypervariable Loops, J. Mol. Biol. 224: 487-499.

Winter, G. et al (1993). Antibody-based Therapy: Humanized Antibodies, Immunology Today 14(6): 243-246.

Final Office Action dated Apr. 9, 2020, for U.S. Appl. No. 15/526,649, filed May 12, 2017, 9 pages.

Bendig, M.M. et al. (1995). "Humanization of rodent monoclonal antibodies by CDR grafting a companion to methods," Methods: A companion to methods in enzymology, pp. 83-93.

Choi, B.D. et al. (2013). "Systemic administration of a bispecific antibody targeting EGFRvIII successfully treats intracerebral glioma," PNAS 110:270-275.

Choi, B.D. et al. (2013). "A novel bispecific antibody recruits T cells to eradicate tumors in the "immunologically privileged" central nervous system," Oncoimmuno. 2:e23639.

Colman, P.M. (1994). "Effects of amino acid sequence changes on antibody-antigen interactions," Res. Immunol. 145:33-36.

Edwards, B.M. et al (2003). "The Remarkable Flexibility of the Human Antibody Repertoire; Isolation of Over One Thousand Different Antibodies to a Single Protein," BLyS J. Mol. Biol. 334:103-118.

Final Office Action dated Sep. 14, 2018, for U.S. Appl. No. 15/402,760, filed Jan. 10, 2017, 18 pages.

Han et al. (2015). "CAR-Engineered NK Cells Targeting Wild-Type EGFR and EGFRvIII Enhance Killing of Glioblastoma and Patient-Derived Glioblastoma Stem Cells," Scientific Reports 5:11483.

International Search Report dated Sep. 16, 2015, for PCT Application No. PCT/EP2015/067439, filed on Jul. 29, 2015, 6 pages.

International Search Report dated Apr. 5, 2017, for PCT Application No. PCT/IB2017/050108, filed on Jan. 10, 2017, 5 pages.

International Search Report dated May 2, 2017, for PCT Application No. PCT/IB2017/050109, filed on Jan. 10, 2017, 5 pages.

Johnson, L.A. et al. (2015). "Rational development and characterization of humanized anti-EGFR variant III chimeric antigen receptor T cells for glioblastoma," Sci. Transl. Med. 7:275(ra22), 16 total pages.

Kimchi-Sarfaty. C. et al. (2007). "A "silent" polymorphism in the MDR1 gene changes substrate specificity," Science 315:525-528.

Lloyd et al., Modelling the human immune response: performance of a 1011 human antibody repertoire against a broad panel of therapeutically relevant antigens Protein Engineering, Design & Selection vol. 22 No. 3 pp. 159-168, 2009.

Mannioui et al. (2013). "Treatment of B ceils malignancies with anti-CD19 CAR+, TCR-, CD52-aiiogenic T cells," J. Immunother. Cancer 1:P34.

Morgan, R.A. et al. (2012). "Recognition of glioma stem cells by genetically modified T cells targeting EGFRvIII and development of adoptive cell therapy for glioma," Human Gene Ther. 23:1043-1053.

Non-Final Office Action dated Jan. 11, 2018, for U.S. Appl. No. 15/402,807, filed Jan. 10, 2017, 7 pages.

Non-Final Office Action dated Mar. 1, 2018, for U.S. Appl. No. 15/402,760, filed Jan. 10, 2017, 28 pages.

Notice of Allowance dated Oct. 11, 2018, for U.S. Appl. No. 15/402,807, filed Jan. 10, 2017, 8 pages.

Notice of Allowance dated Nov. 29, 2018, for U.S. Appl. No. 15/402,760, filed Jan. 10, 2017, 15 pages.

Philip, B. et al. (2014). "A highly compact epitope-based marker/suicide gene for easier and safer T-cell therapy" Blood 124:1277-1287.

Poirot, L. et al. (2014). "521. Multiplex genome editing of TCR alpha/CD52 genes as a platform for off the shelf adoptive t-cell immunotherapies," 17th Annual Meeting of the American Society of Gene and Cell Therapy 22(Suppl. 1):S201-S202.

Poirot, L. et al. (2013). "T-cell engineering for off the shelf adoptive immunotherapy," Blood Journal vol. 122.

Rudikoff, S. et al. (1982). "Single amino acid substitution altering antigen-binding specificity," PNAS 79:1979-1983.

Shen, C.J. et al. (2013). "Chimeric antigen receptor containing ICOS signaling domain mediates specific and efficient antitumor effect of T cells against EGFRvIII expressing glioma," J. Hematol. Oncol. 6:33.

Written Opinion of the International Searching Authority dated Sep. 16, 2015, for PCT Application No. PCT/EP2015/067439, filed on Jul. 29, 2015, 7 pages.

Written Opinion of the International Searching Authority dated Apr. 5, 2017, for PCT Application No. PCT/IB2017/050108, filed on Jan. 10, 2017, 7 pages.

Written Opinion of the International Searching Authority dated May 2, 2017, for PCT Application No. PCT/IB2017/050109, filed on Jan. 10, 2017, 7 pages.

Zitron, I.M. et al. (2013). "Targeting and killing of glioblastoma with activated T cells armed with bispecific antibodies," BMC Cancer 13:83.

\* cited by examiner

```
                        SEQUENCE LISTING

<160> NUMBER OF SEQ ID NOS: 277

<210> SEQ ID NO 1
<211> LENGTH: 115
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
            20                  25                  30

Thr Leu His Trp Val Lys Gln Ser His Val Lys Ser Leu Glu Trp Ile
        35                  40                  45

Gly Gly Ile Asp Pro Ile Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Glu Ala Met Asp Ser Trp Gly Gln Gly Thr Ser Val Thr
            100                 105                 110

Val Ser Ser
        115

<210> SEQ ID NO 2
<211> LENGTH: 112
<212> TYPE: PRT
<213> ORGANISM: Artificial Sequence
<220> FEATURE:
<223> OTHER INFORMATION: Synthetic Construct

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Phe Tyr Tyr Cys Val Gln Asp
                85                  90                  95

Thr His Phe Pro Leu Thr Phe Gly Ala Gly Thr Lys Leu Glu Leu Lys
            100                 105                 110

<210> SEQ ID NO 3
<211> LENGTH: 115
<212> TYPE: PRT
<213> ORGANISM: Artificial Sequence
```

```
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Thr Leu His Trp Val Arg Gln Ala Pro Gly Gln Gly Leu Glu Trp Met
            35                  40                  45

Gly Gly Ile Asn Pro Ile Asn Gly Gly Thr Thr Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Ala Met Asp Ser Trp Gly Gln Gly Thr Leu Val Thr
            100                 105                 110

Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic Construct

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Phe Gln Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asp
                85                  90                  95

Thr His Phe Pro Leu Thr Phe Gly Gly Gly Thr Lys Val Glu Ile Lys
            100                 105                 110

<210> SEQ ID NO 5
<211> LENGTH: 115
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Thr Leu His Trp Val Arg Gln Ala Pro Gly Gln Gly Leu Glu Trp Met
            35                  40                  45
```

```
Gly Gly Ile Trp Pro Ile Thr Gly Gly Thr Thr Tyr Asn Gln Lys Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ala Gln Gly Ser Trp Gly Gln Gly Thr Leu Val Thr
                100                 105                 110

Val Ser Ser
        115

<210> SEQ ID NO 6
<211> LENGTH: 112
<212> TYPE: PRT
<213> ORGANISM: Artificial Sequence
<220> FEATURE:
<223> OTHER INFORMATION: Synthetic Construct

<400> SEQUENCE: 6

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Tyr Ser
                 20                  25                  30

Asn Gly Lys Thr Tyr Leu Asn Trp Phe Gln Gln Arg Pro Gly Gln Ser
             35                  40                  45

Pro Arg Arg Leu Ile Tyr Gln Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Asp
                 85                  90                  95

Thr His Phe Pro Leu Thr Phe Gly Gly Gly Thr Lys Val Glu Ile Lys
                100                 105                 110

<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Thr Leu His Trp Val Arg Gln Ala Pro Gly Gln Gly Leu Glu Trp Met
             35                  40                  45

Gly Gly Ile Trp Pro Ile Thr Gly Gly Thr Thr Tyr Asn Gln Lys Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ala Glu Gly Ser Trp Gly Gln Gly Thr Leu Val Thr
                100                 105                 110

Val Ser Ser
        115
```

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Asp Lys Thr Tyr Thr Asn Trp Phe Gln Gln Arg Pro Gly Gln Ser
        35                  40                  45

Pro Arg Arg Leu Ile Tyr Glu Val Ser Lys Leu Asp Val Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Asp
                85                  90                  95

Thr His Phe Pro Leu Thr Phe Gly Gly Gly Thr Lys Val Glu Ile Lys
            100                 105                 110
```

<210> SEQ ID NO 9
<211> LENGTH: 121
<212> TYPE: PRT
<213> ORGANISM: Artificial Sequence
<220> FEATURE:
<223> OTHER INFORMATION: Synthetic Construct

<400> SEQUENCE: 9

```
Gln Val Thr Leu Lys Glu Ser Gly Pro Val Leu Leu Lys Pro Thr Glu
1               5                   10                  15

Thr Leu Thr Leu Thr Cys Thr Val Ser Gly Phe Ser Leu Ser Asn Pro
            20                  25                  30

Arg Met Gly Val Ser Trp Ile Arg Gln Pro Pro Gly Lys Ala Leu Glu
        35                  40                  45

Trp Phe Ala His Ile Phe Ser Thr Asp Glu Lys Ser Leu Lys Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Ala Pro Val Asp Ser Ala Thr Tyr Tyr
                85                  90                  95

Cys Ala Arg Asp Ser Ser Asn Tyr Glu Gly Tyr Phe Asp Phe Trp Gly
            100                 105                 110

Gln Gly Thr Leu Val Thr Val Ser Ser
            115                 120
```

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

```
Glu Val Val Leu Thr Gln Ser Pro Ala Thr Leu Ser Val Ser Pro Gly
1               5                   10                  15
```

Glu Arg Ala Thr Leu Ser Cys Arg Ala Ser Gln Ser Val Arg Ser Asn
            20                  25                  30

Leu Ala Trp Tyr Gln Gln Lys Ser Gly Gln Ala Pro Arg Leu Leu Ile
        35                  40                  45

Tyr Gly Ser Thr Ile Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asp Trp Pro Phe
                85                  90                  95

Thr Phe Gly Pro Gly Thr Lys Val Asp Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Synthetic Construct

<400> SEQUENCE: 11

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Phe
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

Glu Val Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Phe Ala Trp Tyr Gln Gln Arg Pro Gly Gln Ala Pro Arg Leu Leu Leu
        35                  40                  45

Tyr Gly Ala Thr Thr Arg Ala Thr Gly Leu Pro Gly Arg Phe Ser Gly
    50                  55                  60

Ser Gly Ser Gly Thr Glu Asn Ile Leu Thr Ile Ser Ser Leu Gln Ser
65                  70                  75                  80

Glu Asp Phe Ala Ile Tyr Phe Cys Gln Gln Tyr Lys Asp Trp Pro Phe
                85                  90                  95

```
Thr Phe Gly Pro Gly Ser Lys Val Asp Ile Lys
            100                 105

<210> SEQ ID NO 13
<211> LENGTH: 121
<212> TYPE: PRT
<213> ORGANISM: Artificial Sequence
<220> FEATURE:
<223> OTHER INFORMATION: Synthetic Construct

<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Gly His Ile Phe Ser Thr Asp Glu Lys Ser Tyr Ser Thr Ser
    50                  55                  60

Leu Arg Gly Arg Ile Thr Ile Ser Lys Asp Thr Ser Arg Gly Leu Val
65                  70                  75                  80

Val Leu Thr Leu Thr Asn Met Asp Pro Val Asp Thr Ala Thr Tyr Tyr
                85                  90                  95

Cys Ala Arg Asp Ser Ser Asn Tyr Glu Gly Tyr Phe Asp Phe Trp Gly
            100                 105                 110

Pro Gly Phe Leu Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Arg Val Ser Gln Ser Ile Gly Ala Asn
            20                  25                  30

Leu Ala Trp Tyr Gln Gln Lys Phe Gly Gln Ala Pro Arg Leu Leu Ile
        35                  40                  45

Tyr Gly Ala Ser Thr Arg Ala Thr Gly Ile Pro Val Arg Phe Ser Gly
    50                  55                  60

Gly Gly Ser Gly Thr Glu Phe Thr Leu Thr Ile Ser Ser Leu Gln Ser
65                  70                  75                  80

Glu Asp Phe Ala Ile Tyr Ser Cys Gln Gln Tyr Ile Tyr Trp Pro Phe
                85                  90                  95

Thr Phe Gly Pro Gly Thr Thr Val Asp Ile Lys
            100                 105

<210> SEQ ID NO 15
<211> LENGTH: 121
<212> TYPE: PRT
<213> ORGANISM: Artificial Sequence
<220> FEATURE:
<223> OTHER INFORMATION: Synthetic Construct

<400> SEQUENCE: 15
```

-continued

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Met Gly Val Ser Trp Ile Arg Gln Pro Pro Gly Lys Ala Leu Glu
        35                  40                  45

Trp Phe Ala His Ile Phe Ser Thr Asp Glu Lys Ser Phe Arg Thr Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
                100                 105                 110

Gln Gly Ile Leu Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Asp Ser Gly Thr Glu Phe Ser Leu Thr Ile Ser Ser Leu Gln Ser
65                  70                  75                  80

Glu Asp Phe Ala Val Tyr Phe Cys Gln Gln Tyr Lys Asp Trp Pro Phe
                85                  90                  95

Thr Phe Gly Pro Gly Thr Lys Val Glu Ile Lys
                100                 105

<210> SEQ ID NO 17
<211> LENGTH: 122
<212> TYPE: PRT
<213> ORGANISM: Artificial Sequence
<220> FEATURE:
<223> OTHER INFORMATION: Synthetic Construct

<400> SEQUENCE: 17

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
            20                  25                  30

Arg Met Gly Val Ser Trp Ile Arg Gln Pro Pro Gly Lys Ala Leu Glu
        35                  40                  45

Trp Phe Ala His Ile Phe Ser Ser Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
            85                  90                  95

Cys Ala Arg Asp Ser Ser Asn Tyr Glu Gly Tyr Phe Asp Phe Trp Gly
            100                 105                 110

Gln Gly Thr Leu Val Thr Val Ser Ser Asn
        115                 120

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Met Val Val Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asp
            20                  25                  30

Leu Ala Trp Tyr Gln Gln Pro Pro Gly Gln Ser Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Asp Phe Thr Leu Thr Ile Thr Ser Leu Glu Ser
65                  70                  75                  80

Glu Asp Phe Ala Val Tyr Tyr Cys Gln Gln Tyr Asn Asp Trp Pro Phe
                85                  90                  95

Thr Phe Gly Pro Gly Thr Lys Val Asp Ile Lys
            100                 105

<210> SEQ ID NO 19
<211> LENGTH: 121
<212> TYPE: PRT
<213> ORGANISM: Artificial Sequence
<220> FEATURE:
<223> OTHER INFORMATION: Synthetic Construct

<400> SEQUENCE: 19

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
            20                  25                  30

Arg Met Gly Val Ser Trp Ile Arg Gln Pro Pro Gly Lys Ala Leu Glu
        35                  40                  45

Trp Phe Ala His Ile Phe Ser Ser Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 20
<211> LENGTH: 107
<212> TYPE: PRT

<213> ORGANISM: Artificial Sequence
<220> FEATURE:
<223> OTHER INFORMATION: Synthetic Construct

<400> SEQUENCE: 20

```
Glu Met Glu Val Thr Gln Ser Pro Ala Thr Leu Ser Val Ser Pro Gly
1               5                   10                  15

Glu Arg Ala Thr Leu Ser Cys Arg Ala Ser Gln Asn Ile Gly Ser Asp
            20                  25                  30

Leu Ala Trp Tyr Gln Gln Ser Gly Gln Ala Pro Arg Leu Leu Ile
        35                  40                  45

Ser Gly Ala Ser Thr Arg Ala Thr Gly Val Pro Thr Arg Phe Ser Gly
50                  55                  60

Ser Gly Ser Gly Thr Asp Phe Thr Leu Thr Ile Thr Ser Leu Gln Ser
65                  70                  75                  80

Glu Asp Phe Ala Val Tyr Tyr Cys Gln Gln Tyr Asn Asp Trp Pro Phe
                85                  90                  95

Thr Phe Gly Pro Gly Thr Lys Val Asp Ile Lys
            100                 105
```

<210> SEQ ID NO 21
<211> LENGTH: 121
<212> TYPE: PRT
<213> ORGANISM: Artificial Sequence
<220> FEATURE:
<223> OTHER INFORMATION: Synthetic Construct

<400> SEQUENCE: 21

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
50                  55                  60

Leu Arg Ser Arg Leu Thr Leu Ser Lys Asp Thr Ser Lys Ser Gln Val
65                  70                  75                  80

Val Leu Ile Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120
```

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

```
Glu Val Val Met Thr Gln Ser Pro Pro Asn Leu Ser Val Ser Pro Gly
1               5                   10                  15

Glu Arg Ala Thr Leu Ser Cys Arg Ala Ser Gln Ser Val Thr Ser Asn
            20                  25                  30

Phe Ala Trp Tyr Gln Gln Arg Pro Gly Gln Ser Pro Arg Leu Leu Leu
        35                  40                  45
```

```
Tyr Gly Ala Ser Thr Arg Ala Thr Gly Val Pro Gly Arg Phe Ser Gly
        50                  55                  60

Ser Gly Ser Gly Thr Glu Asn Ile Leu Thr Ile Ser Ser Leu Gln Ser
 65              70                  75                      80

Glu Asp Phe Ala Val Tyr Phe Cys Gln Gln Tyr Lys Asp Trp Pro Phe
                85                  90                  95

Thr Phe Gly Pro Gly Ser Lys Val Asp Ile Lys
            100                 105

<210> SEQ ID NO 23
<211> LENGTH: 121
<212> TYPE: PRT
<213> ORGANISM: Artificial Sequence
<220> FEATURE:
<223> OTHER INFORMATION: Synthetic Construct

<400> SEQUENCE: 23

Gln Val Thr Leu Lys Glu Ser Gly Pro Val Leu Val Lys Pro Thr Glu
  1               5                  10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Thr Asp Glu Lys Ser Ile Arg Arg Ser
 50                  55                  60

Leu Arg Ser Arg Leu Thr Leu Ser Lys Asp Thr Ser Lys Ser Gln Val
 65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Glu Val Val Met Thr Gln Ser Pro Ala Thr Leu Ser Val Ser Pro Gly
  1               5                  10                  15

Glu Arg Ala Thr Leu Ser Cys Arg Ala Ser Gln Gly Val Ser Ser Asn
                20                  25                  30

Phe Ala Trp Tyr Gln Gln Arg Pro Gly Gln Ser Pro Arg Leu Leu Leu
            35                  40                  45

Tyr Gly Ala Ser Thr Arg Ala Thr Gly Val Pro Gly Arg Phe Ser Gly
        50                  55                  60

Ser Gly Ser Gly Thr Glu Asn Ile Leu Thr Ile Ser Ser Leu Gln Ser
 65              70                  75                      80

Glu Asp Phe Ala Ile Tyr Phe Cys Gln Gln Tyr Lys Asp Trp Pro Phe
                85                  90                  95

Thr Phe Gly Pro Gly Ser Lys Val Asp Ile Lys
            100                 105
```

```
<210> SEQ ID NO 25
<211> LENGTH: 121
<212> TYPE: PRT
<213> ORGANISM: Artificial Sequence
<220> FEATURE:
<223> OTHER INFORMATION: Synthetic Construct

<400> SEQUENCE: 25

Gln Val Thr Leu Glu Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Pro Glu
        35                  40                  45

Trp Phe Ala His Ile Phe Ser Thr Asp Glu Lys Ser Leu Arg Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Arg Asn
            20                  25                  30

Leu Ala Trp Tyr Gln Gln Lys Pro Gly Gln Ala Pro Arg Leu Leu Ile
        35                  40                  45

Phe Gly Thr Ser Thr Arg Ala Thr Gly Ile Pro Ala Arg Phe Ser Gly
    50                  55                  60

Ser Gly Ser Gly Thr Glu Phe Thr Leu Thr Ile Asp Ser Leu Gln Ser
65                  70                  75                  80

Glu His Ser Gly Leu Tyr Tyr Cys Gln Gln Tyr Asn Asp Trp Pro Phe
                85                  90                  95

Thr Phe Gly Pro Gly Thr Lys Val Asp Ile Lys
            100                 105

<210> SEQ ID NO 27
<211> LENGTH: 121
<212> TYPE: PRT
<213> ORGANISM: Artificial Sequence
<220> FEATURE:
<223> OTHER INFORMATION: Synthetic Construct

<400> SEQUENCE: 27

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30
```

Lys Met Gly Val Ser Trp Ile Arg Gln Pro Gly Lys Ala Leu Glu
            35                  40                  45

Trp Leu Ala His Ile Phe Ser Thr Asp Glu Lys Ser Ile Arg Arg Ser
    50                  55                  60

Leu Arg Ser Arg Leu Thr Met Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Asp Ser Ser Asn Tyr Glu Gly Tyr Phe Asp Tyr Trp Gly
            100                 105                 110

Gln Gly Thr Leu Val Thr Val Ser Ser
            115                 120

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

Glu Val Leu Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
            20                  25                  30

Phe Ala Trp Tyr Gln Gln Arg Pro Gly Gln Ala Pro Arg Leu Leu Leu
            35                  40                  45

Phe Gly Ala Ser Thr Arg Ala Thr Gly Ile Pro Gly Arg Phe Ser Gly
        50                  55                  60

Ser Gly Ser Gly Thr Glu Asn Ile Leu Thr Ile Ser Ser Leu Gln Ser
65                  70                  75                  80

Glu Asp Phe Ala Ile Tyr Phe Cys Gln Gln Tyr Lys Asp Trp Pro Phe
                85                  90                  95

Thr Phe Gly Pro Gly Ser Lys Val Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic Construct

<400> SEQUENCE: 29

Asp Val Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Asn Pro Gly Gln Ala Pro Arg Leu Leu Ile
            35                  40                  45

Phe Gly Ser Ser Thr Arg Ala Thr Gly Ile Pro Ala Ser Phe Ser Gly
        50                  55                  60

Ser Gly Ser Gly Thr Glu Phe Thr Leu Thr Ile Asn Ser Leu Gln Ser
65                  70                  75                  80

Glu His Ser Ala Val Tyr Tyr Cys Gln Gln Tyr Asn Asp Trp Pro Phe
                85                  90                  95

Thr Phe Gly Pro Gly Thr Lys Val Asp Ile Lys

```
                    100                 105

<210> SEQ ID NO 30
<211> LENGTH: 121
<212> TYPE: PRT
<213> ORGANISM: Artificial Sequence
<220> FEATURE:
<223> OTHER INFORMATION: Synthetic Construct

<400> SEQUENCE: 30

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Pro
            20                  25                  30

Arg Met Gly Val Ser Trp Ile Arg Gln Pro Pro Gly Lys Ala Leu Glu
        35                  40                  45

Trp Leu Gly His Ile Phe Ser Ser Asp Glu Lys Ser Tyr Arg Leu Ser
    50                  55                  60

Leu Arg Ser Arg Leu Ser Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Asp Ser Ser Asn Tyr Gly Tyr Phe Asp Tyr Trp Gly
            100                 105                 110

Gln Gly Thr Leu Val Thr Val Ser Ser
            115                 120

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ile Asn Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asp Tyr Asn Asn Trp Pro Phe
                85                  90                  95

Thr Phe Gly Pro Gly Thr Lys Val Asp Ile Lys
            100                 105

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Gln Val Thr Leu Lys Glu Ser Gly Pro Val Leu Val Lys Pro Ile Glu
1               5                   10                  15
```

```
Thr Leu Thr Leu Thr Cys Thr Val Cys Gly Phe Ser Leu Ser Asn Pro
            20                  25                  30

Arg Met Gly Val Ser Trp Ile Arg Gln Pro Pro Gly Lys Ala Leu Glu
        35                  40                  45

Trp Leu Gly His Ile Phe Ser Ser Asp Glu Lys Ser Tyr Arg Leu Phe
    50                  55                  60

Leu Arg Ser Arg Leu Ser Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asp Tyr Glu Gly Tyr Phe Asp Tyr Trp Gly
            100                 105                 110

Gln Gly Thr Leu Val Thr Val Ser Ser
        115                 120
```

<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

```
Glu Ile Val Met Thr Gln Ser Pro Ala Thr Leu Ser Val Ser Pro Gly
1               5                   10                  15

Glu Arg Thr Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Glu Tyr Asn Asn Trp Pro Phe
                85                  90                  95

Thr Phe Gly Gln Gly Thr Lys Val Glu Ile Lys
            100                 105
```

<210> SEQ ID NO 34
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (83)..(83)
<223> OTHER INFORMATION: Xaa can be any naturally occurring amino acid

<400> SEQUENCE: 34

```
Gln Val Thr Leu Lys Glu Ser Gly Pro Val Leu Val Lys Pro Thr Glu
1               5                   10                  15

Thr Leu Thr Leu Thr Cys Thr Val Phe Gly Phe Ser Leu Ser Asn Pro
            20                  25                  30

Arg Met Gly Val Ser Trp Ile Arg Gln Pro Pro Gly Lys Ala Pro Glu
        35                  40                  45

Trp Leu Gly His Ile Phe Ser Ser Asp Glu Lys Ser Tyr Arg Leu Ser
    50                  55                  60
```

```
Leu Arg Ser Arg Leu Ser Ile Ser Lys Asp Thr Ser Lys Ser Gln Val
 65                  70                  75                  80

Val Phe Xaa Met Thr Asn Met Asp Pro Gly Asp Pro Ala Thr Tyr Tyr
                 85                  90                  95

Cys Val Arg Asp Ser Ser Asn Tyr Glu Glu Tyr Phe Asp Tyr Trp Gly
            100                 105                 110

Gln Gly Thr Leu Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: Synthetic Construct

<400> SEQUENCE: 35

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Pro
                 20                  25                  30

Arg Met Gly Val Ser Trp Leu Arg Gln Pro Pro Gly Lys Ala Leu Glu
             35                  40                  45

Trp Phe Ala His Ile Phe Ser Thr Asp Glu Lys Ser Tyr Ser Pro Ser
 50                  55                  60

Leu Arg Gly Arg Leu Thr Val Ser Lys Asp Thr Ser Lys Ser Gln Val
 65                  70                  75                  80

Val Leu Thr Leu Thr Asn Met Asp Pro Val Asp Thr Ala Thr Tyr Tyr
                 85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
            115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Lys Ile Val Met Thr Gln Ser Pro Ala Thr Leu Ser Val Ser Pro Gly
 1               5                  10                  15

Glu Arg Ala Thr Leu Ser Cys Arg Ala Asn Gln Ile Val Ser Ser Asn
             20                  25                  30

Leu Ala Trp Tyr Gln Gln Lys Pro Gly Gln Ala Pro Arg Leu Leu Val
             35                  40                  45

Phe Gly Thr Ser Thr Arg Ala Thr Gly Ile Pro Ile Arg Phe Ser Gly
 50                  55                  60

Ser Gly Ser Gly Thr Glu Phe Thr Leu Thr Val Ser Ser Leu Gln Ser
 65                  70                  75                  80

Glu Asp Phe Ala Val Tyr Val Cys Gln Gln Tyr Asn Asp Trp Pro Phe
                 85                  90                  95

Thr Phe Gly Pro Gly Thr Lys Val Asp Ile Lys
            100                 105

<210> SEQ ID NO 37
```

```
<211> LENGTH: 118
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Asp Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Val Val
    50                  55                  60

Pro Leu Asn Gly Arg Phe Ile Ile Ser Arg Asp Asp Ser Arg Asn Thr
65                  70                  75                  80

Leu Tyr Leu Gln Leu Asn Asn Leu Lys Thr Glu Asp Thr Ala Val Tyr
                85                  90                  95

Tyr Cys Thr Thr Val Pro Gly Ser Tyr Gly Tyr Trp Gly Gln Gly Thr
            100                 105                 110

Leu Val Thr Val Ser Ser
            115

<210> SEQ ID NO 38
<211> LENGTH: 112
<212> TYPE: PRT
<213> ORGANISM: Artificial Sequence
<220> FEATURE:
<223> OTHER INFORMATION: Synthetic Construct

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Lys Arg Asn Asn Tyr Leu Asp Trp Phe Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110

<210> SEQ ID NO 39
<211> LENGTH: 120
<212> TYPE: PRT
<213> ORGANISM: Artificial Sequence
<220> FEATURE:
<223> OTHER INFORMATION: Synthetic Construct

<400> SEQUENCE: 39

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
            20                  25                  30
```

```
Trp Met Ser Trp Val Arg Gln Ala Pro Gly Lys Gly Leu Glu Trp Val
            35                  40                  45

Gly Arg Ile Lys Ser Ile Ala Asp Gly Gly Ala Thr Asp Tyr Ala Ala
 50                  55                  60

Pro Val Arg Asn Arg Phe Thr Ile Ser Arg Asp Asp Ser Arg Asn Thr
 65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Ala Phe Asp Met Trp Gly Gln
                100                 105                 110

Gly Thr Met Val Thr Val Ser Ser
            115                 120
```

<210> SEQ ID NO 40
<211> LENGTH: 112
<212> TYPE: PRT
<213> ORGANISM: Artificial Sequence
<220> FEATURE:
<223> OTHER INFORMATION: Synthetic Construct

<400> SEQUENCE: 40

```
Asp Ile Val Leu Thr Gln Ser Pro Leu Ser Leu Ser Val Thr Pro Gly
 1               5                  10                  15

Glu Pro Ala Ser Ile Ser Cys Arg Ser Ser Gln Ser Leu Leu Tyr Ser
             20                  25                  30

Asn Gly Lys Asn Tyr Leu Asp Trp Phe Leu His Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Ile Asp Phe Ile Leu Lys Ile
 65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
                100                 105                 110
```

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

```
Glu Val Gln Leu Val Glu Ser Trp Gly Val Leu Val Lys Pro Gly Gly
 1               5                  10                  15

Ser Leu Arg Leu Ser Cys Ala Ala Ser Gly Phe Ile Phe Asn Asn Ala
             20                  25                  30

Trp Met Ser Trp Val Arg Gln Ala Pro Gly Lys Gly Leu Glu Trp Ile
             35                  40                  45

Gly Arg Ile Lys Ser Lys Ser Asp Gly Gly Thr Thr Asp Tyr Ala Ala
 50                  55                  60

Pro Val Lys Asp Arg Phe Thr Ile Ser Arg Asp Asp Ser Lys Asp Thr
 65                  70                  75                  80

Leu Tyr Leu Gln Met Asn Gly Leu Lys Thr Glu Asp Thr Ala Val Tyr
                85                  90                  95

Phe Cys Thr Thr Ala Pro Gly Gly Pro Phe Asp Tyr Trp Gly Gln Gly
                100                 105                 110
```

Thr Leu Val Thr Val Ser Ser
        115

<210> SEQ ID NO 42
<211> LENGTH: 112
<212> TYPE: PRT
<213> ORGANISM: Artificial Sequence
<220> FEATURE:
<223> OTHER INFORMATION: Synthetic Construct

<400> SEQUENCE: 42

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asp Gly Phe Asn Tyr Leu Asp Trp Phe Leu Gln Lys Pro Gly Gln Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Asp Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 43
<211> LENGTH: 120
<212> TYPE: PRT
<213> ORGANISM: Artificial Sequence
<220> FEATURE:
<223> OTHER INFORMATION: Synthetic Construct

<400> SEQUENCE: 43

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
            20                  25                  30

Trp Met Ser Trp Val Arg Gln Ala Pro Gly Lys Gly Leu Glu Trp Val
        35                  40                  45

Gly Arg Ile Lys Ser Ile Thr Asp Gly Gly Val Ile Asp Tyr Ala Ala
    50                  55                  60

Pro Val Arg Asn Arg Cys Thr Ile Ser Arg Asp Asp Ser Arg Asn Thr
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Asp Phe Asp Met Trp Gly Gln
            100                 105                 110

Gly Arg Met Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Synthetic Construct

<400> SEQUENCE: 44

Glu Val Asn Leu Val Glu Ser Gly Gly Leu Val Lys Pro Gly Gly
1               5                   10                  15

Ser Leu Arg Leu Ser Cys Glu Ala Ser Gly Phe Thr Phe Ser Tyr Ala
                20                  25                  30

Trp Met Ser Trp Val Arg Gln Ala Pro Gly Lys Gly Leu Glu Trp Val
            35                  40                  45

Gly Arg Ile Lys Ser Ile Asn Asp Gly Gly Ala Thr Asp Tyr Ala Ser
        50                  55                  60

Pro Val Arg Asn Arg Phe Thr Ile Ser Arg Asp Ser Arg Asn Met
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Ala Phe Asp Met Trp Gly Gln
            100                 105                 110

Gly Thr Leu Val Thr Val Ser Ser
            115                 120

<210> SEQ ID NO 45
<211> LENGTH: 112
<212> TYPE: PRT
<213> ORGANISM: Artificial Sequence
<220> FEATURE:
<223> OTHER INFORMATION: Synthetic Construct

<400> SEQUENCE: 45

Asp Ile Val Leu Thr Gln Ser Pro Leu Ser Leu Ser Val Thr Pro Gly
1               5                   10                  15

Glu Pro Ala Ser Ile Ser Cys Arg Ser Thr Gln Ser Leu Leu Tyr Ser
                20                  25                  30

Asn Gly Lys Asn Tyr Leu Asp Trp Phe Leu His Lys Pro Gly Gln Ser
            35                  40                  45

Pro Gln Leu Leu Ile Phe Leu Gly Ser Ile Arg Ala Ser Gly Val Pro
        50                  55                  60

Asp Arg Phe Ser Gly Ser Gly Ser Gly Ile Asp Phe Ile Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Thr Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Ile Asp Gly Gly Thr Thr Asp Tyr Ala Ala
        50                  55                  60

Pro Val Lys Gly Arg Phe Ile Ile Ser Arg Asp Asp Ser Lys Asn Thr
65                  70                  75                  80

```
Leu Ser Leu Gln Met Asn Ser Leu Lys Thr Glu Asp Thr Ala Met Tyr
                85                  90                  95

Tyr Cys Thr Thr Ala Pro Gly Gly Pro Phe Asp Tyr Trp Gly Gln Gly
            100                 105                 110

Ser Leu Val Thr Val Ser Ser
            115

<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asp Arg Arg Asn Tyr Leu Asp Trp Phe Leu Gln Lys Pro Gly Gln Ser
        35                  40                  45

Pro His Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Ile Thr Phe Gly Gln Gly Thr Arg Leu Glu Ile Lys
            100                 105                 110

<210> SEQ ID NO 48
<211> LENGTH: 126
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Asn
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Tyr His Glu Tyr Ala Gly Gly Tyr Tyr Gly Gly Ala
            100                 105                 110

Met Asp Pro Trp Gly Gln Gly Thr Leu Val Thr Val Ser Ser
            115                 120                 125

<210> SEQ ID NO 49
<211> LENGTH: 112
<212> TYPE: PRT
```

<213> ORGANISM: Artificial Sequence
<220> FEATURE:
<223> OTHER INFORMATION: Synthetic Construct

<400> SEQUENCE: 49

```
Glu Leu Gln Ser Val Leu Thr Gln Pro Pro Ser Ala Ser Gly Thr Pro
1               5                   10                  15
Gly Gln Arg Val Thr Ile Ser Cys Ser Gly Ser Ser Ser Asn Ile Gly
            20                  25                  30
Ser Asn Tyr Val Tyr Trp Tyr Gln Gln Leu Pro Gly Thr Ala Pro Lys
        35                  40                  45
Ile Leu Ile Tyr Arg Asn Asn Gln Arg Pro Ser Gly Val Pro Asp Arg
65                  70                  75                  80
Phe Ser Gly Ser Lys Ser Gly Thr Ser Ala Ser Leu Ala Ile Ser Gly
65                  70                  75                  80
Leu Arg Ser Glu Asp Glu Ala Asp Tyr Tyr Cys Ala Ala Trp Asp Asp
                85                  90                  95
Asn Leu Ser Gly Trp Val Phe Gly Thr Gly Thr Lys Leu Thr Val Leu
            100                 105                 110
```

<210> SEQ ID NO 50
<211> LENGTH: 123
<212> TYPE: PRT
<213> ORGANISM: Artificial Sequence
<220> FEATURE:
<223> OTHER INFORMATION: Synthetic Construct

<400> SEQUENCE: 50

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Asp Ile Ser Gly Gly Gly Arg Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Gly Leu Leu Tyr Gly Gly Val Tyr Pro Met Asp Ile
            100                 105                 110
Trp Gly Gln Gly Thr Leu Val Thr Val Ser Ser
        115                 120
```

<210> SEQ ID NO 51
<211> LENGTH: 107
<212> TYPE: PRT
<213> ORGANISM: Artificial Sequence
<220> FEATURE:
<223> OTHER INFORMATION: Synthetic Construct

<400> SEQUENCE: 51

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys
                100                 105

<210> SEQ ID NO 52
<211> LENGTH: 491
<212> TYPE: PRT
<213> ORGANISM: Artificial Sequence
<220> FEATURE:
<223> OTHER INFORMATION: Synthetic Construct

<400> SEQUENCE: 52

Met Ala Leu Pro Val Thr Ala Leu Leu Leu Pro Leu Ala Leu Leu Leu
 1               5                  10                  15

His Ala Ala Arg Pro Asp Val Val Met Thr Gln Ser Pro Leu Ser Leu
                 20                  25                  30

Pro Val Thr Leu Gly Gln Pro Ala Ser Ile Ser Cys Lys Ser Ser Gln
             35                  40                  45

Ser Leu Leu Tyr Ser Asn Gly Lys Thr Tyr Leu Asn Trp Phe Gln Gln
 50                  55                  60

Arg Pro Gly Gln Ser Pro Arg Arg Leu Ile Tyr Gln Val Ser Lys Leu
 65                  70                  75                  80

Asp Ser Gly Val Pro Asp Arg Phe Ser Gly Ser Gly Ser Gly Thr Asp
                 85                  90                  95

Phe Thr Leu Lys Ile Ser Arg Val Glu Ala Glu Asp Val Gly Val Tyr
                100                 105                 110

Tyr Cys Gly Gln Asp Thr His Phe Pro Leu Thr Phe Gly Gly Gly Thr
             115                 120                 125

Lys Val Glu Ile Lys Gly Gly Gly Gly Ser Gly Gly Gly Gly Ser Gly
130                 135                 140

Gly Gly Ser Gly Gly Gly Gly Ser Gln Val Gln Leu Val Gln Ser
145                 150                 155                 160

Gly Ala Glu Val Lys Lys Pro Gly Ala Ser Val Lys Val Ser Cys Lys
                165                 170                 175

Ala Ser Gly Tyr Thr Phe Thr Asp Tyr Thr Leu His Trp Val Arg Gln
                180                 185                 190

Ala Pro Gly Gln Gly Leu Glu Trp Met Gly Gly Ile Trp Pro Ile Thr
            195                 200                 205

Gly Gly Thr Thr Tyr Asn Gln Lys Phe Lys Gly Arg Val Thr Met Thr
210                 215                 220

Arg Asp Thr Ser Thr Ser Thr Val Tyr Met Glu Leu Ser Ser Leu Arg
225                 230                 235                 240

Ser Glu Asp Thr Ala Val Tyr Tyr Cys Ala Arg Gly Glu Ala Gln Gly
                245                 250                 255

Ser Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
290                 295                 300
```

```
Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
        340                 345                 350

Met Arg Pro Val Gln Thr Thr Gln Glu Glu Asp Gly Cys Ser Cys Arg
    355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 53
<211> LENGTH: 492
<212> TYPE: PRT
<213> ORGANISM: Artificial Sequence
<220> FEATURE:
<223> OTHER INFORMATION: Synthetic Construct

<400> SEQUENCE: 53

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Leu Lys Pro Thr Glu Thr Leu Thr Leu Thr Cys Thr Val Ser Gly Phe
            35                  40                  45

Ser Leu Ser Asn Pro Arg Met Gly Val Ser Trp Ile Arg Gln Pro Pro
50                  55                  60

Gly Lys Ala Leu Glu Trp Phe Ala His Ile Phe Ser Thr Asp Glu Lys
65                  70                  75                  80

Ser Leu Lys Leu Ser Leu Arg Ser Arg Leu Thr Leu Ser Lys Asp Thr
                85                  90                  95

Ser Lys Ser Gln Val Val Leu Thr Met Thr Asn Met Ala Pro Val Asp
            100                 105                 110

Ser Ala Thr Tyr Tyr Cys Ala Arg Asp Ser Ser Asn Tyr Glu Gly Tyr
        115                 120                 125

Phe Asp Phe Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Val Val Leu Thr Gln Ser Pro Ala Thr Leu Ser Val Ser
                165                 170                 175
```

-continued

```
Pro Gly Glu Arg Ala Thr Leu Ser Cys Arg Ala Ser Gln Ser Val Arg
            180                 185                 190

Ser Asn Leu Ala Trp Tyr Gln Gln Lys Ser Gly Gln Ala Pro Arg Leu
        195                 200                 205

Leu Ile Tyr Gly Ser Thr Ile Arg Ala Thr Gly Val Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln Tyr Ser Asp Trp
                245                 250                 255

Pro Phe Thr Phe Gly Pro Gly Thr Lys Val Asp Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 54
<211> LENGTH: 492
<212> TYPE: PRT
<213> ORGANISM: Artificial Sequence
<220> FEATURE:
<223> OTHER INFORMATION: Synthetic Construct

<400> SEQUENCE: 54

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
        35                  40                  45
```

```
Ser Leu Ser Asn Ala Arg Met Gly Val Ser Trp Ile Arg Gln Pro Pro
         50                  55                  60

Gly Lys Ala Leu Glu Trp Leu Ala His Ile Phe Ser Thr Asp Glu Lys
 65                  70                  75                  80

Ser Ile Arg Arg Ser Leu Arg Ser Arg Leu Thr Leu Ser Lys Asp Thr
                 85                  90                  95

Ser Lys Ser Gln Val Val Leu Thr Met Thr Asn Met Asp Pro Val Asp
            100                 105                 110

Thr Ala Thr Tyr Phe Cys Ala Arg Asp Ser Ser Asn Tyr Glu Gly Tyr
        115                 120                 125

Phe Asp Tyr Trp Gly Gln Gly Thr Leu Val Thr Val Ser Ser Gly Gly
    130                 135                 140

Gly Gly Ser Gly Gly Gly Ser Gly Gly Gly Ser Gly Gly Gly
145                 150                 155                 160

Gly Ser Glu Val Val Met Thr Gln Ser Pro Ala Thr Leu Ser Val Ser
                165                 170                 175

Pro Gly Glu Arg Val Thr Leu Ser Cys Arg Ala Ser Gln Ser Val Ser
            180                 185                 190

Ser Asn Phe Ala Trp Tyr Gln Gln Arg Pro Gly Gln Ala Pro Arg Leu
        195                 200                 205

Leu Leu Tyr Gly Ala Thr Thr Arg Ala Thr Gly Leu Pro Gly Arg Phe
    210                 215                 220

Ser Gly Ser Gly Ser Gly Thr Glu Asn Ile Leu Thr Ile Ser Ser Leu
225                 230                 235                 240

Gln Ser Glu Asp Phe Ala Ile Tyr Phe Cys Gln Gln Tyr Lys Asp Trp
                245                 250                 255

Pro Phe Thr Phe Gly Pro Gly Ser Lys Val Asp Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460
```

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 55
<211> LENGTH: 492
<212> TYPE: PRT
<213> ORGANISM: Artificial Sequence
<220> FEATURE:
<223> OTHER INFORMATION: Synthetic Construct

<400> SEQUENCE: 55

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
        35                  40                  45

Ser Leu Ser Asn Ala Arg Met Gly Val Ser Trp Ile Arg Gln Pro Pro
    50                  55                  60

Gly Lys Ala Leu Glu Trp Leu Gly His Ile Phe Ser Thr Asp Glu Lys
65                  70                  75                  80

Ser Tyr Ser Thr Ser Leu Arg Gly Arg Ile Thr Ile Ser Lys Asp Thr
                85                  90                  95

Ser Arg Gly Leu Val Val Leu Thr Leu Thr Asn Met Asp Pro Val Asp
            100                 105                 110

Thr Ala Thr Tyr Tyr Cys Ala Arg Asp Ser Ser Asn Tyr Glu Gly Tyr
        115                 120                 125

Phe Asp Phe Trp Gly Pro Gly Phe Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Val Ser
                165                 170                 175

Pro Gly Glu Arg Ala Thr Leu Ser Cys Arg Val Ser Gln Ser Ile Gly
            180                 185                 190

Ala Asn Leu Ala Trp Tyr Gln Gln Lys Phe Gly Gln Ala Pro Arg Leu
        195                 200                 205

Leu Ile Tyr Gly Ala Ser Thr Arg Ala Thr Gly Ile Pro Val Arg Phe
    210                 215                 220

Ser Gly Gly Gly Ser Gly Thr Glu Phe Thr Leu Thr Ile Ser Ser Leu
225                 230                 235                 240

Gln Ser Glu Asp Phe Ala Ile Tyr Ser Cys Gln Gln Tyr Ile Tyr Trp
                245                 250                 255

Pro Phe Thr Phe Gly Pro Gly Thr Thr Val Asp Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

```
Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
        355                 360                 365

Arg Phe Pro Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 56
<211> LENGTH: 492
<212> TYPE: PRT
<213> ORGANISM: Artificial Sequence
<220> FEATURE:
<223> OTHER INFORMATION: Synthetic Construct

<400> SEQUENCE: 56

Met Ala Leu Pro Val Thr Ala Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Val Lys Pro Thr Glu Thr Leu Thr Leu Thr Cys Thr Val Ser Gly Phe
            35                  40                  45

Ser Leu Asn Asn Ala Arg Met Gly Val Ser Trp Ile Arg Gln Pro Pro
    50                  55                  60

Gly Lys Ala Leu Glu Trp Phe Ala His Ile Phe Ser Thr Asp Glu Lys
65                  70                  75                  80

Ser Phe Arg Thr Ser Leu Arg Ser Arg Leu Thr Leu Ser Lys Asp Thr
                85                  90                  95

Ser Lys Ser Gln Val Val Leu Thr Met Thr Asn Met Asp Pro Val Asp
                100                 105                 110

Thr Ala Thr Tyr Tyr Cys Ala Arg Asp Ser Ser Asn Tyr Glu Gly Tyr
                115                 120                 125

Phe Asp Tyr Trp Gly Gln Gly Ile Leu Val Thr Val Ser Ser Gly Gly
130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
                180                 185                 190

Asn Asn Leu Ala Trp Tyr Gln Gln Lys Pro Gly Gln Ala Pro Arg Leu
                195                 200                 205
```

```
Leu Ile Tyr Gly Ala Ser Thr Arg Ala Thr Gly Val Pro Ala Arg Phe
    210                 215                 220

Ser Gly Ser Asp Ser Gly Thr Glu Phe Ser Leu Thr Ile Ser Ser Leu
225                 230                 235                 240

Gln Ser Glu Asp Phe Ala Val Tyr Phe Cys Gln Gln Tyr Lys Asp Trp
                245                 250                 255

Pro Phe Thr Phe Gly Pro Gly Thr Lys Val Glu Ile Lys Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 57
<211> LENGTH: 496
<212> TYPE: PRT
<213> ORGANISM: Artificial Sequence
<220> FEATURE:
<223> OTHER INFORMATION: Synthetic Construct

<400> SEQUENCE: 57

Met Ala Leu Pro Val Thr Ala Leu Leu Leu Pro Leu Ala Leu Leu Leu
1               5                   10                  15

His Ala Ala Arg Pro Glu Val Asn Leu Val Glu Ser Gly Gly Gly Leu
            20                  25                  30

Val Lys Pro Gly Gly Ser Leu Arg Leu Ser Cys Glu Ala Ser Gly Phe
        35                  40                  45

Thr Phe Ser Tyr Ala Trp Met Ser Trp Val Arg Gln Ala Pro Gly Lys
    50                  55                  60

Gly Leu Glu Trp Val Gly Arg Ile Lys Ser Ile Ala Asp Gly Gly Ala
65                  70                  75                  80
```

```
Thr Asp Tyr Ala Ala Pro Val Arg Asn Arg Phe Thr Ile Ser Arg Asp
                85                  90                  95

Asp Ser Arg Asn Thr Leu Tyr Leu Glu Met His Ser Leu Lys Thr Glu
            100                 105                 110

Asp Thr Ala Val Tyr Tyr Cys Thr Thr Ile Pro Gly Asn Asp Ala Phe
            115                 120                 125

Asp Met Trp Gly Gln Gly Thr Met Val Thr Val Ser Ser Gly Gly Gly
        130                 135                 140

Gly Ser Gly Gly Gly Gly Ser Gly Gly Gly Ser Gly Gly Gly Gly
145                 150                 155                 160

Ser Asp Ile Val Leu Thr Gln Ser Pro Leu Ser Leu Ser Val Thr Pro
                165                 170                 175

Gly Glu Pro Ala Ser Ile Ser Cys Arg Ser Ser Gln Ser Leu Leu Tyr
            180                 185                 190

Ser Asn Gly Lys Asn Tyr Leu Asp Trp Phe Leu His Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Ile Asp Phe Ile Leu Lys
225                 230                 235                 240

Ile Ser Arg Val Glu Ala Glu Asp Val Gly Val Tyr Tyr Cys Met Gln
                245                 250                 255

Ala Gln Gln Thr Pro Ile Thr Phe Gly Gln Gly Thr Arg Leu Glu Ile
            260                 265                 270

Lys Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 58
<211> LENGTH: 496
<212> TYPE: PRT
<213> ORGANISM: Artificial Sequence
<220> FEATURE:
<223> OTHER INFORMATION: Synthetic Construct

<400> SEQUENCE: 58

```
Met Ala Leu Pro Val Thr Ala Leu Leu Leu Pro Leu Ala Leu Leu Leu
1               5                   10                  15

His Ala Ala Arg Pro Glu Val Asn Leu Val Glu Ser Gly Gly Gly Leu
            20                  25                  30

Val Lys Pro Gly Gly Ser Leu Arg Leu Ser Cys Glu Ala Ser Gly Phe
        35                  40                  45

Thr Phe Ser Tyr Ala Trp Met Ser Trp Val Arg Gln Ala Pro Gly Lys
    50                  55                  60

Gly Leu Glu Trp Val Gly Arg Ile Lys Ser Ile Thr Asp Gly Gly Val
65                  70                  75                  80

Ile Asp Tyr Ala Ala Pro Val Arg Asn Arg Cys Thr Ile Ser Arg Asp
                85                  90                  95

Asp Ser Arg Asn Thr Leu Tyr Leu Glu Met His Ser Leu Lys Thr Glu
            100                 105                 110

Asp Thr Ala Val Tyr Tyr Cys Thr Thr Ile Pro Gly Asn Asp Asp Phe
        115                 120                 125

Asp Met Trp Gly Gln Gly Arg Met Val Thr Val Ser Ser Gly Gly Gly
    130                 135                 140

Gly Ser Gly Gly Gly Ser Gly Gly Gly Ser Gly Gly Gly Gly
145                 150                 155                 160

Ser Asp Ile Val Leu Thr Gln Ser Pro Leu Ser Leu Ser Val Thr Pro
                165                 170                 175

Gly Glu Pro Ala Ser Ile Ser Cys Arg Ser Ser Gln Ser Leu Leu Tyr
            180                 185                 190

Ser Asn Gly Lys Asn Tyr Leu Asp Trp Phe Leu His Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Ile Asp Phe Ile Leu Lys
225                 230                 235                 240

Ile Ser Arg Val Glu Ala Glu Asp Val Gly Val Tyr Tyr Cys Met Gln
                245                 250                 255

Ala Gln Gln Thr Pro Ile Thr Phe Gly Gln Gly Thr Arg Leu Glu Ile
            260                 265                 270

Lys Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
```

```
            370                 375                 380
Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
                435                 440                 445

Asp Lys Met Ala Glu Ala Tyr Ser Glu Ile Gly Met Lys Gly Glu Arg
                450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 59
<211> LENGTH: 495
<212> TYPE: PRT
<213> ORGANISM: Artificial Sequence
<220> FEATURE:
<223> OTHER INFORMATION: Synthetic Construct

<400> SEQUENCE: 59

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Trp Gly Val Leu
                20                  25                  30

Val Lys Pro Gly Gly Ser Leu Arg Leu Ser Cys Ala Ala Ser Gly Phe
            35                  40                  45

Ile Phe Asn Asn Ala Trp Met Ser Trp Val Arg Gln Ala Pro Gly Lys
        50                  55                  60

Gly Leu Glu Trp Ile Gly Arg Ile Lys Ser Lys Ser Asp Gly Gly Thr
65                  70                  75                  80

Thr Asp Tyr Ala Ala Pro Val Lys Asp Arg Phe Thr Ile Ser Arg Asp
                85                  90                  95

Asp Ser Lys Asp Thr Leu Tyr Leu Gln Met Asn Gly Leu Lys Thr Glu
                100                 105                 110

Asp Thr Ala Val Tyr Phe Cys Thr Thr Ala Pro Gly Gly Pro Phe Asp
            115                 120                 125

Tyr Trp Gly Gln Gly Thr Leu Val Thr Val Ser Ser Gly Gly Gly Gly
        130                 135                 140

Ser Gly Gly Gly Gly Ser Gly Gly Gly Gly Ser Gly Gly Gly Gly Ser
145                 150                 155                 160

Asp Ile Val Leu Thr Gln Ser Pro Leu Ser Leu Pro Val Thr Pro Gly
                165                 170                 175

Glu Pro Ala Ser Ile Ser Cys Arg Ser Ser Gln Ser Leu Leu His Arg
            180                 185                 190

Asp Gly Phe Asn Tyr Leu Asp Trp Phe Leu Gln Lys Pro Gly Gln Ser
        195                 200                 205

Pro Gln Leu Leu Ile Tyr Leu Ala Ser Ser Arg Ala Ser Gly Val Pro
    210                 215                 220

Asp Arg Phe Ser Gly Ser Asp Ser Gly Thr Asp Phe Thr Leu Lys Ile
225                 230                 235                 240

Ser Arg Val Glu Ala Glu Asp Val Gly Val Tyr Tyr Cys Met Gln Ala
```

```
                245                 250                 255
Leu Gln Thr Pro Ile Thr Phe Gly Gln Gly Thr Arg Leu Glu Ile Lys
                260                 265                 270
Thr Thr Thr Pro Ala Pro Arg Pro Pro Thr Pro Ala Pro Thr Ile Ala
                275                 280                 285
Ser Gln Pro Leu Ser Leu Arg Pro Glu Ala Cys Arg Pro Ala Ala Gly
            290                 295                 300
Gly Ala Val His Thr Arg Gly Leu Asp Phe Ala Cys Asp Ile Tyr Ile
305                 310                 315                 320
Trp Ala Pro Leu Ala Gly Thr Cys Gly Val Leu Leu Leu Ser Leu Val
                325                 330                 335
Ile Thr Leu Tyr Cys Lys Arg Gly Arg Lys Lys Leu Leu Tyr Ile Phe
                340                 345                 350
Lys Gln Pro Phe Met Arg Pro Val Gln Thr Thr Gln Glu Glu Asp Gly
                355                 360                 365
Cys Ser Cys Arg Phe Pro Glu Glu Glu Glu Gly Gly Cys Glu Leu Arg
            370                 375                 380
Val Lys Phe Ser Arg Ser Ala Asp Ala Pro Ala Tyr Gln Gln Gly Gln
385                 390                 395                 400
Asn Gln Leu Tyr Asn Glu Leu Asn Leu Gly Arg Arg Glu Glu Tyr Asp
                405                 410                 415
Val Leu Asp Lys Arg Arg Gly Arg Asp Pro Glu Met Gly Gly Lys Pro
                420                 425                 430
Arg Arg Lys Asn Pro Gln Glu Gly Leu Tyr Asn Glu Leu Gln Lys Asp
                435                 440                 445
Lys Met Ala Glu Ala Tyr Ser Glu Ile Gly Met Lys Gly Glu Arg Arg
            450                 455                 460
Arg Gly Lys Gly His Asp Gly Leu Tyr Gln Gly Leu Ser Thr Ala Thr
465                 470                 475                 480
Lys Asp Thr Tyr Asp Ala Leu His Met Gln Ala Leu Pro Pro Arg
                485                 490                 495

<210> SEQ ID NO 60
<211> LENGTH: 494
<212> TYPE: PRT
<213> ORGANISM: Artificial Sequence
<220> FEATURE:
<223> OTHER INFORMATION: Synthetic Construct

<400> SEQUENCE: 60

Met Ala Leu Pro Val Thr Ala Leu Leu Leu Pro Leu Ala Leu Leu Leu
1               5                   10                  15
His Ala Ala Arg Pro Glu Val Gln Leu Val Glu Ser Gly Gly Gly Leu
                20                  25                  30
Val Lys Pro Gly Gly Ser Leu Arg Leu Ser Cys Glu Ala Ser Gly Phe
            35                  40                  45
Thr Phe Ser Asp Ala Trp Met Ser Trp Val Arg Gln Ala Pro Gly Lys
        50                  55                  60
Gly Leu Glu Trp Val Gly Arg Ile Lys Ser Lys Thr Asp Gly Gly Thr
65                  70                  75                  80
Thr Asp Tyr Val Val Pro Leu Asn Gly Arg Phe Ile Ile Ser Arg Asp
                85                  90                  95
Asp Ser Arg Asn Thr Leu Tyr Leu Gln Leu Asn Asn Leu Lys Thr Glu
                100                 105                 110
Asp Thr Ala Val Tyr Tyr Cys Thr Thr Val Pro Gly Ser Tyr Gly Tyr
```

```
            115                 120                 125
Trp Gly Gln Gly Thr Leu Val Thr Val Ser Ser Gly Gly Gly Ser
            130                 135                 140

Gly Gly Gly Gly Ser Gly Gly Gly Ser Gly Gly Gly Ser Asp
145                 150                 155                 160

Ile Val Met Thr Gln Ser Pro Leu Ser Leu Pro Val Thr Pro Gly Glu
                165                 170                 175

Pro Ala Ser Ile Ser Cys Arg Ser Ser Gln Ser Leu Leu His Asn Lys
                180                 185                 190

Arg Asn Asn Tyr Leu Asp Trp Phe Leu Gln Lys Pro Gly Gln Ser Pro
                195                 200                 205

Gln Leu Leu Ile Tyr Leu Ala Ser Asn Arg Ala Ser Gly Val Pro Asp
                210                 215                 220

Arg Phe Ser Gly Gly Ser Gly Thr Asp Phe Thr Leu Lys Ile Ser
225                 230                 235                 240

Arg Val Glu Ala Glu Asp Val Gly Val Tyr Tyr Cys Met Gln Ala Gln
                245                 250                 255

Gln Thr Pro Ile Thr Phe Gly Gln Gly Thr Arg Leu Glu Ile Lys Thr
                260                 265                 270

Thr Thr Pro Ala Pro Arg Pro Pro Thr Pro Ala Pro Thr Ile Ala Ser
                275                 280                 285

Gln Pro Leu Ser Leu Arg Pro Glu Ala Cys Arg Pro Ala Ala Gly Gly
                290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
                340                 345                 350

Gln Pro Phe Met Arg Pro Val Gln Thr Thr Gln Glu Glu Asp Gly Cys
                355                 360                 365

Ser Cys Arg Phe Pro Glu Glu Glu Glu Gly Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
                450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 61
<211> LENGTH: 502
<212> TYPE: PRT
<213> ORGANISM: Artificial Sequence
<220> FEATURE:
<223> OTHER INFORMATION: Synthetic Construct
```

<400> SEQUENCE: 61

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Asp
        35                  40                  45

Thr Phe Ser Ser Asn Ala Ile Ser Trp Val Arg Gln Ala Pro Gly Gln
    50                  55                  60

Gly Leu Glu Trp Met Gly Val Ile Ile Pro Ile Phe Gly Thr Ala Asp
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg His Thr Tyr His Glu Tyr Ala Gly Gly
        115                 120                 125

Tyr Tyr Gly Gly Ala Met Asp Pro Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Glu Leu Gln Ser Val Leu Thr Gln Pro
                165                 170                 175

Pro Ser Ala Ser Gly Thr Pro Gly Gln Arg Val Thr Ile Ser Cys Ser
            180                 185                 190

Gly Ser Ser Ser Asn Ile Gly Ser Asn Tyr Val Tyr Trp Tyr Gln Gln
        195                 200                 205

Leu Pro Gly Thr Ala Pro Lys Ile Leu Ile Tyr Arg Asn Asn Gln Arg
    210                 215                 220

Pro Ser Gly Val Pro Asp Arg Phe Ser Gly Ser Lys Ser Gly Thr Ser
225                 230                 235                 240

Ala Ser Leu Ala Ile Ser Gly Leu Arg Ser Glu Asp Glu Ala Asp Tyr
                245                 250                 255

Tyr Cys Ala Ala Trp Asp Asp Asn Leu Ser Gly Trp Val Phe Gly Thr
            260                 265                 270

Gly Thr Lys Leu Thr Val Leu Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415
```

-continued

```
Gly Arg Arg Glu Glu Tyr Asp Val Leu Asp Lys Arg Gly Arg Asp
                420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
        450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

Thr Asp Tyr Thr Leu His
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

Gly Tyr Thr Phe Thr Asp
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Gly Tyr Thr Phe Thr Asp Tyr Thr Leu His
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Synthetic Construct

<400> SEQUENCE: 65

Gly Ile Asp Pro Ile Asn Gly Gly Thr Thr Tyr Asn Gln Lys Phe Lys
1               5                   10                  15

Gly

<210> SEQ ID NO 66
<211> LENGTH: 11
<212> TYPE: PRT
<213> ORGANISM: Artificial Sequence
<220> FEATURE:
```

-continued

```
<223> OTHER INFORMATION: Synthetic Construct

<400> SEQUENCE: 66

Gly Ile Asp Pro Ile Asn Gly Gly Thr Thr Tyr
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Gly Glu Ala Met Asp Ser
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Gly Ile Asn Pro Ile Asn Gly Gly Thr Thr Tyr Asn Gln Lys Phe Lys
1               5                   10                  15
Gly

<210> SEQ ID NO 69
<211> LENGTH: 11
<212> TYPE: PRT
<213> ORGANISM: Artificial Sequence
<220> FEATURE:
<223> OTHER INFORMATION: Synthetic Construct

<400> SEQUENCE: 69

Gly Ile Asn Pro Ile Asn Gly Gly Thr Thr Tyr
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Gly Ile Trp Pro Ile Thr Gly Gly Thr Thr Tyr Asn Gln Lys Phe Lys
1               5                   10                  15
Gly

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Gly Ile Trp Pro Ile Thr Gly Gly Thr Thr Tyr
1               5                   10

<210> SEQ ID NO 72
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 72

Gly Glu Ala Glu Gly Ser
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct

<400> SEQUENCE: 73

Gly Glu Ala Gln Gly Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Ser Asn Pro Arg Met Gly Val Ser
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Gly Phe Ser Leu Ser Asn Pro Arg
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Gly Phe Ser Leu Ser Asn Pro Arg Met Gly Val Ser
1               5                   10

<210> SEQ ID NO 77
<211> LENGTH: 16
<212> TYPE: PRT
<213> ORGANISM: Artificial Sequence
<220> FEATURE:
<223> OTHER INFORMATION: Synthetic Construct

<400> SEQUENCE: 77

His Ile Phe Ser Thr Asp Glu Lys Ser Leu Lys Leu Ser Leu Arg Ser
1               5                   10                  15

<210> SEQ ID NO 78
<211> LENGTH: 10
<212> TYPE: PRT
```

<213> ORGANISM: Artificial Sequence
<220> FEATURE:
<223> OTHER INFORMATION: Synthetic Construct

<400> SEQUENCE: 78

His Ile Phe Ser Thr Asp Glu Lys Ser Leu
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Asp Ser Ser Asn Tyr Glu Gly Tyr Phe Asp Phe
1               5                   10

<210> SEQ ID NO 80
<211> LENGTH: 8
<212> TYPE: PRT
<213> ORGANISM: Artificial Sequence
<220> FEATURE:
<223> OTHER INFORMATION: Synthetic Construct

<400> SEQUENCE: 80

Ser Asn Ala Arg Met Gly Val Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Phe Ser Leu Ser Asn Ala Arg
1               5

<210> SEQ ID NO 82
<211> LENGTH: 12
<212> TYPE: PRT
<213> ORGANISM: Artificial Sequence
<220> FEATURE:
<223> OTHER INFORMATION: Synthetic Construct

<400> SEQUENCE: 82

Gly Phe Ser Leu Ser Asn Ala Arg Met Gly Val Ser
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

His Ile Phe Ser Thr Asp Glu Lys Ser Ile Arg Arg Ser Leu Arg Ser
1               5                   10                  15

<210> SEQ ID NO 84
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 84

His Ile Phe Ser Thr Asp Glu Lys Ser Ile
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

Asp Ser Ser Asn Tyr Glu Gly Tyr Phe Asp Tyr
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Synthetic Construct

<400> SEQUENCE: 86

His Ile Phe Ser Thr Asp Glu Lys Ser Tyr Ser Thr Ser Leu Arg Gly
1               5                   10                  15

<210> SEQ ID NO 87
<211> LENGTH: 10
<212> TYPE: PRT
<213> ORGANISM: Artificial Sequence
<220> FEATURE:
<223> OTHER INFORMATION: Synthetic Construct

<400> SEQUENCE: 87

His Ile Phe Ser Thr Asp Glu Lys Ser Tyr
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Asn Asn Ala Arg Met Gly Val Ser
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Gly Phe Ser Leu Asn Asn Ala Arg
1               5

<210> SEQ ID NO 90
<211> LENGTH: 12
<212> TYPE: PRT
<213> ORGANISM: Artificial Sequence
<220> FEATURE:
```

```
<223> OTHER INFORMATION: Synthetic Construct

<400> SEQUENCE: 90

Gly Phe Ser Leu Asn Asn Ala Arg Met Gly Val Ser
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Synthetic Construct

<400> SEQUENCE: 91

His Ile Phe Ser Thr Asp Glu Lys Ser Phe Arg Thr Ser Leu Arg Ser
1               5                   10                  15

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

His Ile Phe Ser Thr Asp Glu Lys Ser Phe
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Ser Asn Val Arg Met Gly Val Ser
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Gly Phe Ser Leu Ser Asn Val Arg
1               5

<210> SEQ ID NO 95
<211> LENGTH: 12
<212> TYPE: PRT
<213> ORGANISM: Artificial Sequence
<220> FEATURE:
<223> OTHER INFORMATION: Synthetic Construct

<400> SEQUENCE: 95

Gly Phe Ser Leu Ser Asn Val Arg Met Gly Val Ser
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 96

His Ile Phe Ser Ser Asp Glu Lys Ser Ile Arg Arg Ser Leu Arg Ser
1               5                   10                  15

<210> SEQ ID NO 97
<211> LENGTH: 10
<212> TYPE: PRT
<213> ORGANISM: Artificial Sequence
<220> FEATURE:
<223> OTHER INFORMATION: Synthetic Construct

<400> SEQUENCE: 97

His Ile Phe Ser Ser Asp Glu Lys Ser Ile
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct

<400> SEQUENCE: 98

His Ile Phe Ser Thr Asp Glu Lys Ser Leu Arg Leu Ser Leu Arg Ser
1               5                   10                  15

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Ser Asn Ala Lys Met Gly Val Ser
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Gly Phe Ser Leu Ser Asn Ala Lys
1               5

<210> SEQ ID NO 101
<211> LENGTH: 12
<212> TYPE: PRT
<213> ORGANISM: Artificial Sequence
<220> FEATURE:
<223> OTHER INFORMATION: Synthetic Construct

<400> SEQUENCE: 101

Gly Phe Ser Leu Ser Asn Ala Lys Met Gly Val Ser
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 102

His Ile Phe Ser Ser Asp Glu Lys Ser Tyr Arg Leu Ser Leu Arg Ser
1               5                   10                  15

<210> SEQ ID NO 103
<211> LENGTH: 10
<212> TYPE: PRT
<213> ORGANISM: Artificial Sequence
<220> FEATURE:
<223> OTHER INFORMATION: Synthetic Construct

<400> SEQUENCE: 103

His Ile Phe Ser Ser Asp Glu Lys Ser Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Construct

<400> SEQUENCE: 104

Asp Ser Ser Asn Tyr Gly Gly Tyr Phe Asp Tyr
1               5                   10

<210> SEQ ID NO 105
<211> LENGTH: 16
<212> TYPE: PRT
<213> ORGANISM: Artificial Sequence
<220> FEATURE:
<223> OTHER INFORMATION: Synthetic Construct

<400> SEQUENCE: 105

His Ile Phe Ser Ser Asp Glu Lys Ser Tyr Arg Leu Phe Leu Arg Ser
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic Construct

<400> SEQUENCE: 106

His Ile Phe Ser Thr Asp Glu Lys Ser Tyr Ser Pro Ser Leu Arg Gly
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Synthetic Construct

<400> SEQUENCE: 107

Asp Ser Ser Asp Tyr Glu Gly Tyr Phe Asp Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Construct

<400> SEQUENCE: 108
```

```
Asp Ser Ser Asn Tyr Glu Glu Tyr Phe Asp Tyr
1               5                   10
```

<210> SEQ ID NO 109
<211> LENGTH: 6
<212> TYPE: PRT
<213> ORGANISM: Artificial Sequence
<220> FEATURE:
<223> OTHER INFORMATION: Synthetic Construct

<400> SEQUENCE: 109

```
Ser Asp Ala Trp Met Ser
1               5
```

<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

```
Gly Phe Thr Phe Ser Asp
1               5
```

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

```
Gly Phe Thr Phe Ser Asp Ala Trp Met Ser
1               5                   10
```

<210> SEQ ID NO 112
<211> LENGTH: 19
<212> TYPE: PRT
<213> ORGANISM: Artificial Sequence
<220> FEATURE:
<223> OTHER INFORMATION: Synthetic Construct

<400> SEQUENCE: 112

```
Arg Ile Lys Ser Lys Thr Asp Gly Gly Thr Thr Asp Tyr Val Val Pro
1               5                   10                  15

Leu Asn Gly
```

<210> SEQ ID NO 113
<211> LENGTH: 13
<212> TYPE: PRT
<213> ORGANISM: Artificial Sequence
<220> FEATURE:
<223> OTHER INFORMATION: Synthetic Construct

<400> SEQUENCE: 113

```
Arg Ile Lys Ser Lys Thr Asp Gly Gly Thr Thr Asp Tyr
1               5                   10
```

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 114

Val Pro Gly Ser Tyr Gly Tyr
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic Construct

<400> SEQUENCE: 115

Ser Tyr Ala Trp Met Ser
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic Construct

<400> SEQUENCE: 116

Gly Phe Thr Phe Ser Tyr
1               5

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Gly Phe Thr Phe Ser Tyr Ala Trp Met Ser
1               5                   10

<210> SEQ ID NO 118
<211> LENGTH: 19
<212> TYPE: PRT
<213> ORGANISM: Artificial Sequence
<220> FEATURE:
<223> OTHER INFORMATION: Synthetic Construct

<400> SEQUENCE: 118

Arg Ile Lys Ser Ile Ala Asp Gly Gly Ala Thr Asp Tyr Ala Ala Pro
1               5                   10                  15

Val Arg Asn

<210> SEQ ID NO 119
<211> LENGTH: 13
<212> TYPE: PRT
<213> ORGANISM: Artificial Sequence
<220> FEATURE:
<223> OTHER INFORMATION: Synthetic Construct

<400> SEQUENCE: 119

Arg Ile Lys Ser Ile Ala Asp Gly Gly Ala Thr Asp Tyr
1               5                   10

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 120

Ile Pro Gly Asn Asp Ala Phe Asp Met
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Construct

<400> SEQUENCE: 121

Asn Asn Ala Trp Met Ser
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic Construct

<400> SEQUENCE: 122

Gly Phe Ile Phe Asn Asn
1               5

<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123

Gly Phe Ile Phe Asn Asn Ala Trp Met Ser
1               5                   10

<210> SEQ ID NO 124
<211> LENGTH: 19
<212> TYPE: PRT
<213> ORGANISM: Artificial Sequence
<220> FEATURE:
<223> OTHER INFORMATION: Synthetic Construct

<400> SEQUENCE: 124

Arg Ile Lys Ser Lys Ser Asp Gly Gly Thr Thr Asp Tyr Ala Ala Pro
1               5                   10                  15

Val Lys Asp

<210> SEQ ID NO 125
<211> LENGTH: 13
<212> TYPE: PRT
<213> ORGANISM: Artificial Sequence
<220> FEATURE:
<223> OTHER INFORMATION: Synthetic Construct

<400> SEQUENCE: 125

Arg Ile Lys Ser Lys Ser Asp Gly Gly Thr Thr Asp Tyr
1               5                   10

<210> SEQ ID NO 126
<211> LENGTH: 8
<212> TYPE: PRT
<213> ORGANISM: Artificial Sequence
<220> FEATURE:

```
<223> OTHER INFORMATION: Synthetic Construct

<400> SEQUENCE: 126

Ala Pro Gly Gly Pro Phe Asp Tyr
1               5

<210> SEQ ID NO 127
<211> LENGTH: 19
<212> TYPE: PRT
<213> ORGANISM: Artificial Sequence
<220> FEATURE:
<223> OTHER INFORMATION: Synthetic Construct

<400> SEQUENCE: 127

Arg Ile Lys Ser Ile Thr Asp Gly Gly Val Ile Asp Tyr Ala Ala Pro
1               5                   10                  15

Val Arg Asn

<210> SEQ ID NO 128
<211> LENGTH: 13
<212> TYPE: PRT
<213> ORGANISM: Artificial Sequence
<220> FEATURE:
<223> OTHER INFORMATION: Synthetic Construct

<400> SEQUENCE: 128

Arg Ile Lys Ser Ile Thr Asp Gly Gly Val Ile Asp Tyr
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Ile Pro Gly Asn Asp Asp Phe Asp Met
1               5

<210> SEQ ID NO 130
<211> LENGTH: 19
<212> TYPE: PRT
<213> ORGANISM: Artificial Sequence
<220> FEATURE:
<223> OTHER INFORMATION: Synthetic Construct

<400> SEQUENCE: 130

Arg Ile Lys Ser Ile Asn Asp Gly Gly Ala Thr Asp Tyr Ala Ser Pro
1               5                   10                  15

Val Arg Asn

<210> SEQ ID NO 131
<211> LENGTH: 13
<212> TYPE: PRT
<213> ORGANISM: Artificial Sequence
<220> FEATURE:
<223> OTHER INFORMATION: Synthetic Construct

<400> SEQUENCE: 131

Arg Ile Lys Ser Ile Asn Asp Gly Gly Ala Thr Asp Tyr
1               5                   10

<210> SEQ ID NO 132
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 132

Thr Asn Ala Trp Met Ser
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133

Gly Phe Thr Phe Thr Asn
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Gly Phe Thr Phe Thr Asn Ala Trp Met Ser
1               5                   10

<210> SEQ ID NO 135
<211> LENGTH: 19
<212> TYPE: PRT
<213> ORGANISM: Artificial Sequence
<220> FEATURE:
<223> OTHER INFORMATION: Synthetic Construct

<400> SEQUENCE: 135

Arg Ile Lys Ser Lys Ile Asp Gly Gly Thr Thr Asp Tyr Ala Ala Pro
1               5                   10                  15

Val Lys Gly

<210> SEQ ID NO 136
<211> LENGTH: 13
<212> TYPE: PRT
<213> ORGANISM: Artificial Sequence
<220> FEATURE:
<223> OTHER INFORMATION: Synthetic Construct

<400> SEQUENCE: 136

Arg Ile Lys Ser Lys Ile Asp Gly Gly Thr Thr Asp Tyr
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Synthetic Construct

<400> SEQUENCE: 137

Ser Ser Asn Ala Ile Ser
1               5

<210> SEQ ID NO 138
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 138

Gly Asp Thr Phe Ser Ser
1               5

<210> SEQ ID NO 139
<211> LENGTH: 10
<212> TYPE: PRT
<213> ORGANISM: Artificial Sequence
<220> FEATURE:
<223> OTHER INFORMATION: Synthetic Construct

<400> SEQUENCE: 139

Gly Asp Thr Phe Ser Ser Asn Ala Ile Ser
1               5                   10

<210> SEQ ID NO 140
<211> LENGTH: 17
<212> TYPE: PRT
<213> ORGANISM: Artificial Sequence
<220> FEATURE:
<223> OTHER INFORMATION: Synthetic Construct

<400> SEQUENCE: 140

Val Ile Ile Pro Ile Phe Gly Thr Ala Asp Tyr Ala Gln Lys Phe Gln
1               5                   10                  15

Gly

<210> SEQ ID NO 141
<211> LENGTH: 11
<212> TYPE: PRT
<213> ORGANISM: Artificial Sequence
<220> FEATURE:
<223> OTHER INFORMATION: Synthetic Construct

<400> SEQUENCE: 141

Val Ile Ile Pro Ile Phe Gly Thr Ala Asp Tyr
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthetic Construct

<400> SEQUENCE: 142

His Thr Tyr His Glu Tyr Ala Gly Gly Tyr Tyr Gly Gly Ala Met Asp
1               5                   10                  15

Pro

<210> SEQ ID NO 143
<211> LENGTH: 6
<212> TYPE: PRT
<213> ORGANISM: Artificial Sequence
<220> FEATURE:
<223> OTHER INFORMATION: Synthetic Construct

<400> SEQUENCE: 143

Ser Asn Tyr Ala Met Ser
1               5
```

```
<210> SEQ ID NO 144
<211> LENGTH: 6
<212> TYPE: PRT
<213> ORGANISM: Artificial Sequence
<220> FEATURE:
<223> OTHER INFORMATION: Synthetic Construct

<400> SEQUENCE: 144

Gly Phe Thr Phe Ser Asn
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic Construct

<400> SEQUENCE: 145

Gly Phe Thr Phe Ser Asn Tyr Ala Met Ser
1               5                   10

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Asp Ile Ser Gly Gly Gly Gly Arg Thr Tyr Tyr Ala Asp Ser Val Lys
1               5                   10                  15

Gly

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Asp Ile Ser Gly Gly Gly Gly Arg Thr Tyr Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic Construct

<400> SEQUENCE: 148

Ala Gly Leu Leu Tyr Gly Gly Gly Val Tyr Pro Met Asp Ile
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Synthetic Construct

<400> SEQUENCE: 149

Lys Ser Ser Gln Ser Leu Leu Tyr Ser Asn Gly Lys Thr Tyr Leu Asn
```

<210> SEQ ID NO 150
<211> LENGTH: 7
<212> TYPE: PRT
<213> ORGANISM: Artificial Sequence
<220> FEATURE:
<223> OTHER INFORMATION: Synthetic Construct

<400> SEQUENCE: 150

Leu Val Ser Lys Leu Asp Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Construct

<400> SEQUENCE: 151

Val Gln Asp Thr His Phe Pro Leu Thr
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 152

Gln Val Ser Lys Leu Asp Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Gly Gln Asp Thr His Phe Pro Leu Thr
1               5

<210> SEQ ID NO 154
<211> LENGTH: 16
<212> TYPE: PRT
<213> ORGANISM: Artificial Sequence
<220> FEATURE:
<223> OTHER INFORMATION: Synthetic Construct

<400> SEQUENCE: 154

Lys Ser Ser Gln Ser Leu Leu Tyr Ser Asn Asp Lys Thr Tyr Thr Asn
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 155

Glu Val Ser Lys Leu Asp Val
1               5

```
<210> SEQ ID NO 156
<211> LENGTH: 11
<212> TYPE: PRT
<213> ORGANISM: Artificial Sequence
<220> FEATURE:
<223> OTHER INFORMATION: Synthetic Construct

<400> SEQUENCE: 156

Arg Ala Ser Gln Ser Val Arg Ser Asn Leu Ala
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Synthetic Construct

<400> SEQUENCE: 157

Gly Ser Thr Ile Arg Ala Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Gln Gln Tyr Ser Asp Trp Pro Phe Thr
1               5

<210> SEQ ID NO 159
<211> LENGTH: 11
<212> TYPE: PRT
<213> ORGANISM: Artificial Sequence
<220> FEATURE:
<223> OTHER INFORMATION: Synthetic Construct

<400> SEQUENCE: 159

Arg Ala Ser Gln Ser Val Ser Ser Asn Phe Ala
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 160

Gly Ala Thr Thr Arg Ala Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Gln Gln Tyr Lys Asp Trp Pro Phe Thr
1               5
```

<210> SEQ ID NO 162
<211> LENGTH: 11
<212> TYPE: PRT
<213> ORGANISM: Artificial Sequence
<220> FEATURE:
<223> OTHER INFORMATION: Synthetic Construct

<400> SEQUENCE: 162

Arg Val Ser Gln Ser Ile Gly Ala Asn Leu Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Synthetic Construct

<400> SEQUENCE: 163

Gly Ala Ser Thr Arg Ala Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Construct

<400> SEQUENCE: 164

Gln Gln Tyr Ile Tyr Trp Pro Phe Thr
1               5

<210> SEQ ID NO 165
<211> LENGTH: 11
<212> TYPE: PRT
<213> ORGANISM: Artificial Sequence
<220> FEATURE:
<223> OTHER INFORMATION: Synthetic Construct

<400> SEQUENCE: 165

Arg Ala Ser Gln Ser Val Ser Asn Asn Leu Ala
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Arg Ala Ser Gln Ser Val Gly Ser Asp Leu Ala
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Synthetic Construct

<400> SEQUENCE: 167

Gln Gln Tyr Asn Asp Trp Pro Phe Thr
1               5

```
<210> SEQ ID NO 168
<211> LENGTH: 11
<212> TYPE: PRT
<213> ORGANISM: Artificial Sequence
<220> FEATURE:
<223> OTHER INFORMATION: Synthetic Construct

<400> SEQUENCE: 168

Arg Ala Ser Gln Asn Ile Gly Ser Asp Leu Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthetic Construct

<400> SEQUENCE: 169

Arg Ala Ser Gln Ser Val Thr Ser Asn Phe Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic Construct

<400> SEQUENCE: 170

Arg Ala Ser Gln Gly Val Ser Ser Asn Phe Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct

<400> SEQUENCE: 171

Arg Ala Ser Gln Ser Val Asn Arg Asn Leu Ala
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Synthetic Construct

<400> SEQUENCE: 172

Gly Thr Ser Thr Arg Ala Thr
1               5

<210> SEQ ID NO 173
<211> LENGTH: 11
<212> TYPE: PRT
<213> ORGANISM: Artificial Sequence
<220> FEATURE:
<223> OTHER INFORMATION: Synthetic Construct

<400> SEQUENCE: 173

Arg Ala Ser Gln Ser Val Ser Thr Asn Phe Ala
1               5                   10

<210> SEQ ID NO 174
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 174

Arg Ala Ser Gln Ser Val Asn Ser Asn Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct

<400> SEQUENCE: 175

Gly Ser Ser Thr Arg Ala Thr
1               5

<210> SEQ ID NO 176
<211> LENGTH: 11
<212> TYPE: PRT
<213> ORGANISM: Artificial Sequence
<220> FEATURE:
<223> OTHER INFORMATION: Synthetic Construct

<400> SEQUENCE: 176

Arg Ala Ser Gln Ser Val Ile Asn Asn Leu Ala
1               5                   10

<210> SEQ ID NO 177
<211> LENGTH: 9
<212> TYPE: PRT
<213> ORGANISM: Artificial Sequence
<220> FEATURE:
<223> OTHER INFORMATION: Synthetic Construct

<400> SEQUENCE: 177

Gln Asp Tyr Asn Asn Trp Pro Phe Thr
1               5

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct

<400> SEQUENCE: 178

Arg Ala Ser Gln Ser Val Gly Ser Asn Leu Ala
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Synthetic Construct

<400> SEQUENCE: 179

Gly Ala Ser Thr Arg Ala Ser Gly
1               5

<210> SEQ ID NO 180
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 180

Gln Glu Tyr Asn Asn Trp Pro Phe Thr
1               5

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct

<400> SEQUENCE: 181

Arg Ala Asn Gln Ile Val Ser Ser Asn Leu Ala
1               5                   10

<210> SEQ ID NO 182
<211> LENGTH: 16
<212> TYPE: PRT
<213> ORGANISM: Artificial Sequence
<220> FEATURE:
<223> OTHER INFORMATION: Synthetic Construct

<400> SEQUENCE: 182

Arg Ser Ser Gln Ser Leu Leu His Asn Lys Arg Asn Asn Tyr Leu Asp
1               5                   10                  15

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct

<400> SEQUENCE: 183

Leu Ala Ser Asn Arg Ala Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Construct

<400> SEQUENCE: 184

Met Gln Ala Gln Gln Thr Pro Ile Thr
1               5

<210> SEQ ID NO 185
<211> LENGTH: 16
<212> TYPE: PRT
<213> ORGANISM: Artificial Sequence
<220> FEATURE:
<223> OTHER INFORMATION: Synthetic Construct

<400> SEQUENCE: 185

Arg Ser Ser Gln Ser Leu Leu Tyr Ser Asn Gly Lys Asn Tyr Leu Asp
1               5                   10                  15

<210> SEQ ID NO 186
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 186

Leu Gly Ser Asn Arg Ala Ser
1               5

<210> SEQ ID NO 187
<211> LENGTH: 16
<212> TYPE: PRT
<213> ORGANISM: Artificial Sequence
<220> FEATURE:
<223> OTHER INFORMATION: Synthetic Construct

<400> SEQUENCE: 187

Arg Ser Ser Gln Ser Leu Leu His Arg Asp Gly Phe Asn Tyr Leu Asp
1               5                   10                  15

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct

<400> SEQUENCE: 188

Leu Ala Ser Ser Arg Ala Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Met Gln Ala Leu Gln Thr Pro Ile Thr
1               5

<210> SEQ ID NO 190
<211> LENGTH: 16
<212> TYPE: PRT
<213> ORGANISM: Artificial Sequence
<220> FEATURE:
<223> OTHER INFORMATION: Synthetic Construct

<400> SEQUENCE: 190

Arg Ser Thr Gln Ser Leu Leu Tyr Ser Asn Gly Lys Asn Tyr Leu Asp
1               5                   10                  15

<210> SEQ ID NO 191
<211> LENGTH: 7
<212> TYPE: PRT
<213> ORGANISM: Artificial Sequence
<220> FEATURE:
<223> OTHER INFORMATION: Synthetic Construct

<400> SEQUENCE: 191

Leu Gly Ser Ile Arg Ala Ser
1               5

<210> SEQ ID NO 192
<211> LENGTH: 16
<212> TYPE: PRT
<213> ORGANISM: Artificial Sequence
```

```
<220> FEATURE:
<223> OTHER INFORMATION: Synthetic Construct

<400> SEQUENCE: 192

Arg Ser Ser Gln Ser Leu Leu Tyr Ser Asp Arg Arg Asn Tyr Leu Asp
1               5                   10                  15

<210> SEQ ID NO 193
<211> LENGTH: 7
<212> TYPE: PRT
<213> ORGANISM: Artificial Sequence
<220> FEATURE:
<223> OTHER INFORMATION: Synthetic Construct

<400> SEQUENCE: 193

Leu Gly Ser Tyr Arg Ala Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Construct

<400> SEQUENCE: 194

Met Gln Ala Leu Gln Ile Pro Ile Thr
1               5

<210> SEQ ID NO 195
<211> LENGTH: 13
<212> TYPE: PRT
<213> ORGANISM: Artificial Sequence
<220> FEATURE:
<223> OTHER INFORMATION: Synthetic Construct

<400> SEQUENCE: 195

Ser Gly Ser Ser Ser Asn Ile Gly Ser Asn Tyr Val Tyr
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Arg Asn Asn Gln Arg Pro Ser
1               5

<210> SEQ ID NO 197
<211> LENGTH: 11
<212> TYPE: PRT
<213> ORGANISM: Artificial Sequence
<220> FEATURE:
<223> OTHER INFORMATION: Synthetic Construct

<400> SEQUENCE: 197

Ala Ala Trp Asp Asp Asn Leu Ser Gly Trp Val
1               5                   10

<210> SEQ ID NO 198
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 198

Arg Ala Ser Gln Ser Ile Ser Ser Tyr Leu Asn
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct

<400> SEQUENCE: 199

Ala Ala Ser Ser Leu Gln Ser
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct

<400> SEQUENCE: 200

Gln Gln Ser Tyr Ser Thr Pro Leu Thr
1               5

<210> SEQ ID NO 201
<211> LENGTH: 943
<212> TYPE: PRT
<213> ORGANISM: Homo sapien

<400> SEQUENCE: 201

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

```
Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
                260                 265                 270

Asn Leu Leu Glu Gly Glu Pro Arg Glu Phe Val Glu Asn Ser Glu Cys
            275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
                340                 345                 350

Cys His Pro Asn Cys Thr Tyr Gly Cys Thr Gly Pro Gly Leu Glu Gly
    355                 360                 365

Cys Pro Thr Asn Gly Pro Lys Ile Pro Ser Ile Ala Thr Gly Met Val
370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
        435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
                500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
                580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
610                 615                 620
```

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
            645                 650                 655

Ser Ser Ile Leu Glu Lys Gly Glu Arg Leu Pro Gln Pro Ile Cys
        660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
            725                 730                 735

Glu Glu Asp Met Asp Asp Val Val Asp Ala Asp Glu Tyr Leu Ile Pro
        740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
            805                 810                 815

Asp Thr Phe Leu Pro Val Pro Glu Tyr Ile Asn Gln Ser Val Pro Lys
        820                 825                 830

Arg Pro Ala Gly Ser Val Gln Asn Pro Val Tyr His Asn Gln Pro Leu
835                 840                 845

Asn Pro Ala Pro Ser Arg Asp Pro His Tyr Gln Asp Pro His Ser Thr
850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
            885                 890                 895

Gln Ile Ser Leu Asp Asn Pro Asp Tyr Gln Gln Asp Phe Phe Pro Lys
        900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
930                 935                 940

<210> SEQ ID NO 202
<211> LENGTH: 20
<212> TYPE: PRT
<213> ORGANISM: Artificial Sequence
<220> FEATURE:
<223> OTHER INFORMATION: Synthetic Construct

<400> SEQUENCE: 202

Gly Gly Gly Gly Ser Gly Gly Gly Gly Ser Gly Gly Gly Gly Ser Gly
1               5                   10                  15

Gly Gly Gly Ser
            20

<210> SEQ ID NO 203
<211> LENGTH: 42

<212> TYPE: PRT
<213> ORGANISM: Homo sapien

<400> SEQUENCE: 203

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 204
<211> LENGTH: 42
<212> TYPE: PRT
<213> ORGANISM: Homo sapien

<400> SEQUENCE: 204

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 205
<211> LENGTH: 112
<212> TYPE: PRT
<213> ORGANISM: Homo sapien

<400> SEQUENCE: 205

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 206
<211> LENGTH: 21
<212> TYPE: PRT
<213> ORGANISM: Homo sapien

<400> SEQUENCE: 206

Met Ala Leu Pro Val Thr Ala Leu Leu Leu Pro Leu Ala Leu Leu Leu
1               5                   10                  15

His Ala Ala Arg Pro
            20

<210> SEQ ID NO 207
<211> LENGTH: 16
<212> TYPE: PRT
<213> ORGANISM: Homo sapien

<400> SEQUENCE: 207

Gly Leu Ala Val Ser Thr Ile Ser Ser Phe Phe Pro Pro Gly Tyr Gln
1               5                   10                  15

<210> SEQ ID NO 208
<211> LENGTH: 45
<212> TYPE: PRT
<213> ORGANISM: Homo sapien

<400> SEQUENCE: 208

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 209
<211> LENGTH: 231
<212> TYPE: PRT
<213> ORGANISM: Homo sapien

<400> SEQUENCE: 209

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 210
<211> LENGTH: 24

<212> TYPE: PRT
<213> ORGANISM: Homo sapien

<400> SEQUENCE: 210

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 211
<211> LENGTH: 52
<212> TYPE: PRT
<213> ORGANISM: Homo sapien

<400> SEQUENCE: 211

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
            20                  25                  30

Arg Thr Arg Lys Gly Phe Arg Leu Leu Asn Pro His Pro Lys Pro Asn
        35                  40                  45

Pro Lys Asn Asn
    50

<210> SEQ ID NO 212
<211> LENGTH: 215
<212> TYPE: PRT
<213> ORGANISM: Homo sapien

<400> SEQUENCE: 212

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu

<210> SEQ ID NO 213
<211> LENGTH: 41
<212> TYPE: PRT
<213> ORGANISM: Homo sapien

<400> SEQUENCE: 213

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 214
<211> LENGTH: 18
<212> TYPE: PRT
<213> ORGANISM: Homo sapien

<400> SEQUENCE: 214

Met Ile Pro Ala Val Val Leu Leu Leu Leu Leu Val Glu Gln Ala
1               5                   10                  15

Ala Ala

<210> SEQ ID NO 215
<211> LENGTH: 43
<212> TYPE: PRT
<213> ORGANISM: Artificial Sequence
<220> FEATURE:
<223> OTHER INFORMATION: Synthetic Construct

<400> SEQUENCE: 215

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser
        35                  40

<210> SEQ ID NO 216
<211> LENGTH: 22
<212> TYPE: PRT
<213> ORGANISM: Homo sapien

<400> SEQUENCE: 216

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 217
<211> LENGTH: 21
<212> TYPE: PRT
<213> ORGANISM: Homo sapien

<400> SEQUENCE: 217

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 218
<211> LENGTH: 530
<212> TYPE: PRT
<213> ORGANISM: Homo sapien

<400> SEQUENCE: 218

```
Leu Thr Pro Gln Gln Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Ala Ile Ala Ser Asn Asn Gly
        35                  40                  45

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
370                 375                 380
```

```
Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
        420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 219
<211> LENGTH: 530
<212> TYPE: PRT
<213> ORGANISM: Artificial Sequence
<220> FEATURE:
<223> OTHER INFORMATION: Synthetic Construct

<400> SEQUENCE: 219

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205
```

```
Gln Val Val Ala Ile Ala Ser Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
            245                 250                 255
Leu Glu Thr Val Gln Arg Leu Leu Pro Val Leu Cys Gln Ala His Gly
        260                 265                 270
Leu Thr Pro Gln Gln Val Val Ala Ile Ala Ser Asn Asn Gly Gly Lys
    275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
            325                 330                 335
Gln Ala His Gly Leu Thr Pro Glu Gln Val Val Ala Ile Ala Ser Asn
        340                 345                 350
Ile Gly Gly Lys Gln Ala Leu Glu Thr Val Gln Ala Leu Leu Pro Val
    355                 360                 365
Leu Cys Gln Ala His Gly Leu Thr Pro Glu Gln Val Val Ala Ile Ala
370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
            405                 410                 415
Ile Ala Ser Asn Ile Gly Gly Lys Gln Ala Leu Glu Thr Val Gln Ala
        420                 425                 430
Leu Leu Pro Val Leu Cys Gln Ala His Gly Leu Thr Pro Glu Gln Val
    435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
            485                 490                 495
Thr Val Gln Arg Leu Leu Pro Val Leu Cys Gln Ala His Gly Leu Thr
        500                 505                 510
Pro Gln Gln Val Val Ala Ile Ala Ser Asn Gly Gly Arg Pro Ala
    515                 520                 525
Leu Glu
    530

<210> SEQ ID NO 220
<211> LENGTH: 530
<212> TYPE: PRT
<213> ORGANISM: Artificial Sequence
<220> FEATURE:
<223> OTHER INFORMATION: Synthetic Construct

<400> SEQUENCE: 220

Leu Thr Pro Gln Gln Val Val Ala Ile Ala Ser Asn Asn Gly Gly Lys
1               5                   10                  15
Gln Ala Leu Glu Thr Val Gln Arg Leu Leu Pro Val Leu Cys Gln Ala
            20                  25                  30
```

-continued

His Gly Leu Thr Pro Gln Gln Val Ala Ile Ala Ser Asn Gly Gly
            35                  40                  45

Gly Lys Gln Ala Leu Glu Thr Val Gln Arg Leu Leu Pro Val Leu Cys
 50                  55                  60

Gln Ala His Gly Leu Thr Pro Gln Gln Val Val Ala Ile Ala Ser Asn
 65                  70                  75                  80

Asn Gly Gly Lys Gln Ala Leu Glu Thr Val Gln Arg Leu Leu Pro Val
                 85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
            370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 221
<211> LENGTH: 539
<212> TYPE: PRT
<213> ORGANISM: Artificial Sequence
<220> FEATURE:
<223> OTHER INFORMATION: Synthetic Construct

<400> SEQUENCE: 221

Asn Pro Gln Arg Ser Thr Val Trp Tyr Leu Thr Pro Gln Gln Val Val
1               5                   10                  15

Ala Ile Ala Ser Asn Asn Gly Gly Lys Gln Ala Leu Glu Thr Val Gln
            20                  25                  30

Arg Leu Leu Pro Val Leu Cys Gln Ala His Gly Leu Thr Pro Gln Gln
        35                  40                  45

Val Val Ala Ile Ala Ser Asn Gly Gly Gly Lys Gln Ala Leu Glu Thr
    50                  55                  60

Val Gln Arg Leu Leu Pro Val Leu Cys Gln Ala His Gly Leu Thr Pro
65                  70                  75                  80

Gln Gln Val Val Ala Ile Ala Ser Asn Gly Gly Lys Gln Ala Leu
                85                  90                  95

Glu Thr Val Gln Arg Leu Leu Pro Val Leu Cys Gln Ala His Gly Leu
            100                 105                 110

Thr Pro Gln Gln Val Val Ala Ile Ala Ser Asn Gly Gly Lys Gln
        115                 120                 125

Ala Leu Glu Thr Val Gln Arg Leu Leu Pro Val Leu Cys Gln Ala His
130                 135                 140

Gly Leu Thr Pro Glu Gln Val Val Ala Ile Ala Ser His Asp Gly Gly
145                 150                 155                 160

Lys Gln Ala Leu Glu Thr Val Gln Arg Leu Leu Pro Val Leu Cys Gln
                165                 170                 175

Ala His Gly Leu Thr Pro Glu Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Ala His Gly Leu Thr Pro Gln Gln Val Val Ala Ile Ala Ser
    210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Gln Gln Val Val Ala Ile
                245                 250                 255

Ala Ser Asn Gly Gly Gly Lys Gln Ala Leu Glu Thr Val Gln Arg Leu
            260                 265                 270

```
Leu Pro Val Leu Cys Gln Ala His Gly Leu Thr Pro Gln Gln Val Val
            275                 280                 285

Ala Ile Ala Ser Asn Gly Gly Lys Gln Ala Leu Glu Thr Val Gln
    290                 295                 300

Arg Leu Leu Pro Val Leu Cys Gln Ala His Gly Leu Thr Pro Gln Gln
305                 310                 315                 320

Val Val Ala Ile Ala Ser Asn Gly Gly Lys Gln Ala Leu Glu Thr
                325                 330                 335

Val Gln Arg Leu Leu Pro Val Leu Cys Gln Ala His Gly Leu Thr Pro
            340                 345                 350

Gln Gln Val Val Ala Ile Ala Ser Asn Gly Gly Lys Gln Ala Leu
        355                 360                 365

Glu Thr Val Gln Arg Leu Leu Pro Val Leu Cys Gln Ala His Gly Leu
    370                 375                 380

Thr Pro Gln Gln Val Val Ala Ile Ala Ser Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Gln Gln Val Val Ala Ile Ala Ser Asn Asn Gly Gly
            420                 425                 430

Lys Gln Ala Leu Glu Thr Val Gln Arg Leu Leu Pro Val Leu Cys Gln
        435                 440                 445

Ala His Gly Leu Thr Pro Gln Gln Val Val Ala Ile Ala Ser Asn Gly
    450                 455                 460

Gly Gly Lys Gln Ala Leu Glu Thr Val Gln Arg Leu Leu Pro Val Leu
465                 470                 475                 480

Cys Gln Ala His Gly Leu Thr Pro Gln Gln Val Val Ala Ile Ala Ser
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Gln Gln Val Val Ala Ile
        515                 520                 525

Ala Ser Asn Gly Gly Gly Arg Pro Ala Leu Glu
    530                 535

<210> SEQ ID NO 222
<211> LENGTH: 530
<212> TYPE: PRT
<213> ORGANISM: Artificial Sequence
<220> FEATURE:
<223> OTHER INFORMATION: Synthetic Construct

<400> SEQUENCE: 222

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95
```

-continued

```
Leu Cys Gln Ala His Gly Leu Thr Pro Glu Gln Val Val Ala Ile Ala
                100                 105                 110
Ser Asn Ile Gly Gly Lys Gln Ala Leu Glu Thr Val Gln Ala Leu Leu
            115                 120                 125
Pro Val Leu Cys Gln Ala His Gly Leu Thr Pro Glu Gln Val Val Ala
        130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Glu
        195                 200                 205
Gln Val Val Ala Ile Ala Ser His Asp Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Glu Gln Val Val Ala Ile Ala Ser Asn Ile Gly Gly Lys
        275                 280                 285
Gln Ala Leu Glu Thr Val Gln Ala Leu Leu Pro Val Leu Cys Gln Ala
    290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Gln Gln Val Val Ala Ile Ala Ser Asn
            340                 345                 350
Asn Gly Gly Lys Gln Ala Leu Glu Thr Val Gln Arg Leu Leu Pro Val
        355                 360                 365
Leu Cys Gln Ala His Gly Leu Thr Pro Gln Gln Val Val Ala Ile Ala
    370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly Leu Thr Pro Gln Gln Val
        435                 440                 445
Val Ala Ile Ala Ser Asn Asn Gly Gly Lys Gln Ala Leu Glu Thr Val
    450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
```

Leu Glu
    530

<210> SEQ ID NO 223
<211> LENGTH: 530
<212> TYPE: PRT
<213> ORGANISM: Artificial Sequence
<220> FEATURE:
<223> OTHER INFORMATION: Synthetic Construct

<400> SEQUENCE: 223

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser Asn Ile Gly Gly Lys Gln Ala Leu Glu Thr Val
        180                 185                 190

Gln Ala Leu Leu Pro Val Leu Cys Gln Ala His Gly Leu Thr Pro Gln
    195                 200                 205

Gln Val Val Ala Ile Ala Ser Asn Gly Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Gly Lys
    275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn

```
            340                 345                 350
Gly Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
                435                 440                 445

Val Ala Ile Ala Ser Asn Gly Gly Gly Lys Gln Ala Leu Glu Thr Val
            450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
                515                 520                 525

Leu Glu
    530

<210> SEQ ID NO 224
<211> LENGTH: 530
<212> TYPE: PRT
<213> ORGANISM: Artificial Sequence
<220> FEATURE:
<223> OTHER INFORMATION: Synthetic Construct

<400> SEQUENCE: 224

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
```

```
                165                 170                 175
Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
            275                 280                 285

Gln Ala Leu Glu Thr Val Gln Arg Leu Leu Pro Val Leu Cys Gln Ala
            290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
        370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 225
<211> LENGTH: 530
<212> TYPE: PRT
<213> ORGANISM: Artificial Sequence
<220> FEATURE:
<223> OTHER INFORMATION: Synthetic Construct
```

```
<400> SEQUENCE: 225

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415
```

Ile Ala Ser Asn Gly Gly Lys Gln Ala Leu Glu Thr Val Gln Arg
            420             425             430

Leu Leu Pro Val Leu Cys Gln Ala His Gly Leu Thr Pro Glu Gln Val
        435             440             445

Val Ala Ile Ala Ser Asn Ile Gly Gly Lys Gln Ala Leu Glu Thr Val
450             455             460

Gln Ala Leu Leu Pro Val Leu Cys Gln Ala His Gly Leu Thr Pro Glu
465             470             475             480

Gln Val Val Ala Ile Ala Ser His Asp Gly Gly Lys Gln Ala Leu Glu
                485             490             495

Thr Val Gln Arg Leu Leu Pro Val Leu Cys Gln Ala His Gly Leu Thr
        500             505             510

Pro Gln Gln Val Val Ala Ile Ala Ser Asn Gly Gly Gly Arg Pro Ala
        515             520             525

Leu Glu
    530

<210> SEQ ID NO 226
<211> LENGTH: 135
<212> TYPE: PRT
<213> ORGANISM: Homo sapien

<400> SEQUENCE: 226

Cys Pro Tyr Ser Asn Pro Ser Leu Cys Ser Gly Gly Gly Gly Ser Glu
1               5               10              15

Leu Pro Thr Gln Gly Thr Phe Ser Asn Val Ser Thr Asn Val Ser Pro
            20              25              30

Ala Lys Pro Thr Thr Thr Ala Cys Pro Tyr Ser Asn Pro Ser Leu Cys
        35              40              45

Ser Gly Gly Gly Gly Ser Pro Ala Pro Arg Pro Pro Thr Pro Ala Pro
    50              55              60

Thr Ile Ala Ser Gln Pro Leu Ser Leu Arg Pro Glu Ala Cys Arg Pro
65              70              75              80

Ala Ala Gly Gly Ala Val His Thr Arg Gly Leu Asp Phe Ala Cys Asp
                85              90              95

Ile Tyr Ile Trp Ala Pro Leu Ala Gly Thr Cys Gly Val Leu Leu Leu
            100             105             110

Ser Leu Val Ile Thr Leu Tyr Cys Asn His Arg Asn Arg Arg Arg Val
        115             120             125

Cys Lys Cys Pro Arg Pro Trp
    130             135

<210> SEQ ID NO 227
<211> LENGTH: 19
<212> TYPE: PRT
<213> ORGANISM: Artificial Sequence
<220> FEATURE:
<223> OTHER INFORMATION: Synthetic Construct

<400> SEQUENCE: 227

Cys Gly Ser Gly Ser Gly Leu Glu Glu Lys Lys Gly Asn Tyr Val Val
1               5               10              15

Thr Asp His

<210> SEQ ID NO 228
<211> LENGTH: 804
<212> TYPE: DNA

<213> ORGANISM: Artificial Sequence
<220> FEATURE:
<223> OTHER INFORMATION: Synthetic Construct

<400> SEQUENCE: 228

| | | | | | |
|---|---|---|---|---|---|
| atggctctgc | ccgtcaccgc | tctgctgctg | cccctggctc | tgctgctgca | cgctgctcgc | 60 |
| cctgatgtgg | tcatgactca | gtctcccctg | tctctgcccg | tcaccctggg | acagcccgcc | 120 |
| agcatctcct | gcaagagctc | ccagagcctg | ctgtactcca | acggcaagac | ctatctgaat | 180 |
| tggttccagc | agagacccgg | ccagagccct | cggagactga | tctaccaggt | gtctaagctg | 240 |
| gacagcggcg | tgcctgatcg | cttctctgga | agcggatccg | gaaccgactt | tacactgaag | 300 |
| atcagccggg | tggaggcaga | ggacgtgggc | gtgtactatt | gcgccaggga | tacccacttc | 360 |
| ccactgacat | ttggcggcgg | caccaaggtg | gagatcaagg | gaggaggagg | aagcggagga | 420 |
| ggaggaagcg | gcggcggcgg | ctctggcggc | ggcggcagcc | aggtgcagct | ggtgcagagc | 480 |
| ggagcagagg | tgaagaagcc | tggcgcctcc | gtgaaggtgt | cttgtaaggc | cagcggctac | 540 |
| acattcaccg | attatacact | gcactgggtg | cggcaggccc | ctggccaggg | actggagtgg | 600 |
| atgggaggaa | tctggcctat | caccggagga | accacataca | accagaagtt | taagggcaga | 660 |
| gtgacaatga | ccagggacac | atctaccagc | acagtgtata | tggagctgtc | tagcctgcgc | 720 |
| tccgaggata | cagccgtgta | ctattgcgcc | agaggcgagg | cacagggatc | ttggggacag | 780 |
| ggcaccctgg | tgacagtgtc | ctct | | | | 804 |

<210> SEQ ID NO 229
<211> LENGTH: 807
<212> TYPE: DNA
<213> ORGANISM: Artificial Sequence
<220> FEATURE:
<223> OTHER INFORMATION: Synthetic Construct

<400> SEQUENCE: 229

| | | | | | |
|---|---|---|---|---|---|
| atggctctgc | ccgtcaccgc | tctgctgctg | ccactggccc | tgctgctgca | cgcagcaagg | 60 |
| cctcaggtga | ccctgaagga | gagcggccct | gtgctgctga | agccaacaga | gaccctgaca | 120 |
| ctgacctgca | cagtgtctgg | cttcagcctg | tccaaccccc | ggatgggcgt | gagctggatc | 180 |
| agacagcccc | ctggcaaggc | cctggagtgg | ttcgcccaca | tcttttctac | cgatgagaag | 240 |
| agcctgaagc | tgtccctgag | atctaggctg | accctgagca | aggacacatc | taagagccag | 300 |
| gtggtgctga | ccatgacaaa | catggcccct | gtggactccg | ccacatacta | ttgcgccaga | 360 |
| gacagctcca | attacgaggg | ctatttcgac | ttttggggcc | agggcaccct | ggtgacagtg | 420 |
| tctagcggcg | gaggaggatc | cggaggagga | ggatctggcg | gcggcggctc | cggcggcggc | 480 |
| ggctccgagg | tggtgctgac | ccagagccct | gccacactgt | ccgtgtctcc | aggcgagaga | 540 |
| gccaccctgt | cttgtagggc | cagccagtcc | gtgcgcagca | atctggcctg | gtaccagcag | 600 |
| aagtccggcc | aggcccccaa | gactgctgat | ctatggctcca | ccatcagggc | cacaggagtg | 660 |
| ccagcacgct | tctctggaag | cggatccggc | acagagttta | ccctgacaat | ctcctctctg | 720 |
| cagtccgagg | atttcgccgt | gtactattgc | cagcagtact | ctgactggcc | cttcaccttt | 780 |
| ggccctggca | aaaggtggaa | tatcaag | | | | 807 |

<210> SEQ ID NO 230
<211> LENGTH: 807
<212> TYPE: DNA
<213> ORGANISM: Artificial Sequence
<220> FEATURE:
<223> OTHER INFORMATION: Synthetic Construct

<400> SEQUENCE: 230

```
atggctctgc ccgtcaccgc tctgctgctg ccactggccc tgctgctgca cgcagcaagg      60
ccacaggtga ccctgaagga gtccggcccc gtgctggtga agcctacaga gaccctgaca     120
ctgacctgca cagtgtccgg cttctctctg agcaacgccc gcatgggcgt gtcttggatc     180
aggcagcccc ctggcaaggc cctggagtgg ctggcccaca tcttttccac cgacgagaag     240
tctatccgga gaagcctgcg ctccaggctg accctgagca aggatacatc caagtctcag     300
gtggtgctga ccatgacaaa catggacccc gtggataccg ccacatactt ctgcgccaga     360
gacagctcca attacgaggg ctattttgat tactggggcc agggcaccct ggtgacagtg     420
tctagcggag gaggaggaag cggaggagga ggatctggcg gcggcggctc tggcggcggc     480
ggcagcgagg tggtcatgac ccagagccca gccacactga gcgtgtcccc tggcgagagg     540
gtgaccctgt cctgtagggc atctcagagc gtgtcctcta acttcgcctg gtatcagcag     600
agaccaggcc aggcaccaag gctgctgctg tacggagcaa ccacaagagc cacaggactg     660
cccggcaggt tttccggatc tggaagcggc accgagaata tcctgacaat cagctccctg     720
cagtctgagg acttcgccat ctattttgc cagcagtaca aggattggcc attcaccttt     780
ggccccggca gcaaggtgga catcaag                                          807
```

<210> SEQ ID NO 231
<211> LENGTH: 807
<212> TYPE: DNA
<213> ORGANISM: Artificial Sequence
<220> FEATURE:
<223> OTHER INFORMATION: Synthetic Construct

<400> SEQUENCE: 231

```
atggctctgc ccgtcaccgc tctgctgctg ccactggccc tgctgctgca cgcagcaaga      60
cctcaggtga ccctgaagga gtccggccct gtgctggtga agccaacaga gaccctgaca     120
ctgacctgca cagtgtctgg cttcagcctg tccaacgcaa ggatgggcgt gagctggatc     180
aggcagcccc ctggcaaggc cctggagtgg ctgggccaca tctttagcac cgacgagaag     240
tcttacagca catccctgag aggcaggatc accatctcta aggatacaag cagaggcctg     300
gtggtgctga ccctgacaaa catggacccc gtggataccg ccacatacta ttgcgccagg     360
gacagctcca attacgaggg ctatttcgat ttttggggcc ctggcttcct ggtgaccgtg     420
tctagcggcg gcggcggctc tggaggagga ggaagcggag gaggaggatc cggcggcggc     480
ggctctgaga tcgtgatgac ccagtcccct gccacactgt ctgtgagccc aggcgagaga     540
gccaccctgt cttgtagggt gtcccagtct atcggcgcca atctggcctg gtaccagcag     600
aagttcggcc aggccccaag gctgctgatc tatggagcat ccaccagagc cacaggaatc     660
cccgtgaggt tctccggagg aggatctgga accgagttta ccctgacaat ctcctctctg     720
cagagcgagg actttgccat ctactcctgc agcagtaca tctattggcc cttcacatttt    780
ggccctggca ccacagtgga tatcaag                                          807
```

<210> SEQ ID NO 232
<211> LENGTH: 807
<212> TYPE: DNA
<213> ORGANISM: Artificial Sequence
<220> FEATURE:
<223> OTHER INFORMATION: Synthetic Construct

<400> SEQUENCE: 232

```
atggctctgc cgtcaccgc tctgctgctg ccactggccc tgctgctgca cgcagcaaga    60
ccacaggtga ccctgaagga gagcggaccc gtgctggtga agcctacaga gaccctgaca   120
ctgacctgca cagtgagcgg cttctccctg aacaatgcaa ggatgggcgt gtcctggatc   180
aggcagcccc ctggcaaggc cctggagtgg ttcgcccaca tctttagcac cgacgagaag   240
tcctttcgca catctctgag aagcaggctg accctgagca aggatacaag caagtcccag   300
gtggtgctga ccatgacaaa catggacccc gtggataccg ccacatacta ttgcgccaga   360
gacagctcca attacgaggg ctatttcgat tactggggcc agggcatcct ggtgaccgtg   420
tctagcggcg gcggcggctc tggaggagga ggaagcggag gaggaggatc cggcggcggc   480
ggctctgaga tcgtgatgac ccagtctccc gccacactgt ctgtgagccc tggcgagaga   540
gccacactga ctgtagggc ctcccagtct gtgagcaaca atctggcctg gtatcagcag   600
aagccaggcc aggcaccaag gctgctgatc tacggagcat ccaccagagc cacaggagtg   660
ccagcaaggt tctccggatc tgacagcggc accgagttta gcctgacaat ctcctctctg   720
cagtccgagg acttcgccgt gtattttgc cagcagtaca aggattggcc attcaccttt   780
ggccccggca caaggtgga gatcaag                                        807
```

<210> SEQ ID NO 233
<211> LENGTH: 819
<212> TYPE: DNA
<213> ORGANISM: Artificial Sequence
<220> FEATURE:
<223> OTHER INFORMATION: Synthetic Construct

<400> SEQUENCE: 233

```
atggctctgc ccgtcaccgc tctgctgctg ccactggccc tgctgctgca cgcagcaagg    60
ccagaggtga acctggtgga gtccggcggc ggcctggtga agcctggcgg atccctgagg   120
ctgtcttgcg aggcaagcgg cttcaccttc agctacgcct ggatgtcctg ggtgcgccag   180
gccccccggca agggactgga gtgggtggga cggatcaagt ccatcgcaga cggaggagca   240
accgattacg cagcccctgt gagaaacagg ttcacaatct ccagagacga ttctaggaat   300
accctgtatc tggagatgca ctctctgaag acagaggaca ccgccgtgta ctattgcacc   360
acaatccctg caacgacgc cttgatatg tggggccagg gcacaatggt gaccgtgagc   420
tccggcggcg gcggctctgg aggaggagga agcggaggag gaggaagcgg gggcggcggc   480
tctgacatcg tgctgacaca gtccccactg tccctgtctg taccccccgg cgagcctgca   540
agcatctcct gtagatctag ccagagcctg ctgtactcca cggcaagaa ttatctggat   600
tggttcctgc acaagccagg ccagtctccc cagctgctga tctacctggg atctaatagg   660
gcaagcggag tgccagaccg gttctctgga agcggatccg gcatcgactt catcctgaag   720
atcagcaggg tggaggccga ggatgtgggc gtgtactatt gcatgcaggc ccagcagaca   780
cccatcacct tcggccaggg cacaagactg gagatcaag                          819
```

<210> SEQ ID NO 234
<211> LENGTH: 819
<212> TYPE: DNA
<213> ORGANISM: Artificial Sequence
<220> FEATURE:
<223> OTHER INFORMATION: Synthetic Construct

<400> SEQUENCE: 234

```
atggctctgc ccgtcaccgc tctgctgctg ccactggccc tgctgctgca cgcagcaagg    60
ccagaggtga acctggtgga gtccggcggc ggcctggtga agcctggcgg atccctgagg   120
```

```
ctgtcttgcg aggcaagcgg cttcaccttc agctacgcct ggatgtcctg ggtgcgccag    180
gcccccggca agggactgga gtgggtgggc cggatcaagt ccatcaccga cggaggcgtg    240
atcgattacg cagcacctgt gagaaacagg tgcacaatct ccagagacga ttctaggaat    300
accctgtatc tggagatgca ctctctgaag acagaggaca ccgccgtgta ctattgtacc    360
acaatccctg gcaacgacga tttcgatatg tggggccagg gcagaatggt gaccgtgagc    420
tccggcggcg gcggctctgg aggaggagga agcggaggag gaggaagcgg gggcggcggc    480
tctgacatcg tgctgacaca gtccccactg tccctgtctg tgaccccggg cgagcctgca    540
agcatctcct gtaggtctag ccagagcctg ctgtactcca acggcaagaa ttatctggat    600
tggtttctgc acaagccagg ccagtctccc cagctgctga tctacctggg atctaatagg    660
gcaagcggag tgccagaccg gttctctgga agcggatccg gcatcgactt catcctgaag    720
atcagccgcg tggaggcaga ggacgtgggc gtgtactatt gcatgcaggc ccagcagaca    780
cccatcacct tcggccaggg cacaagactg gagatcaag                          819
```

<210> SEQ ID NO 235
<211> LENGTH: 816
<212> TYPE: DNA
<213> ORGANISM: Artificial Sequence
<220> FEATURE:
<223> OTHER INFORMATION: Synthetic Construct

<400> SEQUENCE: 235

```
atggctctgc ccgtcaccgc tctgctgctg ccactggccc tgctgctgca cgcagcaagg     60
ccagaggtgc agctggtgga gtcttggggc gtgctggtga agcctggcgg atctctgagg    120
ctgagctgcg cagcatccgg cttcatcttt aacaatgcct ggatgtcctg ggtgcgccag    180
gcccccggca agggactgga gtggatcggc cggatcaaga gcaagtccga cggaggaacc    240
acagattacg cagcacctgt gaaggaccgc ttcacaatct ctcgggacga tagcaaggat    300
accctgtatc tgcagatgaa cggcctgaag acagaggaca ccgccgtgta cttctgcacc    360
acagcccctg gcggcccttt tgattattgg ggccagggca cactggtgac cgtgagctcc    420
ggaggaggag gaagcggcgg aggaggcagc ggcggcggcg gctctggcgg cggcggcagc    480
gacatcgtgc tgacacagag ccctctgtcc ctgccagtga ccccggcga gcctgcctct    540 atcagctgtc gctctagcca gagcctgctg caccggacg gcttcaatta cctggattgg    600
tttctgcaga agccaggcca gtcccccag ctgctgatct atctggcctc ctctagagcc    660
tctggcgtgc cagacaggtt ctccggctct gacagcggca cagacttcac cctgaagatc    720
agcagagtgg aggccgagga tgtgggcgtg tactattgca tgcaggccct gcagacaccc    780
atcaccttcg gccagggcac aagactggag atcaag                             816
```

<210> SEQ ID NO 236
<211> LENGTH: 813
<212> TYPE: DNA
<213> ORGANISM: Artificial Sequence
<220> FEATURE:
<223> OTHER INFORMATION: Synthetic Construct

<400> SEQUENCE: 236

```
atggctctgc ccgtcaccgc tctgctgctg ccactggccc tgctgctgca cgcagcaagg     60
cctgaggtgc agctggtgga gagcggcggc ggcctggtga agcctggcgg atccctgagg    120
ctgtcttgcg aggcaagcgg cttcaccttt agcgacgcat ggatgtcctg ggtgcgccag    180
```

| | |
|---|---|
| gccctggca agggactgga gtgggtggga cggatcaaga gcaagacaga cggcggcacc | 240 |
| acagattacg tggtgccact gaacggccgc ttcatcatct cccgcgacga ttctcggaat | 300 |
| accctgtatc tgcagctgaa caatctgaag acagaggata ccgccgtgta ctattgcacc | 360 |
| acagtgccag gctcctacgg ctattgggc cagggcacac tggtgaccgt gagctccggc | 420 |
| ggcggcggct ctggaggagg aggaagcgga ggaggaggaa gcggggggcgg cggctctgac | 480 |
| atcgtgatga cacagtctcc actgagcctg ccagtgaccc ctggcgagcc agcctccatc | 540 |
| tcttgtcgct ctagccagag cctgctgcac aacaagcgga caattacct ggattggttt | 600 |
| ctgcagaagc ctggccagtc ccctcagctg ctgatctatc tggccagcaa tagagcctcc | 660 |
| ggagtgccag acaggttctc tggaggagga agcggaacag acttcaccct gaagatcagc | 720 |
| agagtggagg ccgaggacgt gggcgtgtac tattgcatgc aggcccagca gacacctatc | 780 |
| accttcggcc agggcacaag actggagatc aag | 813 |

<210> SEQ ID NO 237
<211> LENGTH: 837
<212> TYPE: DNA
<213> ORGANISM: Artificial Sequence
<220> FEATURE:
<223> OTHER INFORMATION: Synthetic Construct

<400> SEQUENCE: 237

| | |
|---|---|
| atggctctgc ccgtcaccgc tctgctgctg cctctggccc tgctgctgca cgcagcaagg | 60 |
| ccacaggtgc agctggtgca gtccggagca gaggtgaaga gcctggcag ctccgtgaag | 120 |
| gtgagctgca aggcctccgg cgacacattc tctagcaacg caatcagctg ggtgcgccag | 180 |
| gcccctggcc agggactgga gtggatgggc gtgatcatcc ctatcttcgg caccgccgac | 240 |
| tatgcccaga gtttcagggg ccgggtgaca atcaccgccg atgagtctac aagcaccgcc | 300 |
| tacatggagc tgtcctctct gagatccgag gacacagccg tgtactattg ccaggcac | 360 |
| acctatcacg agtacgcagg aggatactat ggaggagcaa tggatccttg gggacagggc | 420 |
| acactggtga ccgtgagctc cggcggcggc ggctctggag gaggaggaag cggaggagga | 480 |
| ggaagcgggg cggcggctc tgagctgcag agcgtgctga cccagccacc ttccgcctct | 540 |
| ggaacaccag gccagagggt gaccatcagc tgctccggat ctagctccaa catcggctcc | 600 |
| aattacgtgt attggtacca gcagctgcca ggcacagccc caagatcct gatctaccgc | 660 |
| aacaatcagc ggccttctgg cgtgccagat agattctctg gcagcaagtc cggcacctct | 720 |
| gccagcctgg caatctccgg cctgaggtct gaggacgagg ccgattacta ttgcgccgcc | 780 |
| tgggacgata acctgagcgg ctgggtgttt ggcacaggca ccaagctgac agtgctg | 837 |

<210> SEQ ID NO 238
<211> LENGTH: 1476
<212> TYPE: DNA
<213> ORGANISM: Artificial Sequence
<220> FEATURE:
<223> OTHER INFORMATION: Synthetic Construct

<400> SEQUENCE: 238

| | |
|---|---|
| atggctctgc ccgtcaccgc tctgctgctg ccctggctc tgctgctgca cgctgctcgc | 60 |
| cctgatgtgg tcatgactca gtctcccctg tctctgcccg tcaccctggg acagcccgcc | 120 |
| agcatctcct gcaagagctc ccagagcctg ctgtactcca cggcaagac ctatctgaat | 180 |
| tggttccagc agagacccgg ccagagccct cggagactga tctaccaggt gtctaagctg | 240 |
| gacagcggcg tgcctgatcg cttctctgga agcggatccg gaaccgactt tacactgaag | 300 |

```
atcagccggg tggaggcaga ggacgtgggc gtgtactatt gcggccagga tacccacttc      360
ccactgacat ttggcggcgg caccaaggtg gagatcaagg gaggaggagg aagcggagga      420
ggaggaagcg gcggcggcgg ctctggcggc ggcggcagcc aggtgcagct ggtgcagagc      480
ggagcagagg tgaagaagcc tggcgcctcc gtgaaggtgt cttgtaaggc cagcggctac      540
acattcaccg attatacact gcactgggtg cggcaggccc ctggccaggg actggagtgg      600
atgggaggaa tctggcctat caccggagga accacataca accagaagtt taagggcaga      660
gtgacaatga ccagggacac atctaccagc acagtgtata tggagctgtc tagcctgcgc      720
tccgaggata cagccgtgta ctattgcgcc agaggcgagg cacagggatc ttggggacag      780
ggcaccctgg tgacagtgtc ctctaccaca accccagcac caagaccacc taccccctgca     840 ccaacaatcg cctcccagcc tctgtctctg cgcccagagg catgtaggcc agcagcagga      900
ggagcagtgc acaccagggg cctggacttt gcctgcgata tctacatctg gcaccactg      960 gcaggaacat gtggcgtgct gctgctgagc ctggtcatca ccctgtactg caagcgcggc     1020
cggaagaagc tgctgtatat cttcaagcag cccttcatga cccgtgca gacaacccag       1080 gaggaggacg gctgctcctg taggttccca gaagaagagg agggcggctg tgagctgaga     1140
gtgaagtttt ccaggtctgc cgatgcacca gcataccagc agggacagaa tcagctgtat     1200
aacgagctga atctgggcag gcgcgaggag tatgacgtgc tggataagag agaggaagg      1260 gaccctgaga tgggaggcaa gcctaggcgc aagaacccac aggagggcct gtacaatgag     1320
ctgcagaagg ataagatggc cgaggcctat tccgagatcg gcatgaaggg cgagcggaga     1380
aggggcaagg gccacgacgg gctgtaccag ggactgtcaa ccgctaccaa ggatacttac     1440
gacgccctgc atatgcaggc actgcctcca aggtga                              1476
```

<210> SEQ ID NO 239
<211> LENGTH: 1479
<212> TYPE: DNA
<213> ORGANISM: Artificial Sequence
<220> FEATURE:
<223> OTHER INFORMATION: Synthetic Construct

<400> SEQUENCE: 239

```
atggctctgc ccgtcaccgc tctgctgctg ccactggccc tgctgctgca cgcagcaagg       60
cctcaggtga ccctgaagga gagcggccct gtgctgctga agccaacaga gaccctgaca      120
ctgacctgca cagtgtctgg cttcagcctg tccaaccccc ggatgggcgt gagctggatc      180
agacagcccc ctggcaaggc cctggagtgg ttcgcccaca tctttttctac cgatgagaag      240 agcctgaagc tgtccctgag atctaggctg accctgagca aggacacatc taagagccag      300
gtggtgctga ccatgacaaa catggcccct gtggactccg ccacatacta ttgcgccaga      360
gacagctcca attacgaggg ctatttcgac ttttggggcc agggcaccct ggtgacagtg      420
tctagcggcg gaggaggatc cggaggagga ggatctggcg gcggcggctc cggcggcggc      480
ggctccgagg tggtgctgac ccagagccct gccacactgt ccgtgtctcc aggcgagaga     540
gccaccctgt cttgtagggc cagccagtcc gtgcgcagca atctggcctg gtaccagcag     600
aagtccggcc aggcccccaa gctgctgatc tatggctcca ccatcagggc cacaggagtg     660
ccagcacgct ctctctggaag cggatccggc acagagttta ccctgacaat ctcctctctg      720
cagtccgagg atttcgccgt gtactattgc cagcagtact ctgactggcc cttcaccttt      780
ggccctggca caaaggtgga tatcaagacc acaacccctg caccaaggcc accaacccca     840
```

```
gcacctacaa tcgcaagcca gccactgtcc ctgagacccg aggcctgtag gcctgcagca      900
ggaggagcag tgcacacccg cggcctggac tttgcctgcg atatctatat ctgggcacca      960
ctggcaggaa cctgtggcgt gctgctgctg agcctggtca tcaccctgta ctgcaagcgc     1020
ggccggaaga agctgctgta tatcttcaag cagcccttca tgcggcccgt gcagacaacc     1080
caggaggagg atggctgctc ctgtagattc cctgaggagg aggagggagg atgtgagctg     1140
agggtgaagt tttctcggag cgccgacgca ccagcatacc agcagggaca gaaccagctg     1200
tataacgagc tgaatctggg ccggagagag gagtacgacg tgctggataa gaggaggggga    1260 agagacccag atgggagg caagccacgg agaaagaacc cccaggaggg cctgtacaat       1320
gagctgcaga aggataagat ggccgaggcc tattctgaga tcggcatgaa gggagagagg     1380
cgccggggca agggacacga cggactgtac cagggactgt ccaccgcaac aaaggacacc     1440
tatgatgccc tgcatatgca ggcactgcct ccaaggtga                            1479
```

<210> SEQ ID NO 240  
<211> LENGTH: 1479  
<212> TYPE: DNA  
<213> ORGANISM: Artificial Sequence  
<220> FEATURE:  
<223> OTHER INFORMATION: Synthetic Construct

<400> SEQUENCE: 240

```
atggctctgc ccgtcaccgc tctgctgctg ccactggccc tgctgctgca cgcagcaagg       60
ccacaggtga ccctgaagga gtccggcccc gtgctggtga agcctacaga gaccctgaca      120
ctgacctgca gtgtccggg cttctctctg agcaacgccc gcatgggcgt gtcttggatc      180
aggcagcccc ctggcaaggc cctggagtgg ctggcccaca tcttttccac cgacgagaag      240
tctatccgga gaagcctgcg ctccaggctg accctgagca aggatacatc caagtctcag     300
gtggtgctga ccatgacaaa catggacccc gtggataccg ccacatactt ctgcgccaga     360
gacagctcca attacgaggg ctatttgat tactggggcc agggcaccct ggtgacagtg      420
tctagcggag gaggaggaag cggaggagga ggatctggcg gcggcggctc tggcggcggc     480
ggcagcgagg tggtcatgac ccagagccca gccacactga gcgtgtcccc tggcgagagg     540
gtgaccctgt cctgtagggc atctcagagc gtgtcctcta acttcgcctg gtatcagcag     600
agaccaggcc aggcaccaag gctgctgctg tacggagcaa ccacaagagc cacaggactg     660
cccggcaggt tttccggatc tggaagcggc accgagaata tcctgacaat cagctccctg     720
cagtctgagg acttcgccat ctattttgc cagcagtaca aggattggcc attcaccttt     780
ggccccggca gcaaggtgga catcaagacc acaaccctg caccaagacc accaaccca      840 gcacctacaa tcgcctctca gcctctgagc ctgcgcccag aggcatgtag gccagcagca    900
ggaggagcag tgcacacaag gggcctggac ttcgcctgcg atatctatat ctgggcacct    960
ctggcaggaa cctgtggcgt gctgctgctg agcctggtca tcaccctgta ttgcaagaga   1020
ggcaggaaga agctgctgta catcttcaag cagcctttta tgcgcccagt gcagacaacc   1080
caggaggagg acggctgcag ctgtcggttc cctgaagagg aggagggcgg ctgtgagctg   1140
agagtgaagt tttccaggtc tgccgatgcc cagcctatc agcagggcca gaatcagctg   1200
tacaacgagc tgaatctggg caggcgcgag gagtacgacg tgctggataa gaggagagga   1260
agggatccag atgggaggag caagcctagg cgcaagaacc cacaggaggg cctgtataat    1320
gagctgcaga aggacaagat ggccgaggcc tactccgaga tcggcatgaa gggagagcgg   1380
agaaggggca agggacacga tggcctgtat cagggcctgt ctaccgccac aaaggacacc   1440
```

-continued

```
tacgatgccc tgcatatgca ggcactgcct ccaaggtga                        1479
```

<210> SEQ ID NO 241
<211> LENGTH: 1479
<212> TYPE: DNA
<213> ORGANISM: Artificial Sequence
<220> FEATURE:
<223> OTHER INFORMATION: Synthetic Construct

<400> SEQUENCE: 241

```
atggctctgc ccgtcaccgc tctgctgctg ccactggccc tgctgctgca cgcagcaaga      60
cctcaggtga ccctgaagga gtccggccct gtgctggtga agccaacaga gaccctgaca     120
ctgacctgca cagtgtctgg cttcagcctg tccaacgcaa ggatgggcgt gagctggatc     180
aggcagcccc ctggcaaggc cctggagtgg ctgggccaca tctttagcac cgacgagaag     240
tcttacagca catccctgag aggcaggatc accatctcta aggatacaag cagaggcctg     300
gtggtgctga ccctgacaaa catggacccc gtggataccg ccacatacta ttgcgccagg     360
gacagctcca attacgaggg ctatttcgat ttttggggcc ctggcttcct ggtgaccgtg     420
tctagcggcg gcggcggctc tggaggagga ggaagcggag gaggaggatc cggcggcggc     480
ggctctgaga tcgtgatgac ccagtcccct gccacactgt ctgtgagccc aggcgagaga     540
gccaccctgt cttgtagggt gtcccagtct atcggcgcca atctggcctg gtaccagcag     600
aagttcggcc aggccccaag gctgctgatc tatggagcat ccaccagagc cacaggaatc     660
cccgtgaggt tctccggagg aggatctgga accgagttta ccctgacaat ctcctctctg     720
cagagcgagg actttgccat ctactcctgc agcagtaca  tctattggcc cttcacattt     780
ggccctggca ccacagtgga tatcaagacc acaaccctg  caccaaggcc accaacccca     840
gcacctacaa tcgcaagcca gccactgtcc ctgagaccag aggcatgtag gcctgcagca     900
ggaggagccg tgcacaccag aggcctggac tttgcctgcg atatctatat ctgggccaca     960
ctggcaggaa cctgtggcgt gctgctgctg agcctggtca tcaccctgta ctgcaagcgc    1020
ggccggaaga gctgctgta  tatcttcaag cagcccttca tgcgcccgt gcagacaacc     1080
caggaggagg acggctgcag ctgtcggttc cctgaagagg aggaggagg  atgtgagctg    1140
agggtgaagt ttagccggtc cgccgatgca ccagcatacc agcagggcca gaaccagctg    1200
tataacgagc tgaatctggg ccggagagag gagtacgacg tgctggataa gaggagggga    1260
agagacccag agatgggagg caagccacgg agaagaacc  cccaggaggg cctgtacaat    1320
gagctgcaga aggacaagat ggccgaggcc tatagcgaga tcggcatgaa gggagagagg    1380
cgccggggca agggacacga tggcctgtac cagggcctgt ccaccgccac aaaggacacc    1440
tatgatgccc tgcatatgca ggcactgcct ccaaggtga                          1479
```

<210> SEQ ID NO 242
<211> LENGTH: 1479
<212> TYPE: DNA
<213> ORGANISM: Artificial Sequence
<220> FEATURE:
<223> OTHER INFORMATION: Synthetic Construct

<400> SEQUENCE: 242

```
atggctctgc ccgtcaccgc tctgctgctg ccactggccc tgctgctgca cgcagcaaga      60
ccacaggtga ccctgaagga gagcggaccc gtgctggtga agcctacaga gaccctgaca     120
ctgacctgca cagtgagcgg cttctcccctg aacaatgcaa ggatgggcgt gtcctggatc    180
```

```
aggcagcccc ctggcaaggc cctggagtgg ttcgcccaca tctttagcac cgacgagaag      240
tcctttcgca catctctgag aagcaggctg accctgagca aggatacaag caagtcccag      300
gtggtgctga ccatgacaaa catggacccc gtggataccg ccacatacta ttgcgccaga      360
gacagctcca attacgaggg ctatttcgat tactggggcc agggcatcct ggtgaccgtg      420
tctagcggcg gcggcggctc tggaggagga ggaagcggag gaggaggatc cggcggcggc      480
ggctctgaga tcgtgatgac ccagtctccc gccacactgt ctgtgagccc tggcgagaga      540
gccacactga gctgtagggc ctcccagtct gtgagcaaca atctggcctg gtatcagcag      600
aagccaggcc aggcaccaag gctgctgatc tacggagcat ccaccagagc cacaggagtg      660
ccagcaaggt tctccggatc tgacagcggc accgagttta gcctgacaat ctcctctctg      720
cagtccgagg acttcgccgt gtatttttgc cagcagtaca aggattggcc attcaccttt      780
ggccccggca caaaggtgga gatcaagacc acaacccctg caccaagacc accaacccca      840
gcacctacaa tcgcatccca gcctctgtct ctgagaccag aggcatgtag gccagcagca      900
ggaggagcag tgcacaccag gggcctggac tttgcctgcg atatctatat ctgggcacct      960
ctggcaggaa cctgtggcgt gctgctgctg agcctggtca tcaccctgta ttgcaagcgc     1020
ggccggaaga agctgctgta catcttcaag cagcctttta tgcgcccagt gcagacaacc     1080
caggaggagg acggctgctc ctgtcggttc cctgaagagg aggagggagg atgtgagctg     1140
agggtgaagt tttcccggtc tgccgatgcc ccagcctatc agcagggcca gaaccagctg     1200
tacaacgagc tgaatctggg ccggagagag gagtacgacg tgctggataa gaggagggga     1260
agagatccag agatgggagg caagcctcgg agaaagaacc cacaggaggg cctgtataat     1320
gagctgcaga aggacaagat ggccgaggcc tactccgaga tcggcatgaa gggagagagg     1380
cgccggggca aggacacga tggcctgtat cagggcctgt ctaccgccac aaaggacacc     1440
tacgatgccc tgcatatgca ggcactgcct ccaaggtga                            1479
```

<210> SEQ ID NO 243
<211> LENGTH: 1491
<212> TYPE: DNA
<213> ORGANISM: Artificial Sequence
<220> FEATURE:
<223> OTHER INFORMATION: Synthetic Construct

<400> SEQUENCE: 243

```
atggctctgc ccgtcaccgc tctgctgctg ccactggccc tgctgctgca cgcagcaagg       60
ccagaggtga acctggtgga gtccggcggc ggcctggtga gcctggcgg atccctgagg      120 ctgtcttgcg caggcaagcgg cttcaccttc agctacgcct ggatgtcctg ggtgcgccag      180
gccccgggca agggactgga gtgggtggga cggatcaagt ccatcgcaga cggaggagca      240
accgattacg cagcccctgt gagaaacagg ttcacaatct ccagagacga ttctaggaat      300
accctgtatc tggagatgca ctctctgaag acagaggaca ccgccgtgta ctattgcacc      360
acaatccctg gcaacgacgc ctttgatatg tggggccagg gcacaatggt gaccgtgagc      420
tccggcggcg gcggctctgg aggaggagga agcggaggag gaggaagcgg gggcggcggc      480
tctgacatcg tgctgacaca gtccccactg tccctgtctg tgaccccgg cgagcctgca      540 agcatctcct gtagatctag ccagagcctg ctgtactcca acggcaagaa ttatctggat      600
tggttcctgc acaagccagg ccagtctccc cagctgctga tctacctggg atctaatagg      660
gcaagcggag tgccagaccg gttctctgga agcggatccg gcatcgactt catcctgaag     720
atcagcaggg tggaggccga ggatgtgggc gtgtactatt gcatgcaggc ccagcagaca     780
```

```
cccatcacct tcggccaggg cacaagactg gagatcaaga ccacaacccc agcaccaagg    840
ccacctacac ctgcaccaac catcgcatcc cagccactgt ctctgaggcc tgaggcatgt    900
cggccagcag caggaggagc agtgcacacc cgcggcctgg actttgcctg cgatatctac    960
atctgggcac cactggcagg aacatgtggc gtgctgctgc tgagcctggt catcaccctg   1020
tactgcaagc gcggccggaa gaagctgctg tatatcttca agcagccttt tatgagacca   1080
gtgcagacaa cccaggagga ggacggctgc tcctgtaggt tccctgaaga ggaggagggc   1140
ggctgtgagc tgagagtgaa gttttctagg agcgccgatg caccagcata ccagcaggga   1200
cagaatcagc tgtataacga gctgaatctg gccggagag aggagtatga cgtgctggat    1260
aagaggaggg aagggaccc tgagatggga ggcaagcccc ggagaaagaa ccctcaggag     1320
ggcctgtaca atgagctgca aaggacaag atggccgagg cctatagcga gatcggcatg    1380
aagggagaga ggcgccgggg caagggacac gatggcctgt accagggcct gtccacagcc   1440
accaaggaca cctatgatgc cctgcatatg caggcactgc ctccaaggtg a            1491
```

<210> SEQ ID NO 244
<211> LENGTH: 1491
<212> TYPE: DNA
<213> ORGANISM: Artificial Sequence
<220> FEATURE:
<223> OTHER INFORMATION: Synthetic Construct

<400> SEQUENCE: 244

```
atggctctgc ccgtcaccgc tctgctgctg ccactggccc tgctgctgca cgcagcaagg     60
ccagaggtga actggtgga gtccggcggc ggcctggtga gcctggcgg atccctgagg     120 ctgtcttgcg aggcaagcgg cttcaccttc agctacgcct ggatgtcctg ggtgcgccag    180
gcccccggca agggactgga gtgggtgggc cggatcaagt ccatcaccga cggaggcgtg    240
atcgattacg cagcacctgt gagaaacagg tgcacaatct ccagagacga ttctaggaat    300
accctgtatc tggagatgca ctctctgaag acagaggaca ccgccgtgta ctattgtacc    360
acaatccctg caacgacga tttcgatatg tggggccagg gcagaatggt gaccgtgagc    420
tccggcggcg gcggctctgg aggaggagga agcggaggag gaggaagcgg gggcggcggc    480
tctgacatcg tgctgacaca gtccccactg tccctgtctg tgaccccgg cgagcctgca    540 agcatctcct gtaggtctag ccagagcctg ctgtactcca acggcaagaa ttatctggat    600
tggtttctgc acaagccagg ccagtctccc cagctgctga tctacctggg atctaatagg    660
gcaagcggag tgccagaccg gttctctgga agcggatccg gcatcgactt catcctgaag    720
atcagccgcg tggaggcaga ggacgtgggc gtgtactatt gcatgcaggc ccagcagaca    780
cccatcaccT tcggccaggg cacaagactg gagatcaaga ccacaacccc agcaccaagg    840
ccacctacac ctgcaccaac catcgcatcc cagccactgt ctctgaggcc tgaggcatgt    900
aggccagcag caggaggagc agtgcacacc agaggcctgg actttgcctg cgatatctac    960
atctgggcac cactggcagg aacatgtggc gtgctgctgc tgagcctggt catcaccctg   1020
tactgcaagc gcggccggaa gaagctgctg tatatcttca agcagccttt tatgagacca   1080
gtgcagacaa cccaggagga ggacggctgc tcctgtaggt tccctgaaga ggaggagggc   1140
ggctgtgagc tgagagtgaa gttttctagg agcgccgatg caccagcata ccagcaggga   1200
cagaatcagc tgtataacga gctgaatctg gccggagag aggagtatga cgtgctggat    1260
aagaggaggg aagggatcc tgagatggga ggcaagcccc ggagaaagaa ccctcaggag    1320
```

```
ggcctgtaca atgagctgca gaaggacaag atggccgagg cctatagcga gatcggcatg      1380
aagggagaga ggcgccgggg caagggacac gatggcctgt accagggcct gtccacagcc      1440
accaaggaca cctatgatgc cctgcatatg caggcactgc ctccaaggtg a               1491

<210> SEQ ID NO 245
<211> LENGTH: 1488
<212> TYPE: DNA
<213> ORGANISM: Artificial Sequence
<220> FEATURE:
<223> OTHER INFORMATION: Synthetic Construct

<400> SEQUENCE: 245
atggctctgc ccgtcaccgc tctgctgctg ccactggccc tgctgctgca cgcagcaagg       60
ccagaggtgc agctggtgga gtcttggggc gtgctggtga agcctggcgg atctctgagg      120
ctgagctgcg cagcatccgg cttcatcttt aacaatgcct ggatgtcctg ggtgcgccag      180 gccccccggca agggactgga gtggatcggc cggatcaaga gcaagtccga cggaggaacc      240
acagattacg cagcacctgt gaaggaccgc ttcacaatct ctcgggacga tagcaaggat      300
accctgtatc tgcagatgaa cggcctgaag acagaggaca ccgccgtgta cttctgcacc      360
acagcccctg gcggcccttt tgattattgg ggccagggca cactggtgac cgtgagctcc      420
ggaggaggag gaagcggcgg aggaggcagc ggcggcggcg gctctggcgg cggcggcagc      480
gacatcgtgc tgacacagag ccctctgtcc ctgccagtga ccccggcga gcctgcctct      540 atcagctgtc gctctagcca gagcctgctg caccgggacg gcttcaatta cctggattgg      600
tttctgcaga agccaggcca gtcccccag ctgctgatct atctggcctc ctctagagcc       660
tctggcgtgc cagacaggtt ctccggctct gacagcggca cagacttcac cctgaagatc      720
agcagagtgg aggccgagga tgtgggcgtg tactattgca tgcaggccct gcagacaccc      780
atcaccttcg gccagggcac aaagactgga gatcaagacca caaccccagc accaaggcca      840
cctacacctg caccaaccat cgcatcccag ccactgtctc tgagacctga ggcctgtagg      900
ccagcagcag gaggagcagt gcacaccagg ggcctggact ttgcctgcga tatctacatc      960
tgggcacctc tggcaggaac atgtggcgtg ctgctgctga gcctggtcat cacccctgtac    1020 tgcaagagag gcaggaagaa gctgctgtat atcttcaagc agccttttat gagaccagtg      1080
cagacaaccc aggaggagga cggctgctcc tgtaggttcc ctgaagagga ggagggagga      1140
tgtgagctga gggtgaagtt ttcccggtct gccgatgcac cagcatacca gcagggacag      1200
aaccagctgt ataacgagct gaatctgggc cggagagagg agtacgacgt gctggataag      1260
aggcgcggca gagatccaga gatgggcggc aagccccgga aagaaccc tcaggagggc        1320 ctgtacaatg agctgcagaa ggacaagatg gccgaggcct atagcgagat cggcatgaag      1380
ggagagaggc gccggggcaa gggcacgat ggcctgtacc agggcctgtc cacagccacc        1440
aaggacacct atgatgccct gcatatgcag gcactgcctc caaggtga                  1488

<210> SEQ ID NO 246
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 246
atggctctgc ccgtcaccgc tctgctgctg ccactggccc tgctgctgca cgcagcaagg       60
cctgaggtgc agctggtgga gagcggcggc ggcctggtga agcctggcgg atccctgagg      120
```

```
ctgtcttgcg aggcaagcgg cttcaccttt agcgacgcat ggatgtcctg ggtgcgccag    180
gcccctggca agggactgga gtgggtggga cggatcaaga gcaagacaga cggcggcacc    240
acagattacg tggtgccact gaacggccgc ttcatcatct cccgcgacga ttctcggaat    300
accctgtatc tgcagctgaa caatctgaag acagaggata ccgccgtgta ctattgcacc    360
acagtgccag gctcctacgg ctattggggc agggcacac tggtgaccgt gagctccggc     420
ggcggcggct ctgaggagg aggaagcgga ggaggaggaa gcggggcgg cggctctgac      480 atcgtgatga cacagtctcc actgagcctg ccagtgaccc ctggcgagcc agcctccatc    540
tcttgtcgct ctagccagag cctgctgcac aacaagcgga caattacct ggattggttt     600 ctgcagaagc ctggccagtc ccctcagctg ctgatctatc tggccagcaa tagagcctcc    660
ggagtgccag acaggttctc tggaggagga agcggaacag acttcaccct gaagatcagc    720
agagtggagg ccgaggacgt gggcgtgtac tattgcatgc aggcccagca gacacctatc    780
accttcggcc agggcacaag actggagatc aagaccacaa ccccagcacc aaggccacct    840
acacctgcac caaccatcgc ctcccagcct ctgtctctga ccagaggc atgtaggcca      900 gcagcaggag gagcagtgca caccagggc ctggactttg cctgcgatat ctacatctgg     960
gcacctctgg caggaacatg tggcgtgctg ctgctgagcc tggtcatcac cctgtactgc   1020
aagagaggca ggaagaagct gctgtatatc ttcaagcagc ccttcatgag acccgtgcag   1080
acaacccagg aggaggacgg ctgctcttgt aggttcccag aagaggagga gggaggatgt   1140
gagctgaggg tgaagtttag ccggtccgcc gatgcaccag cataccagca gggacagaac   1200
cagctgtata cgagctgaa tctgggccgg agagaggagt acgacgtgct ggataagagg    1260
aggggaaggg atccagagat gggaggcaag cctcggagaa agaacccaca ggagggcctg   1320
tacaatgagc tgcagaagga caagatggcc gaggcctatt ctgagatcgg catgaaggga   1380
gagaggcgcc ggggcaaggg acacgatggc ctgtaccagg gcctgagcac agccaccaag   1440
gacacctatg atgccctgca tatgcaggca ctgcctccaa ggtga                   1485
```

<210> SEQ ID NO 247
<211> LENGTH: 1508
<212> TYPE: DNA
<213> ORGANISM: Artificial Sequence
<220> FEATURE:
<223> OTHER INFORMATION: Synthetic Construct

<400> SEQUENCE: 247

```
atggctctgc ccgtcaccgc tctgctgctg cctctggccc tgctgctgca cgcagcaagg     60
ccacaggtgc agctggtgca gtccggagca gaggtgaaga gcctggcag ctccgtgaag     120 gtgagctgca aggcctccgg cgacacattc tctagcaacg caatcagctg ggtgcgccag    180
gcccctggcc agggactgga gtggatgggc gtgatcatcc ctatcttcgg caccgccgac    240
tatgcccaga gtttcagggg ccgggtgaca atcaccgccg atgagtctac aagcaccgcc    300
tacatggagc tgtcctctct gagatccgag gacacagccg tgtactattg tgccaggcac    360
acctatcacg agtacgcagg aggatactat ggaggagcaa tggatccttg gggacagggc    420
acactggtga ccgtgagctc cggcggcggc ggctctggag aggaggaag cggaggagga    480 ggaagcgggg cggcggctc tgagctgcag agcgtgctga cccagccacc ttccgcctct    540
ggaacaccag gccagagggt gaccatcagc tgctccggat ctagctccaa catcggctcc    600
aattacgtgt attggtacca gcagctgcca ggcacagccc ccaagatcct gatctaccgc    660
```

```
aacaatcagc ggccttctgg cgtgccagat agattctctg gcagcaagtc cggcacctct    720
gccagcctgg caatctccgg cctgaggtct gaggacgagg ccgattacta ttgcgccgcc    780
tgggacgata acctgagcgg ctgggtgttt ggcacaggca ccaagctgac agtgctgacc    840
acaacccctg caccaagacc accaacacca gcacctacca tcgcaagcca gccactgtcc    900
ctgagacccg aggcctgtag gcctgcagca ggaggagcag tgcacaccag gggcctggac    960
tttgcctgcg atatctatat ctgggcacca ctggcaggaa catgtggcgt gctgctgctg   1020
agcctggtca tcaccctgta ttgcaagaga ggcaggaaga agctgctgta catcttcaag   1080 cagccctttα tgcgccctgt gcagacaacc caggaggagg acggctgcag ctgtcggttc   1140
ccagaagagg aggagggagg atgtgagctg agggtgaagt tttcccggtc tgccgatgca   1200
ccagcatatc agcagggaca gaatcagctg tacaacgagc tgaatctggg ccggagagag   1260
gagtacgacg tgctggataa gaggagggga agggaccctg agatgggagg caagccacgg   1320
agaaaaaccc ccaggagggc ctgtataatg agctgcagaa ggacaagatg gccgaggcct   1380
actctgagat cggcatgaag ggagagaggc gccggggcaa gggacacgat ggcctgtatc   1440
agggcctgag cacagccacc aaggacacct acgatgccct gcatatgcag gcactgcctc   1500
caaggtga                                                            1508
```

<210> SEQ ID NO 248
<211> LENGTH: 529
<212> TYPE: PRT
<213> ORGANISM: Artificial Sequence
<220> FEATURE:
<223> OTHER INFORMATION: Synthetic Construct

<400> SEQUENCE: 248

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
        35                  40                  45

Ser Leu Asn Asn Ala Arg Met Gly Val Ser Trp Ile Arg Gln Pro Pro
    50                  55                  60

Gly Lys Ala Leu Glu Trp Phe Ala His Ile Phe Ser Thr Asp Glu Lys
65                  70                  75                  80

Ser Phe Arg Thr Ser Leu Arg Ser Arg Leu Thr Leu Ser Lys Asp Thr
                85                  90                  95

Ser Lys Ser Gln Val Val Leu Thr Met Thr Asn Met Asp Pro Val Asp
            100                 105                 110

Thr Ala Thr Tyr Tyr Cys Ala Arg Asp Ser Ser Asn Tyr Glu Gly Tyr
        115                 120                 125

Phe Asp Tyr Trp Gly Gln Gly Ile Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Asn Asn Leu Ala Trp Tyr Gln Gln Lys Pro Gly Gln Ala Pro Arg Leu
        195                 200                 205
```

```
Leu Ile Tyr Gly Ala Ser Thr Arg Ala Thr Gly Val Pro Ala Arg Phe
210                 215                 220

Ser Gly Ser Asp Ser Gly Thr Glu Phe Ser Leu Thr Ile Ser Ser Leu
225                 230                 235                 240

Gln Ser Glu Asp Phe Ala Val Tyr Phe Cys Gln Gln Tyr Lys Asp Trp
            245                 250                 255

Pro Phe Thr Phe Gly Pro Gly Thr Lys Val Glu Ile Lys Gly Ser Gly
        260                 265                 270

Gly Gly Gly Ser Cys Pro Tyr Ser Asn Pro Ser Leu Cys Ser Gly Gly
            275                 280                 285

Gly Gly Ser Cys Pro Tyr Ser Asn Pro Ser Leu Cys Ser Gly Gly Gly
        290                 295                 300

Gly Ser Thr Thr Thr Pro Ala Pro Arg Pro Pro Thr Pro Ala Pro Thr
305                 310                 315                 320

Ile Ala Ser Gln Pro Leu Ser Leu Arg Pro Glu Ala Cys Arg Pro Ala
                325                 330                 335

Ala Gly Gly Ala Val His Thr Arg Gly Leu Asp Phe Ala Cys Asp Ile
            340                 345                 350

Tyr Ile Trp Ala Pro Leu Ala Gly Thr Cys Gly Val Leu Leu Leu Ser
        355                 360                 365

Leu Val Ile Thr Leu Tyr Cys Lys Arg Gly Arg Lys Lys Leu Leu Tyr
370                 375                 380

Ile Phe Lys Gln Pro Phe Met Arg Pro Val Gln Thr Thr Gln Glu Glu
385                 390                 395                 400

Asp Gly Cys Ser Cys Arg Phe Pro Glu Glu Glu Glu Gly Gly Cys Glu
                405                 410                 415

Leu Arg Val Lys Phe Ser Arg Ser Ala Asp Ala Pro Ala Tyr Gln Gln
            420                 425                 430

Gly Gln Asn Gln Leu Tyr Asn Glu Leu Asn Leu Gly Arg Arg Glu Glu
        435                 440                 445

Tyr Asp Val Leu Asp Lys Arg Gly Arg Asp Pro Glu Met Gly Gly
        450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 249
<211> LENGTH: 529
<212> TYPE: PRT
<213> ORGANISM: Artificial Sequence
<220> FEATURE:
<223> OTHER INFORMATION: Synthetic Construct

<400> SEQUENCE: 249

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
```

-continued

```
                35                  40                  45
Ser Leu Ser Asn Ala Arg Met Gly Val Ser Trp Ile Arg Gln Pro Pro
 50                  55                  60
Gly Lys Ala Leu Glu Trp Leu Ala His Ile Phe Ser Thr Asp Glu Lys
 65                  70                  75                  80
Ser Ile Arg Arg Ser Leu Arg Ser Arg Leu Thr Leu Ser Lys Asp Thr
                 85                  90                  95
Ser Lys Ser Gln Val Val Leu Thr Met Thr Asn Met Asp Pro Val Asp
                100                 105                 110
Thr Ala Thr Tyr Phe Cys Ala Arg Asp Ser Ser Asn Tyr Glu Gly Tyr
                115                 120                 125
Phe Asp Tyr Trp Gly Gln Gly Thr Leu Val Thr Val Ser Ser Gly Gly
                130                 135                 140
Gly Gly Ser Gly Gly Gly Ser Gly Gly Gly Ser Gly Gly
145                 150                 155                 160
Gly Ser Glu Val Val Met Thr Gln Ser Pro Ala Thr Leu Ser Val Ser
                165                 170                 175
Pro Gly Glu Arg Val Thr Leu Ser Cys Arg Ala Ser Gln Ser Val Ser
                180                 185                 190
Ser Asn Phe Ala Trp Tyr Gln Gln Arg Pro Gly Gln Ala Pro Arg Leu
                195                 200                 205
Leu Leu Tyr Gly Ala Thr Thr Arg Ala Thr Gly Leu Pro Gly Arg Phe
                210                 215                 220
Ser Gly Ser Gly Ser Gly Thr Glu Asn Ile Leu Thr Ile Ser Ser Leu
225                 230                 235                 240
Gln Ser Glu Asp Phe Ala Ile Tyr Phe Cys Gln Gln Tyr Lys Asp Trp
                245                 250                 255
Pro Phe Thr Phe Gly Pro Gly Ser Lys Val Asp Ile Lys Gly Ser Gly
                260                 265                 270
Gly Gly Gly Ser Cys Pro Tyr Ser Asn Pro Ser Leu Cys Ser Gly Gly
                275                 280                 285
Gly Gly Ser Cys Pro Tyr Ser Asn Pro Ser Leu Cys Ser Gly Gly Gly
                290                 295                 300
Gly Ser Thr Thr Thr Pro Ala Pro Arg Pro Pro Thr Pro Ala Pro Thr
305                 310                 315                 320
Ile Ala Ser Gln Pro Leu Ser Leu Arg Pro Glu Ala Cys Arg Pro Ala
                325                 330                 335
Ala Gly Gly Ala Val His Thr Arg Gly Leu Asp Phe Ala Cys Asp Ile
                340                 345                 350
Tyr Ile Trp Ala Pro Leu Ala Gly Thr Cys Gly Val Leu Leu Leu Ser
                355                 360                 365
Leu Val Ile Thr Leu Tyr Cys Lys Arg Gly Arg Lys Lys Leu Leu Tyr
                370                 375                 380
Ile Phe Lys Gln Pro Phe Met Arg Pro Val Gln Thr Thr Gln Glu Glu
385                 390                 395                 400
Asp Gly Cys Ser Cys Arg Phe Pro Glu Glu Glu Glu Gly Gly Cys Glu
                405                 410                 415
Leu Arg Val Lys Phe Ser Arg Ser Ala Asp Ala Pro Ala Tyr Gln Gln
                420                 425                 430
Gly Gln Asn Gln Leu Tyr Asn Glu Leu Asn Leu Gly Arg Arg Glu Glu
                435                 440                 445
Tyr Asp Val Leu Asp Lys Arg Arg Gly Arg Asp Pro Glu Met Gly Gly
450                 455                 460
```

```
Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
            485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 250
<211> LENGTH: 532
<212> TYPE: PRT
<213> ORGANISM: Artificial Sequence
<220> FEATURE:
<223> OTHER INFORMATION: Synthetic Construct

<400> SEQUENCE: 250

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Trp Gly Val Leu
            20                  25                  30

Val Lys Pro Gly Gly Ser Leu Arg Leu Ser Cys Ala Ala Ser Gly Phe
        35                  40                  45

Ile Phe Asn Asn Ala Trp Met Ser Trp Val Arg Gln Ala Pro Gly Lys
    50                  55                  60

Gly Leu Glu Trp Ile Gly Arg Ile Lys Ser Lys Ser Asp Gly Gly Thr
65                  70                  75                  80

Thr Asp Tyr Ala Ala Pro Val Lys Asp Arg Phe Thr Ile Ser Arg Asp
                85                  90                  95

Asp Ser Lys Asp Thr Leu Tyr Leu Gln Met Asn Gly Leu Lys Thr Glu
            100                 105                 110

Asp Thr Ala Val Tyr Phe Cys Thr Thr Ala Pro Gly Gly Pro Phe Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Asp Ile Val Leu Thr Gln Ser Pro Leu Ser Leu Pro Val Thr Pro Gly
                165                 170                 175

Glu Pro Ala Ser Ile Ser Cys Arg Ser Ser Gln Ser Leu Leu His Arg
            180                 185                 190

Asp Gly Phe Asn Tyr Leu Asp Trp Phe Leu Gln Lys Pro Gly Gln Ser
        195                 200                 205

Pro Gln Leu Leu Ile Tyr Leu Ala Ser Ser Arg Ala Ser Gly Val Pro
    210                 215                 220

Asp Arg Phe Ser Gly Ser Asp Ser Gly Thr Asp Phe Thr Leu Lys Ile
225                 230                 235                 240

Ser Arg Val Glu Ala Glu Asp Val Gly Val Tyr Tyr Cys Met Gln Ala
                245                 250                 255

Leu Gln Thr Pro Ile Thr Phe Gly Gln Gly Thr Arg Leu Glu Ile Lys
            260                 265                 270

Gly Ser Gly Gly Gly Ser Cys Pro Tyr Ser Asn Pro Ser Leu Cys
        275                 280                 285
```

Ser Gly Gly Gly Ser Cys Pro Tyr Ser Asn Pro Ser Leu Cys Ser
    290                 295                 300

Gly Gly Gly Gly Ser Thr Thr Thr Pro Ala Pro Arg Pro Pro Thr Pro
305                 310                 315                 320

Ala Pro Thr Ile Ala Ser Gln Pro Leu Ser Leu Arg Pro Glu Ala Cys
                325                 330                 335

Arg Pro Ala Ala Gly Gly Ala Val His Thr Arg Gly Leu Asp Phe Ala
            340                 345                 350

Cys Asp Ile Tyr Ile Trp Ala Pro Leu Ala Gly Thr Cys Gly Val Leu
        355                 360                 365

Leu Leu Ser Leu Val Ile Thr Leu Tyr Cys Lys Arg Gly Arg Lys Lys
    370                 375                 380

Leu Leu Tyr Ile Phe Lys Gln Pro Phe Met Arg Pro Val Gln Thr Thr
385                 390                 395                 400

Gln Glu Glu Asp Gly Cys Ser Cys Arg Phe Pro Glu Glu Glu Glu Gly
                405                 410                 415

Gly Cys Glu Leu Arg Val Lys Phe Ser Arg Ser Ala Asp Ala Pro Ala
            420                 425                 430

Tyr Gln Gln Gly Gln Asn Gln Leu Tyr Asn Glu Leu Asn Leu Gly Arg
        435                 440                 445

Arg Glu Glu Tyr Asp Val Leu Asp Lys Arg Arg Gly Arg Asp Pro Glu
    450                 455                 460

Met Gly Gly Lys Pro Arg Arg Lys Asn Pro Gln Glu Gly Leu Tyr Asn
465                 470                 475                 480

Glu Leu Gln Lys Asp Lys Met Ala Glu Ala Tyr Ser Glu Ile Gly Met
                485                 490                 495

Lys Gly Glu Arg Arg Arg Gly Lys Gly His Asp Gly Leu Tyr Gln Gly
            500                 505                 510

Leu Ser Thr Ala Thr Lys Asp Thr Tyr Asp Ala Leu His Met Gln Ala
        515                 520                 525

Leu Pro Pro Arg
    530

<210> SEQ ID NO 251
<211> LENGTH: 531
<212> TYPE: PRT
<213> ORGANISM: Artificial Sequence
<220> FEATURE:
<223> OTHER INFORMATION: Synthetic Construct

<400> SEQUENCE: 251

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Lys Pro Gly Gly Ser Leu Arg Leu Ser Cys Glu Ala Ser Gly Phe
            35                  40                  45

Thr Phe Ser Asp Ala Trp Met Ser Trp Val Arg Gln Ala Pro Gly Lys
        50                  55                  60

Gly Leu Glu Trp Val Gly Arg Ile Lys Ser Lys Thr Asp Gly Gly Thr
65                  70                  75                  80

Thr Asp Tyr Val Val Pro Leu Asn Gly Arg Phe Ile Ile Ser Arg Asp
                85                  90                  95

Asp Ser Arg Asn Thr Leu Tyr Leu Gln Leu Asn Asn Leu Lys Thr Glu
            100                 105                 110

```
Asp Thr Ala Val Tyr Tyr Cys Thr Val Pro Gly Ser Tyr Gly Tyr
            115                 120                 125

Trp Gly Gln Gly Thr Leu Val Thr Val Ser Ser Gly Gly Gly Ser
    130                 135                 140

Gly Gly Gly Gly Ser Gly Gly Gly Ser Gly Gly Gly Ser Asp
145                 150                 155                 160

Ile Val Met Thr Gln Ser Pro Leu Ser Leu Pro Val Thr Pro Gly Glu
            165                 170                 175

Pro Ala Ser Ile Ser Cys Arg Ser Gln Ser Leu Leu His Asn Lys
            180                 185                 190

Arg Asn Asn Tyr Leu Asp Trp Phe Leu Gln Lys Pro Gly Gln Ser Pro
        195                 200                 205

Gln Leu Leu Ile Tyr Leu Ala Ser Asn Arg Ala Ser Gly Val Pro Asp
        210                 215                 220

Arg Phe Ser Gly Gly Gly Ser Gly Thr Asp Phe Thr Leu Lys Ile Ser
225                 230                 235                 240

Arg Val Glu Ala Glu Asp Val Gly Val Tyr Tyr Cys Met Gln Ala Gln
                245                 250                 255

Gln Thr Pro Ile Thr Phe Gly Gln Gly Thr Arg Leu Glu Ile Lys Gly
            260                 265                 270

Ser Gly Gly Gly Gly Ser Cys Pro Tyr Ser Asn Pro Ser Leu Cys Ser
    275                 280                 285

Gly Gly Gly Ser Cys Pro Tyr Ser Asn Pro Ser Leu Cys Ser Gly
        290                 295                 300

Gly Gly Gly Ser Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
            325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
            355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
            435                 440                 445

Glu Glu Tyr Asp Val Leu Asp Lys Arg Arg Gly Arg Asp Pro Glu Met
        450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
            485                 490                 495

Gly Glu Arg Arg Arg Gly Lys Gly His Asp Gly Leu Tyr Gln Gly Leu
                500                 505                 510

Ser Thr Ala Thr Lys Asp Thr Tyr Asp Ala Leu His Met Gln Ala Leu
            515                 520                 525

Pro Pro Arg
```

<210> SEQ ID NO 252
<211> LENGTH: 1590
<212> TYPE: DNA
<213> ORGANISM: Artificial Sequence
<220> FEATURE:
<223> OTHER INFORMATION: Synthetic Construct

<400> SEQUENCE: 252

| | |
|---|---|
| atggcactgc cagtgaccgc cctgctgctg cctctggccc tgctgctgca cgcagccaga | 60 |
| ccccaggtga cactgaagga gagcggcccc gtgctggtga agcctacaga gacactgacc | 120 |
| ctgacctgca cagtgagcgg cttctccctg aacaatgcaa ggatgggcgt gtcctggatc | 180 |
| aggcagccac ctggcaaggc cctggagtgg ttcgcccaca tctttagcac cgacgagaag | 240 |
| tcctttcgca catctctgag aagcaggctg accctgagca aggatacaag caagtcccag | 300 |
| gtggtgctga ccatgacaaa catggaccct gtggataccg ccacatacta ttgtgcccgg | 360 |
| gacagctcca attacgaggg ctatttcgat tactgggggcc agggcatcct ggtgaccgtg | 420 |
| tctagcggcg gcggcggctc tggaggagga ggaagcggag aggaggatc cggcggcggc | 480 |
| ggctctgaga tcgtgatgac ccagtcccca gccacactgt ctgtgagccc aggagagaga | 540 |
| gccaccctgt cttgcagggc ctcccagtct gtgagcaaca tctggcctg gtatcagcag | 600 |
| aagcctggcc aggccccaag gctgctgatc tacgagcaa gcaccagagc aacaggagtg | 660 |
| cctgcaaggt tctccggatc tgacagcggc accgagtttt ctctgacaat ctcctctctg | 720 |
| cagagcgagg acttcgccgt gtattttttgt cagcagtaca aggattggcc attcaccttt | 780 |
| ggccccggca caaggtgga gatcaagggc tccggaggag gaggatcctg ccctattcc | 840 |
| aacccttctc tgtgcagcgg aggaggagga agctgtccat actccaatcc ctccctgtgc | 900 |
| tccggcggcg gaggatccac cacaaccca gcacctagac caccaacccc agcaccaaca | 960 |
| atcgcatccc agcctctgtc tctgcggccc gaggcatgca ggccagcagc aggcggcgcc | 1020 |
| gtgcacacca ggggcctgga ctttgcctgc gatatctata tctgggcacc actggcagga | 1080 |
| acctgtggcg tgctgctgct gagcctggtc atcaccctgt attgcaagcg cggccggaag | 1140 |
| aagctgctgt acatcttcaa gcagcctttt atgcgcccag tgcagacaac ccaggaggag | 1200 |
| gacggctgct cctgtcggtt ccctgaagag gaggagggag gatgtgagct gcgcgtgaag | 1260 |
| ttttcccggt ctgccgatgc cccagcctat cagcagggcc agaaccagct gtacaacgag | 1320 |
| ctgaatctgg gccggagaga ggagtacgac gtgctggata gaggaggggg aagagatccc | 1380 |
| gagatgggag gcaagcctcg gagaaagaac ccacaggagg gcctgtataa tgagctgcag | 1440 |
| aaggacaaga tggccgaggc ctactctgag atcggcatga aggagagag gcgccggggc | 1500 |
| aagggacacg atggcctgta tcagggcctg tccaccgcca caaggacac ctacgatgcc | 1560 |
| ctgcacatgc aggccctgcc tccaaggtga | 1590 |

<210> SEQ ID NO 253
<211> LENGTH: 1590
<212> TYPE: DNA
<213> ORGANISM: Artificial Sequence
<220> FEATURE:
<223> OTHER INFORMATION: Synthetic Construct

<400> SEQUENCE: 253

| | |
|---|---|
| atggcactgc cagtgaccgc cctgctgctg cctctggccc tgctgctgca cgcagccaga | 60 |
| ccccaggtga cactgaagga gtccggcccc gtgctggtga agcctacaga gacactgacc | 120 |

```
ctgacctgca cagtgagcgg cttctctctg agcaacgcaa ggatgggcgt gtcctggatc        180
aggcagccac ctggcaaggc cctggagtgg ctggcccaca tcttttccac cgacgagaag        240
tctatccgga gaagcctgcg ctcccggctg accctgagca aggatacatc caagtctcag        300
gtggtgctga ccatgacaaa catgaccct gtggataccg ccacatactt ctgtgcccgg         360
gacagctcca attacgaggg ctattttgat tactggggcc agggcaccct ggtgacagtg        420
tctagcggag gaggaggaag cggaggagga ggatcaggcg cggcggctc tggcggcggc         480 ggcagcgagg tggtcatgac ccagtctcca gccacactga gcgtgtcccc aggagagcgc        540
gtgaccctga gctgccgggc ctctcagagc gtgtcctcta acttcgcctg gtatcagcag        600
cggccccgga caggcaccaag gctgctgctg tacggagcaa ccacaagagc aacaggcctg        660
cctggcaggt tttccggctc tggcagcggc accgagaata tcctgacaat cagctccctg        720
cagagcgagg acttcgccat ctattttgt cagcagtaca aggattggcc attcaccttt         780
ggccccggct ccaaggtgga catcaaggga tccggaggag gaggatcttg cccctattct        840
aaccctagcc tgtgctccgg aggaggagga tcctgtccat actctaatcc atccctgtgc        900
agcggaggag gaggatctac cacaaccccca gcacctagac caccaacccc agcacccaca       960
atcgcctctc agcctctgag cctgcgccca gaggcatgca ggccagcagc aggaggagca       1020
gtgcacacca ggggcctgga cttcgcctgc gatatctata tctgggcacc actggcagga       1080
acctgtggcg tgctgctgct gtccctggtc atcaccctgt attgcaagag aggcaggaag       1140
aagctgctgt acatcttcaa gcagccttt atgcgcccag tgcagacaac ccaggaggag         1200
gacggctgca gctgtcggtt ccctgaagag gaggagggcg gctgtgagct gagagtgaag       1260
ttttccaggt ctgccgatgc cccagcctat cagcagggcc agaatcagct gtacaacgag       1320
ctgaatctgg gcaggcgcga ggagtacgac gtgctggata gaggagagg acgcgatccc        1380 gagatgggag gcaagcctag gcgcaagaac ccacaggagg gcctgtataa tgagctgcag       1440
aaggacaaga tggccgaggc ctactctgag atcggcatga agggagagcg gagaagggc        1500 aagggacacg atggcctgta tcagggcctg agcaccgcca caaaggacac ctacgatgcc       1560
ctgcacatgc aggccctgcc tccaaggtga                                        1590
```

<210> SEQ ID NO 254
<211> LENGTH: 1599
<212> TYPE: DNA
<213> ORGANISM: Artificial Sequence
<220> FEATURE:
<223> OTHER INFORMATION: Synthetic Construct

<400> SEQUENCE: 254

```
atggccctgc cagtgaccgc cctgctgctg ccactggccc tgctgctgca cgccgccaga         60
cctgaggtgc agctggtgga gagctgggc gtgctggtga agccaggagg ctctctgagg        120
ctgagctgcg cagcatccgg cttcatcttt aacaatgcct ggatgtcctg ggtgagacag        180
gcaccaggca agggcctgga gtggatcggc aggatcaaga gcaagtccga cggaggaacc        240
acagattacg cagcacccgt gaaggaccgc ttcacaatct ctcgggacga tagcaaggat        300
accctgtatc tgcagatgaa cggcctgaag acagaggaca ccgccgtgta cttctgcacc        360
acagccccag gcggccctt tgattattgg ggccagggca cactggtgac cgtgagctcc         420
ggaggaggag gaagcggcgg aggaggcagc ggcggcggcg gctctggcgg cggcggcagc        480
gacatcgtgc tgacacagag cccactgtcc ctgcctgtga ccccaggaga gcccgcctct        540
```

| | |
|---|---|
| atcagctgtc gctctagcca gagcctgctg caccgggacg gcttcaatta cctggattgg | 600 |
| tttctgcaga agcctggcca gagcccacag ctgctgatct atctggcctc ctctagagca | 660 |
| tccggagtgc ctgacaggtt ctccggatct gacagcggca cagacttcac cctgaagatc | 720 |
| tcccgcgtgg aggcagagga tgtgggcgtg tactattgca tgcaggccct gcagacacca | 780 |
| atcaccttcg gccagggcac acggctggag atcaagggat ccggaggagg aggatcttgc | 840 |
| ccctactcta accctagcct gtgcagcggc ggaggaggat cttgtccata ttctaatcca | 900 |
| agcctgtgca gcggggagg aggaagcacc acaacccctg caccaagacc ccctacacca | 960 |
| gcacctacca tcgcatccca gccactgtct ctgcggcccg aggcatgtag gccagcagca | 1020 |
| ggaggagcag tgcacaccag gggcctggac tttgcctgcg atatctacat ctgggcacca | 1080 |
| ctggcaggaa catgtggcgt gctgctgctg agcctggtca tcaccctgta ctgcaagaga | 1140 |
| ggcaggaaga agctgctgta tatcttcaag cagccttta tgcgcccagt gcagacaacc | 1200 |
| caggaggagg acggctgctc ctgtaggttc ccagaagagg aggagggagg atgtgagctg | 1260 |
| cgcgtgaagt tttcccggtc tgccgatgca cctgcatacc agcagggaca gaaccagctg | 1320 |
| tataacgagc tgaatctggg ccggagagag gagtacgacg tgctggataa gaggagggga | 1380 |
| cgcgatcctg agatgggagg caagccccgg agaaagaacc ctcaggaggg cctgtacaat | 1440 |
| gagctgcaga aggacaagat ggccgaggcc tattccgaga tcggcatgaa gggagagagg | 1500 |
| cgccggggca agggacacga tggcctgtac cagggcctgt ctacagccac caaggacacc | 1560 |
| tatgatgccc tgcacatgca ggccctgcca ccaaggtga | 1599 |

<210> SEQ ID NO 255
<211> LENGTH: 1596
<212> TYPE: DNA
<213> ORGANISM: Artificial Sequence
<220> FEATURE:
<223> OTHER INFORMATION: Synthetic Construct

<400> SEQUENCE: 255

| | |
|---|---|
| atggcactgc cagtgacagc cctgctgctg cctctggccc tgctgctgca cgcagccaga | 60 |
| ccagaggtgc agctggtgga gtccggagga ggcctggtga agccaggagg ctccctgagg | 120 |
| ctgtcttgcg aggccagcgg cttcaccttt agcgacgcct ggatgtcctg ggtgagacag | 180 |
| gcaccaggca agggcctgga gtgggtgggc aggatcaaga gcaagacaga cggcggcacc | 240 |
| acagattacg tggtgcctct gaacggccgg ttcatcatct cccgcgacga ttctcggaat | 300 |
| accctgtatc tgcagctgaa caatctgaag acagaggata ccgccgtgta ctattgcacc | 360 |
| acagtgcctg gctcctacgg ctattgggc cagggcacac tggtgaccgt gagctccggc | 420 |
| ggcggcggct ctggaggagg aggaagcgga ggaggaggaa gcggggcgg cggctctgac | 480 |
| atcgtgatga cacagtctcc actgagcctg ccagtgaccc caggagagcc tgcctccatc | 540 |
| tcttgtcgct ctagccagtc cctgctgcac aacaagcgga caattaccct ggattggttc | 600 |
| ctgcagaagc caggccagtc tccccagctg ctgatctatc tggccagcaa tagagcctcc | 660 |
| ggagtgccag acaggttctc tggaggagga agcggaacag acttcaccct gaagatcagc | 720 |
| cgcgtggagc agaggacgt gggcgtgtac tattgcatgc aggcccagca gacacccatc | 780 |
| acctttggcc agggaacccg gctggagatc aagggctccg gaggaggagg atcctgccct | 840 |
| tactccaacc catctctgtg cagcggagga ggaggatctt gtccatattc caatccttcc | 900 |
| ctgtgctccg gaggaggagg aagcaccaca cccctgcac aagacccc tacaccagca | 960 |
| cctaccatcg catcccagcc tctgtctctg cggcccgagg catgtaggcc agcagcaggc | 1020 |

```
ggcgccgtgc acaccagggg cctggacttt gcctgcgata tctacatctg ggcaccactg   1080
gcaggaacat gtggcgtgct gctgctgtct ctggtcatca ccctgtactg caagagaggc   1140
aggaagaagc tgctgtatat cttcaagcag cccttcatgc ggcccgtgca gacaacccag   1200
gaggaggacg gctgcagctg tcggttccct gaagaggagg agggaggatg tgagctgcgc   1260
gtgaagttta gccggtccgc cgatgcacca gcataccagc agggccagaa ccagctgtat   1320
aacgagctga atctgggccg gagagaggag tacgacgtgc tggataagag gaggggacgc   1380
gatcctgaga tgggaggcaa gcctcggaga aagaacccac aggagggcct gtacaatgag   1440
ctgcagaagg acaagatggc cgaggcctat agcgagatcg gcatgaaggg agagaggcgc   1500
cggggcaagg acacgatgg cctgtaccag ggcctgtcca cagccaccaa ggacacctat   1560
gatgccctgc acatgcaggc cctgccacca aggtga                             1596
```

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

```
Cys Pro Tyr Ser Asn Pro Ser Leu Cys
 1               5
```

<210> SEQ ID NO 257
<211> LENGTH: 255
<212> TYPE: PRT
<213> ORGANISM: Artificial Sequence
<220> FEATURE:
<223> OTHER INFORMATION: Synthetic Construct

<400> SEQUENCE: 257

```
Met Ala Leu Pro Val Thr Ala Leu Leu Leu Pro Leu Ala Leu Leu Leu
 1               5                  10                  15

His Ala Ala Arg Pro Asp Val Val Met Thr Gln Ser Pro Leu Ser Leu
                20                  25                  30

Pro Val Thr Leu Gly Gln Pro Ala Ser Ile Ser Cys Lys Ser Ser Gln
            35                  40                  45

Ser Leu Leu Tyr Ser Asn Gly Lys Thr Tyr Leu Asn Trp Phe Gln Gln
        50                  55                  60

Arg Pro Gly Gln Ser Pro Arg Arg Leu Ile Tyr Gln Val Ser Lys Leu
 65                  70                  75                  80

Asp Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Gly Gln Asp Thr His Phe Pro Leu Thr Phe Gly Gly Gly Thr
        115                 120                 125

Lys Val Glu Ile Lys Gly Gly Gly Ser Gly Gly Gly Gly Ser Gly
    130                 135                 140

Gly Gly Gly Ser Gly Gly Gly Gly Ser Gln Val Gln Leu Val Gln Ser
145                 150                 155                 160

Gly Ala Glu Val Lys Lys Pro Gly Ala Ser Val Lys Val Ser Cys Lys
                165                 170                 175

Ala Ser Gly Tyr Thr Phe Thr Asp Tyr Thr Leu His Trp Val Arg Gln
            180                 185                 190
```

```
Ala Pro Gly Gln Gly Leu Glu Trp Met Gly Ile Trp Pro Ile Thr
            195                 200                 205

Gly Gly Thr Thr Tyr Asn Gln Lys Phe Lys Gly Arg Val Thr Met Thr
210                 215                 220

Arg Asp Thr Ser Thr Ser Thr Val Tyr Met Glu Leu Ser Ser Leu Arg
225                 230                 235                 240

Ser Glu Asp Thr Ala Val Tyr Tyr Cys Ala Arg Gly Glu Ala Gln
            245                 250                 255
```

<210> SEQ ID NO 258
<211> LENGTH: 255
<212> TYPE: PRT
<213> ORGANISM: Artificial Sequence
<220> FEATURE:
<223> OTHER INFORMATION: Synthetic Construct

<400> SEQUENCE: 258

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Leu Lys Pro Thr Glu Thr Leu Thr Leu Thr Cys Thr Val Ser Gly Phe
            35                  40                  45

Ser Leu Ser Asn Pro Arg Met Gly Val Ser Trp Ile Arg Gln Pro Pro
        50                  55                  60

Gly Lys Ala Leu Glu Trp Phe Ala His Ile Phe Ser Thr Asp Glu Lys
65                  70                  75                  80

Ser Leu Lys Leu Ser Leu Arg Ser Arg Leu Thr Leu Ser Lys Asp Thr
                85                  90                  95

Ser Lys Ser Gln Val Val Leu Thr Met Thr Asn Met Ala Pro Val Asp
            100                 105                 110

Ser Ala Thr Tyr Tyr Cys Ala Arg Asp Ser Ser Asn Tyr Glu Gly Tyr
        115                 120                 125

Phe Asp Phe Trp Gly Gln Gly Thr Leu Val Thr Val Ser Ser Gly Gly
130                 135                 140

Gly Gly Ser Gly Gly Gly Gly Ser Gly Gly Gly Gly Ser Gly Gly Gly
145                 150                 155                 160

Gly Ser Glu Val Val Leu Thr Gln Ser Pro Ala Thr Leu Ser Val Ser
                165                 170                 175

Pro Gly Glu Arg Ala Thr Leu Ser Cys Arg Ala Ser Gln Ser Val Arg
            180                 185                 190

Ser Asn Leu Ala Trp Tyr Gln Gln Lys Ser Gly Gln Ala Pro Arg Leu
        195                 200                 205

Leu Ile Tyr Gly Ser Thr Ile Arg Ala Thr Gly Val Pro Ala Arg Phe
210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln Tyr Ser Asp
                245                 250                 255
```

<210> SEQ ID NO 259
<211> LENGTH: 255
<212> TYPE: PRT
<213> ORGANISM: Artificial Sequence
<220> FEATURE:
<223> OTHER INFORMATION: Synthetic Construct

<400> SEQUENCE: 259

```
Met Ala Leu Pro Val Thr Ala Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Val Lys Pro Thr Glu Thr Leu Thr Leu Thr Cys Thr Val Ser Gly Phe
            35                  40                  45

Ser Leu Ser Asn Ala Arg Met Gly Val Ser Trp Ile Arg Gln Pro Pro
    50                  55                  60

Gly Lys Ala Leu Glu Trp Leu Ala His Ile Phe Ser Thr Asp Glu Lys
65                  70                  75                  80

Ser Ile Arg Arg Ser Leu Arg Ser Arg Leu Thr Leu Ser Lys Asp Thr
                85                  90                  95

Ser Lys Ser Gln Val Val Leu Thr Met Thr Asn Met Asp Pro Val Asp
            100                 105                 110

Thr Ala Thr Tyr Phe Cys Ala Arg Asp Ser Ser Asn Tyr Glu Gly Tyr
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Val Val Met Thr Gln Ser Pro Ala Thr Leu Ser Val Ser
                165                 170                 175

Pro Gly Glu Arg Val Thr Leu Ser Cys Arg Ala Ser Gln Ser Val Ser
            180                 185                 190

Ser Asn Phe Ala Trp Tyr Gln Gln Arg Pro Gly Gln Ala Pro Arg Leu
        195                 200                 205

Leu Leu Tyr Gly Ala Thr Thr Arg Ala Thr Gly Leu Pro Gly Arg Phe
    210                 215                 220

Ser Gly Ser Gly Ser Gly Thr Glu Asn Ile Leu Thr Ile Ser Ser Leu
225                 230                 235                 240

Gln Ser Glu Asp Phe Ala Ile Tyr Phe Cys Gln Gln Tyr Lys Asp
                245                 250                 255
```

<210> SEQ ID NO 260
<211> LENGTH: 255
<212> TYPE: PRT
<213> ORGANISM: Artificial Sequence
<220> FEATURE:
<223> OTHER INFORMATION: Synthetic Construct

<400> SEQUENCE: 260

```
Met Ala Leu Pro Val Thr Ala Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Val Lys Pro Thr Glu Thr Leu Thr Leu Thr Cys Thr Val Ser Gly Phe
            35                  40                  45

Ser Leu Ser Asn Ala Arg Met Gly Val Ser Trp Ile Arg Gln Pro Pro
    50                  55                  60

Gly Lys Ala Leu Glu Trp Leu Gly His Ile Phe Ser Thr Asp Glu Lys
65                  70                  75                  80

Ser Tyr Ser Thr Ser Leu Arg Gly Arg Ile Thr Ile Ser Lys Asp Thr
                85                  90                  95

Ser Arg Gly Leu Val Val Leu Thr Leu Thr Asn Met Asp Pro Val Asp
```

```
                  100                 105                 110
Thr Ala Thr Tyr Tyr Cys Ala Arg Asp Ser Ser Asn Tyr Glu Gly Tyr
            115                 120                 125

Phe Asp Phe Trp Gly Pro Gly Phe Leu Val Thr Val Ser Ser Gly Gly
        130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Val Ser
                165                 170                 175

Pro Gly Glu Arg Ala Thr Leu Ser Cys Arg Val Ser Gln Ser Ile Gly
            180                 185                 190

Ala Asn Leu Ala Trp Tyr Gln Gln Lys Phe Gly Gln Ala Pro Arg Leu
        195                 200                 205

Leu Ile Tyr Gly Ala Ser Thr Arg Ala Thr Gly Ile Pro Val Arg Phe
    210                 215                 220

Ser Gly Gly Ser Gly Thr Glu Phe Thr Leu Thr Ile Ser Ser Leu
225                 230                 235                 240

Gln Ser Glu Asp Phe Ala Ile Tyr Ser Cys Gln Gln Tyr Ile Tyr
                245                 250                 255

<210> SEQ ID NO 261
<211> LENGTH: 255
<212> TYPE: PRT
<213> ORGANISM: Artificial Sequence
<220> FEATURE:
<223> OTHER INFORMATION: Synthetic Construct

<400> SEQUENCE: 261

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
        35                  40                  45

Ser Leu Asn Asn Ala Arg Met Gly Val Ser Trp Ile Arg Gln Pro Pro
    50                  55                  60

Gly Lys Ala Leu Glu Trp Phe Ala His Ile Phe Ser Thr Asp Glu Lys
65                  70                  75                  80

Ser Phe Arg Thr Ser Leu Arg Ser Arg Leu Thr Leu Ser Lys Asp Thr
                85                  90                  95

Ser Lys Ser Gln Val Val Leu Thr Met Thr Asn Met Asp Pro Val Asp
            100                 105                 110

Thr Ala Thr Tyr Tyr Cys Ala Arg Asp Ser Ser Asn Tyr Glu Gly Tyr
        115                 120                 125

Phe Asp Tyr Trp Gly Gln Gly Ile Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Asn Asn Leu Ala Trp Tyr Gln Gln Lys Pro Gly Gln Ala Pro Arg Leu
        195                 200                 205

Leu Ile Tyr Gly Ala Ser Thr Arg Ala Thr Gly Val Pro Ala Arg Phe
```

```
                210                 215                 220
Ser Gly Ser Asp Ser Gly Thr Glu Phe Ser Leu Thr Ile Ser Ser Leu
225                 230                 235                 240

Gln Ser Glu Asp Phe Ala Val Tyr Phe Cys Gln Gln Tyr Lys Asp
                245                 250                 255

<210> SEQ ID NO 262
<211> LENGTH: 255
<212> TYPE: PRT
<213> ORGANISM: Artificial Sequence
<220> FEATURE:
<223> OTHER INFORMATION: Synthetic Construct

<400> SEQUENCE: 262

Met Ala Leu Pro Val Thr Ala Leu Leu Leu Pro Leu Ala Leu Leu Leu
1               5                   10                  15

His Ala Ala Arg Pro Glu Val Asn Leu Val Glu Ser Gly Gly Gly Leu
                20                  25                  30

Val Lys Pro Gly Gly Ser Leu Arg Leu Ser Cys Glu Ala Ser Gly Phe
            35                  40                  45

Thr Phe Ser Tyr Ala Trp Met Ser Trp Val Arg Gln Ala Pro Gly Lys
        50                  55                  60

Gly Leu Glu Trp Val Gly Arg Ile Lys Ser Ile Ala Asp Gly Gly Ala
65                  70                  75                  80

Thr Asp Tyr Ala Ala Pro Val Arg Asn Arg Phe Thr Ile Ser Arg Asp
                85                  90                  95

Asp Ser Arg Asn Thr Leu Tyr Leu Glu Met His Ser Leu Lys Thr Glu
                100                 105                 110

Asp Thr Ala Val Tyr Tyr Cys Thr Thr Ile Pro Gly Asn Asp Ala Phe
            115                 120                 125

Asp Met Trp Gly Gln Gly Thr Met Val Thr Val Ser Ser Gly Gly Gly
        130                 135                 140

Gly Ser Gly Gly Gly Gly Ser Gly Gly Gly Gly Ser Gly Gly Gly Gly
145                 150                 155                 160

Ser Asp Ile Val Leu Thr Gln Ser Pro Leu Ser Leu Ser Val Thr Pro
                165                 170                 175

Gly Glu Pro Ala Ser Ile Ser Cys Arg Ser Ser Gln Ser Leu Leu Tyr
                180                 185                 190

Ser Asn Gly Lys Asn Tyr Leu Asp Trp Phe Leu His Lys Pro Gly Gln
            195                 200                 205

Ser Pro Gln Leu Leu Ile Tyr Leu Gly Ser Asn Arg Ala Ser Gly Val
        210                 215                 220

Pro Asp Arg Phe Ser Gly Ser Gly Ser Gly Ile Asp Phe Ile Leu Lys
225                 230                 235                 240

Ile Ser Arg Val Glu Ala Glu Asp Val Gly Val Tyr Tyr Cys Met
                245                 250                 255

<210> SEQ ID NO 263
<211> LENGTH: 255
<212> TYPE: PRT
<213> ORGANISM: Artificial Sequence
<220> FEATURE:
<223> OTHER INFORMATION: Synthetic Construct

<400> SEQUENCE: 263

Met Ala Leu Pro Val Thr Ala Leu Leu Leu Pro Leu Ala Leu Leu Leu
1               5                   10                  15
```

His Ala Ala Arg Pro Glu Val Asn Leu Val Glu Ser Gly Gly Gly Leu
            20                  25                  30

Val Lys Pro Gly Gly Ser Leu Arg Leu Ser Cys Glu Ala Ser Gly Phe
        35                  40                  45

Thr Phe Ser Tyr Ala Trp Met Ser Trp Val Arg Gln Ala Pro Gly Lys
    50                  55                  60

Gly Leu Glu Trp Val Gly Arg Ile Lys Ser Ile Thr Asp Gly Gly Val
65                  70                  75                  80

Ile Asp Tyr Ala Ala Pro Val Arg Asn Arg Cys Thr Ile Ser Arg Asp
                85                  90                  95

Asp Ser Arg Asn Thr Leu Tyr Leu Glu Met His Ser Leu Lys Thr Glu
            100                 105                 110

Asp Thr Ala Val Tyr Tyr Cys Thr Thr Ile Pro Gly Asn Asp Asp Phe
        115                 120                 125

Asp Met Trp Gly Gln Gly Arg Met Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Val Leu Thr Gln Ser Pro Leu Ser Leu Ser Val Thr Pro
                165                 170                 175

Gly Glu Pro Ala Ser Ile Ser Cys Arg Ser Ser Gln Ser Leu Leu Tyr
            180                 185                 190

Ser Asn Gly Lys Asn Tyr Leu Asp Trp Phe Leu His Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Ile Asp Phe Ile Leu Lys
225                 230                 235                 240

Ile Ser Arg Val Glu Ala Glu Asp Val Gly Val Tyr Tyr Cys Met
                245                 250                 255

<210> SEQ ID NO 264
<211> LENGTH: 255
<212> TYPE: PRT
<213> ORGANISM: Artificial Sequence
<220> FEATURE:
<223> OTHER INFORMATION: Synthetic Construct

<400> SEQUENCE: 264

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Trp Gly Val Leu
            20                  25                  30

Val Lys Pro Gly Gly Ser Leu Arg Leu Ser Cys Ala Ala Ser Gly Phe
        35                  40                  45

Ile Phe Asn Asn Ala Trp Met Ser Trp Val Arg Gln Ala Pro Gly Lys
    50                  55                  60

Gly Leu Glu Trp Ile Gly Arg Ile Lys Ser Lys Ser Asp Gly Gly Thr
65                  70                  75                  80

Thr Asp Tyr Ala Ala Pro Val Lys Asp Arg Phe Thr Ile Ser Arg Asp
                85                  90                  95

Asp Ser Lys Asp Thr Leu Tyr Leu Gln Met Asn Gly Leu Lys Thr Glu
            100                 105                 110

Asp Thr Ala Val Tyr Phe Cys Thr Thr Ala Pro Gly Gly Pro Phe Asp
        115                 120                 125

```
Tyr Trp Gly Gln Gly Thr Leu Val Thr Val Ser Ser Gly Gly Gly
    130                 135                 140

Ser Gly Gly Gly Gly Ser Gly Gly Gly Ser Gly Gly Gly Gly Ser
145                 150                 155                 160

Asp Ile Val Leu Thr Gln Ser Pro Leu Ser Leu Pro Val Thr Pro Gly
                165                 170                 175

Glu Pro Ala Ser Ile Ser Cys Arg Ser Ser Gln Ser Leu Leu His Arg
                180                 185                 190

Asp Gly Phe Asn Tyr Leu Asp Trp Phe Leu Gln Lys Pro Gly Gln Ser
                195                 200                 205

Pro Gln Leu Leu Ile Tyr Leu Ala Ser Ser Arg Ala Ser Gly Val Pro
    210                 215                 220

Asp Arg Phe Ser Gly Ser Asp Ser Gly Thr Asp Phe Thr Leu Lys Ile
225                 230                 235                 240

Ser Arg Val Glu Ala Glu Asp Val Gly Val Tyr Tyr Cys Met Gln
                245                 250                 255
```

<210> SEQ ID NO 265
<211> LENGTH: 255
<212> TYPE: PRT
<213> ORGANISM: Artificial Sequence
<220> FEATURE:
<223> OTHER INFORMATION: Synthetic Construct

<400> SEQUENCE: 265

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Lys Pro Gly Gly Ser Leu Arg Leu Ser Cys Glu Ala Ser Gly Phe
            35                  40                  45

Thr Phe Ser Asp Ala Trp Met Ser Trp Val Arg Gln Ala Pro Gly Lys
        50                  55                  60

Gly Leu Glu Trp Val Gly Arg Ile Lys Ser Lys Thr Asp Gly Gly Thr
65                  70                  75                  80

Thr Asp Tyr Val Val Pro Leu Asn Gly Arg Phe Ile Ile Ser Arg Asp
                85                  90                  95

Asp Ser Arg Asn Thr Leu Tyr Leu Gln Leu Asn Asn Leu Lys Thr Glu
                100                 105                 110

Asp Thr Ala Val Tyr Tyr Cys Thr Thr Val Pro Gly Ser Tyr Gly Tyr
            115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gly Gly Gly Gly Ser Asp
145                 150                 155                 160

Ile Val Met Thr Gln Ser Pro Leu Ser Leu Pro Val Thr Pro Gly Glu
                165                 170                 175

Pro Ala Ser Ile Ser Cys Arg Ser Ser Gln Ser Leu Leu His Asn Lys
            180                 185                 190

Arg Asn Asn Tyr Leu Asp Trp Phe Leu Gln Lys Pro Gly Gln Ser Pro
                195                 200                 205

Gln Leu Leu Ile Tyr Leu Ala Ser Asn Arg Ala Ser Gly Val Pro Asp
    210                 215                 220

Arg Phe Ser Gly Gly Ser Gly Thr Asp Phe Thr Leu Lys Ile Ser
225                 230                 235                 240
```

```
Arg Val Glu Ala Glu Asp Val Gly Val Tyr Tyr Cys Met Gln Ala
                245                 250                 255

<210> SEQ ID NO 266
<211> LENGTH: 255
<212> TYPE: PRT
<213> ORGANISM: Artificial Sequence
<220> FEATURE:
<223> OTHER INFORMATION: Synthetic Construct

<400> SEQUENCE: 266

Met Ala Leu Pro Val Thr Ala Leu Leu Leu Pro Leu Ala Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Asp
            35                  40                  45

Thr Phe Ser Ser Asn Ala Ile Ser Trp Val Arg Gln Ala Pro Gly Gln
        50                  55                  60

Gly Leu Glu Trp Met Gly Val Ile Ile Pro Ile Phe Gly Thr Ala Asp
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg His Thr Tyr His Glu Tyr Ala Gly Gly
        115                 120                 125

Tyr Tyr Gly Gly Ala Met Asp Pro Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Glu Leu Gln Ser Val Leu Thr Gln Pro
                165                 170                 175

Pro Ser Ala Ser Gly Thr Pro Gly Gln Arg Val Thr Ile Ser Cys Ser
            180                 185                 190

Gly Ser Ser Asn Ile Gly Ser Asn Tyr Val Tyr Trp Tyr Gln Gln
        195                 200                 205

Leu Pro Gly Thr Ala Pro Lys Ile Leu Ile Tyr Arg Asn Asn Gln Arg
    210                 215                 220

Pro Ser Gly Val Pro Asp Arg Phe Ser Gly Ser Lys Ser Gly Thr Ser
225                 230                 235                 240

Ala Ser Leu Ala Ile Ser Gly Leu Arg Ser Glu Asp Glu Ala Asp
                245                 250                 255

<210> SEQ ID NO 267
<211> LENGTH: 9
<212> TYPE: PRT
<213> ORGANISM: Artificial Sequence
<220> FEATURE:
<223> OTHER INFORMATION: Synthetic Construct

<400> SEQUENCE: 267

Gly Phe Thr Phe Ser Tyr Ala Trp Met
1               5

<210> SEQ ID NO 268
<211> LENGTH: 255
<212> TYPE: PRT
<213> ORGANISM: Homo sapien
```

```
<400> SEQUENCE: 268

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln
                245                 250                 255

<210> SEQ ID NO 269
<211> LENGTH: 255
<212> TYPE: PRT
<213> ORGANISM: Artificial Sequence
<220> FEATURE:
<223> OTHER INFORMATION: Synthetic Construct

<400> SEQUENCE: 269

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95
```

```
Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln
                245                 250                 255
```

<210> SEQ ID NO 270
<211> LENGTH: 255
<212> TYPE: PRT
<213> ORGANISM: Artificial Sequence
<220> FEATURE:
<223> OTHER INFORMATION: Synthetic Construct

<400> SEQUENCE: 270

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205
```

Gln Val Val Ala Ile Ala Ser Asn Asn Gly Gly Lys Gln Ala Leu Glu
          210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln
                245                 250                 255

<210> SEQ ID NO 271
<211> LENGTH: 255
<212> TYPE: PRT
<213> ORGANISM: Artificial Sequence
<220> FEATURE:
<223> OTHER INFORMATION: Synthetic Construct

<400> SEQUENCE: 271

Asn Pro Gln Arg Ser Thr Val Trp Tyr Leu Thr Pro Gln Gln Val Val
1               5                   10                  15

Ala Ile Ala Ser Asn Asn Gly Gly Lys Gln Ala Leu Glu Thr Val Gln
            20                  25                  30

Arg Leu Leu Pro Val Leu Cys Gln Ala His Gly Leu Thr Pro Gln Gln
        35                  40                  45

Val Val Ala Ile Ala Ser Asn Gly Gly Gly Lys Gln Ala Leu Glu Thr
    50                  55                  60

Val Gln Arg Leu Leu Pro Val Leu Cys Gln Ala His Gly Leu Thr Pro
65                  70                  75                  80

Gln Gln Val Val Ala Ile Ala Ser Asn Asn Gly Gly Lys Gln Ala Leu
                85                  90                  95

Glu Thr Val Gln Arg Leu Leu Pro Val Leu Cys Gln Ala His Gly Leu
            100                 105                 110

Thr Pro Gln Gln Val Val Ala Ile Ala Ser Asn Asn Gly Gly Lys Gln
        115                 120                 125

Ala Leu Glu Thr Val Gln Arg Leu Leu Pro Val Leu Cys Gln Ala His
    130                 135                 140

Gly Leu Thr Pro Glu Gln Val Val Ala Ile Ala Ser His Asp Gly Gly
145                 150                 155                 160

Lys Gln Ala Leu Glu Thr Val Gln Arg Leu Leu Pro Val Leu Cys Gln
                165                 170                 175

Ala His Gly Leu Thr Pro Glu Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Ala His Gly Leu Thr Pro Gln Gln Val Val Ala Ile Ala Ser
    210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Gln Gln Val Val Ala
                245                 250                 255

<210> SEQ ID NO 272
<211> LENGTH: 255
<212> TYPE: PRT
<213> ORGANISM: Artificial Sequence
<220> FEATURE:
<223> OTHER INFORMATION: Synthetic Construct

<400> SEQUENCE: 272

Leu Thr Pro Glu Gln Val Val Ala Ile Ala Ser His Asp Gly Gly Lys
1               5                   10                  15

```
Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
               100                 105                 110

Ser Asn Ile Gly Gly Lys Gln Ala Leu Glu Thr Val Gln Ala Leu Leu
           115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln
                245                 250                 255

<210> SEQ ID NO 273
<211> LENGTH: 255
<212> TYPE: PRT
<213> ORGANISM: Artificial Sequence
<220> FEATURE:
<223> OTHER INFORMATION: Synthetic Construct

<400> SEQUENCE: 273

Leu Thr Pro Gln Gln Val Val Ala Ile Ala Ser Asn Asn Gly Gly Lys
 1               5                  10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
 50                  55                  60

Gln Ala His Gly Leu Thr Pro Gln Gln Val Val Ala Ile Ala Ser Asn
 65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
               100                 105                 110

Ser Asn Ile Gly Gly Lys Gln Ala Leu Glu Thr Val Gln Ala Leu Leu
           115                 120                 125
```

```
Pro Val Leu Cys Gln Ala His Gly Leu Thr Pro Gln Gln Val Val Ala
    130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser Asn Ile Gly Gly Lys Gln Ala Leu Glu Thr Val
            180                 185                 190
Gln Ala Leu Leu Pro Val Leu Cys Gln Ala His Gly Leu Thr Pro Gln
        195                 200                 205
Gln Val Val Ala Ile Ala Ser Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Glu Gln Val Val Ala Ile Ala Ser His Asp Gly Gly Lys Gln
                245                 250                 255
```

<210> SEQ ID NO 274
<211> LENGTH: 255
<212> TYPE: PRT
<213> ORGANISM: Artificial Sequence
<220> FEATURE:
<223> OTHER INFORMATION: Synthetic Construct

<400> SEQUENCE: 274

```
Leu Thr Pro Gln Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Glu Gln Val Val Ala Ile Ala Ser His Asp Gly
            35                  40                  45
Gly Lys Gln Ala Leu Glu Thr Val Gln Arg Leu Leu Pro Val Leu Cys
        50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Gln Gln Val Val Ala Ile Ala
            100                 105                 110
Ser Asn Gly Gly Gly Lys Gln Ala Leu Glu Thr Val Gln Arg Leu Leu
        115                 120                 125
Pro Val Leu Cys Gln Ala His Gly Leu Thr Pro Glu Gln Val Val Ala
    130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Gly Lys Gln Ala Leu Glu
    210                 215                 220
Thr Val Gln Arg Leu Leu Pro Val Leu Cys Gln Ala His Gly Leu Thr
225                 230                 235                 240
```

-continued

Pro Glu Gln Val Val Ala Ile Ala Ser Asn Ile Gly Gly Lys Gln
            245                 250                 255

<210> SEQ ID NO 275
<211> LENGTH: 255
<212> TYPE: PRT
<213> ORGANISM: Artificial Sequence
<220> FEATURE:
<223> OTHER INFORMATION: Synthetic Construct

<400> SEQUENCE: 275

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln
            245                 250                 255

<210> SEQ ID NO 276
<211> LENGTH: 136
<212> TYPE: PRT
<213> ORGANISM: Homo sapien

<400> SEQUENCE: 276

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
            35                  40                  45

```
Ser Gly Gly Gly Gly Ser Pro Ala Pro Arg Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Val
            115                 120                 125

Cys Lys Cys Pro Arg Pro Val Val
            130             135

<210> SEQ ID NO 277
<211> LENGTH: 1509
<212> TYPE: DNA
<213> ORGANISM: Artificial Sequence
<220> FEATURE:
<223> OTHER INFORMATION: Synthetic Construct

<400> SEQUENCE: 277
atggctctgc cgtcaccgc tctgctgctg cctctggccc tgctgctgca cgcagcaagg      60
ccacaggtgc agctggtgca gtccggagca gaggtgaaga agcctggcag ctccgtgaag    120
gtgagctgca aggcctccgg cgacacattc tctagcaacg caatcagctg ggtgcgccag    180
gcccctggcc agggactgga gtggatgggc gtgatcatcc ctatcttcgg caccgccgac    240
tatgcccaga gtttcagggg ccgggtgaca atcaccgccg atgagtctac aagcaccgcc    300
tacatggagc tgtcctctct gagatccgag gacacagccg tgtactattg ccaggcac      360 acctatcacg agtacgcagg aggatactat ggaggagcaa tggatccttg gggacagggc    420
acactggtga ccgtgagctc cggcggcggc ggctctggag aggaggaag cggaggagga    480 ggaagcgggg gcggcggctc tgagctgcag agcgtgctga cccagccacc ttccgcctct    540
ggaacaccag gccagagggt gaccatcagc tgctccggat ctagctccaa catcggctcc    600
aattacgtgt attggtacca gcagctgcca ggcacagccc caagatcct gatctaccgc    660 aacaatcagc ggccttctgg cgtgccagat agattctctg gcagcaagtc cggcacctct    720
gccagcctgg caatctccgg cctgaggtct gaggacgagg ccgattacta ttgcgccgcc    780
tgggacgata acctgagcgg ctgggtgttt ggcacaggca ccaagctgac agtgctgacc    840 acaaccccctg caccaagacc accaacacca gcacctacca tcgcaagcca gccactgtcc    900
ctgagacccg aggcctgtag gcctgcagca ggaggagcag tgcacaccag gggcctggac    960
tttgcctgcg atatctatat ctgggcacca ctggcaggaa catgtggcgt gctgctgctg   1020
agcctggtca tcacccctgta ttgcaagaga ggcaggaaga agctgctgta catcttcaag   1080 cagccctta tgcgccctgt gcagacaacc caggaggagg acggctgcag ctgtcggttc   1140
ccagaagagg aggagggagg atgtgagctg agggtgaagt tttcccggtc tgccgatgca   1200
ccagcatatc agcagggaca gaatcagctg tacaacgagc tgaatctggg ccggagagag   1260
gagtacgacg tgctggataa gaggagggga agggaccctg agatgggagg caagccacgg   1320
agaaagaacc cccaggaggg cctgtataat gagctgcaga aggacaagat ggccgaggcc   1380
```

-continued

```
tactctgaga tcggcatgaa gggagagagg cgccggggca agggacacga tggcctgtat    1440
cagggcctga gcacagccac caaggacacc tacgatgccc tgcatatgca ggcactgcct    1500
ccaaggtga                                                            1509
```

CHIMERIC ANTIGEN RECEPTORS TARGETING EPIDERMAL GROWTH FACTOR RECEPTOR VARIANT III

CROSS-REFERENCE TO RELATED APPLICATIONS

This application is a divisional of U.S. patent application Ser. No. 15/402,760 filed Jan. 10, 2017, now issued as U.S. Pat. No. 10,259,876, which claims the benefit of U.S. Provisional Application No. 62/431,758 filed Dec. 8, 2016, and U.S. Provisional Application No. 62/281,533 filed Jan. 21, 2016, all of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "ALGN_006_03US_SeqList_ST25.txt" created on Apr. 2, 2020 and having a size of 284 KB. The sequence listing contained in this .txt file is part of the specification and is incorporated herein by reference in its entirety.

FIELD

The invention relates to chimeric antigen receptors (CAR). CARs are able to redirect immune cell specificity and reactivity toward a selected target exploiting the ligand-binding domain properties. In particular, the invention relates to CARs that specifically bind to Epidermal Growth Factor Receptor Variant III (EGFRvIII specific CARs). The invention further relates to polynucleotides encoding EGFRvIII specific CAR and isolated cells expressing EGFRvIII specific CARs at their surface. The invention further relates to methods for engineering immune cells expressing EGFRvIII specific CARs at their surface. The invention is particularly useful for the treatment of solid tumors such as glioblastoma multiforme (GBM), non-small cell lung cancer, head and neck cancer, breast cancer, ovarian cancer, and prostate cancer. The invention further relates to immune cells comprising the EGFRvIII specific CARs (EGFRvIII specific CAR-T cells), compositions comprising the EGFRvIII specific CAR-T cells, and methods of using the EGFRvIII specific CAR-T cells for treating EGFRvIII-mediated pathologies.

BACKGROUND

EGFR variant III (EGFRvIII), a tumor specific mutant of EGFR, is a product of genomic rearrangement which is often associated with wild-type EGFR gene amplification. EGFRvIII is formed by an in-frame deletion of exons 2-7, leading to deletion of 267 amino acids with a glycine substitution at the junction. The truncated receptor loses its ability to bind ligands but acquires constitutive kinase activity. Interestingly, EGFRvIII always co-expresses with full length wild-type EGFR in the same tumor cells. Moreover, EGFRvIII expressing cells exhibit increased proliferation, invasion, angiogenesis and resistance to apoptosis.

EGFRvIII is most often found in glioblastoma multiforme (GBM). It is estimated that 25-35% of GBM carries this truncated receptors. Moreover, its expression often reflects a more aggressive phenotype and poor prognosis. Besides GBM, expression of EGFRvIII has also been reported in other solid tumors such as non-small cell lung cancer, head and neck cancer, breast cancer, ovarian cancer and prostate cancer. In contrast, EGFRvIII is not expressed in healthy tissues. The lack of expression in normal tissues makes EGFRvIII an ideal target for developing tumor specific targeted therapy.

Adoptive transfer of T cells genetically modified to recognize malignancy-associated antigens has shown promise as a new approach to treating cancer (see, e.g., Brenner et al., Current Opinion in Immunology, 22(2): 251-257 (2010); Rosenberg et al., Nature Reviews Cancer, 8(4): 299-308 (2008)). T cells can be genetically modified to express chimeric antigen receptors (CARs), which are fusion proteins comprised of an antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)). Accordingly, treatment to a solid tumor such as glioblastoma multiforme using an anti-EGFRvIII antagonist including EGFRvIII specific CARs and EGFRvIII specific CAR-T cells would make a promising therapeutic agent.

SUMMARY

Chimeric antigen receptors (CARs) that bind to EGFRvIII are provided. It is demonstrated that certain EGFRvIII specific CARs are effective when expressed in T cells to activate T cells upon contact with EGFRvIII. Advantageously, the EGFRvIII specific CARs provided herein bind human EGFRvIII. Also advantageously, the EGFRvIII specific CAR-T cells provided herein exhibit degranulation activity, increased interferon gamma production, and/or cytotoxic activity upon contact with EGFRvIII-expressing cells.

In one aspect, the invention provides an EGFRvIII specific CAR comprising an extracellular ligand-binding domain, a first transmembrane domain, and an intracellular signaling domain, wherein the extracellular ligand-binding domain comprises (a) a heavy chain variable (VH) region comprising (i) a VH complementarity determining region one (CDR1) comprising the sequence shown in SEQ ID NO: 62, 63, 64, 74, 75, 76, 80, 81, 82, 88, 89, 90, 109, 110, 111, 115, 116, 117, 121, 122, 123, 137, 138, or 139; (ii) a VH CDR2 comprising the sequence shown in SEQ ID NO: 70, 71, 77, 78, 83, 84, 86, 87, 91, 92, 112, 113, 118, 119, 124, 125, 127, 128, 140, or 141; and iii) a VH CDR3 comprising the sequence shown in SEQ ID NO: 73, 79, 85, 114, 120, 126, 129, or 142, and/or (b) a light chain variable (VL) region comprising (i) a VL CDR1 comprising the sequence shown in SEQ ID NO: 149, 156, 159, 162, 165, 182, 185, 187, or 195; (ii) a VL CDR2 comprising the sequence shown in SEQ ID NO: 152, 157, 160, 163, 183, 186, 188, or 196; and (iii) a VL CDR3 comprising the sequence shown in SEQ ID NO: 153, 158, 161, 164, 184, 189, or 197.

In another aspect, the invention provides an EGFRvIII specific CAR comprising an extracellular ligand-binding domain, a first transmembrane domain, and an intracellular signaling domain, wherein the extracellular ligand-binding domain comprises a single chain Fv fragment (scFv) comprising a heavy chain variable (VH) region comprising three CDRs from the VH region comprising the sequence shown in SEQ ID NO: 5, 9, 11, 13, 15, 37, 39, 41, 43, or 48; and/or a light chain variable (VL) region comprising three CDRs from the VL region comprising the sequence shown in SEQ ID NO: 6, 10, 12, 14, 16, 38, 40, 42, or 49. In some embodiments, the VH region can comprise the sequence shown in SEQ ID NO: 5, 9, 11, 13, 15, 37, 39, 41, 43, or 48, or a variant thereof with one or several conservative amino acid substitutions in residues that are not within a CDR and/or the VL region can comprise the amino acid sequence shown in SEQ ID NO: 6, 10, 12, 14, 16, 38, 40, 42, or 49, or a variant thereof with one or several amino acid substitutions in amino acids that are not within a CDR. For example, in some embodiments, the VH or VL region of the scFv can comprise an amino acid sequence described above or a variant thereof with no more than 10, 9, 8, 7, 6, 5, 4, 3, 2, or 1 conservative substitutions in residues that are not within a CDR.

In some embodiments, the invention provides an EGFRvIII specific CAR comprising an extracellular ligand-binding domain, a first transmembrane domain, and an intracellular signaling domain, wherein the extracellular ligand-binding domain comprises a single chain Fv fragment (scFv) comprising a heavy chain variable (VH) region comprising the sequence shown in SEQ ID NO: 11, 15, 30, 37, or 41; and/or a light chain variable (VL) region comprising the sequence shown in SEQ ID NO: 12, 16, 31, 38, or 42. In some embodiments, the VH comprises the sequence shown in SEQ ID NO: 11 and the VL comprises the sequence shown in SEQ ID NO: 12. In some embodiments, the VH comprises the sequence shown in SEQ ID NO: 15 and the VL comprises the sequence shown in SEQ ID NO: 16. In some embodiments, the VH comprises the sequence shown in SEQ ID NO: 30 and the VL comprises the sequence shown in SEQ ID NO: 31. In some embodiments, the VH comprises the sequence shown in SEQ ID NO: 37 and the VL comprises the sequence shown in SEQ ID NO: 38. In some embodiments, the VH comprises the sequence shown in SEQ ID NO: 41 and the VL comprises the sequence shown in SEQ ID NO: 42.

In some embodiments, the intracellular signaling domain comprises a CD3zeta signaling domain. In some embodiments, the intracellular signaling domain comprises a 4-1BB signaling domain. In some embodiments, the CAR can further comprise a second intracellular signaling domain. In some embodiments, the second intracellular signaling domain can comprise a 4-1BB signaling domain. In some embodiments the first intracellular signaling domain comprises a CD3zeta signaling domain and the second intracellular signaling domain comprises a 4-1BB signaling domain.

In some embodiments, the CAR can comprise a stalk domain between the extracellular ligand-binding domain and the first transmembrane domain. In some embodiments, the stalk domain can be selected from the group consisting of: a human CD8α hinge, a human CD28 hinge, an IgG1 hinge, and an FcγRIIIα hinge.

In some embodiments, the first transmembrane domain can comprise a CD8α chain transmembrane domain.

In some embodiments, the CAR can comprise another extracellular ligand-binding domain which is not specific for EGFRvIII.

In some embodiments of a CAR, the extracellular ligand-binding domain(s), the first transmembrane domain, and intracellular signaling domain(s) are on a single polypeptide.

In some embodiments, the CAR can comprise a second transmembrane domain, wherein the first transmembrane domain and the extracellular ligand-binding domain(s) are on a first polypeptide, and wherein the second transmembrane domain and the intracellular signaling domain(s) are on a second polypeptide, wherein the first transmembrane domain comprises a transmembrane domain from the α chain of the high-affinity IgE receptor (FcεRI) and the second transmembrane domain comprises a transmembrane domain from the γ or β chain of FcεRI. In some embodiments, the CAR can comprise a third polypeptide comprising a third transmembrane domain fused to an intracellular signaling domain from a co-stimulatory molecule, wherein the third transmembrane domain comprises a transmembrane domain from the γ or β chain of FcεRI.

In another aspect, the invention provides an isolated polynucleotide comprising a nucleic acid sequence encoding an EGFRvIII specific CAR as described herein.

In another aspect, the invention provides an expression vector comprising a nucleic acid sequence encoding an EGFRvIII specific CAR antibody as described herein.

In another aspect, the invention provides an engineered immune cell expressing at its cell surface membrane an EGFRvIII specific CAR as described herein. In some embodiments, the engineered immune cell can comprise another CAR which is not specific for EGFRvIII.

In some embodiments, the engineered immune cell can comprise a polynucleotide encoding a suicide polypeptide. In some embodiments, the suicide polypeptide is RQR8. In some embodiments, the polynucleotide encoding the suicide polypeptide is in a different nucleic acid molecule than the polynucleotide comprising a nucleic acid sequence encoding the EGFRvIII specific CAR. In some embodiments, the polynucleotide encoding the suicide polypeptide is part of the same nucleic acid molecule as the polynucleotide comprising a nucleic acid sequence encoding the EGFRvIII specific CAR.

In some embodiments, an engineered immune cell containing an EGFRvIII-specific CAR can comprise a suicide polypeptide in a separate polypeptide chain from the polypeptide chain of the EGFRvIII-specific CAR.

In some embodiments, an EGFRvIII specific CAR as described herein also comprises a suicide polypeptide in the same polypeptide chain as the CAR. For example, the suicide polypeptide may be between the scFv and hinge sequence of the CAR. In some embodiments, a suicide polypeptide in a CAR may have the R2 format as provided herein. In some embodiments, a suicide polypeptide comprises an epitope that is recognized by rituximab.

Also provided herein is a polynucleotide encoding an EGFRvIII specific CAR which also encodes a suicide polypeptide in the CAR.

In some embodiments, an engineered immune cell can be derived from an inflammatory T-lymphocyte, a cytotoxic T-lymphocyte, a regulatory T-lymphocyte, a memory T-lymphocyte, a helper T-lymphocyte, a natural killer T-lymphocyte, or a natural killer cell.

In some embodiments, the engineered immune cell can comprise a disruption in one or more endogenous genes, wherein the endogenous gene encodes TCRα, TCRβ, CD52, glucocorticoid receptor (GR), deoxycytidine kinase (dCK), or an immune checkpoint protein such as for example programmed death-1 (PD-1).

In some embodiments, the immune cell is obtained from a healthy donor. In some embodiments, the immune cell is obtained from a patient.

In another aspect, the invention provides an engineered immune cell expressing at its cell surface membrane an EGFRvIII specific CAR as described herein for use as a medicament. In some embodiments, the medicament is for use in treatment of an EGFRvIII related cancer (e.g., any cancer with EGFRvIII expression) selecting from the group consisting of glioblastoma multiform, anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, mixed glioma, head and neck cancer, non-small cell lung cancer, breast cancer, ovarian cancer, prostate cancer, medulloblastoma, colorectal cancer, anal cancer, cervical cancer, renal cancer, skin cancer, pancreatic cancer, liver cancer, bladder cancer, gastric cancer, thyroid cancer, mesothelioma, uterine cancer, lymphoma, and leukemia.

In another aspect, the invention provides a method of engineering an immune cell comprising: providing an immune cell; and expressing at the surface of the cell at least one EGFRvIII specific CAR as described herein.

In some embodiments, the method comprises: providing an immune cell; introducing into the cell at least one polynucleotide encoding said EGFRvIII specific CAR; and expressing said polynucleotide into the cell.

In some embodiments, the method comprises providing an immune cell; introducing into the cell at least one polynucleotide encoding said EGFRvIII specific CAR; and introducing at least one other CAR which is not specific for EGFRvIII.

In another aspect, the invention provides a method of treating a subject suffering from a condition associated with malignant cells, the method comprising: providing an immune cell expressing at the surface an EGFRvIII specific CAR as described herein; and administering said immune cells to said patient.

In another aspect, the invention provides a pharmaceutical composition comprising an engineered immune cell as described herein.

In another aspect, the invention provides a method of treating a condition associated with malignant cells expressing EGFRvIII in a subject comprising administering to a subject in need thereof an effective amount of a pharmaceutical composition of claim comprising an engineered immune cell as described herein. In some embodiments, the condition is a cancer. In some embodiments, the cancer is an EGFRvIII related cancer selecting from the group consisting of glioblastoma multiform, anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, mixed glioma, head and neck cancer, non-small cell lung cancer, breast cancer, ovarian cancer, prostate cancer, medulloblastoma, colorectal cancer, anal cancer, renal cancer, cervical cancer, liver cancer, pancreatic cancer, gastric cancer, thyroid cancer, mesothelioma, uterine cancer, and bladder cancer.

In another aspect, the invention provides a method of inhibiting tumor growth or progression in a subject who has malignant cells expressing EGFRvIII, comprising administering to the subject in need thereof an effective amount of a pharmaceutical composition comprising an engineered immune cell as described herein.

In another aspect, the invention provides a method of inhibiting metastasis of malignant cells expressing EGFRvIII in a subject, comprising administering to the subject in need thereof an effective amount of a pharmaceutical composition comprising an engineered immune cell as described herein.

In another aspect, the invention provides a method inducing tumor regression in a subject who has malignant cells expressing EGFRvIII, comprising administering to the subject in need thereof an effective amount of a pharmaceutical composition comprising an engineered immune cell as described herein.

BRIEF DESCRIPTION OF THE FIGURES/DRAWINGS

FIG. 1A, FIG. 1B, and FIG. 1C show examples of FACS binding histograms of three EGFRvIII antibodies: mAb 42G9 (FIG. 1A), 32A10 (FIG. 1B) and 32G8 (FIG. 1C), to three F98 cell lines: F98 (EGFR negative), F98-EGFRwt, and F98-EGFRvIII. The X-axis is fluorescence intensity; the Y-axis is percentage of maximum/normalized to mode.

Figure 3:
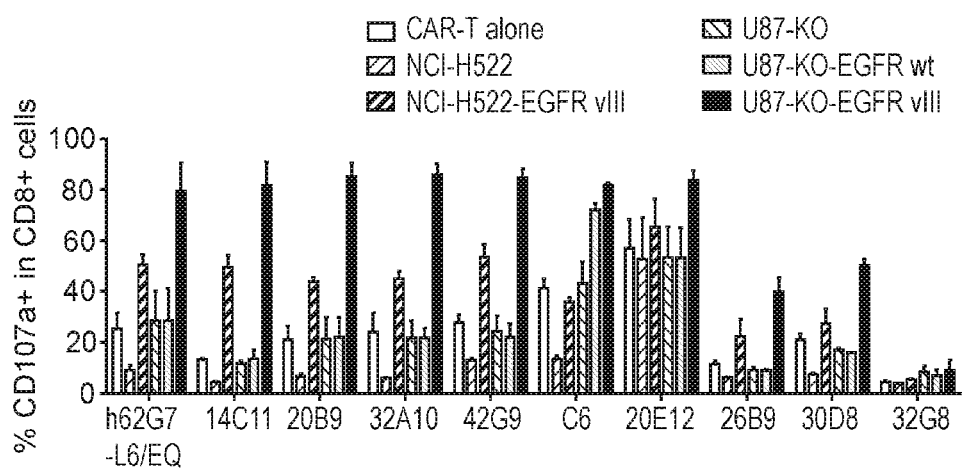

FIG. 3 shows a bar graph summarizing degranulation activities of EGFRvIII specific CAR T cells expressing different EGFRvIII specific clones, alone or upon co-culture with various cell lines: cells that do not express any EGFR protein (NCI-H522 and U87-KO), cells express high level of wild-type EGFR (U87-KO-EGFRwt), or cells that express low (NCI-H522-EGFRvIII) and high (U87-KO-EGFRvIII) levels of EGFRvIII.

Figure 4:
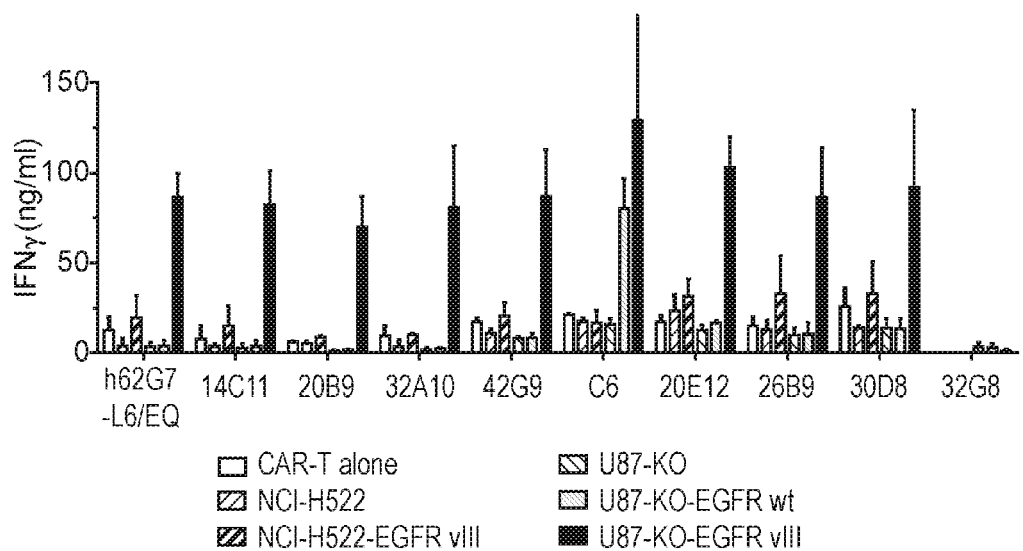

FIG. 4 shows a bar graph summarizing IFNγ secretion by EGFRvIII specific CAR T cells expressing different EGFRvIII specific clones, alone or upon co-culture with various cell lines: cells that do not express any EGFR protein (NCI-H522 and U87-KO), cells express high level of wild-type EGFR (U87-KO-EGFRwt), or cells that express low (NCI-H522-EGFRvII) and high (U87-KO-EGFRvIII) levels of EGFRvIII.

Figure 5:
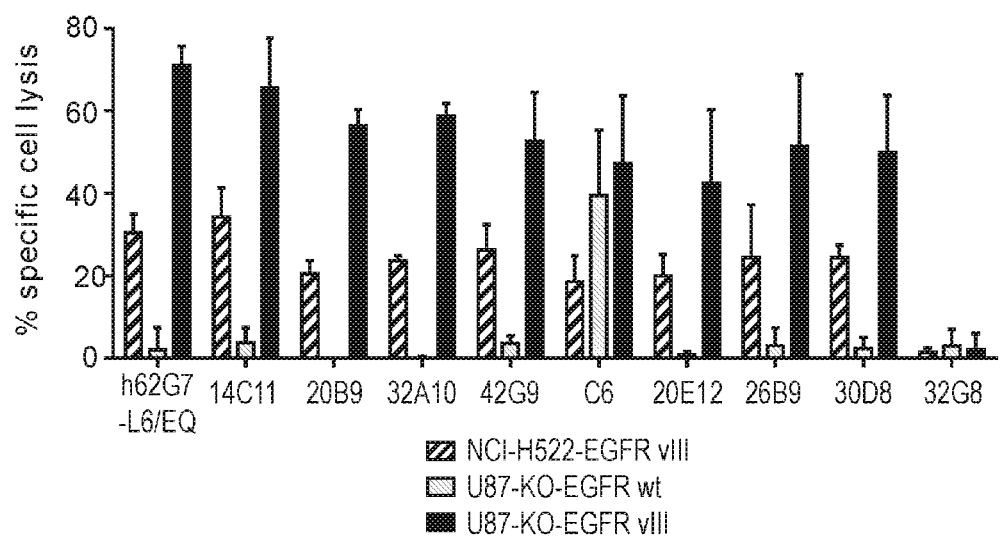

FIG. 5 shows a bar graph comparing the cytotoxicity of EGFRvIII specific CAR T cells expressing different EGFRvIII specific clones towards a wild-type EGFR expressing cell line (U87-KO-EGFRwt) vs high (U87-KO-EGFRvIII) and low EGFRvIII (NCI-H522-EGFRvIII) expressing cell lines.

Figure 6:
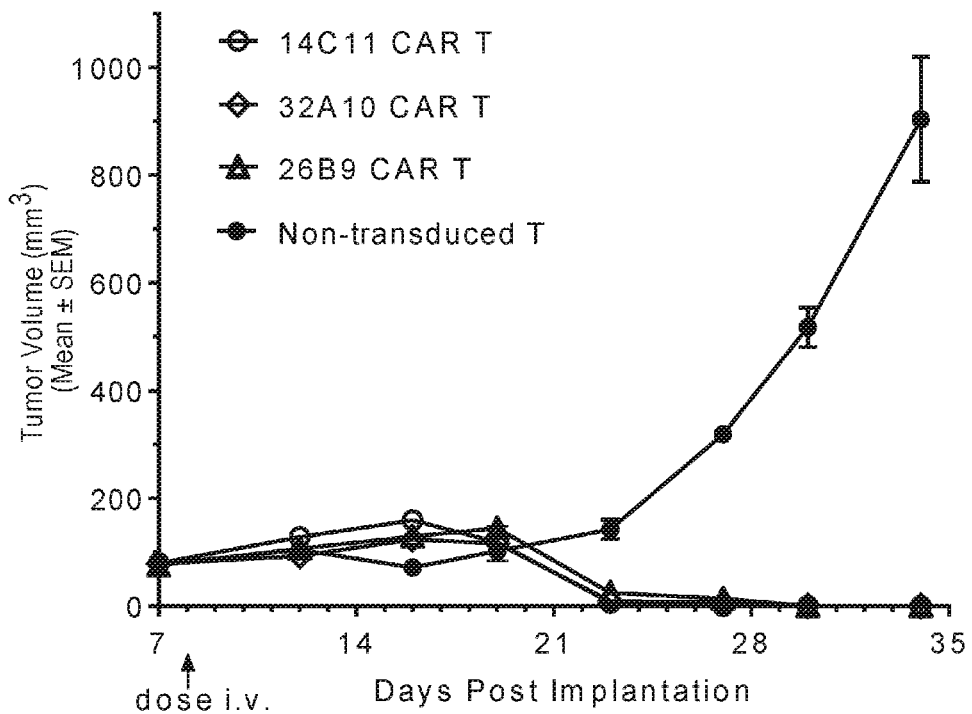

FIG. 6 shows a graph summarizing the anti-tumor activities of EGFRvIII specific CAR T cells expressing different EGFRvIII specific clones against GBM cells in a subcutaneous GBM xenograft model.

Figure 7:
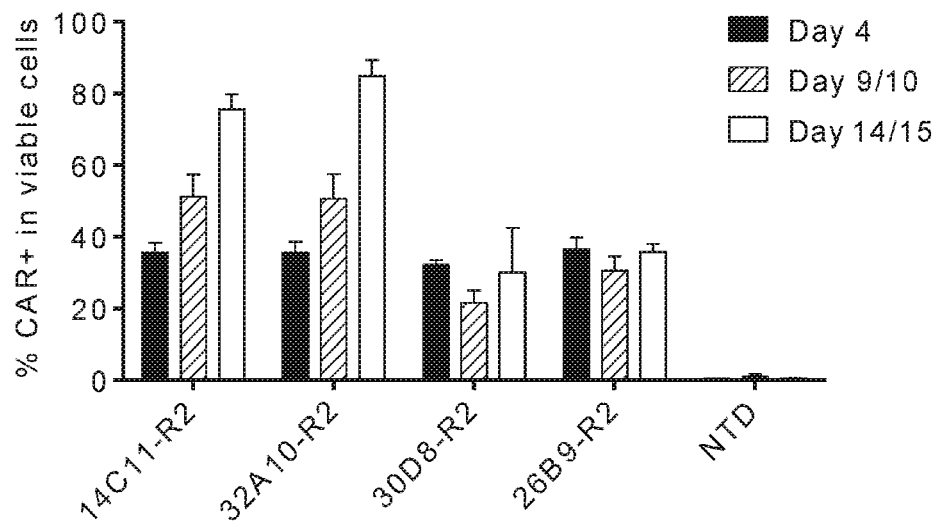

FIG. 7 shows a bar graph summarizing the CAR expression by CAR T cells expressing four different EGFRvIII specific clones in the CAR and carrying the intra-CAR suicide sequence R2 in the CAR on Day 4, Day 9/10, and Day 14/15 post-T cell transduction.

Figure 8:
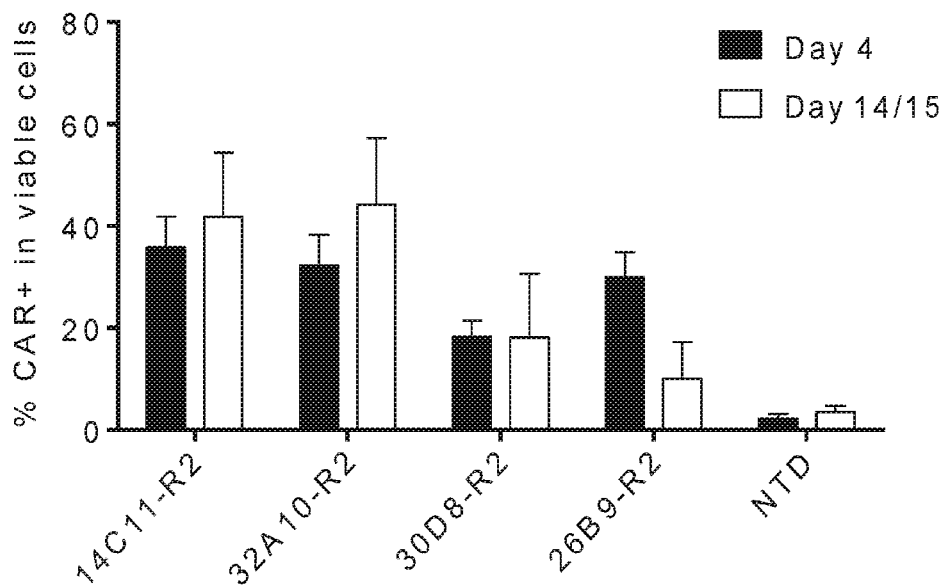

FIG. 8 shows a bar graph summarizing the CAR expression by CAR T cells expressing four different EGFRvIII specific clones in the CAR and carrying the intra-CAR suicide sequence R2 on Day 4 and Day 14/15 post-T cell transduction.

Figure 9:
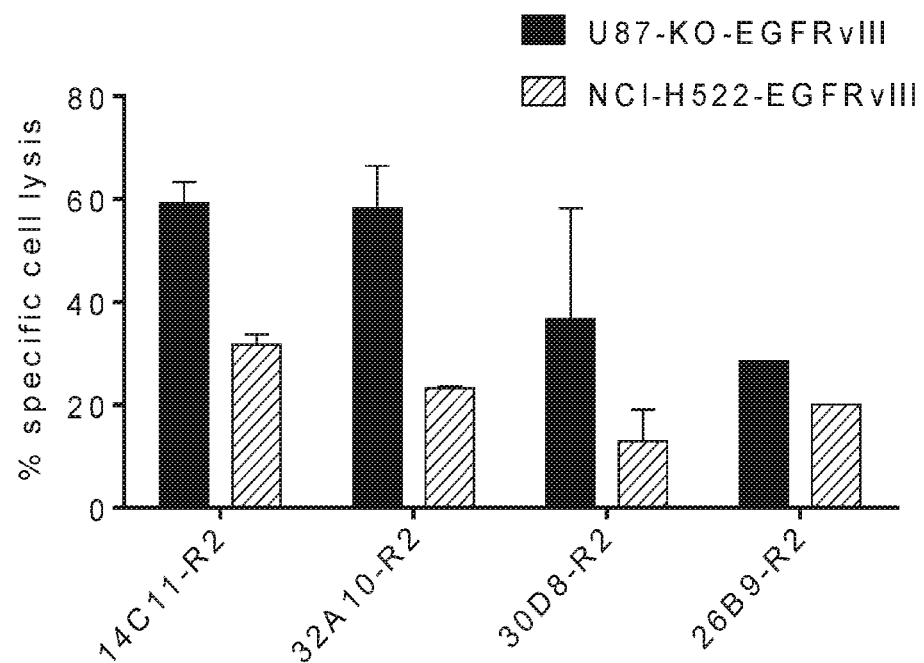

FIG. 9 shows a bar graph summarizing the cytotoxicity of CAR T cells expressing four different EGFRvIII specific clones and carrying the intra-CAR suicide sequence R2 against a high level (U87-KO-EGFRvIII) and a low level EGFRvIII (NCI-H522-EGFRvIII) expressing cell line.

DETAILED DESCRIPTION

The invention disclosed herein provides chimeric antigen receptors (CARs) and immune cells comprising CARs (e.g.

CAR-T cells) that specifically bind to EGFRvIII (e.g., human EGFRvIII). The invention also provides polynucleotides encoding these CARs, compositions comprising these CAR-T cells, and methods of making and using these CARs and CAR-T cells. The invention also provides methods for treating a condition associated with EGFRvIII-mediated pathologies in a subject, such as cancer.

General Techniques

The practice of the invention will employ, unless otherwise indicated, conventional techniques of molecular biology (including recombinant techniques), microbiology, cell biology, biochemistry, immunology, virology, monoclonal antibody generation and engineering, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The term "extracellular ligand-binding domain" as used herein refers to an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

The term "stalk domain" or "hinge domain" are used interchangeably herein to refer to any oligo- or polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector function signal and directs the cell to perform a specialized function.

A "co-stimulatory molecule" as used herein refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation, cytokine production, and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., EGFRvIII). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., EGFRvIII protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an EGFRvIII epitope is an antibody that binds this epitope with greater affinity, avidity, more readily, and/or with greater duration than it binds to other EGFRvIII epitopes or non-EGFRvIII epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "bivalent antibody" comprises two antigen binding sites per molecule (e.g., IgG). In some instances, the two binding sites have the same antigen specificities. However, bivalent antibodies may be bispecific.

A "bispecific" or "dual-specific" is a hybrid antibody having two different antigen binding sites. The two antigen binding sites of a bispecific antibody bind to two different epitopes, which may reside on the same or different protein targets.

A "bifunctional" is an antibody having identical antigen binding sites (i.e., identical amino acid sequences) in the two arms but each binding site can recognize two different antigens.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "immune cell" refers to a cell of hematopoietic origin functionally involved in the initiation and/or execution of innate and/or adaptative immune response.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, $CH_2$ and $CH_3$.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "autologous" means that cells, a cell line, or population of cells used for treating patients are originating from said patient or from a Human Leucocyte Antigen (HLA) compatible donor.

As used herein "allogeneic" means that cells or population of cells used for treating patients are not originating from said patient but from a donor.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of EGFRvIII expressing tumor, remission of an EGFRvIII associated disease (e.g., cancer), decreasing symptoms resulting from an EGFRvIII associated disease (e.g., cancer), increasing the quality of life of those suffering from an EGFRvIII associated disease (e.g., cancer), decreasing the dose of other medications required to treat an EGFRvIII associated disease (e.g., cancer), delaying the progression of an EGFRvIII associated disease (e.g., cancer), curing an EGFRvIII associated disease (e.g., cancer), and/or prolong survival of patients having an EGFRvIII associated disease (e.g., cancer).

"Ameliorating" means a lessening or improvement of one or more symptoms as compared to not administering an EGFRvIII specific CAR. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various EGFRvIII associated diseases or conditions (such as for example glioblastoma multiform), decreasing the dose of other medications required to treat the disease, enhancing the effect of another medication, and/or delaying the progression of the EGFRvIII associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants may be measured using, for example, full-length antibodies and/or Fab antibody fragments and corresponding antigen.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Determinations of the association and dissociation rate constants, $k_{on}$ and $k_{off}$ respectively, may be made using a surface plasmon resonance-based biosensor to characterize an analyte/ligand interaction under conditions where the analyte is monovalent with respect to binding a ligand that is immobilized at low capacity onto a sensor surface via a capture reagent. The analysis is performed using a kinetic titration methodology as described in Karlsson et al., Anal. Biochem 349, 136-147, 2006. The sensor chip, capturing reagent, and assay buffer employed for a given assay are chosen to give stable capture of ligand onto the sensor surface, minimize non-specific binding of the analyte to the surfaces, and yield analyte-binding responses that are appropriate for kinetic analysis, per the recommendations in Myszka, J. Mol. Recognit 12, 279-284, 1999. The analyte-binding responses per analyte/ligand interaction are double referenced and fit to a 1:1 Langmuir "mass transport limited model" with $k_a$, $k_d$ and $R_{max}$ as global parameters as described in Myszka & Morton et al., Biophys. Chem 64, 127-137 (1997). The equilibrium dissociation constant, $K_D$, is deduced from the ratio of the kinetic rate constants, $K_D=k_{off}/k_{on}$. Such determinations preferably take place at 25° C. or 37° C.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the invention encompasses not only the entire group listed as a whole, but each member of the group individually and all possible subgroups of the main group, but also the main group absent one or more of the group members. The invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the invention. The materials, methods, and examples are illustrative only and not intended to be limiting.

EGFRvIII Specific CARs and Methods of Making Thereof

The invention provides CARs that bind to EGFRvIII (e.g., human EGFRvIII (e.g., SEQ ID NO: 201, accession number: P00533 Feature Identifier VAR_066493, or GenBank Accession No. AJN69267)). EGFRvIII specific CARs provided herein include single chain CARS and multichain CARs. The CARs have the ability to redirect T cell specificity and reactivity toward EGFRvIII in a non-MHC-restricted manner, exploiting the antigen-binding properties of monoclonal antibodies. The non-MHC-restricted antigen recognition gives T cells expressing CARs the ability to recognize an antigen independent of antigen processing, thus bypassing a major mechanism of tumor escape.

In some embodiments, CARs provided herein comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

In some embodiments, an EGFRvIII specific multichain CAR is based on the high affinity receptor for IgE (FcεRI). The FcεRI expressed on mast cells and basophiles triggers allergic reactions. FcεRI is a tetrameric complex composed of a single α subunit, a single β subunit, and two disulfide-linked γ subunits. The α subunit contains the IgE-binding domain. The β and γ subunits contain ITAMs that mediate signal transduction. In some embodiments, the extracellular domain of the FcRα chain is deleted and replaced by an EGFRvIII specific extracellular ligand-binding domain. In some embodiments, the multichain EGFRvIII specific CAR comprises an scFv that binds specifically to EGFRvIII, the CD8α hinge, and the ITAM of the FcRβ chain. In some embodiments, the CAR may or may not comprise the FcRγ chain.

In some embodiments, the extracellular ligand-binding domain comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)$_4$ (SEQ ID NO: 202), which bridges approximately 3.5 nm between the carboxyl terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In some embodiments, the extracellular ligand-binding domain comprises (a) a VH region comprising (i) a VH complementarity determining region one (CDR1) comprising the sequence shown in SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, or 145; (ii) a VH CDR2 comprising the sequence shown in SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, or 147; and iii) a VH CDR3 comprising the sequence shown in SEQ ID NO: 67, 72, 73, 79, 85, 104, 107, 108, 114, 120, 126, 129, 142, or 148; and/or a VL region comprising (i) a VL CDR1 comprising the sequence shown in SEQ ID NO: 149, 154, 156, 159, 162, 165, 166, 168, 169, 170, 171, 173, 174, 176, 178, 181, 182, 185, 187, 190, 192, 195, or 198; (ii) a VL CDR2 comprising the sequence shown in SEQ ID NO: 150, 152, 155, 157, 160, 163, 172, 175, 179, 183, 186, 188, 191, 193, 196, or 199; and (iii) a VL CDR3 comprising the sequence shown in SEQ ID NO: 151, 153, 158, 161, 164, 167, 177, 180, 184, 189, 194, 197, or 200. In some embodiments, the VH and VL are linked together by a flexible linker. In some embodiments a flexible linker comprises the amino acid sequence shown in SEQ ID NO: 202.

In some embodiments, the extracellular ligand-binding domain comprises (a) a VH region comprising (i) a VH complementarity determining region one (CDR1) comprising the sequence shown in SEQ ID NO: 62, 63, 64, 74, 75, 76, 80, 81, 82, 88, 89, 90, 109, 110, 111, 115, 116, 117, 121, 122, 123, 137, 138, or 139; (ii) a VH CDR2 comprising the sequence shown in SEQ ID NO: 70, 71, 77, 78, 83, 84, 86, 87, 91, 92, 112, 113, 118, 119, 124, 125, 127, 128, 140, or 141; and iii) a VH CDR3 comprising the sequence shown in SEQ ID NO: 73, 79, 85, 114, 120, 126, 129, or 142, and/or (b) a VL region comprising (i) a VL CDR1 comprising the sequence shown in SEQ ID NO: 149, 156, 159, 162, 165, 182, 185, 187, or 195; (ii) a VL CDR2 comprising the sequence shown in SEQ ID NO: 152, 157, 160, 163, 183, 186, 188, or 196; and (iii) a VL CDR3 comprising the sequence shown in SEQ ID NO: 153, 158, 161, 164, 184, 189, or 197.

In another aspect, provided is CAR, which specifically binds to EGFRvIII, wherein the CAR comprises an extracellular ligand-binding domain comprising: a VH region comprising a VH CDR1, VH CDR2, and VH CDR3 of the VH sequence shown in SEQ ID NO: 1, 3, 5, 7, 9, 11, 13, 15, 17, 19, 21, 23, 25, 27, 30, 32, 34, 35, 37, 39, 41, 43, 44, 46, 48, or 50; and/or a VL region comprising VL CDR1, VL CDR2, and VL CDR3 of the VL sequence shown in SEQ ID NO: 2, 4, 6, 8, 10, 12, 14, 16, 18, 20, 22, 24, 26, 28, 29, 31, 33, 36, 38, 40, 42, 45, 47, 49, or 51. In some embodiments, the VH and VL are linked together by a flexible linker. In some embodiments a flexible linker comprises the amino acid sequence shown in SEQ ID NO: 202.

In some embodiments, the CAR comprises an extracellular ligand-binding domain comprising: a VH region comprising a VH CDR1, VH CDR2, and VH CDR3 of the VH sequence shown in SEQ ID NO: 5, 9, 11, 13, 15, 37, 39, 41, 43, or 48; and/or a VL region comprising VL CDR1, VL CDR2, and VL CDR3 of the VL sequence shown in SEQ ID NO: 6, 10, 12, 14, 16, 38, 40, 42, or 49. In some embodiments, the VH and VL are linked together by a flexible linker. In some embodiments a flexible linker comprises the amino acid sequence shown in SEQ ID NO: 202.

In some embodiments, a CAR of the invention comprises an extracellular ligand-binding domain having any one of partial light chain sequence as listed in Table 1 and/or any one of partial heavy chain sequence as listed in Table 1. In Table 1, the underlined sequences are CDR sequences according to Kabat and in bold according to Chothia. The different mAbs of Table 1 may also be referred to herein as different anti-EGFRvIII antibody "clones".

TABLE 1

| mAb | Light Chain | Heavy Chain |
|---|---|---|
| m62G7 | DVVMTQTPLTLSVTIGQPASISCKSSQSLLYSNGKTYLNWLLQRPGQSPKRLIYLVSKLDSGVPDRFTGSGSGTDFTLKISRVEAEDLGFYYCVQDTHFPLTFGAGTKLELK (SEQ ID NO: 2) | EVQLQQSGPELVKPGASVKISCKTSGYTFTDYTLHWVKQSHVKSLEWIGGIDPINGGTTYNQKFKGKATLTVDKSSSTAYMELRSLTSEDSAVYYCARGEAMDSWGQGTSVTVSS (SEQ ID NO: 1) |
| h62G7 | DVVMTQSPLSLPVTLGQPASISCKSSQSLLYSNGKTYLNWFQQRPGQSPRRLIYLVSKLDSGVPDRFSGSGSGTDFTLKISRVEAEDVGVYYCVQDTHFPLTFGGGTKVEIK (SEQ ID NO: 4) | QVQLVQSGAEVKKPGASVKVSCKASGYTFTDYTLHWVRQAPGQGLEWMGGINPINGGTTYNQKFKGRVTMTRDTSTSTVYMELSSLRSEDTAVYYCARGEAMDSWGQGTLVTVSS (SEQ ID NO: 3) |
| h62G7-L6/EQ | DVVMTQSPLSLPVTLGQPASISCKSSQSLLYSNGKTYLNWFQQRPGQSPRRLIYQVSKLDSGVPDRFSGSGSGTDFTLKISRVEAEDVGVYYCGQDTHFPLTFGGGTKVEIK (SEQ ID NO: 6) | QVQLVQSGAEVKKPGASVKVSCKASGYTFTDYTLHWVRQAPGQGLEWMGGIWPITGGTTYNQKFKGRVTMTRDTSTSTVYMELSSLRSEDTAVYYCARGEAQGSWGQGTLVTVSS (SEQ ID NO: 5) |
| h62G7-H14/L1-DV | DVVMTQSPLSLPVTLGQPASISCKSSQSLLYSNDKTYTNWFQQRPGQSPRRLIYEVSKLDVGVPDRFSGSGSGTDFTLKISRVEAEDVGVYYCGQDTHFPLTFGGGTKVEIK (SEQ ID NO: 8) | QVQLVQSGAEVKKPGASVKVSCKASGYTFTDYTLHWVRQAPGQGLEWMGGIWPITGGTTYNQKFKGRVTMTRDTSTSTVYMELSSLRSEDTAVYYCARGEAEGSWGQGTLVTVSS (SEQ ID NO: 7) |
| 42G9 | EVVLTQSPATLSVSPGERATLSCRASQSVRSNLAWYQQKSGQAPRLLIYGSTIRATGVPARFSGSGSGTEFTLTISSLQSEDFAVYYCQQYSDWPFTFGPGTKVDIK (SEQ ID NO: 10) | QVTLKESGPVLLKPTETLTLTCTVSGFSLSNPRMGVSWIRQPPGKALEWFAHIFSTDEKSLKLSLIRASRLTLSKDTSKSQVVLTMTNMAPVDSATYYCARDSSNYEGYFDFWGQGTLVTVSS (SEQ ID NO: 9) |
| 32A10 | EVVMTQSPATLSVSPGERVTLSCRASQSVSSNFAWYQQRPGQAPRLLLYGATTRATGLPGRFSGSGSGTENILTISSLQSEDFAIYFCQQYKDWPFTFGPGSKVDIK (SEQ ID NO: 12) | QVTLKESGPVLVKPTETLTLTCTVSGFSLSNARMGVSWIRQPPGKALEWLAHIFSTDEKSIRRSLRSRLTLSKDTSKSQVVLTMTNMDPVDTATYFCARDSSNYEGYFDYWGQGTLVTVSS (SEQ ID NO: 11) |
| 20B9 | EIVMTQSPATLSVSPGERATLSCRVSQSIGANLAWYQQKFGQAPRLLIYGASTRATGIPVRFSGGGSGTEFTLTISSLQSEDFAIYSCQQYIYWPFTFGPGTTVDIK (SEQ ID NO: 14) | QVTLKESGPVLVKPTETLTLTCTVSGFSLSNARMGVSWIRQPPGKALEWLGHIFSTDEKSYSTSLRGRITISKDTSRGLVVLTLTMDPVDTATYYCARDSSNYEGYFDFWGPGFLVTVSS (SEQ ID NO: 13) |
| 14C11 | EIVMTQSPATLSVSPGERATLSCRASQSVSNNLAWYQQKPGQAPRLLIYGASTRATGVPARFSGSDSGTEFSLTISSLQSEDFAVYFCQQYKDWPFTFGPGTKVEIK (SEQ ID NO: 16) | QVTLKESGPVLVKPTETLTLTCTVSGFSLNNARMGVSWIRQPPGKALEWFAHIFSTDEKSFRTSLRSRLTLSKDTSKSQVVLTMTNMDPVDTATYYCARDSSNYEGYFDYWGQGILVTVSS (SEQ ID NO: 15) |
| 21E11 | DMVVTQSPATLSVSPGERATLSCRASQSVGSDLAWYQQPPGQSPRLLIYGASTRATGVPARFSGSGSGTDFTLTITSLESEDFAVYYCQQYNDWPFTFGPGTKVDIK (SEQ ID NO: 18) | QVTLKESGPVLVKPTETLTLTCTVSGFSLSNVRMGVSWIRQPPGKALEWFAHIFSSDEKSIRRSLRSRLTLSKDTSKSQVVLTMTNMDPVDTATYYCARDSSNYEGYFDFWGQGTLVTVSSN (SEQ ID NO: 17) |
| 49B11 | EMEVTQSPATLSVSPGERATLSCRASQNIGSDLAWYQQQSGQAPRLLISGASTRATGVPTRFSGSGSGTDFTLTITSLQSEDFAVYYCQQYNDWPFTFGPGTKVDIK (SEQ ID NO: 20) | QVTLKESGPVLVKPTETLTLTCTVSGFSLSNVRMGVSWIRQPPGKALEWFAHIFSSDEKSIRRSLRSRLTLSKDTSKSQVVLTMTNMDPVDTATYYCARDSSNYEGYFDYWGQGTLVTVSS (SEQ ID NO: 19) |
| 46E10 | EVVMTQSPPNLSVSPGERATLSCRASQSVTSNFAWYQQRPGQSPRL | QVTLKESGPVLVKPTETLTLTCTVSGFSLSNARMGVSWIRQPPGKA |

TABLE 1-continued

| mAb | Light Chain | Heavy Chain |
|---|---|---|
| | LLYGASTRATGVPGRFSGSGSGT ENILTISSLQSEDFAVYFCQQYK DWPFTFGPGSKVDIK (SEQ ID NO: 22) | LEWLAHIFSTDEKSIRRSLRSRL TLSKDTSKSQVVLIMTNMDPVDT ATYYCARDSSNYEGYFDYWGQGT LVTVSS (SEQ ID NO: 21) |
| 12H6 | EVVMTQSPATLSVSPGERATLSC RASQGVSSNFAWYQQRPGQSPRL LLYGASTRATGVPGRFSGSGSGT ENILTISSLQSEDFAIYFCQQYK DWPFTFGPGSKVDIK (SEQ ID NO: 24) | QVTLKESGPVLVKPTETLTLTCT VSGFSLSNARMGVSWIRQPPGKA LEWLAHIFSTDEKSIRRSLRSRL TLSKDTSKSQVVLTMTNMDPVDT ATYYCARDSSNYEGYFDYWGQGT LVTVSS (SEQ ID NO: 23) |
| 19A9 | EVVMTQSPATLSVSPGERATLSC RASQSVNRNLAWYQQKPGQAPRL LIFGTSTRATGIPARFSGSGSGT EFTLTIDSLQSEHSGLYYCQQYN DWPFTFGPGTKVDIK (SEQ ID NO: 26) | QVTLEESGPVLVKPTETLTLTCT VSGFSLSNARMGVSWIRQPPGKA PEWFAHIFSTDEKSLRLSLRSRL TLSKDTSKSQVVLTMTNMDPVDT ATYYCARDSSNYEGYFDYWGQGT LVTVSS (SEQ ID NO: 25) |
| 11B11 | EVLMTQSPATLSVSPGERATLSC RASQSVSTNFAWYQQRPGQAPRL LLFGASTRATGIPGRFSGSGSGT ENILTISSLQSEDFAIYFCQQYK DWPFTFGPGSKVEIK (SEQ ID NO: 28) | QVTLKESGPVLVKPTETLTLTCT VSGFSLSNAKMGVSWIRQPPGKA LEWLAHIFSTDEKSIRRSLRSRL TMSKDTSKSQVVLTMTNMDPVDT ATYYCVRDSSNYEGYFDYWGQGT LVTVSS (SEQ ID NO: 27) |
| 21E7 | DVVLTQSPATLSVSPGERATLSC RASQSVNSNLAWYQQNPGQAPRL LIFGSSTRATGIPASFSGSGSGT EFTLTINSLQSEHSAVYYCQQYN DWPFTFGPGTKVDIK (SEQ ID NO: 29) | QVTLEESGPVLVKPTETLTLTCT VSGFSLSNARMGVSWIRQPPGKA PEWFAHIFSTDEKSLRLSLRSRL TLSKDTSKSQVVLTMTNMDPVDT ATYYCARDSSNYEGYFDYWGQGT LVTVSS (SEQ ID NO: 25) |
| 12B2 | EVVMTQSPATLSVSPGERATLSC RASQSVINNLAWYQQKPGQAPRL LIYGTSTRATDIPARFSGSGSGT EFTLTISSLQSEDFAVYYCQDYN NWPFTFGPGTKVDIK (SEQ ID NO: 31) | QVTLKESGPVLVKPTETLTLTCT VSGFSLSNPRMGVSWIRQPPGKA LEWLGHIFSSDEKSYRLSLRSRL SISKDTSKSQVVLTMTNMDPVDT ATYYCVRDSSNYGGYFDYWGQGT LVTVSS (SEQ ID NO: 30) |
| 11F10 | EIVMTQSPATLSVSPGERTTLSC RASQSVGSNLAWYQQKPGQAPRL LIYGASTRASGVPARFSGSGSGT EFTLTISSLQSEDFAVYSCQEYN NWPFTFGQGTKVEIK (SEQ ID NO: 33) | QVTLKESGPVLVKPIETLTLTCT VCGFSLSNPRMGVSWIRQPPGKA LEWLGHIFSSDEKSYRLFLRSRL SISKDTSKSQVVLTMTNMDPVDT ATYYCARDSSDYEGYFDYWGQGT LVTVSS (SEQ ID NO: 32) |
| 17G11 | EVVMTQSPATLSVSPGERATLSC RASQSVINNLAWYQQKPGQAPRL LIYGTSTRATDIPARFSGSGSGT EFTLTISSLQSEDFAVYYCQDYN NWPFTFGPGTKVDIK (SEQ ID NO: 31) | QVTLKESGPVLVKPTETLTLTCT VFGFSLSNPRMGVSWIRQPPGKA PEWLGHIFSSDEKSYRLSLRSRL SISKDTSKSQVVFXMTNMDPGDP ATYYCVRDSSNYEEYFDYWGQGT LVTVSS (SEQ ID NO: 34) |
| 29D5 | KIVMTQSPATLSVSPGERATLSC RANQIVSSNLAWYQQKPGQAPRL LVFGTSTRATGIPIRFSGSGSGT EFTLTVSSLQSEDFAVYVCQQYN DWPFTFGPGTKVDIK (SEQ ID NO: 36) | QVTLKESGPVLVKPTETLTLTCT VSGFSLSNPRMGVSWLRQPPGKA LEWFAHIFSTDEKSYSPSLRGRL TVSKDTSKSQVVLTLTNMDPVDT ATYYCARDSSNYEGYFDYWGQGT LVTVSS (SEQ ID NO: 35) |
| 30D8 | DIVMTQSPLSLPVTPGEPASISC RSSQSLLHNKRNNYLDWFLQKPG QSPQLLIYLASNRASGVPDRFSG GGSGTDFTLKISRVEAEDVGVYY CMQAQQTPITFGQGTRLEIK (SEQ ID NO: 38) | EVQLVESGGGLVKPGGSLRLSCE ASGFTFSDAWMSWVRQAPGKGLE WVGRIKSKTDGGTTDYVVPLNGR FIISRDDSRNTLYLQLNNLKTED TAVYYCTTVPGSYGYWGQGTLVT VSS (SEQ ID NO: 37) |

TABLE 1-continued

| mAb | Light Chain | Heavy Chain |
|---|---|---|
| 20E12 | DIVLTQSPLSLSVTPGEPASISCRSSQSLLYSNGKNYLDWFLHKPGQSPQLLIYLGSNRASGVPDRFSGSGSGIDFILKISRVEAEDVGVYYCMQAQQTPITFGQGTRLEIK (SEQ ID NO: 40) | EVNLVESGGGLVKPGGSLRLSCEASGFTFSYAWMSWVRQAPGKGLEWVGRIKSIADGGATDYAAPVRNRFTISRDDSRNTLYLEMHSLKTEDTAVYYCTTIPGNDAFDMWGQGTMVTVSS (SEQ ID NO: 39) |
| 26B9 | DIVLTQSPLSLPVTPGEPASISCRSSQSLLHRDGFNYLDWFLQKPGQSPQLLIYLASSRASGVPDRFSGSDSGTDFTLKISRVEAEDVGVYYCMQALQTPITFGQGTRLEIK (SEQ ID NO: 42) | EVQLVESWGVLVKPGGSLRLSCAASGFIFNNAWMSWVRQAPGKGLEWIGRIKSKSDGGTTDYAAPVKDRFTISRDDSKDTLYLQMNGLKTEDTAVYFCTTAPGGPFDYWGQGTLVTVSS (SEQ ID NO: 41) |
| 32G8 | DIVLTQSPLSLSVTPGEPASISCRSSQSLLYSNGKNYLDWFLHKPGQSPQLLIYLGSNRASGVPDRFSGSGSGIDFILKISRVEAEDVGVYYCMQAQQTPITFGQGTRLEIK (SEQ ID NO: 40) | EVNLVESGGGLVKPGGSLRLSCEASGFTFSYAWMSWVRQAPGKGLEWVGRIKSITDGGVIDYAAPVRNRCTISRDDSRNTLYLEMHSLKTEDTAVYYCTTIPGNDDFDMWGQGRMVTVSS (SEQ ID NO: 43) |
| 34E7 | DIVLTQSPLSLSVTPGEPASISCRSTQSLLYSNGKNYLDWFLHKPGQSPQLLIFLGSIRASGVPDRFSGSGSGIDFILKISRVEAEDVGVYYCMQAQQTPITFGQGTRLEIK (SEQ ID NO: 45) | EVNLVESGGGLVKPGGSLRLSCEASGFTFSYAWMSWVRQAPGKGLEWVGRIKSINDGGATDYASPVRNRFTISRDDSRNMLYLEMHSLKTEDTAVYYCTTIPGNDAFDMWGQGTLVTVSS (SEQ ID NO: 44) |
| 20G5 | DIVLTQSPLSLPVTPGEPASISCRSSQSLLYSDRRNYLDWFLQKPGQSPHLLIYLGSYRASGVPDRFSGSGSGTDFTLKISRVEAEDVGVYYCMQALQIPITFGQGTRLEIK (SEQ ID NO: 47) | EVQLVESGGDLVKPGGSLRLSCAASGFTFTNAWMSWVRQAPGKGLEWVGRIKSKIDGGTTDYAAPVKGRFIISRDDSKNTLSLQMNSLKTEDTAMYYCTTAPGGPFDYWGQGSLVTVSS (SEQ ID NO: 46) |
| C6 | ELQSVLTQPPSASGTPGQRVTISCSGSSSNIGSNYVYWYQQLPGTAPKILIYRNNQRPSGVPDRFSGSKSGTSASLAISGLRSEDEADYYCAAWDDNLSGWVFGTGTKLTVL (SEQ ID NO: 49) | QVQLVQSGAEVKKPGSSVKVSCKASGDTFSSNAISWVRQAPGQGLEWMGVIIPIFGTADYAQKFQGRVTITADESTSTAYMELSSLRSEDTAVYYCARHTYHEYAGGYYGGAMDPWGQGTLVTVSS (SEQ ID NO: 48) |
| B5 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK (SEQ ID NO: 51) | EVQLLESGGGLVQPGGSLRLSCAASGFTFSNYAMSWVRQAPGKGLEWVSDISGGGGRTYYADSVKGRFTISRDNSKNTLYLQMNSLRAEDTAVYYCARAGLLYGGGVYPMDIWGQGTLVTVSS (SEQ ID NO: 50) |

Also provided herein are CDR portions of extracellular ligand-binding domains of CARs to EGFRvIII (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| m62G7 | TDYTLH (SEQ ID NO: 62) (Kabat); GYTFTD | GIDPINGGTTYNQKFKG (SEQ ID NO: 65) (Kabat) GIDPINGGTTY | GEAMDS (SEQ ID NO: 67) |

TABLE 2-continued

| | | | |
|---|---|---|---|
| | (SEQ ID NO: 63) (Chothia); GYTFTDYTLH (SEQ ID NO: 64) (extended) | (SEQ ID NO: 66) (Chothia) | |
| h62G7 | TDYTLH (SEQ ID NO: 62) (Kabat); GYTFTD (SEQ ID NO: 63) (Chothia); GYTFTDYTLH (SEQ ID NO: 64) (extended) | GINPINGGTTYNQKFKG (SEQ ID NO: 68) (Kabat) GINPINGGTTY (SEQ ID NO: 69) (Chothia) | GEAMDS (SEQ ID NO: 67) |
| h62G7-H14 | TDYTLH (SEQ ID NO: 62) (Kabat); GYTFTD (SEQ ID NO: 63) (Chothia); GYTFTDYTLH (SEQ ID NO: 64) (extended) | GIWPITGGTTYNQKFKG (SEQ ID NO: 70) (Kabat) GIWPITGGTTY (SEQ ID NO: 71) (Chothia) | GEAEGS (SEQ ID NO: 72) |
| h62G7-EQ | TDYTLH (SEQ ID NO: 62) (Kabat); GYTFTD (SEQ ID NO: 63) (Chothia); GYTFTDYTLH (SEQ ID NO: 64) (extended) | GIWPITGGTTYNQKFKG (SEQ ID NO: 70) (Kabat) GIWPITGGTTY (SEQ ID NO: 71) (Chothia) | GEAQGS (SEQ ID NO: 73) |
| 42G9 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSTDEKSLKLSLRS (SEQ ID NO: 77) (Kabat) HIFSTDEKSL (SEQ ID NO: 78) (Chothia) | DSSNYEGYFDF (SEQ ID NO: 79) |
| 32A10 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 20B9 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSYSTSLRG (SEQ ID NO: 86) (Kabat) HIFSTDEKSY (SEQ ID NO: 87) (Chothia) | DSSNYEGYFDF (SEQ ID NO: 79) |
| 14C11 | NNARMGVS (SEQ ID NO: 88) (Kabat); GFSLNNAR (SEQ ID NO: 89) (Chothia); GFSLNNARMGVS (SEQ ID NO: 90) (extended) | HIFSTDEKSFRTSLRS (SEQ ID NO: 91) (Kabat) HIFSTDEKSF (SEQ ID NO: 92) (Chothia) | DSSNYEGYFDY (SEQ ID NO: 85) |
| 21E11 | SNVRMGVS (SEQ ID NO: 93) (Kabat); GFSLSNVR | HIFSSDEKSIRRSLRS (SEQ ID NO: 96) (Kabat) HIFSSDEKSI | DSSNYEGYFDF (SEQ ID NO: 79) |

TABLE 2-continued

| | | | |
|---|---|---|---|
| | (SEQ ID NO: 94) (Chothia); GFSLSNVRMGVS (SEQ ID NO: 95) (extended) | (SEQ ID NO: 97) (Chothia) | |
| 49B11 | SNVRMGVS (SEQ ID NO: 93) (Kabat); GFSLSNVR (SEQ ID NO: 94) (Chothia); GFSLSNVRMGVS (SEQ ID NO: 95) (extended) | HIFSSDEKSIRRSLRS (SEQ ID NO: 96) (Kabat) HIFSSDEKSI (SEQ ID NO: 97) (Chothia) | DSSNYEGYFDY (SEQ ID NO: 85) |
| 46E10 12H6 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 19A9 21E7 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSLRLSLRS (SEQ ID NO: 98) (Kabat) HIFSTDEKSL (SEQ ID NO: 78) (Chothia) | DSSNYEGYFDY (SEQ ID NO: 85) |
| 11B11 | SNAKMGVS (SEQ ID NO: 99) (Kabat); GFSLSNAK (SEQ ID NO: 100) (Chothia); GFSLSNAKMGVS (SEQ ID NO: 101) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 12B2 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | DSSNYGGYFDY (SEQ ID NO: 104) |
| 11F10 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLFLRS (SEQ ID NO: 105) (Kabat) HIFSSDEKSY (SEQ ID NO: 103) (Chothia) | DSSDYEGYFDY (SEQ ID NO: 107) |
| 17G11 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | DSSNYEEYFDY (SEQ ID NO: 108) |
| 29D5 | SNPRMGVS (SEQ ID NO: 74) (Kabat); GFSLSNPR | HIFSTDEKSYSPSLRG (SEQ ID NO: 106) (Kabat) HIFSTDEKSY | DSSNYEGYFDY (SEQ ID NO: 85) |

TABLE 2-continued

| | | | |
|---|---|---|---|
| | (SEQ ID NO: 75) (Chothia); GFSLSNPRMGVS (SEQ ID NO: 76) (extended) | (SEQ ID NO: 87) (Chothia) | |
| 30D8 | SDAWMS (SEQ ID NO: 109) (Kabat); GFTFSD (SEQ ID NO: 110) (Chothia); GFTFSDAWMS (SEQ ID NO: 111) (extended) | RIKSKTDGGTTDYVVPLNG (SEQ ID NO: 112) (Kabat) RIKSKTDGGTTDY (SEQ ID NO: 113) (Chothia) | VPGSYGY (SEQ ID NO: 114) |
| 20E12 | SYAWMS (SEQ ID NO: 115) (Kabat); GFTFSY (SEQ ID NO: 116) (Chothia); GFTFSYAWMS (SEQ ID NO: 117) (extended) | RIKSIADGGATDYAAPVRN (SEQ ID NO: 118) (Kabat) RIKSIADGGATDY (SEQ ID NO: 119) (Chothia) | IPGNDAFDM (SEQ ID NO: 120) |
| 26B9 | NNAWMS (SEQ ID NO: 121) (Kabat); GFIFNN (SEQ ID NO: 122) (Chothia); GFIFNNAWMS (SEQ ID NO: 123) (extended) | RIKSKSDGGTTDYAAPVKD (SEQ ID NO: 124) (Kabat) RIKSKSDGGTTDY (SEQ ID NO: 125) (Chothia) | APGGPFDY (SEQ ID NO: 126) |
| 32G8 | SYAWMS (SEQ ID NO: 115) (Kabat); GFTFSY (SEQ ID NO: 116) (Chothia); GFTFSYAWMS (SEQ ID NO: 117) (extended) | RIKSITDGGVIDYAAPVRN (SEQ ID NO: 127) (Kabat) RIKSITDGGVIDY (SEQ ID NO: 128) (Chothia) | IPGNDDFDM (SEQ ID NO: 129) |
| 34E7 | SYAWMS (SEQ ID NO: 115) (Kabat); GFTFSY (SEQ ID NO: 116) (Chothia); GFTFSYAWMS (SEQ ID NO: 117) (extended) | RIKSINDGGATDYASPVRN (SEQ ID NO: 130) (Kabat) RIKSINDGGATDY (SEQ ID NO: 131 (Chothia) | IPGNDAFDM (SEQ ID NO: 120) |
| 20G5 | TNAWMS (SEQ ID NO: 132) (Kabat); GFTFTN (SEQ ID NO: 133) (Chothia); GFTFTNAWMS (SEQ ID NO: 134) (extended) | RIKSKIDGGTTDYAAPVKG (SEQ ID NO: 135) (Kabat) RIKSKIDGGTTDY (SEQ ID NO: 136) (Chothia) | APGGPFDY (SEQ ID NO: 126) |
| C6 | SSNAIS (SEQ ID NO: 137) (Kabat); GDTFSS (SEQ ID NO: 138) (Chothia); GDTFSSNAIS (SEQ ID NO: 139) (extended) | VIIPIFGTADYAQKFQG (SEQ ID NO: 140) (Kabat) VIIPIFGTADY (SEQ ID NO: 141) (Chothia) | HTYHEYAGGYYGGAMDP (SEQ ID NO: 142) |
| B5 | SNYAMS (SEQ ID NO: 143) (Kabat); GFTFSN | DISGGGGRTYYADSVKG (SEQ ID NO: 146) (Kabat) DISGGGGRTYY | AGLLYGGGVYPMDI (SEQ ID NO: 148) |

TABLE 2-continued

|  | (SEQ ID NO: 144) (Chothia); GFTFSNYAMS (SEQ ID NO: 145) (extended) | (SEQ ID NO: 147) (Chothia) |  |
| --- | --- | --- | --- |

| Light Chain | | | |
| --- | --- | --- | --- |
| mAb | CDRL1 | CDRL2 | CDRL3 |
| m62G7 h62G7 | KSSQSLLYSNGKTYLN (SEQ ID NO: 149) | LVSKLDS (SEQ ID NO: 150) | VQDTHFPLT (SEQ ID NO: 151) |
| h62G7-L6 | KSSQSLLYSNGKTYLN (SEQ ID NO: 149) | QVSKLDS (SEQ ID NO: 152) | GQDTHFPLT (SEQ ID NO: 153) |
| h62G7-L1-DV | KSSQSLLYSNDKTYTN (SEQ ID NO: 154) | EVSKLDV (SEQ ID NO: 155) | GQDTHFPLT (SEQ ID NO: 153) |
| 42G9 | RASQSVRSNLA (SEQ ID NO: 156) | GSTIRAT (SEQ ID NO: 157) | QQYSDWPFT (SEQ ID NO: 158) |
| 32A10 | RASQSVSSNFA (SEQ ID NO: 159) | GATTRAT (SEQ ID NO: 160) | QQYKDWPFT (SEQ ID NO: 161) |
| 20B9 | RVSQSIGANLA (SEQ ID NO: 162) | GASTRAT (SEQ ID NO: 163) | QQYIYWPFT (SEQ ID NO: 164) |
| 14C11 | RASQSVSNNLA (SEQ ID NO: 165) | GASTRAT (SEQ ID NO: 163) | QQYKDWPFT (SEQ ID NO: 161) |
| 21E11 | RASQSVGSDLA (SEQ ID NO: 166) | GASTRAT (SEQ ID NO: 163) | QQYNDWPFT (SEQ ID NO: 167) |
| 49B11 | RASQNIGSDLA (SEQ ID NO: 168) | GASTRAT (SEQ ID NO: 163) | QQYNDWPFT (SEQ ID NO: 167) |
| 46E10 | RASQSVTSNFA (SEQ ID NO: 169) | GASTRAT (SEQ ID NO: 163) | QQYKDWPFT (SEQ ID NO: 161) |
| 12H6 | RASQGVSSNFA (SEQ ID NO: 170) | GASTRAT (SEQ ID NO: 163) | QQYKDWPFT (SEQ ID NO: 161) |
| 19A9 | RASQSVNRNLA (SEQ ID NO: 171) | GTSTRAT (SEQ ID NO: 172) | QQYNDWPFT (SEQ ID NO: 167) |
| 11B11 | RASQSVSTNFA (SEQ ID NO: 173) | GASTRAT (SEQ ID NO: 163) | QQYKDWPFT (SEQ ID NO: 161) |
| 21E7 | RASQSVNSNLA (SEQ ID NO: 174) | GSSTRAT (SEQ ID NO: 175) | QQYNDWPFT (SEQ ID NO: 167) |
| 12B2 17G11 | RASQSVINNLA (SEQ ID NO: 176) | GTSTRAT (SEQ ID NO: 172) | QDYNNWPFT (SEQ ID NO: 177) |
| 11F10 | RASQSVGSNLA (SEQ ID NO: 178) | GASTRASG (SEQ ID NO: 179) | QEYNNWPFT (SEQ ID NO: 180) |
| 29D5 | RANQIVSSNLA (SEQ ID NO: 181) | GTSTRAT (SEQ ID NO: 172) | QQYNDWPFT (SEQ ID NO: 167) |
| 30D8 | RSSQSLLHNKRNNYLD (SEQ ID NO: 182) | LASNRAS (SEQ ID NO: 183) | MQAQQTPIT (SEQ ID NO: 184) |
| 20E12 32G8 | RSSQSLLYSNGKNYLD (SEQ ID NO: 185) | LGSNRAS (SEQ ID NO: 186) | MQAQQTPIT (SEQ ID NO: 184) |
| 26B9 | RSSQSLLHRDGFNYLD (SEQ ID NO: 187) | LASSRAS (SEQ ID NO: 188) | MQALQTPIT (SEQ ID NO: 189) |
| 34E7 | RSTQSLLYSNGKNYLD (SEQ ID NO: 190) | LGSIRAS (SEQ ID NO: 191) | MQAQQTPIT (SEQ ID NO: 184) |
| 20G5 | RSSQSLLYSDRRNYLD (SEQ ID NO: 192) | LGSYRAS (SEQ ID NO: 193) | MQALQIPIT (SEQ ID NO: 194) |

TABLE 2-continued

| | | | |
|---|---|---|---|
| C6 | SGSSSNIGSNYVY (SEQ ID NO: 195) | RNNQRPS (SEQ ID NO: 196) | AAWDDNLSGWV (SEQ ID NO: 197) |
| B5 | RASQSISSYLN (SEQ ID NO: 198) | AASSLQS (SEQ ID NO: 199) | QQSYSTPLT (SEQ ID NO: 200) |

The invention encompasses modifications to the CARs and polypeptides of the invention variants shown in Table 1, including functionally equivalent CARs having modifications which do not significantly affect their properties and variants which have enhanced or decreased activity and/or affinity. For example, the amino acid sequence may be mutated to obtain an antibody with the desired binding affinity to EGFRvIII. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened. In some embodiments, substitution variants of antibodies provided herein have no more than 15, 14, 13, 12, 11, 10, 9, 8, 7, 6, 5, 4, 3, 2, or 1 conservative substitution in the VH or VL region as compared to the reference parent antibody. In some embodiments, the substitutions are not within a CDR of the VH or VL region.

TABLE 3

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |

TABLE 3-continued

Amino Acid Substitutions

| Original Residue (naturally occurring amino acid) | Conservative Substitutions | Exemplary Substitutions |
|---|---|---|
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

In some embodiments, the invention provides a CAR comprising an extracellular ligand-binding domain that binds to EGFRvIII and competes for binding to EGFRvIII with the antibodies described herein or the CARs described herein (e.g., Table 5A), including m62G7, h62G7, h62G7-H14/L1-DV, h62G7-L6/EQ, 42G9, 32A10, 20B9, 14C11, 21E11, 49B11, 46E10, 12H6, 19A9, 21E7, 11B11, 12B2, 11F10, 17G11, 29D5, 30D8, 20E12, 26B9, 32G8, 34E7, 20G5, C6, and B5.

In some embodiments, the invention provides CARs comprising CDR portions of antibodies to EGFRvIII antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the EGFRvIII specific CAR as described herein to EGFRvIII (such as human EGFRvIII (e.g., (SEQ ID NO: 201)) can be about 0.001 to about 5000 nM. In some embodiments, the binding affinity is about any of 5000 nM, 4500 nM, 4000 nM, 3500 nM, 3000 nM, 2500 nM, 2000 nM, 1789 nM, 1583 nM, 1540 nM, 1500 nM, 1490 nM, 1064 nM, 1000 nM, 933 nM, 894 nM, 750 nM, 705 nM, 678 nM, 532 nM, 500 nM, 494 nM, 400 nM, 349 nM, 340 nM, 353 nM, 300 nM, 250 nM, 244 nM, 231 nM, 225 nM, 207 nM, 200 nM, 186 nM, 172 nM, 136 nM, 113 nM, 104 nM, 101 nM, 100 nM, 90 nM, 83 nM, 79 nM, 74 nM, 54 nM, 50 nM, 45 nM, 42 nM, 40 nM, 35 nM, 32 nM, 30 nM, 25 nM, 24 nM, 22 nM, 20 nM, 19 nM, 18 nM, 17 nM, 16 nM, 15 nM, 12 nM, 10 nM, 9 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.001 nM. In some embodiments, the binding affinity is less than about any of 5000 nM, 4000 nM, 3000 nM, 2000 nM, 1000 nM, 900 nM, 800 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

The intracellular signaling domain of a CAR according to the invention is responsible for intracellular signaling following the binding of extracellular ligand-binding domain to the target resulting in the activation of the immune cell and immune response. The intracellular signaling domain has the ability to activate of at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3, (zeta) signaling domain which has amino acid sequence with at least about 70%, preferably at least 80%, more preferably at least 90%, 95%, 97%, or 99% sequence identity with an amino acid sequence shown in SEQ. ID NO: 205. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of a fragment of 41BB (GenBank: AAA53133.) and CD28 (NP_006130.1). In some embodiments, the intracellular signaling domain of the CAR of the invention comprises amino acid sequence which comprises at least 70%, preferably at least 80%, more preferably at least 90%, 95%, 97%, or 99% sequence identity with an amino acid sequence shown in SEQ. ID NO: 213 (CD28 signaling domain) or SEQ. ID NO: 204 (4-1BB signaling domain).

CARs are expressed on the surface membrane of the cell. Thus, the CAR can comprise a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The CAR can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, said transmembrane and hinge domains comprise a part of human CD8α chain, preferably which comprise at least 70%, preferably at least 80%, more preferably at least 90%, 95%, 97%, or 99% sequence identity with the amino acid sequence shown in SEQ ID NO: 210 and SEQ ID NO: 208, respectively. In some embodiments, CARs disclosed herein can comprise an extracellular ligand-binding domain that specifically binds EGFRvIII, CD8α human hinge and transmembrane domains, the CD3ζ, signaling domain, and the 4-1BB signaling domain.

Table 4 provides exemplary sequences of domains which can be used in the CARs disclosed herein.

TABLE 4

Exemplary sequences of CAR Components

| Domain | Amino Acid Sequence | SEQ ID NO: |
|---|---|---|
| CD8α signal peptide | MALPVTALLLPLALLLHAA RP | 206 |
| FcγRIIIα hinge | GLAVSTISSFFPPGYQ | 207 |
| CD8α hinge | TTTPAPRPPTPAPTIASQP LSLRPEACRPAAGGAVHTR GLDFACD | 208 |
| IgG1 hinge | EPKSPDKTHTCPPCPAPPV AGPSVFLFPPKPKDTLMIA RTPEVTCVVVDVSHEDPEV KFNWYVDGVEVHNAKTKPR EEQYNSTYRVVSVLTVLHQ DWLNGKEYKCKVSNKALPA PIEKTISKAKGQPREPQVY TLPPSRDELTKNQVSLTCL VKGFYPSDIAVEWESNGQP ENNYKTTPPVLDSDGSFFL YSKLTVDKSRWQQGNVFSC SVMHEALHNHYTQKSLSLS PGK | 209 |
| CD8α transmembrane (TM) domain | IYIWAPLAGTCGVLLLSLV ITLYC | 210 |
| 41BB intracellular signaling domain (ISD) | KRGRKKLLYIFKQPFMRPV QTTQEEDGCSCRFPEEEEG GCEL | 203 |

TABLE 4-continued

Exemplary sequences of CAR Components

| Domain | Amino Acid Sequence | SEQ ID NO: |
|---|---|---|
| CD3ζ intracellular signaling domain (ISD) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 205 |
| FcεRI α-TM-IC (FcεRI α chain trans-membrane and intracellular domain) | FFIPLLVVILFAVDTGLFISTQQQVTFLLKIKRTRKGFRLLNPHPKPNPKNN | 211 |
| FcεRI β-ΔITAM (FcεRI β chain without ITAM) | MDTESNRRANLALPQEPSSVPAFEVLEISPQEVSSGRLLKSASSPPLHTWLTVLKKEQEFLGVTQILTAMICLCFGTVVCSVLDISHIEGDIFSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVPE | 212 |

TABLE 4-continued

Exemplary sequences of CAR Components

| Domain | Amino Acid Sequence | SEQ ID NO: |
|---|---|---|
| 41BB-IC (41BB co-signaling domain) | KRGRKKLLYIFKQPFMRPVQTTQEEDGCSCRFPEEEEGGCEL | 204 |
| CD28-IC (CD28 co-signaling domain) | RSKRSRGGHSDYMNMTPRRPGPTRKHYQPYAPPRDFAAYRS | 213 |
| FcεRIγ-SP (signal peptide) | MIPAVVLLLLLLVEQAAA | 214 |
| FcεRI γ-ΔITAM (FcεRI γ chain without ITAM) | LGEPQLCYILDAILFLYGIVLTLLYCRLKIQVRKAAITSYEKS | 215 |
| GSG-P2A (GSG-P2A ribosomal skip polypeptide) | GSGATNFSLLKQAGDVEENPGP | 216 |
| GSG-T2A (GSG-T2A ribosomal skip polypeptide) | GSGEGRGSLLTCGDVEENPGP | 217 |

Table 5A provides amino acid sequences of exemplary EGFRvIII specific CARs of the present invention. In Table 5A, the signal/leader peptide sequence is in bold, and GS linker [(GGGGS)$_4$ (SEQ ID NO: 202)] is underlined.

TABLE 5A

Amino acid sequences of exemplary EGFRvIII specific CARs

| CAR | CAR Amino Acid Sequence | Components (in order, N-terminus to C-terminus) |
|---|---|---|
| h62G7-L6/EQ | MALPVTALLLPLALLLHAARPDVVMTQSPLSLPVTLGQPASISCKSSQSLLYSNGKTYLNWFQQRPGQSPRRLIYQVSKLDSGVPDRFSGSGSGTDFTLKISRVEAEDVGVYYCGQDTHFPLTFGGGTKVEI<u>GGGGSGGGGSGGGGSGGGGS</u>QVQLVQSGAEVKKPGASVKVSCKASGYTFTDYTLHWVRQAPGQGLEWMGGIWPITGGTTYNQKFKGRVTMTRDTSTSTVYMELSSLRSEDTAVYYCARGEAQGSWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 52) | CD8α signal peptide; h62G7-L6/EQ VL (Table 1 SEQ ID NO: 6); GS linker [(GGGGS)$_4$ (SEQ ID NO: 202)]; h62G7-L6/EQ VH (Table 1 SEQ ID NO: 5); CD8α hinge; CD8α TM; 4-1BB signaling domain; CD3zeta signaling domain |
| 42G9 | MALPVTALLLPLALLLHAARPQVTLKESGPVLLKPTETLTLTCTVSGFSLSNPRMGVSWIRQPPGKALEWFAHIFSTDEKSLKLSLRSRLTLSKDTSKSQVVLTMTNMAPVDSATYYCARDSSNYEGYFDFWGQGTLVTVSS<u>GGGGSGGGGSGGGGSGGGGS</u>EVVLTQSPATLSVSPGERATLSCRASQSVRSNLAWYQQKSGQAPRLLIYGSTIRATGVPARFSGSGSGTEFTLIISSLQSEDFAVYYCQQYSDWPFTFGPGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 53) | CD8α signal peptide; 42G9 VH (Table 1 SEQ ID NO: 9); GS linker; 42G9 VL (Table 1 SEQ ID NO: 10); CD8α hinge; CD8α TM; 4-1BB signaling domain; CD3zeta signaling domain |
| 32A10 | MALPVTALLLPLALLLHAARPQVTLKESGPVLVKPTETLTLTCTVSGFSLSNARMGVSWIRQPPGKALEWLAHIFSTDEKSIRRSLRSRLTLSKDTSKSQVVLTMTNMDPVDTATYFCARDSSNYEGYFDYWGQGTLVTVSS<u>GGGGSGGGGSGGGGSGGGGS</u>EVVLTQSPATLSVSPGERVTLSCRASQSVSSNFAWYQQRPGQAPRLLLYGATTRATGLPGRFSGSGSGTENILTISSLQSEDFAIYFCQQYKDWPFTFGPGSKVDIKTTTP | CD8α signal peptide; 32A10 VH (Table 1 SEQ ID NO: 11); GS linker; 32A10 VL (Table 1 SEQ ID NO: 12); CD8α hinge; |

TABLE 5A-continued

Amino acid sequences of exemplary EGFRvIII specific CARs

| CAR | CAR Amino Acid Sequence | Components (in order, N-terminus to C-terminus) |
|---|---|---|
| | APRPPTPAPTIASQPLSLRPEACRPAAGGAVHTRGLDFA<br>CDIYIWAPLAGTCGVLLLSLVITLYCKRGRKKLLYIFKQ<br>PFMRPVQTTQEEDGCSCRFPEEEEGGCELRVKFSRSADA<br>PAYQQGQNQLYNELNLGRREEYDVLDKRRGRDPEMGGKP<br>RRKNPQEGLYNELQKDKMAEAYSEIGMKGERRRGKGHDG<br>LYQGLSTATKDTYDALHMQALPPR<br>(SEQ ID NO: 54) | CD8α TM;<br>4-1BB signaling domain;<br>CD3zeta signaling domain |
| 20B9 | MALPVTALLLPLALLLHAARPQVTLKESGPVLVKPTETL<br>TLTCTVSGFSLSNARMGVSWIRQPPGKALEWLGHIFSTD<br>EKSYSTSLRGRITISKDTSRGLVVLTLTNMDPVDTATYY<br>CARDSSNYEGYFDFWGPGFLVTVSS<u>GGGGSGGGGSGGGG</u><br><u>SGGGGS</u>EIVMTQSPATLSVSPGERATLSCRVSQSIGANL<br>AWYQQKFGQAPRLLIYGASTRATGIPVRFSGGGSGTEFT<br>LTISSLQSEDFAIYSCQQYIYWPFTFGPGTTVDIKTTTP<br>APRPPTPAPTIASQPLSLRPEACRPAAGGAVHTRGLDFA<br>CDIYIWAPLAGTCGVLLLSLVITLYCKRGRKKLLYIFKQ<br>PFMRPVQTTQEEDGCSCRFPEEEEGGCELRVKFSRSADA<br>PAYQQGQNQLYNELNLGRREEYDVLDKRRGRDPEMGGKP<br>RRKNPQEGLYNELQKDKMAEAYSEIGMKGERRRGKGHDG<br>LYQGLSTATKDTYDALHMQALPPR<br>(SEQ ID NO: 55) | CD8α signal peptide;<br>20B9 VH (Table 1, SEQ ID NO: 13);<br>GS linker;<br>20B9 VL (Table 1, SEQ ID NO: 14);<br>CD8α hinge;<br>CD8α TM;<br>4-1BB signaling domain;<br>CD3zeta signaling domain |
| 14C11 | MALPVTALLLPLALLLHAARPQVTLKESGPVLVKPTETL<br>TLTCTVSGFSLNNARMGVSWIRQPPGKALEWFAHIFSTD<br>EKSFRTSLRSRLTLSKDTSKSQVVLTMTNMDPVDTATYY<br>CARDSSNYEGYFDYWGQGILVTVSS<u>GGGGSGGGGSGGGG</u><br><u>SGGGGS</u>EIVMTQSPATLSVSPGERATLSCRASQSVSNNL<br>AWYQQKPGQAPRLLIYGASTRATGVPARFSGSDSGTEFS<br>LIISSLQSEDFAVYFCQQYKDWPFTFGPGTKVEIKTTTP<br>APRPPTPAPTIASQPLSLRPEACRPAAGGAVHTRGLDFA<br>CDIYIWAPLAGTCGVLLLSLVITLYCKRGRKKLLYIFKQ<br>PFMRPVQTTQEEDGCSCRFPEEEEGGCELRVKFSRSADA<br>PAYQQGQNQLYNELNLGRREEYDVLDKRRGRDPEMGGKP<br>RRKNPQEGLYNELQKDKMAEAYSEIGMKGERRRGKGHDG<br>LYQGLSTATKDTYDALHMQALPPR<br>(SEQ ID NO: 56) | CD8α signal peptide;<br>14C11 VH (Table 1, SEQ ID NO: 15);<br>GS linker;<br>14C11 VL (Table 1, SEQ ID NO: 16);<br>CD8α hinge;<br>CD8α TM;<br>4-1BB signaling domain;<br>CD3zeta signaling domain |
| 20E12 | MALPVTALLLPLALLLHAARPEVNLVESGGGLVKPGGSL<br>RLSCEASGFTFSYAWMSWVRQAPGKGLEWVGRIKSIADG<br>GATDYAAPVRNRFTISRDDSRNTLYLEMHSLKTEDTAVY<br>YCTTIPGNDAFDMWGQGTMVTVSS<u>GGGGSGGGGSGGGGS</u><br><u>GGGGS</u>DIVLTQSPLSLSVTPGEPASISCRSSQSLLYSNG<br>KNYLDWFLHKPGQSPQLLIYLGSNRASGVPDRFSGSGSG<br>IDFILKISRVEAEDVGVYYCMQAQQTPITFGQGTRLEIK<br>TTTPAPRPPTPAPTIASQPLSLRPEACRPAAGGAVHTRG<br>LDFACDIYIWAPLAGTCGVLLLSLVITLYCKRGRKKLLY<br>IFKQPFMRPVQTTQEEDGCSCRFPEEEEGGCELRVKFSR<br>SADAPAYQQGQNQLYNELNLGRREEYDVLDKRRGRDPEM<br>GGKPRRKNPQEGLYNELQKDKMAEAYSEIGMKGERRRGK<br>GHDGLYQGLSTATKDTYDALHMQALPPR<br>(SEQ ID NO: 57) | CD8α signal peptide;<br>20E12 VH (Table 1, SEQ ID NO: 39);<br>GS linker;<br>20E12 VL (Table 1, SEQ ID NO: 40);<br>CD8α hinge;<br>CD8α TM;<br>4-1BB signaling domain;<br>CD3zeta signaling domain |
| 32G8 | MALPVTALLLPLALLLHAARPEVNLVESGGGLVKPGGSL<br>RLSCFASGFTFSYAWMSWVRQAPGKGLEWVGRIKSITDG<br>GVIDYAAPVRNRCTISRDDSRNTLYLEMHSLKTEDTAVY<br>YCTTIPGNDDFDMWGQGRMVTVSS<u>GGGGSGGGGSGGGGS</u><br><u>GGGGS</u>DIVLTQSPLSLSVTPGEPASISCRSSQSLLYSNG<br>KNYLDWFLHKPGQSPQLLIYLGSNRASGVPDRFSGSGSG<br>IDFILKISRVEAEDVGVYYCMQAQQTPITFGQGTRLEIK<br>TTTPAPRPPTPAPTIASQPLSLRPEACRPAAGGAVHTRG<br>LDFACDIYIWAPLAGTCGVLLLSLVITLYCKRGRKKLLY<br>IFKQPFMRPVQTTQEEDGCSCRFPEEEEGGCELRVKFSR<br>SADAPAYQQGQNQLYNELNLGRREEYDVLDKRRGRDPEM<br>GGKPRRKNPQEGLYNELQKDKMAEAYSEIGMKGERRRGK<br>GHDGLYQGLSTATKDTYDALHMQALPPR<br>(SEQ ID NO: 58) | CD8α signal peptide;<br>32G8 VH (Table 1, SEQ ID NO: 43);<br>GS linker;<br>32G8 VL (Table 1, SEQ ID NO: 40);<br>CD8α hinge;<br>CD8α TM;<br>4-1BB signaling domain;<br>CD3zeta signaling domain |
| 26B9 | MALPVTALLLPLALLLHAARPEVQLVESWGVLVKPGGSL<br>RLSCAASGFIFNNAWMSWVRQAPGKGLEWIGRIKSKSDG<br>GTTDYAAPVKDRFTISRDDSKDTLYLQMNGLKTEDTAVY<br>FCTTAPGGPFDYWGQGTLVTVSS<u>GGGGSGGGGSGGGGSG</u><br><u>GGGS</u>DIVLTQSPLSLPVTPGEPASISCRSSQSLLHRDGF<br>NYLDWFLQKPGQSPQLLIYLASSRASGVPDRFSGSDSGT | CD8α signal peptide;<br>26B9 VH (Table 1, SEQ ID NO: 41);<br>GS linker;<br>26B9 VL (Table 1, SEQ ID NO: 42); |

TABLE 5A-continued

Amino acid sequences of exemplary EGFRvIII specific CARs

| CAR | CAR Amino Acid Sequence | Components (in order, N-terminus to C-terminus) |
|---|---|---|
|  | DFTLKISRVEAEDVGVYYCMQALQTPITFGQGTRLEIK TTTPAPRPPTPAPTIASQPLSLRPEACRPAAGGAVHTRG LDFACDIYIWAPLAGTCGVLLLSLVITLYCKRGRKKLLY IFKQPFMRPVQTTQEEDGCSCRFPEEEEGGCELRVKFSR SADAPAYQQGQNQLYNELNLGRREEYDVLDKRRGRDPEM GGKPRRKNPQEGLYNELQKDKMAEAYSEIGMKGERRRGK GHDGLYQGLSTATKDTYDALHMQALPPR (SEQ ID NO: 59) | CD8α hinge; CD8α TM; 4-1BB signaling domain; CD3zeta signaling domain |
| 30D8 | MALPVTALLLPLALLLHAARPEVQLVESGGGLVKPGGSL RLSCEASGFTFSDAWMSWVRQAPGKGLEWVGRIKSKTDG GTTDYVVPLNGRFIISRDDSRNTLYLQLNNLKTEDTAVY YCTTVPGSYGYWGQGTLVTVSS<u>GGGGSGGGGSGGGGSGG GGS</u>DIVMTQSPLSLPVTPGEPASISCRSSQSLLHNKRNN YLDWFLQKPGQSPQLLIYLASNRASGVPDRFSGGSGTD FTLKISRVEAEDVGVYYCMQAQQTPITFGQGTRLEIKTT TPAPRPPTPAPTIASQPLSLRPEACRPAAGGAVHTRGLD FACDIYIWAPLAGTCGVLLLSLVITLYCKRGRKKLLYIF KQPFMRPVQTTQEEDGCSCRFPEEEEGGCELRVKFSRSA DAPAYQQGQNQLYNELNLGRREEYDVLDKRRGRDPEMGG KPRRKNPQEGLYNELQKDKMAEAYSEIGMKGERRRGKGH DGLYQGLSTATKDTYDALHMQALPPR (SEQ ID NO: 60) | CD8α signal peptide; 30D8 VH (Table 1, SEQ ID NO: 37); GS linker; 30D8 VL (Table 1, SEQ ID NO: 38); CD8α hinge; CD8α TM; 4-1BB signaling domain; CD3zeta signaling domain |
| C6 | MALPVTALLLPLALLLHAARPQVQLVQSGAEVKKPGSSV KVSCKASGDTFSSNAISWVRQAPGQGLEWMGVIIPIFGT ADYAQKFQGRVTITADESTSTAYMELSSLRSEDTAVYYC ARHTYHEYAGGYYGGAMDPWGQGTLVTVSS<u>GGGGSGGGG SGGGGSGGGGS</u>ELQSVLTQPPSASGTPGQRVTISCSGSS SNIGSNYVYWYQQLPGTAPKILIYRNNQRPSGVPDRFSG SKSGTSASLAISGLRSEDEADYYCAAWDDNLSGWVFGTG TKLTVLTTTPAPRPPTPAPTIASQPLSLRPEACRPAAGG AVHTRGLDFACDIYIWAPLAGTCGVLLLSLVITLYCKRG RKKLLYIFKQPFMRPVQTTQEEDGCSCRFPEEEEGGCEL RVKFSRSADAPAYQQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR (SEQ ID NO: 61) | CD8α signal peptide; C6 VH (Table 1, SEQ ID NO: 48); GS linker; C6 VL (Table 1, SEQ ID NO: 49); CD8α hinge; CD8α TM; 4-1BB signaling domain; CD3zeta signaling domain |

Table 5B provides nucleic acid sequences of exemplary scFvs of EGFRvIII specific CARs of the present invention. In Table 5B, the sequence encoding the CD8α signal/leader peptide is underlined.

TABLE 5B

Nucleic acid sequences of exemplary EGFRvIII specific scFvs

| CAR | scFv Nucleic Acid Sequence |
|---|---|
| h62G7-L6/EQ scFv | <u>ATGGCTCTGCCCGTCACCGCTCTGCTGCTGCCCCTGGCTCTGCTGCTGCACG CTGCTCGCCCT</u>GATGTGGTCATGACTCAGTCTCCCCTGTCTCTGCCCGTCAC CCTGGGACAGCCCGCCAGCATCTCCTGCAAGAGCTCCCAGAGCCTGCTGTAC TCCAACGGCAAGACCTATCTGAATTGGTTCCAGCAGAGACCCGGCCAGAGCC CTCGGAGACTGATCTACCAGGTGTCTAAGCTGGACAGCGGCGTGCCTGATCG CTTCTCTGGAAGCGGATCCGGAACCGACTTTACACTGAAGATCAGCCGGGTG GAGGCAGAGGACGTGGGCGTGTACTATTGCGGCCAGGATACCCACTTCCCAC TGACATTTGGCGGCGGCACCAAGGTGGAGATCAAGGGAGGAGGAGGAAGCGG AGGAGGAGGAAGCGGCGGCGGCGGCTCTGGCGGCGGCGGCAGCCAGGTGCAG CTGGTGCAGAGCGGAGCAGAGGTGAAGAAGCCTGGCGCCTCCGTGAAGGTGT CTTGTAAGGCCAGCGGCTACACCATTCACCGATTATACACTGCACTGGGTGCG GCAGGCCCCTGGCCAGGGACTGGAGTGGATGGGAGGAATCTGGCCTATCACC GGAGGAACCACATACAACCAGAAGTTTAAGGGCAGAGTGACAATGACCAGGG ACACATCTACCAGCACAGTGTATATGGAGCTGTCTAGCCTGCGCTCCGAGGA TACAGCCGTGTACTATTGCGCCAGAGGCGAGGCACAGGGATCTTGGGGACAG GGCACCCTGGTGACAGTGTCCTCT (SEQ ID NO: 228) |
| 42G9 scFv | <u>ATGGCTCTGCCCGTCACCGCTCTGCTGCTGCCACTGGCCCTGCTGCTGCACG CAGCAAGGCCT</u>CAGGTGACCCTGAAGGAGAGCGGCCCTGTGCTGCTGAAGCC AACAGAGACCCTGACACTGACCTGCACAGTGTCTGGCTTCAGCCTGTCCAAC CCCCGGATGGGCGTGAGCTGGATCAGACAGCCCCCTGGCAAGGCCCTGGAGT |

TABLE 5B-continued

Nucleic acid sequences of exemplary EGFRvIII specific scFvs

| CAR | scFv Nucleic Acid Sequence |
|---|---|
| | GGTTCGCCCACATCTTTTCTACCGATGAGAAGAGCCTGAAGCTGTCCCTGAG<br>ATCTAGGCTGACCCTGAGCAAGGACACATCTAAGAGCCAGGTGGTGCTGACC<br>ATGACAAACATGGCCCCTGTGGACTCCGCCACATACTATTGCGCCAGAGACA<br>GCTCCAATTACGAGGGCTATTTCGACTTTTGGGGCCAGGGCACCCTGGTGAC<br>AGTGTCTAGCGGCGGAGGAGGATCCGGAGGAGGAGGATCTGGCGGCGGCGGC<br>TCCGGCGGCGGCGGCTCCGAGGTGGTGCTGACCCAGAGCCCTGCCACACTGT<br>CCGTGTCTCCAGGCGAGAGAGCCACCCTGTCTTGTAGGGCCAGCCAGTCCGT<br>GCGCAGCAATCTGGCCTGGTACCAGCAGAAGTCCGGCCAGGCCCCAAGACTG<br>CTGATCTATGGCTCCACCATCAGGGCCACAGGAGTGCCAGCACGCTTCTCTG<br>GAAGCGGATCCGGCACAGAGTTTACCCTGACAATCTCCTCTCTGCAGTCCGA<br>GGATTTCGCCGTGTACTATTGCCAGCAGTACTCTGACTGGCCCTTCACCTTT<br>GGCCCTGGCACAAAGGTGGATATCAAG (SEQ ID NO: 229) |
| 32A10<br>scFv | <u>ATGGCTCTGCCCGTCACCGCTCTGCTGCTGCCACTGGCCCTGCTGCTGCACG</u><br><u>CAGCAAGGCCA</u>CAGGTGACCCTGAAGGAGTCCGGCCCCGTGCTGGTGAAGCC<br>TACAGAGACCCTGACACTGACCTGCACAGTGTCCGGCTTCTCTCTGAGCAAC<br>GCCCGCATGGGCGTGTCTTGGATCAGGCAGCCCCCTGGCAAGGCCCTGGAGT<br>GGCTGGCCCACATCTTTTCCACCGACGAGAAGTCTATCCGGAGAAGCCTGCG<br>CTCCAGGCTGACCCTGAGCAAGGATACATCCAAGTCTCAGGTGGTGCTGACC<br>ATGACAAACATGGACCCCGTGGATACCGCCACATACTTCTGCGCCAGAGACA<br>GCTCCAATTACGAGGGCTATTTTGATTACTGGGGCCAGGGCACCCTGGTGAC<br>AGTGTCTAGCGGAGGAGGAGGAAGCGGAGGAGGAGGATCTGGCGGCGGCGGC<br>TCTGGCGGCGGCGGCAGCGAGGTGGTCATGACCCAGAGCCCAGCCACACTGA<br>GCGTGTCCCCTGGCGAGAGGGTGACCCTGTCCTGTAGGGCATCTCAGAGCGT<br>GTCCTCTAACTTCGCCTGGTATCAGCAGAGACCAGGCCAGGCCCAAGGCTG<br>CTGCTGTACGGAGCAACCACAAGAGCCACAGGACTGCCCGGCAGGTTTTCCG<br>GATCTGGAAGCGGCACCGAGAATATCCTGACAATCAGCTCCCTGCAGTCTGA<br>GGACTTCGCCATCTATTTTGCCAGCAGTACAAGGATTGGCCATTCACCTTT<br>GGCCCCGGCAGCAAGGTGGACATCAAG (SEQ ID NO: 230) |
| 20B9<br>scFv | <u>ATGGCTCTGCCCGTCACCGCTCTGCTGCTGCCACTGGCCCTGCTGCTGCACG</u><br><u>CAGCAAGACCT</u>CAGGTGACCCTGAAGGAGTCCGGCCCCGTGCTGGTGAAGCC<br>AACAGAGACCCTGACACTGACCTGCACAGTGTCTGGCTTCAGCCTGTCCAAC<br>GCAAGGATGGGCGTGAGCTGGATCAGGCAGCCCCCTGGCAAGGCCCTGGAGT<br>GGCTGGGCCACATCTTTAGCACCGACGAGAAGTCTTACAGCACATCCCTGAG<br>AGGCAGGATCACCATCTCTAAGGATACAAGCAGAGGCCTGGTGGTGCTGACC<br>CTGACAAACATGGACCCCGTGGATACCGCCACATACTATTGCGCCAGGGACA<br>GCTCCAATTACGAGGGCTATTTCGATTTTTGGGGCCCTGGCTTCCTGGTGAC<br>CGTGTCTAGCGGCGGCGGCGGCTCTGGAGGAGGAGGAAGCGGAGGAGGAGGA<br>TCCGGCGGCGGCGGCTCTGAGATCGTGATGACCCAGTCCCCTGCCACACTGT<br>CTGTGAGCCCAGGCGAGAGAGCCACCCTGTCTTGTAGGGTGTCCCAGTCTAT<br>CGGCGCCAATCTGGCCTGGTACCAGCAGAAGTTCGGCCAGGCCCCAAGGCTG<br>CTGATCTATGGAGCATCCACCAGAGCCCACAGGAATCCCCGTGAGGTTCTCCG<br>GAGGAGGATCTGGAACCGAGTTTACCCTGACAATCTCCTCTCTGCAGAGCGA<br>GGACTTTGCCATCTACTCCTGCCAGCAGTACATCTATTGGCCCTTCACATTT<br>GGCCCTGGCACCACAGTGGATATCAAG (SEQ ID NO: 231) |
| 14C11<br>scFv | <u>ATGGCTCTGCCCGTCACCGCTCTGCTGCTGCCACTGGCCCTGCTGCTGCACG</u><br><u>CAGCAAGACCA</u>CAGGTGACCCTGAAGGAGAGCGGACCCGTGCTGGTGAAGCC<br>TACAGAGACCCTGACACTGACCTGCACAGTGAGCGGCTTCTCCCTGAACAAT<br>GCAAGGATGGGCGTGTCCTGGATCAGGCAGCCCCCTGGCAAGGCCCTGGAGT<br>GGTTCGCCCACATCTTTAGCACCGACGAGAAGTCCTTTCGCACATCTCTGAG<br>AAGCAGGCTGACCCTGAGCAAGGATACAAGCAAGTCCCAGGTGGTGCTGACC<br>ATGACAAACATGGACCCCGTGGATACCGCCACATACTATTGCGCCAGAGACA<br>GCTCCAATTACGAGGGCTATTTCGATTACTGGGGCCAGGGCATCCTGGTGAC<br>CGTGTCTAGCGGCGGCGGCGGCTCTGGAGGAGGAGGAAGCGGAGGAGGAGGA<br>TCCGGCGGCGGCGGCTCTGAGATCGTGATGACCCAGTCTCCCGCCACACTGT<br>CTGTGAGCCCTGGCGAGAGAGCCACACTGAGCTGTAGGGCCTCCCAGTCTGT<br>GAGCAACAATCTGGCCTGGTATCAGCAGAAGCCAGGCCAGGCACCAAGGCTG<br>CTGATCTACGGAGCATCCACCAGAGCCCACAGGAGTGCCAGCAAGGTTCTCCG<br>GATCTGACAGCGGCACCGAGTTTAGCCTGACAATCTCCTCTCTGCAGTCCGA<br>GGACTTCGCCGTGTATTTTGCCAGCAGTACAAGGATTGGCCATTCACCTTT<br>GGCCCCGGCACAAAGGTGGAGATCAAG (SEQ ID NO: 232) |
| 20E12<br>scFv | <u>ATGGCTCTGCCCGTCACCGCTCTGCTGCTGCCACTGGCCCTGCTGCTGCACG</u><br><u>CAGCAAGGCCA</u>GAGGTGAACCTGGTGGAGTCCGGCGGCGCCTGGTGAAGCC<br>TGGCGGATCCCTGAGGCTGTCTTGCGAGGCAAGCGGCTTCACCTTCAGCTAC<br>GCCTGGATGTCCTGGGTGCGCCAGGCCCCCGGCAAGGGACTGGAGTGGGTGG<br>GACGGATCAAGTCCATCGCAGACGGAGGAGCAACCGATTACGCAGCCCCTGT<br>GAGAAACAGGTTCACAATCTCCAGAGACGATTCTAGGAATACCCTGTATCTG<br>GAGATGCACTCTCTGAAGACAGAGGACACCGCCGTGTACTATTGCACCACAA<br>TCCCTGGCAACGACGCCTTTGATATGTGGGGCCAGGGCACAATGGTGACCGT<br>GAGCTCCGGCGGCGGCGGCTCTGGAGGAGGAGGAAGCGGAGGAGGAGGAAGC<br>GGGGGCGGCGGCTCTGACATCGTGCTGACACAGTCCCCACTGTCCCTGTCTG<br>TGACCCCCGGCGAGCCTGCAAGCATCTCCTGTAGATCTAGCCAGAGCCTGCT<br>GTACTCCAACGGCAAGAATTATCTGGATTGGTTCCTGCACAAGCCAGGCCAG TABLE 5B-continued Nucleic acid sequences of exemplary EGFRvIII specific scFvs

| CAR | scFv Nucleic Acid Sequence |
|---|---|
| | TCTCCCCAGCTGCTGATCTACCTGGGATCTAATAGGGCAAGCGGAGTGCCAG<br>ACCGGTTCTCTGGAAGCGGATCCGGCATCGACTTCATCCTGAAGATCAGCAG<br>GGTGGAGGCCGAGGATGTGGGCGTGTACTATTGCATGCAGGCCCAGCAGACA<br>CCCATCACCTTCGGCCAGGGCACAAGACTGGAGATCAAG (SEQ ID NO: 233) |
| 32G8 scFv | <u>ATGGCTCTGCCCGTCACCGCTCTGCTGCTGCCACTGGCCCTGCTGCTGCACG</u><br><u>CAGCAAGGCCA</u>GAGGTGAACCTGGTGGAGTCCGGCGGCGGCCTGGTGAAGCC<br>TGGCGGATCCCTGAGGCTGTCTTGCGAGGCAAGCGGCTTCACCTTCAGCTAC<br>GCCTGGATGTCCTGGGTGCGCCAGGCCCCCGGCAAGGGACTGGAGTGGGTGG<br>GCCGGATCAAGTCCATCACCGACGGAGGCGTGATCGATTACGCAGCACCTGT<br>GAGAAACAGGTGCACAATCTCCAGAGACGATTCTAGGAATACCCTGTATCTG<br>GAGATGCACTCTCTGAAGACAGAGGACACCGCCGTGTACTATTGTACCACAA<br>TCCCTGGCAACGACGATTTCGATATGTGGGGCCAGGGCAGAATGGTGACCGT<br>GAGCTCCGGCGGCGGCGGCTCTGGAGGAGGAGGAAGCGGAGGAGGAGGAAGC<br>GGGGGCGGCGGCTCTGACATCGTGCTGACACAGTCCCCACTGTCCCTGTCTG<br>TGACCCCCGGCGAGCCTGCAAGCATCTCCTGTAGGTCTAGCCAGAGCCTGCT<br>GTACTCCAACGGCAAGAATTATCTGGATTGGTTTCTGCACAAGCCAGGCCAG<br>TCTCCCCAGCTGCTGATCTACCTGGGATCTAATAGGGCAAGCGGAGTGCCAG<br>ACCGGTTCTCTGGAAGCGGATCCGGCATCGACTTCATCCTGAAGATCAGCCG<br>CGTGGAGGCAGAGGACGTGGGCGTGTACTATTGCATGCAGGCCCAGCAGACA<br>CCCATCACCTTCGGCCAGGGCACAAGACTGGAGATCAAG (SEQ ID NO: 234) |
| 26B9 scFv | <u>ATGGCTCTGCCCGTCACCGCTCTGCTGCTGCCACTGGCCCTGCTGCTGCACG</u><br><u>CAGCAAGGCCA</u>GAGGTGCAGCTGGTGGAGTCTTGGGGCGTGCTGGTGAAGCC<br>TGGCGGATCTCTGAGGCTGAGCTGCGCAGCATCCGGCTTCATCTTTAACAAT<br>GCCTGGATGTCCTGGGTGCGCCAGGCCCCCGGCAAGGGACTGGAGTGGATCG<br>GCCGGATCAAGAGCAAGTCCGACGGAGGAACCACAGATTACGCAGCACCTGT<br>GAAGGACCGCTTCACAATCTCTCGGGACGATAGCAAGGATACCCTGTATCTG<br>CAGATGAACGGCCTGAAGACAGAGGACACCGCCGTGTACTTCTGCACCACAG<br>CCCCTGGCGGCCCTTTTGATTATTGGGGCCAGGGCACACTGGTGACCGTGAG<br>CTCCGGAGGAGGAGGAAGCGGCGGAGGAGGCAGCGGCGGCGGCGGCTCTGGC<br>GGCGGCGGCAGCGACATCGTGCTGACACAGAGCCCTCTGTCCCTGCCAGTGA<br>CCCCCGGCGAGCCTGCCTCTATCAGCTGTCGCTCTAGCCAGAGCCTGCTGCA<br>CCGGGACGGCTTCAATTACCTGGATTGGTTTCTGCAGAAGCCAGGCCAGTCC<br>CCCCAGCTGCTGATCTATCTGGCCTCCTCTAGAGCCTCTGGCGTGCCAGACA<br>GGTTCTCCGGCTCTGACAGCGGCACAGACTTCACCCTGAAGATCAGCAGAGT<br>GGAGGCCGAGGATGTGGGCGTGTACTATTGCATGCAGGCCCTGCAGACACCC<br>ATCACCTTCGGCCAGGGCACAAGACTGGAGATCAAG (SEQ ID NO: 235) |
| 30D8 scFv | <u>ATGGCTCTGCCCGTCACCGCTCTGCTGCTGCCACTGGCCCTGCTGCTGCACG</u><br><u>CAGCAAGGCCT</u>GAGGTGCAGCTGGTGGAGAGCGGCGGCGGCCTGGTGAAGCC<br>TGGCGGATCCCTGAGGCTGTCTTGCGAGGCAAGCGGCTTCACCTTTAGCGAC<br>GCATGGATGTCCTGGGTGCGCCAGGCCCCTGGCAAGGGACTGGAGTGGGTGG<br>GACGGATCAAGAGCAAGACAGACGGCGGCACCACAGATTACGTGGTGCCACT<br>GAACGGCCGCTTCATCATCTCCCGCGACGATTCTCGGAATACCCTGTATCTG<br>CAGCTGAACAATCTGAAGACAGAGGATACCGCCGTGTACTATTGCACCACAG<br>TGCCAGGCTCCTACGGCTATTGGGGCCAGGGCACACTGGTGACCGTGAGCTC<br>CGGCGGCGGCGGCTCTGGAGGAGGAGGAAGCGGAGGAGGAGGAAGCGGGGGC<br>GGCGGCTCTGACATCGTGATGACACAGTCTCCACTGAGCCTGCCAGTGACCC<br>CTGGCGAGCCAGCCTCCATCTCTTGTCGCTCTAGCCAGAGCCTGCTGCACAA<br>CAAGCGGAACAATTACCTGGATTGGTTTCTGCAGAAGCCTGGCCAGTCCCCT<br>CAGCTGCTGATCTATCTGGCCAGCAATAGAGCCTCCGGAGTGCCAGACAGGT<br>TCTCTGGAGGAGAAGCGGAACAGACTTCACCCTGAAGATCAGCAGAGTGGA<br>GGCCGAGGACGTGGGCGTGTACTATTGCATGCAGGCCCAGCAGACACCTATC<br>ACCTTCGGCCAGGGCACAAGACTGGAGATCAAG (SEQ ID NO: 236) |
| C6 scFv | <u>ATGGCTCTGCCCGTCACCGCTCTGCTGCTGCCTCTGGCCCTGCTGCTGCACG</u><br><u>CAGCAAGGCCA</u>CAGGTGCAGCTGGTGCAGTCCGGAGCAGAGGTGAAGAAGCC<br>TGGCAGCTCCGTGAAGGTGAGCTGCAAGGCCTCCGGCGACACATTCTCTAGC<br>AACGCAATCAGCTGGGTGCGCCAGGCCCCTGGCCAGGGACTGGAGTGGATGG<br>GCGTGATCATCCCTATCTTCGGCACCGCCGACTATGCCCAGAAGTTTCAGGG<br>CCGGGTGACAATCACCGCCGATGAGTCTACAAGCACCGCCTACATGGAGCTG<br>TCCCTCTCTGAGATCCGAGGACACAGCCGTGTACTATTGTGCCAGGCACACCT<br>ATCACGAGTACGCAGGAGGATACTATGGAGGAGCAATGGATCCTTGGGGACA<br>GGGCACACTGGTGACCGTGAGCTCCGGCGGCGGCGGCTCTGGAGGAGGAGGA<br>AGCGGAGGAGGAGGAAGCGGGGGCGGCGGCTCTGAGCTGCAGAGCGTGCTGA<br>CCCAGCCACCTTCCGCCTCTGGAACACCAGGCCAGAGGGTGACCATCAGCTG<br>CTCCGGATCTAGCTCCAACATCGGCTCCAATTACGTGTATTGGTACCAGCAG |

TABLE 5B-continued

Nucleic acid sequences of exemplary EGFRvIII specific scFvs

| CAR | scFv Nucleic Acid Sequence |
|---|---|
| | CTGCCAGGCACAGCCCCCAAGATCCTGATCTACCGCAACAATCAGCGGCCTT<br>CTGGCGTGCCAGATAGATTCTCTGGCAGCAAGTCCGGCACCTCTGCCAGCCT<br>GGCAATCTCCGGCCTGAGGTCTGAGGACGAGGCCGATTACTATTGCGCCGCC<br>TGGGACGATAACCTGAGCGGCTGGGTGTTTGGCACAGGCACCAAGCTGACAG<br>TGCTG (SEQ ID NO: 237) |

Table 5C provides exemplary nucleic acid sequences of exemplary EGFRvIII specific CARs of the present invention.

TABLE 5C

Nucleic acid sequences of exemplary EGFRvIII specific CARs

| CAR | CAR Nucleic Acid Sequence | Components |
|---|---|---|
| h62G7-L6/EQ | ATGGCTCTGCCCGTCACCGCTCTGCTGCTGCCCCTGGCT<br>CTGCTGCTGCACGCTGCTCGCCCTGATGTGGTCATGACT<br>CAGTCTCCCCTGTCTCTGCCCGTCACCCTGGGACAGCCC<br>GCCAGCATCTCCTGCAAGAGCTCCCAGAGCCTGCTGTAC<br>TCCAACGGCAAGACCTATCTGAATTGGTTCCAGCAGAGA<br>CCCGGCCAGAGCCCTCGGAGACTGATCTACCAGGTGTCT<br>AAGCTGGACAGCGGCGTGCCTGATCGCTTCTCTGGAAGC<br>GGATCCGGAACCGACTTTACACTGAAGATCAGCCGGGTG<br>GAGGCAGAGGACGTGGGCGTGTACTATTGCGCCGCAGGAT<br>ACCCACTTCCCACTGACATTTGGCGGCGGCACCAAGGTG<br>GAGATCAAGGGAGGAGGAGGAAGCGGAGGAGGAGGAAGC<br>GGCGGCGGCGGCTCTGGCGGCGGCGGCAGCCAGGTGCAG<br>CTGGTGCAGAGCGGAGCAGAGGTGAAGAAGCCTGGCGCC<br>TCCGTGAAGGTGTCTTGTAAGGCCAGCGGCTACACATTC<br>ACCGATTATACACTGCACTGGGTGCGGCAGGCCCCTGGC<br>CAGGGACTGGAGTGGATGGGAGGAATCTGGCCTATCACC<br>GGAGGAACCACATACAACCAGAAGTTTAAGGGCAGAGTG<br>ACAATGACCAGGGACACATCTACCAGCACAGTGTATATG<br>GAGCTGTCTAGCCTGCGCTCCGAGGATACAGCCGTGTAc<br>TATTGCGCCAGAGGCGAGGCACAGGGATCTTGGGGACAG<br>GGCACCCTGGTGACAGTGTCCTCTACCACAACCCCAGCA<br>CCAAGACCACCTACCCCTGCACCAACAATCGCCTCCCAG<br>CCTCTGTCTCTGCGCCCAGAGGCATGTAGGCCAGCAGCA<br>GGAGGAGCAGTGCACACCAGGGGCCTGGACTTTGCCTGC<br>GATATCTACATCTGGGCACCACTGGCAGGAACATGTGGC<br>GTGCTGCTGCTGAGCCTGGTCATCACCCTGTACTGCAAG<br>CGCGGCCGGAAGAAGCTGCTGTATATCTTCAAGCAGCCC<br>TTCATGAGACCCGTGCAGACAACCCAGGAGGAGGACGGC<br>TGCTCCTGTAGGTTCCCAGAAGAAGAGGAGGGCGGCTGT<br>GAGCTGAGAGTGAAGTTTTCCAGGTCTGCCGATGCACCA<br>GCATACCAGCAGGGACAGAATCAGCTGTATAACGAGCTG<br>AATCTGGGCAGGCGCGAGGAGTATGACGTGCTGGATAAG<br>AGGAGAGGAAGGGACCCTGAGATGGGAGGCAAGCCTAGG<br>CGCAAGAACCCACAGGAGGGCCTGTACAATGAGCTGCAG<br>AAGGATAAGATGGCCGAGGCCTATTCCGAGATCGGCATG<br>AAGGGCGAGCGGAGAAGGGGCAAGGGCCACGACGGGCTG<br>TACCAGGGACTGTCAACCGCTACCAAGGATACTTACGAC<br>GCCCTGCATATGCAGGCACTGCCTCCAAGGTGA (SEQ<br>ID NO: 238) | CD8α signal peptide;<br>h62G7-L6/EQ VL (Table 1 SEQ ID NO: 6);<br>GS linker [(GGGGS)<sub>4</sub> (SEQ ID NO: 202)];<br>h62G7-L6/EQ VH (Table 1 SEQ ID NO: 5);<br>CD8α hinge;<br>CD8α TM;<br>4-1BB signaling domain;<br>CD3zeta signaling domain |
| 42G9 | ATGGCTCTGCCCGTCACCGCTCTGCTGCTGCCACTGGCC<br>CTGCTGCTGCACGCAGCAAGGCCTCAGGTGACCCTGAAG<br>GAGAGCGGCCCTGTGCTGCTGAAGCCAACAGAGACCCTG<br>ACACTGACCTGCACAGTGTCTGGCTTCAGCCTGTCCAAC<br>CCCCGGATGGGCGTGAGCTGGATCAGACAGCCCCCTGGC<br>AAGGCCCTGGAGTGGTTCGCCCACATCTTTTCTACCGAT<br>GAGAAGAGCCTGAAGCTGTCCCTGAGATCTAGGCTGACC<br>CTGAGCAAGGACACATCTAAGAGCCAGGTGGTGCTGACC<br>ATGACAAACATGGCCCCTGTGGACTCCGCCACATACTAT<br>TGCGCCAGAGACAGCTCCAATTACGAGGGCTATTTCGAC<br>TTTTGGGGCCAGGGCACCCTGGTGACAGTGTCTAGCGGC<br>GGAGGAGGATCCGGAGGAGGAGGATCTGGCGGCGGCGGC<br>TCCGGCGGCGGCGGCTCCGAGGTGGTGCTGACCCAGAGC<br>CCTGCCACACTGTCCGTGTCTCCAGGCGAGAGAGCCACC<br>CTGTCTTGTAGGGCCAGCCAGTCCGTGCGCAGCAATCTG<br>GCCTGGTACCAGCAGAAGTCCGGCCAGGCCCCAAGACTG<br>CTGATCTATGGCTCCACCATCAGGGCCACAGGAGTGCCA | CD8α signal peptide;<br>42G9 VH (Table 1 SEQ ID NO: 9);<br>GS linker;<br>42G9 VL (Table 1 SEQ ID NO: 10);<br>CD8α hinge;<br>CD8α TM;<br>4-1BB signaling domain;<br>CD3zeta signaling domain |

TABLE 5C-continued

Nucleic acid sequences of exemplary EGFRvIII specific CARs

| CAR | CAR Nucleic Acid Sequence | Components |
|---|---|---|
| | GCACGCTTCTCTGGAAGCGGATCCGGCACAGAGTTTACC<br>CTGACAATCTCCTCTCTGCAGTCCGAGGATTTCGCCGTG<br>TACTATTGCCAGCAGTACTCTGACTGGCCCTTCACCTTT<br>GGGCCTGGCACAAAGGTGGATATCAAGACCACAACCCCT<br>GCACCAAGGCCACCAACCCCAGCACCTACAATGCAAGC<br>CAGCCACTGTCCCTGAGACCCGAGGCCTGTAGGCCTGCA<br>GCAGGAGGAGCAGTGCACACCCGCGGCCTGGACTTTGCC<br>TGCGATATCTATATCTGGGCACCACTGGCAGGAACCTGT<br>GGCGTGCTGCTGCTGAGCCTGGTCATCACCCTGTACTGC<br>AAGCGCGGCCGGAAGAAGCTGCTGTATATCTTCAAGCAG<br>CCCTTCATGCGGCCCGTGCAGACAACCCAGGAGGAGGAT<br>GGCTGCTCCTGTAGATTCCCTGAGGAGGAGGAGGGAGGA<br>TGTGAGCTGAGGGTGAAGTTTTCTCGGAGCGCCGACGCA<br>CCAGCATACCAGCAGGGACAGAACCAGCTGTATAACGAG<br>CTGAATCTGGGCCGGAGAGAGGAGTACGACGTGCTGGAT<br>AAGAGGAGGGGAAGAGACCCAGAGATGGGAGGCAAGCCA<br>CGGAGAAAGAACCCCCAGGAGGGCCTGTACAATGAGCTG<br>CAGAAGGATAAGATGGCCGAGGCCTATTCTGAGATCGGC<br>ATGAAGGGAGAGAGGCGCCGGGGCAAGGGACACGACGGA<br>CTGTACCAGGGACTGTCCACCGCAACAAAGGACACCTAT<br>GATGCCCTGCATATGCAGGCACTGCCTCCAAGGTGA<br>(SEQ ID NO: 239) | |
| 32A10 | ATGGCTCTGCCCGTCACCGCTCTGCTGCTGCCACTGGCC<br>CTGCTGCTGCACGCAGCAAGGCCACAGGTGACCCTGAAG<br>GAGTCCGGCCCCGTGCTGGTGAAGCCTACAGAGACCCTG<br>ACACTGACCTGCACAGTGTCCGGCTTCTCTCTGAGCAAC<br>GCCCGCATGGGCGTGTCTTGGATCAGGCAGCCCCCTGGC<br>AAGGCCCTGGAGTGGCTGGCCCACATCTTTTCCACCGAC<br>GAGAAGTCTATCCGGAGAAGCCTGCGCTCCAGGCTGACC<br>CTGAGCAAGGATACATCCAAGTCTCAGGTGGTGCTGACC<br>ATGACAAACATGGACCCCGTGGATACCGCCACATACTTC<br>TGCGCCAGAGACAGCTCCAATTACGAGGGCTATTTTGAT<br>TACTGGGGCCAGGGCACCCTGGTGACAGTGTCTAGCGGA<br>GGAGGAGGAAGCGGAGGAGGAGGATCTGGCGGCGGCGGC<br>TCTGGCGGCGGCGGCAGCGAGGTGGTCATGACCCAGAGC<br>CCAGCCACACTGAGCGTGTCCCCTGGCGAGAGGGTGACC<br>CTGTCCTGTAGGGCATCTCAGAGCGTGTCCTCTAACTTC<br>GCCTGGTATCAGCAGAGACCAGGCCAGGCACCAAGGCTG<br>CTGCTGTACGGAGCAACCACAAGAGCCACAGGACTGCCC<br>GGCAGGTTTTCCGGATCTGGAAGCGGCACCGAGAATATC<br>CTGACAATCAGCTCCCTGCAGTCTGAGGACTTCGCCATC<br>TATTTTTGCCAGCAGTACAAGGATTGGCCATTCACCTTT<br>GGCCCCGGCAGCAAGGTGGACATCAAGACCACAACCCCT<br>GCACCAAGACCACCAACCCCAGCACCTACAATGCCTCT<br>CAGCCTCTGAGCCTGCGCCCAGAGGCATGTAGGCCAGCA<br>GCAGGAGGAGCAGTGCACACAAGGGGCCTGGACTTCGCC<br>TGCGATATCTATATCTGGGCACCTCTGGCAGGAACCTGT<br>GGCGTGCTGCTGCTGAGCCTGGTCATCACCCTGTATTGC<br>AAGAGAGGCAGGAAGAAGCTGCTGTACATCTTCAAGCAG<br>CCTTTTATGCGCCCAGTGCAGACACCCAGGAGGAGGAC<br>GGCTGCAGCTGTCGGTTCCCTGAAGAGGAGGAGGGCGGC<br>TGTGAGCTGAGAGTGAAGTTTTCCAGGTCTGCCGATGCC<br>CCAGCCTATCAGCAGGGCCAGAATCAGCTGTACAACGAG<br>CTGAATCTGGGCAGGCGCGAGGAGTACGACGTGCTGGAT<br>AAGAGGAGAGGAAGGGATCCAGAGATGGGAGGCAAGCCT<br>AGGCGCAAGAACCCACAGGAGGGCCTGTATAATGAGCTG<br>CAGAAGGACAAGATGGCCGAGGCCTACTCCGAGATCGGC<br>ATGAAGGGAGAGCGGAGAAGGGGCAAGGGACACGATGGC<br>CTGTATCAGGGCCTGTCTACCGCCACAAAGGACACCTAC<br>GATGCCCTGCATATGCAGGCACTGCCTCCAAGGTGA<br>(SEQ ID NO: 240) | CD8α signal peptide;<br>32A10 VH (Table 1 SEQ ID NO: 11);<br>GS linker;<br>32A10 VL (Table 1 SEQ ID NO: 12);<br>CD8α hinge;<br>CD8α TM;<br>4-1BB signaling domain;<br>CD3zeta signaling domain |
| 20B9 | ATGGCTCTGCCCGTCACCGCTCTGCTGCTGCCACTGGCC<br>CTGCTGCTGCACGCAGCAAGACCTCAGGTGACCCTGAAG<br>GAGTCCGGCCCCTGTGCTGGTGAAGCCAACAGAGACCCTG<br>ACACTGACCTGCACAGTGTCTGGCTTCAGCCTGTCCAAC<br>GCAAGGATGGGCGTGAGCTGGATCAGGCAGCCCCCTGGC<br>AAGGCCCTGGAGTGGCTGGCCACATCTTTAGCACCGAC<br>GAGAAGTCTTACAGCACATCCCTGAGAGGCAGGATCACC<br>TCTCTAAGGATACAAGCAGAGGCTTGGTGGTGCTGACC<br>CTGACAAACATGGACCCCGTGGATACCGCCACATACTAT<br>TGCGCCAGGGACAGCTCCAATTACGAGGGCTATTTCGAT<br>TTTTGGGGCCCCTGGCTTCCTGGTGACCGTGTCTAGCGGC<br>GGCGGCGGCTCTGGAGGAGGAGGAAGCGGAGGAGGAGGA<br>TCCGGCGGCGGCGGCTCTGAGATCGTGATGACCCAGTCC | CD8α signal peptide;<br>20B9 VH (Table 1, SEQ ID NO: 13);<br>GS linker;<br>20B9 VL (Table 1, SEQ ID NO: 14);<br>CD8α hinge;<br>CD8α TM;<br>4-1BB signaling domain;<br>CD3zeta signaling domain |

TABLE 5C-continued

Nucleic acid sequences of exemplary EGFRvIII specific CARs

| CAR | CAR Nucleic Acid Sequence | Components |
|---|---|---|
| | CCTGCCACACTGTCTGTGAGCCCAGGCGAGAGAGCCACC<br>CTGTCTTGTAGGGTGTCCCAGTCTATCGGCGCCAATCTG<br>GCCTGGTACCAGCAGAAGTTCGGCCAGGCCCCAAGGCTG<br>CTGATCTATGGAGCATCCACCAGAGCCACAGGAATCCCC<br>GTGAGGTTCTCCGGAGGAGGATCTGGAACCGAGTTTACC<br>CTGACAATCTCCTCTCTGCAGAGCGAGGACTTTGCCATC<br>TACTCCTGCCAGCAGTACATCTATTGGCCCTTCACATTT<br>GGCCCTGGCACCACAGTGGATATCAAGACCACAACCCCT<br>GCACCAAGGCCACCAACCCCAGCACCTACAATCGCAAGC<br>CAGCCACTGTCCCTGAGACCAGAGGCATGTAGGCCTGCA<br>GCAGGAGGAGCCGTGCACACCAGAGGCCTGGACTTTGCC<br>TGCGATATCTATATCTGGGCACCACTGGCAGGAACCTGT<br>GGCGTGCTGCTGCTGAGCCTGGTCATCACCCTGTACTGC<br>AAGCGCGGCCGGAAGAAGCTGCTGTATATCTTCAAGCAG<br>CCCTTCATGCGCCCCGTGCAGACAACCCAGGAGGAGGAC<br>GGCTGCAGCTGTCGGTTCCCTGAAGAGGAGGAGGGAGGA<br>TGTGAGCTGAGGGTGAAGTTTAGCCGGTCCGCCGATGCA<br>CCAGCATACCAGCAGGGCCAGAACCAGCTGTATAACGAG<br>CTGAATCTGGGCCGGAGAGAGGAGTACGACGTGCTGGAT<br>AAGAGGAGGGGAAGAGACCCAGAGATGGGAGGCAAGCCA<br>CGGAGAAAGAACCCCCAGGAGGGCCTGTACAATGAGCTG<br>CAGAAGGACAAGATGGCCGAGGCCTATAGCGAGATCGGC<br>ATGAAGGGAGAGAGGCGCCGGGGCAAGGGACACGATGGC<br>CTGTACCAGGGCCTGTCCACCGCCACAAAGGACACCTAT<br>GATGCCCTGCATATGCAGGCACTGCCTCCAAGGTGA<br>(SEQ ID NO: 241) | |
| 14C11 | ATGGCTCTGCCCGTCACCGCTCTGCTGCTGCCACTGGCC<br>CTGCTGCTGCACGCAGCAAGACCACAGGTGACCCTGAAG<br>GAGAGCGGACCCGTGCTGGTGAAGCCTACAGAGACCCTG<br>ACACTGACCTGCACAGTGAGCGGCTTCTCCCTGAACAAT<br>GCAAGGATGGGCGTGTCCTGGATCAGGCAGCCCCCTGGC<br>AAGGCCCTGGAGTGGTTCGCCCACATCTTTAGCACCGAC<br>GAGAAGTCCTTTCGCACATCTCTGAGAAGCAGGCTGACC<br>CTGAGCAAGGATACAAGCAAGTCCCAGGTGGTGCTGACC<br>ATGACAAACATGGACCCCGTGGATACCGCCACATACTAT<br>TGCGCCAGAGACAGCTCCAATTACGAGGGCTATTTCGAT<br>TACTGGGGCCAGGGCATCCTGGTGACCGTGTCTAGCGGC<br>GGCGGCGGCTCTGGAGGAGGAGGAAGCGGAGGAGGAGGA<br>TCCGGCGGCGGCGGCTCTGAGATCGTGATGACCCAGTCT<br>CCCGCCACACTGTCTGTGAGCCCTGGCGAGAGAGCCACA<br>CTGAGCTGTAGGGCCTCCCAGTCTGTGAGCAACAATCTG<br>GCCTGGTATCAGCAGAAGCCAGGCCAGGCACCAAGGCTG<br>CTGATCTACGGAGCATCCACCAGAGCCACAGGAGTGCCA<br>GCAAGGTTCTCCGGATCTGACAGCGGCACCGAGTTTAGC<br>CTGACAATCTCCTCTCTGCAGTCCGAGGACTTCGCCGTG<br>TATTTTTGCCAGCAGTACAAGGATTGGCCATTCACCTTT<br>GGCCCCGGCACAAAGGTGGAGATCAAGACCACAACCCCT<br>GCACCAAGACCACCAACCCCAGCACCTACAATCGCATCC<br>CAGCCTCTGTCTCTGAGACCAGAGGCATGTAGGCCAGCA<br>GCAGGAGGAGCAGTGCACACCAGGGGCCTGGACTTTGCC<br>TGCGATATCTATATCTGGGCACCTCTGGCAGGAACCTGT<br>GGCGTGCTGCTGCTGAGCCTGGTCATCACCCTGTATTGC<br>AAGCGCGGCCGGAAGAAGCTGCTGTACATCTTCAAGCAG<br>CCTTTTATGCGCCCAGTGCAGACAACCCAGGAGGAGGAC<br>GGCTGCTCCTGTCGGTTCCCTGAAGAGGAGGAGGGAGGA<br>TGTGAGCTGAGGGTGAAGTTTTCCCGGTCTGCCGATGCC<br>CCAGCCTATCAGCAGGGCCAGAACCAGCTGTACAACGAG<br>CTGAATCTGGGCCGGAGAGAGGAGTACGACGTGCTGGAT<br>AAGAGGAGGGGAAGAGATCCAGAGATGGGAGGCAAGCCT<br>CGGAGAAAGAACCCACAGGAGGGCCTGTATAATGAGCTG<br>CAGAAGGACAAGATGGCCGAGGCCTACTCCGAGATCGGC<br>ATGAAGGGAGAGAGGCGCCGGGGCAAGGGACACGATGGC<br>CTGTATCAGGGCCTGTCTACCGCCACAAAGGACACCTAC<br>GATGCCCTGCATATGCAGGCACTGCCTCCAAGGTGA<br>(SEQ ID NO: 242) | CD8α signal peptide;<br>14C11 VH (Table 1, SEQ<br>ID NO: 15);<br>GS linker;<br>14C11 VL (Table 1, SEQ<br>ID NO: 16);<br>CD8α hinge;<br>CD8α TM;<br>4-1BB signaling<br>domain;<br>CD3zeta signaling<br>domain |

TABLE 5C-continued

Nucleic acid sequences of exemplary EGFRvIII specific CARs

| CAR | CAR Nucleic Acid Sequence | Components |
|---|---|---|
| 20E12 | ATGGCTCTGCCCGTCACCGCTCTGCTGCTGCCACTGGCC<br>CTGCTGCTGCACGCAGCAAGGCCAGAGGTGAACCTGGTG<br>GAGTCCGGCGGCGGCCTGGTGAAGCCTGGCGGATCCCTG<br>AGGCTGTCTTGCGAGGCAAGCGGCTTCACCTTCAGCTAC<br>GCCTGGATGTCCTGGGTGCGCCAGGCCCCCGGCAAGGGA<br>CTGGAGTGGGTGGGACGGATCAAGTCCATCGCAGACGGA<br>GGAGCAACCGATTACGCAGCCCCTGTGAGAAACAGGTTC<br>ACAATCTCCAGAGACGATTCTAGGAATACCCTGTATCTG<br>GAGATGCACTCTCTGAAGACAGAGGACACCGCCGTGTAC<br>TATTGCACCACAATCCCTGGCAACGACGCCTTTGATATG<br>TGGGGCCAGGGCACAATGGTGACCGTGAGCTCCGGCGGC<br>GGCGGCTCTGGAGGAGGAGGAAGCGGAGGAGGAGGAAGC<br>GGGGGCGGCGGCTCTGACATCGTGCTGACACAGTCCCCA<br>CTGTCCCTGTCTGTGACCCCCGGCGAGCCTGCAAGCATC<br>TCCTGTAGATCTAGCCAGAGCCTGCTGTACTCCAACGGC<br>AAGAATTATCTGGATTGGTTCCTGCACAAGCCAGGCCAG<br>TCTCCCCAGCTGCTGATCTACCTGGGATCTAATAGGGCA<br>AGCGGAGTGCCAGACCGGTTCTCTGGAAGCGGATCCGGC<br>ATCGACTTCATCCTGAAGATCAGCAGGGTGGAGGCCGAG<br>GATGTGGGCGTGTACTATTGCATGCAGGCCCAGCAGACA<br>CCCATCACCTTCGGCCAGGGCACAAGACTGGAGATCAAG<br>ACCACAACCCCAGCACCAAGGCCACCTACACCTGCACCA<br>ACCATCGCATCCCAGCCACTGTCTCTGAGGCCTGAGGCA<br>TGTCGGCCAGCAGCAGGAGGAGCAGTGCACACCCGCGGC<br>CTGGACTTTGCCTGCGATATCTACATCTGGGCACCACTG<br>GCAGGAACATGTGGCGTGCTGCTGCTGAGCCTGGTCATC<br>ACCCTGTACTGCAAGCGCGGCCGGAAGAAGCTGCTGTAT<br>ATCTTCAAGCAGCCTTTTATGAGACCAGTGCAGACAACC<br>CAGGAGGAGGACGGCTGCTCCTGTAGGTTCCCTGAAGAG<br>GAGGAGGGCGGCTGTGAGCTGAGAGTGAAGTTTTCTAGG<br>AGCGCCGATGCACCAGCATACCAGCAGGGACAGAATCAG<br>CTGTATAACGAGCTGAATCTGGGCCGGAGAGAGGAGTAT<br>GACGTGCTGGATAAGAGGAGGGGAAGGGACCCTGAGATG<br>GGAGGCAAGCCCCGGAGAAAGAACCCTCAGGAGGGCCTG<br>TACAATGAGCTGCAGAAGGACAAGATGGCCGAGGCCTAT<br>AGCGAGATCGGCATGAAGGGAGAGAGGCGCCGGGGCAAG<br>GGACACGATGGCCTGTACCAGGGCCTGTCCACAGCCACC<br>AAGGACACCTATGATGCCCTGCATATGCAGGCACTGCCT<br>CCAAGGTGA<br>(SEQ ID NO: 243) | CD8α signal peptide;<br>20E12 VH (Table 1, SEQ<br>ID NO: 39);<br>GS linker;<br>20E12 VL (Table 1, SEQ<br>ID NO: 40);<br>CD8α hinge;<br>CD8α TM;<br>4-1BB signaling<br>domain;<br>CD3zeta signaling<br>domain |
| 32G8 | ATGGCTCTGCCCGTCACCGCTCTGCTGCTGCCACTGGCC<br>CTGCTGCTGCACGCAGCAAGGCCAGAGGTGAACCTGGTG<br>GAGTCCGGCGGCGGCCTGGTGAAGCCTGGCGGATCCCTG<br>AGGCTGTCTTGCGAGGCAAGCGGCTTCACCTTCAGCTAC<br>GCCTGGATGTCCTGGGTGCGCCAGGCCCCCGGCAAGGGA<br>CTGGAGTGGGTGGGCCGGATCAAGTCCATCACCGACGGA<br>GGCGTGATCGATTACGCAGCACCTGTGAGAAACAGGTGC<br>ACAATCTCCAGAGACGATTCTAGGAATACCCTGTATCTG<br>GAGATGCACTCTCTGAAGACAGAGGACACCGCCGTGTAC<br>TATTGTACCACAATCCCTGGCAACGACGATTTCGATATG<br>TGGGGCCAGGGCAGAATGGTGACCGTGAGCTCCGGCGGC<br>GGCGGCTCTGGAGGAGGAGGAAGCGGAGGAGGAGGAAGC<br>GGGGGCGGCGGCTCTGACATCGTGCTGACACAGTCCCCA<br>CTGTCCCTGTCTGTGACCCCCGGCGAGCCTGCAAGCATC<br>TCCTGTAGGTCTAGCCAGAGCCTGCTGTACTCCAACGGC<br>AAGAATTATCTGGATTGGTTTCTGCACAAGCCAGGCCAG<br>TCTCCCCAGCTGCTGATCTACCTGGGATCTAATAGGGCA<br>AGCGGAGTGCCAGACCGGTTCTCTGGAAGCGGATCCGGC<br>ATCGACTTCATCCTGAAGATCAGCCGCGTGGAGGCAGAG<br>GACGTGGGCGTGTACTATTGCATGCAGGCCCAGCAGACA<br>CCCATCACCTTCGGCCAGGGCACAAGACTGGAGATCAAG<br>ACCACAACCCCAGCACCAAGGCCACCTACACCTGCACCA<br>ACCATCGCATCCCAGCCACTGTCTCTGAGGCCTGAGGCA<br>TGTAGGCCAGCAGCAGGAGGAGCAGTGCACACCAGAGGC<br>CTGGACTTTGCCTGCGATATCTACATCTGGGCACCACTG<br>GCAGGAACATGTGGCGTGCTGCTGCTGAGCCTGGTCATC<br>ACCCTGTACTGCAAGCGCGGCCGGAAGAAGCTGCTGTAT<br>ATCTTCAAGCAGCCTTTTATGAGACCAGTGCAGACAACC<br>CAGGAGGAGGACGGCTGCTCCTGTAGGTTCCCTGAAGAG<br>GAGGAGGGCGGCTGTGAGCTGAGAGTGAAGTTTTCTAGG<br>AGCGCCGATGCACCAGCATACCAGCAGGGACAGAATCAG<br>CTGTATAACGAGCTGAATCTGGGCCGGAGAGAGGAGTAT<br>GACGTGCTGGATAAGAGGAGGGGAAGGGATCCTGAGATG<br>GGAGGCAAGCCCCGGAGAAAGAACCCTCAGGAGGGCCTG | CD8α signal Peptide;<br>32G8 VH (Table 1, SEQ<br>ID NO: 43);<br>GS linker;<br>32G8 VL (Table 1, SEQ<br>ID NO: 40);<br>CD8α hinge;<br>CD8α TM;<br>4-1BB signaling<br>domain;<br>CD3zeta signaling<br>domain |

TABLE 5C-continued

Nucleic acid sequences of exemplary EGFRvIII specific CARs

| CAR | CAR Nucleic Acid Sequence | Components |
|---|---|---|
| | TACAATGAGCTGCAGAAGGACAAGATGGCCGAGGCCTAT<br>AGCGAGATCGGCATGAAGGGAGAGAGGCGCCGGGGCAAG<br>GGACACGATGGCCTGTACCAGGGCCTGTCCACAGCCACC<br>AAGGACACCTATGATGCCCTGCATATGCAGGCACTGCCT<br>CCAAGGTGA<br>(SEQ ID NO: 244) | |
| 26B9 | ATGGCTCTGCCCGTCACCGCTCTGCTGCTGCCACTGGCC<br>CTGCTGCTGCACGCAGCAAGGCCAGAGGTGCAGCTGGTG<br>GAGTCTTGGGGCGTGCTGGTGAAGCCTGGCGGATCTCTG<br>AGGCTGAGCTGCGCAGCATCCGGCTTCATCTTTAACAAT<br>GCCTGGATGTCCTGGGTGCGCCAGGCCCCCGGCAAGGGA<br>CTGGAGTGGATCGGCCGGATCAAGAGCAAGTCCGACGGA<br>GGAACCACAGATTACGCAGCACCTGTGAAGGACCGCTTC<br>ACAATCTCTCGGGACGATAGCAAGGATACCCTGTATCTG<br>CAGATGAACGGCCTGAAGACAGAGGACACCGCCGTGTAC<br>TTCTGCACCACAGCCCCTGGCGGCCCCTTTTGATTATTGG<br>GGCCAGGGCACACTGGTGACCGTGAGCTCCGGAGGAGGA<br>GGAAGCGGCGGAGGAGGCAGCGGCGGCGGCGGCTCTGGC<br>GGCGGCGGCAGCGACATCGTGCTGACACAGAGCCCTCTG<br>TCCCTGCCAGTGACCCCCGGCGAGCCTGCCTCTATCAGC<br>TGTCGCTCTAGCCAGAGCCTGCTGCACCGGGACGGCTTC<br>AATTACCTGGATTGGTTTCTGCAGAAGCCAGGCCAGTCC<br>CCCCAGCTGCTGATCTATCTGGCCTCCTCTAGAGCCTCT<br>GGCGTGCCAGACAGGTTCTCCGGCTCTGACAGCGGCACA<br>GACTTCACCCTGAAGATCAGCAGAGTGGAGGCCGAGGAT<br>GTGGGCGTGTACTATTGCATGCAGGCCCTGCAGACACCC<br>ATCACCTTCGGCCAGGGCACAAGACTGGAGATCAAGACC<br>ACAACCCCAGCACCAAGGCCACCTACACCTGCACCAACC<br>ATCGCATCCCAGCCACTGTCTCTGAGACCTGAGGCCTGT<br>AGGCCAGCAGCAGGAGGAGCAGTGCACACCAGGGGCCTG<br>GACTTTGCCTGCGATATCTACATCTGGGCACCTCTGGCA<br>GGAACATGTGGCGTGCTGCTGCTGAGCCTGGTCATCACC<br>CTGTACTGCAAGAGAGGCAGGAAGAAGCTGCTGTATATC<br>TTCAAGCAGCCTTTTATGAGACCAGTGCAGACAACCCAG<br>GAGGAGGACGGCTGCTCCTGTAGGTTCCCTGAAGAGGAG<br>GAGGGAGGATGTGAGCTGAGGGTGAAGTTTTCCCGGTCT<br>GCCGATGCACCAGCATACCAGCAGGGACAGAACCAGCTG<br>TATAACGAGCTGAATCTGGGCCGGAGAGAGGAGTACGAC<br>GTGCTGGATAAGAGGCGCGGCAGAGATCCAGAGATGGGC<br>GGCAAGCCCCGGAGAAAGAACCCTCAGGAGGGCCTGTAC<br>AATGAGCTGCAGAAGGACAAGATGGCCGAGGCCTATAGC<br>GAGATCGGCATGAAGGGAGAGAGGCGCCGGGGCAAGGGA<br>CACGATGGCCTGTACCAGGGCCTGTCCACAGCCACCAAG<br>GACACCTATGATGCCCTGCATATGCAGGCACTGCCTCCA<br>AGGTGA<br>(SEQ ID NO: 245) | CD8α signal peptide;<br>26B9 VH (Table 1, SEQ<br>ID NO: 41);<br>GS linker;<br>26B9 VL (Table 1, SEQ<br>ID NO: 42);<br>CD8α hinge;<br>CD8α TM;<br>4-1BB signaling<br>domain;<br>CD3zeta signaling<br>domain |
| 30D8 | ATGGCTCTGCCCGTCACCGCTCTGCTGCTGCCACTGGCC<br>CTGCTGCTGCACGCAGCAAGGCCTGAGGTGCAGCTGGTG<br>GAGAGCGGCGGCGGCCTGGTGAAGCCTGGCGGATCCCTG<br>AGGCTGTCTTGCGAGGCAAGCGGCTTCACCTTTAGCGAC<br>GCATGGATGTCCTGGGTGCGCCAGGCCCCTGGCAAGGGA<br>CTGGAGTGGGTGGGACGGATCAAGAGCAAGACAGACGGC<br>GGCACCACAGATTACGTGGTGCCACTGAACGGCCGCTTC<br>ATCATCTCCCGCGACGATTCTCGGAATACCCTGTATCTG<br>CAGCTGAACAATCTGAAGACAGAGGATACCGCCGTGTAC<br>TATTG0ACCACAGTGCCAGGCTCCTACGGCTATTGGGGC<br>CAGGGCACACTGGTGACCGTGAGCTCCGGCGGCGGCGGC<br>TCTGGAGGAGGAGGAAGCGGAGGAGGAGGAAGCGGGGGC<br>GGCGGCTCTGACATCGTGATGACACAGTCTCCACTGAGC<br>CTGCCAGTGACCCCTGGCGAGCCAGCCTCCATCTCTTGT<br>CGCTCTAGCCAGAGCCTGCTGCACAACAAGCGGAACAAT<br>TACCTGGATTGGTTTCTGCAGAAGCCTGGCCAGTCCCCT<br>CAGCTGCTGATCTATCTGGCCAGCAATAGAGCCTCCGGA<br>GTGCCAGACAGGTTCTCTGGAGGAGGAAGCGGAACAGAC<br>TTCACCCTGAAGATCAGCAGAGTGGAGGCCGAGGACGTG<br>GGCGTGTACTATTGCATGCAGGCCCAGCAGACACCTATC<br>ACCTTCGGCCAGGGCACAAGACTGGAGATCAAGACCACA<br>ACCCCAGCACCAAGGCCACCTACACCTGCACCAACCATC<br>GCCTCCCAGCCTCTGTCTCTGAGACCAGAGGCATGTAGG<br>CCAGCAGCAGGAGGAGCAGTGCACACCAGGGGCCTGGAC<br>TTTGCCTGCGATATCTACATCTGGGCACCTCTGGCAGGA<br>ACATGTGGCGTGCTGCTGCTGAGCCTGGTCATCACCCTG<br>TACTGCAAGAGAGGCAGGAAGAAGGTGGTGTATATCTTC<br>AAGCAGCCCTTCATGAGACCCGTGCAGACAACCCAGGAG | CD8α signal peptide;<br>30D8 VH (Table 1, SEQ<br>ID NO: 37);<br>GS linker;<br>30D8 VL (Table 1, SEQ<br>ID NO: 38);<br>CD8α hinge;<br>CD8α TM;<br>4-1BB signaling<br>domain;<br>CD3zeta signaling<br>domain |

TABLE 5C-continued

Nucleic acid sequences of exemplary EGFRvIII specific CARs

| CAR | CAR Nucleic Acid Sequence | Components |
|---|---|---|
| | GAGGACGGCTGCTCTTGTAGGTTCCCAGAAGAGGAGGAG<br>GGAGGATGTGAGCTGAGGGTGAAGTTTAGCCGGTCCGCC<br>GATGCACCAGCATACCAGCAGGGACAGAACCAGCTGTAT<br>AACGAGCTGAATCTGGGCCGGAGAGAGGAGTACGACGTG<br>CTGGATAAGAGGAGGGGAAGGGATCCAGAGATGGGAGGC<br>AAGCCTCGGAGAAAGAACCCACAGGAGGGCCTGTACAAT<br>GAGCTGCAGAAGGACAAGATGGCCGAGGCCTATTCTGAG<br>ATCGGCATGAAGGGAGAGAGGCGCCGGGGCAAGGGACAC<br>GATGGCCTGTACCAGGGCCTGAGCACAGCCACCAAGGAC<br>ACCTATGATGCCCTGCATATGCAGGCACTGCCTCCAAGG<br>TGA<br>(SEQ ID NO: 246) | |
| C6 | ATGGCTCTGCCCGTCACCGCTCTGCTGCTGCCTCTGGCC<br>CTGCTGCTGCACGCAGCAAGGCCACAGGTGCAGCTGGTG<br>CAGTCCGGAGCAGAGGTGAAGAAGCCTGGCAGCTCCGTG<br>AAGGTGAGCTGCAAGGCCTCCGGCGACACATTCTCTAGC<br>AACGCAATCAGCTGGGTGCGCCAGGCCCCTGGCCAGGGA<br>CTGGAGTGGATGGGCGTGATCATCCCTATCTTCGGCACC<br>GCCGACTATGCCCAGAAGTTTCAGGGCCGGGTGACAATC<br>ACCGCCGATGAGTCTACAAGCACCGCCTACATGGAGCTG<br>TCCTCTCTGAGATCCGAGGACACAGCCGTGTACTATTGT<br>GCCAGGCACACCTATCACGAGTACGCAGGAGGATACTAT<br>GGAGGAGCAATGGATCCTTGGGGACAGGGCACACTGGTG<br>ACCGTGAGCTCCGGCGGCGGCGGCTCTGGAGGAGGAGGA<br>AGCGGAGGAGGAGGAAGCGGGGGCGGCGGCTCTGAGCTG<br>CAGAGCGTGCTGACCCAGCCACCTTCCGCCTCTGGAACA<br>CCAGGCCAGAGGGTGACCATCAGCTGCTCCGGATCTAGC<br>TCCAACATCGGCTCCAATTACGTGTATTGGTACCAGCAG<br>CTGCCAGGCACAGCCCCCAAGATCCTGATCTACCGCAAC<br>AATCAGCGGCCTTCTGGCGTGCCAGATAGATTCTCTGGC<br>AGCAAGTCCGGCACCTCTGCCAGCCTGGCAATCTCCGGC<br>CTGAGGTCTGAGGACGAGGCCGATTACTATTGCGCCGCC<br>TGGGACGATAACCTGAGCGGCTGGGTGTTTGGCACAGGC<br>ACCAAGCTGACAGTGCTGACCACAACCCCTGCACCAAGA<br>CCACCAACACCAGCACCTACCATCGCAAGCCAGCCACTG<br>TCCCTGAGACCCGAGGCCTGTAGGCCTGCAGCAGGAGGA<br>GCAGTGCACACCAGGGGCCTGGACTTTGCCTGCGATATC<br>TATATCTGGGCACCACTGGCAGGAACATGTGGCGTGCTG<br>CTGCTGAGCCTGGTCATCACCCTGTATTGCAAGAGAGGC<br>AGGAAGAAGCTGCTGTACATCTTCAAGCAGCCCTTTATG<br>CGCCCTGTGCAGACAACCCAGGAGGAGGACGGCTGCAGC<br>TGTCGGTTCCCAGAAGAGGAGGAGGGAGGATGTGAGCTG<br>AGGGTGAAGTTTTCCCGGTCTGCCGATGCACCAGCATAT<br>CAGCAGGGACAGAATCAGCTGTACAACGAGCTGAATCTG<br>GGCCGGAGAGAGGAGTACGACGTGCTGGATAAGAGGAGG<br>GGAAGGGACCCTGAGATGGGAGGCAAGCCACGGAGAAAA<br>ACCCCCAGGAGGGCCTGTATAATGAGCTGCAGAAGGACA<br>AGATGGCCGAGGCCTACTCTGAGATCGGCATGAAGGGAG<br>AGAGGCGCCGGGGCAAGGGACACGATGGCCTGTATCAGG<br>GCCTGAGCACAGCCACCAAGGACACCTACGATGCCCTGC<br>ATATGCAGGCACTGCCTCCAAGGTGA<br>(SEQ ID NO: 247) | CD8α signal peptide;<br>C6 VH (Table 1, SEQ ID<br>NO: 48);<br>GS linker;<br>C6 VL (Table 1, SEQ ID<br>NO: 49);<br>CD8α hinge;<br>CD8α TM;<br>4-1BB signaling<br>domain;<br>CD3zeta signaling<br>domain |

Downregulation or mutation of target antigens is commonly observed in cancer cells, creating antigen-loss escape variants. Thus, to offset tumor escape and render immune cell more specific to target, the EGFRvIII specific CAR can comprise one or more additional extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In some embodiments, said different extracellular ligand-binding domains can be placed on different transmembrane polypeptides composing the CAR. In some embodiments, the invention relates to a population of CARs, each CAR comprising a different extracellular ligand-binding domain. In a particular, the invention relates to a method of engineering immune cells comprising providing an immune cell and expressing at the surface of the cell a population of CARs, each CAR comprising different extracellular ligand-binding domains. In another particular embodiment, the invention relates to a method of engineering an immune cell comprising providing an immune cell and introducing into the cell polynucleotides encoding polypeptides composing a population of CARs each one comprising different extracellular ligand-binding domains. By population of CARs, it is meant at least two, three, four, five, six or more CARs each one comprising different extracellular ligand-binding domains. The different extracellular ligand-binding domains according to the invention can preferably simultaneously bind different elements in target thereby augmenting immune cell activation and function. The invention also relates to an isolated immune cell which comprises a population of CARs each one comprising different extracellular ligand-binding domains.

In another aspect, the invention provides polynucleotides encoding any of the CARs and polypeptides described herein. Polynucleotides can be made and expressed by procedures known in the art.

In another aspect, the invention provides compositions (such as a pharmaceutical compositions) comprising any of the cells of the invention. In some embodiments, the composition comprises a cell comprising a polynucleotide encoding any of the CARs described herein.

Expression vectors, and administration of polynucleotide compositions are further described herein.

In another aspect, the invention provides a method of making any of the polynucleotides described herein.

Polynucleotides complementary to any such sequences are also encompassed by the invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the invention. Further, alleles of the genes comprising the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratogene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding an EGFRvIII specific CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a signal peptide, leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In some embodiments the signal peptide comprises the amino acid sequence shown in SEQ ID NO: 206 or 214. Those skilled in the art will recognize that, in view of the degeneracy of the genetic code, considerable sequence variation is possible among these polynucleotide molecules. In some embodiments, nucleic acid sequences of the invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding identical amino acids as the codons that are being exchanged.

Methods of Engineering an Immune Cell

Methods of preparing immune cells for use in immunotherapy are provided herein. In some embodiments, the methods comprise introducing a CAR according to the invention into immune cells, and expanding the cells. In some embodiments, the invention relates to a method of engineering an immune cell comprising: providing a cell and expressing at the surface of the cell at least one CAR as described above. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the method comprises: transforming the cell with at least one polynucleotide encoding CAR as described above, and expressing the polynucleotides in the cell.

In some embodiments, the polynucleotides are present in lentiviral vectors for stable expression in the cells.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, dCK, CD52, GR, PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or Cas9 endonuclease.

In some embodiments, an additional catalytic domain is used with a rare-cutting endonuclease to enhance its capacity to inactivate targeted genes. For example, an additional catalytic domain can be a DNA end-processing enzyme. Non-limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non-limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In some embodiments, an additional catalytic domain can have a 3'-5'-exonuclease activity, and in some embodiments, said additional catalytic domain is TREX, more preferably TREX2 catalytic domain (WO2012/058458). In some embodiments, said catalytic domain is encoded by a single chain TREX polypeptide. The additional catalytic domain may be fused to a nuclease fusion protein or chimeric protein. In some embodiments, the additional catalytic domain is fused using, for example, a peptide linker.

In some embodiments, the method further comprises a step of introducing into cells an exogeneous nucleic acid comprising at least a sequence homologous to a portion of the target nucleic acid sequence, such that homologous recombination occurs between the target nucleic acid sequence and the exogeneous nucleic acid. In some embodimentss, said exogenous nucleic acid comprises first and second portions which are homologous to region 5' and 3' of the target nucleic acid sequence, respectively. The exogenous nucleic acid may also comprise a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. In some embodiments, homologous sequences of at least about 50 bp, greater than about 100 bp, or greater than about 200 bp can be used within the donor matrix. The exogenous nucleic acid can be, for example without limitation, from about 200 bp to about 6000 bp, more preferably from about 1000 bp to about 2000 bp. Shared nucleic acid homologies are located in regions flanking upstream and downstream the site of the break, and the nucleic acid sequence to be introduced is located between the two arms.

In some embodiments, a nucleic acid successively comprises a first region of homology to sequences upstream of said cleavage; a sequence to inactivate a targeted gene selected from the group consisting of TCRα, TCRβ, CD52, glucocorticoid receptor (GR), deoxycytidine kinase (dCK), and an immune checkpoint protein such as for example programmed death-1 (PD-1); and a second region of homology to sequences downstream of the cleavage. The polynucleotide introduction step can be simultaneous, before or after the introduction or expression of the rare-cutting endonuclease. Depending on the location of the target nucleic acid sequence wherein break event has occurred, such exogenous nucleic acid can be used to knock-out a gene, e.g. when exogenous nucleic acid is located within the open reading frame of the gene, or to introduce new sequences or genes of interest. Sequence insertions by using such exogenous nucleic acid can be used to modify a targeted existing gene, by correction or replacement of the gene (allele swap as a non-limiting example), or to up- or down-regulate the expression of the targeted gene (promoter swap as non-limiting example), the targeted gene correction or replacement. In some embodiments, inactivation of a genes selected from the group consisting of TCRα, TCRβ, CD52, GR, dCK, and immune checkpoint proteins, can be done at a precise genomic location targeted by a specific TALE-nuclease, wherein said specific TALE-nuclease catalyzes a cleavage and wherein the exogenous nucleic acid successively comprising at least a region of homology and a sequence to inactivate one targeted gene selected from the group consisting of TCRα, TCRβ, CD52, GR, dCK, immune checkpoint proteins which is integrated by homologous recombination. In some embodiments, several genes can be, successively or at the same time, inactivated by using several TALE-nucleases respectively and specifically targeting one defined gene and several specific polynucleotides for specific gene inactivation.

In some embodiments, the method comprises inactivation of one or more additional genes selected from the group consisting of TCRα, TCRβ, CD52, GR, dCK, and immune checkpoint proteins. In some embodiments, inactivation of a gene can be accomplished by introducing into the cells at least one rare-cutting endonuclease such that the rare-cutting endonuclease specifically catalyzes cleavage in a targeted sequence of the cell genome; and optionally, introducing into the cells an exogenous nucleic acid successively comprising a first region of homology to sequences upstream of the cleavage, a sequence to be inserted in the genome of the cell, and a second region of homology to sequences downstream of the cleavage; wherein the introduced exogenous nucleic acid inactivates a gene and integrates at least one exogenous polynucleotide sequence encoding at least one recombinant protein of interest. In some embodiments, the exogenous polynucleotide sequence is integrated within a gene encoding a protein selected from the group consisting of TCRα, TCRβ, CD52, GR, dCK, and immune checkpoint protein.

In another aspect, a step of genetically modifying cells can comprise: modifying T cells by inactivating at least one gene expressing a target for an immunosuppressive agent, and; expanding the cells, optionally in presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others may act through activation of T cells or by inhibiting the activation of helper cells. The methods according to the invention allow conferring immunosuppressive resistance to T cells for immunotherapy by inactivating the target of the immunosuppressive agent in T cells. As non-limiting examples, targets for immunosuppressive agent can be a receptor for an immunosuppressive agent such as for example without limitation CD52, glucocorticoid receptor (GR), FKBP family gene members, and cyclophilin family gene members.

In some embodiments, the genetic modification of the method involves expression, in provided cells to engineer, of one rare-cutting endonuclease such that the rare-cutting endonuclease specifically catalyzes cleavage in one targeted gene thereby inactivating the targeted gene. In some embodiments, a method of engineering cells comprises at least one of the following steps: providing a T cell, such as from a cell culture or from a blood sample; selecting a gene in the T cell expressing a target for an immunosuppressive agent; introducing into the T cell a rare-cutting endonuclease able to selectively inactivate by DNA cleavage, preferably by double-strand break the gene encoding a target for the immunosuppressive agent, and expanding the cells, optionally in presence of the immunosuppressive agent.

In some embodiments, the method comprises: providing a T cell, such as from a cell culture or from a blood sample; selecting a gene in the T cell wherein the gene expresses a target for an immunosuppressive agent; transforming the T cell with nucleic acid encoding a rare-cutting endonuclease able to selectively inactivate by DNA cleavage, preferably by double-strand break the gene encoding a target for the immunosuppressive agent, and expressing the rare-cutting endonucleases into the T cells; and expanding the cells, optionally in presence of the immunosuppressive agent.

In some embodiments, the rare-cutting endonuclease specifically targets CD52 or GR. In some embodiments, the gene selected for inactivation encodes CD52, and the immunosuppressive treatment comprises a humanized antibody targeting CD52 antigen. In some embodiments, the gene selected for inactivation encodes GR, and the immunosuppressive treatment comprises a corticosteroid such as dexamethasone. In some embodiments, the gene selected for inactivation is a FKBP family gene member or a variant thereof and the immunosuppressive treatment comprises FK506, also known as Tacrolimus or fujimycin. In some embodiments, the FKBP family gene member is FKBP12 or a variant thereof. In some embodiments, gene selected for inactivation is a cyclophilin family gene member or a variant thereof and the immunosuppressive treatment comprises cyclosporine.

In some embodiments, the rare-cutting endonuclease can be, for example, a meganuclease, a zinc finger nuclease, or a TALE-nuclease. In some embodiments, the rare-cutting endonuclease is a TALE-nuclease.

Also provided herein are methods of engineering T cells, suitable for immunotherapy, wherein the methods comprise: genetically modifying T cells by inactivating at least one immune checkpoint protein. In some embodiments the immune checkpoint protein is, for example, PD-1 and/or CTLA-4. In some embodiments, methods of genetically modifying a cell comprises: modifying T cells by inactivating at least one immune checkpoint protein; and expanding the cells. Immune checkpoint proteins include, but are not limited to Programmed Death 1 (PD-1, also known as PDCD1 or CD279, accession number: NM-005018), Cytotoxic T-Lymphocyte Antigen 4 (CTLA-4, also known as CD152, GenBank accession number AF414120.1), LAG3 (also known as CD223, accession number: NM-002286.5), Tim3 (also known as HAVCR2, GenBank accession number: JX049979.1), BTLA (also known as CD272, accession number: NM-181780.3), BY55 (also known as CD160, GenBank accession number: CR541888.1), TIGIT (also known as VSTM3, accession number: NM-173799), B7H5 (also known as C10orf54, homolog of mouse vista gene, accession number: NM-022153.1), LAIR1 (also known as CD305, GenBank accession number: CR542051.1), SIGLEC10 (GeneBank accession number: AY358337.1), 2B4 (also known as CD244, accession number: NM-001166664.1), which directly inhibit immune cells. For example, CTLA-4 is a cell-surface protein expressed on certain CD4 and CD8 T cells; when engaged by its ligands (B7-1 and B7-2) on antigen presenting cells, T cell activation and effector function are inhibited.

In some embodiments, said method to engineer cells comprises at least one of the following steps: providing a T cell, such as from a cell culture or from a blood sample; introducing into the T cell a rare-cutting endonuclease able to selectively inactivate by DNA cleavage, preferably by double-strand break one gene encoding an immune checkpoint protein; and expanding the cells. In some embodiments, the method comprises: providing a T cell, such as from a cell culture or from a blood sample; transfecting said T cell with nucleic acid encoding a rare-cutting endonuclease able to selectively inactivate by DNA cleavage, preferably by double-strand break a gene encoding an immune checkpoint protein; expressing the rare-cutting endonucleases into the T cells; expanding the cells. In some embodiments, the rare-cutting endonuclease specifically targets a gene selected from the group consisting of: PD-1, CTLA-4, LAG3, Tim3, BTLA, BY55, TIGIT, B7H5, LAIR1, SIGLEC10, 2B4, TCRα, and TCRβ. In some embodiments, the rare-cutting endonuclease can be a meganuclease, a zinc finger nuclease or a TALE-nuclease. In some embodiments, the rare-cutting endonuclease is a TALE-nuclease.

In some embodiments, the present invention can be particularly suitable for allogeneic immunotherapy. In such embodiments, cells may be modified by a method comprising: inactivating at least one gene encoding a component of the T cell receptor (TCR) in T cells; and expanding the T cells. In some embodiments, the genetic modification of the method relies on the expression, in provided cells to engineer, of one rare-cutting endonuclease such that the rare-cutting endonuclease specifically catalyzes cleavage in one targeted gene thereby inactivating the targeted gene. In some embodiments, said method to engineer cells comprises at least one of the following steps: providing a T cell, such as from a cell culture or from a blood sample; introducing into the T cell a rare-cutting endonuclease able to selectively inactivate by DNA cleavage, preferably by double-strand break at least one gene encoding a component of the T cell receptor (TCR), and expanding the cells.

In some embodiments, the method comprises: providing a T cell, such as from a cell culture or from a blood sample; transfecting said T cell with nucleic acid encoding a rare-cutting endonuclease able to selectively inactivate by DNA cleavage, preferably by double-strand break at least one gene encoding a component of the T cell receptor (TCR); expressing the rare-cutting endonucleases into the T cells;

sorting the transfected T cells, which do not express TCR on their cell surface; and expanding the cells.

In some embodiments, the rare-cutting endonuclease can be a meganuclease, a zinc finger nuclease or a TALE-nuclease. In some embodiments, the rare-cutting endonuclease is a TALE-nuclease. In some embodiments the TALE-nucleases recognize and cleave a sequence encoding TCRα or TCRβ. In some embodiments a TALE-nuclease comprises a polypeptide sequence selected from the amino acid sequence shown in SEQ ID NO: 218, 219, 220, 221, 222, 223, 224, or 225.

```
TALE-nuclease polypeptide sequences:
Repeat TRAC T01-L
                                                         (SEQ ID NO: 218)
LTPQQVVAIASNGGGKQALETVQRLLPVLCQAHGLTPQQVVAIASNNGGKQALETVQRLL

PVLCQAHGLTPQQVVAIASNGGGKQALETVQRLLPVLCQAHGLTPEQVVAIASHDGGKQ

ALETVQRLLPVLCQAHGLTPEQVVAIASHDGGKQALETVQRLLPVLCQAHGLTPEQVVAIA

SHDGGKQALETVQRLLPVLCQAHGLTPEQVVAIASNIGGKQALETVQALLPVLCQAHGLT

PEQVVAIASHDGGKQALETVQRLLPVLCQAHGLTPEQVVAIASNIGGKQALETVQALLPVL

CQAHGLTPQQVVAIASNNGGKQALETVQRLLPVLCQAHGLTPEQVVAIASNIGGKQALET

VQALLPVLCQAHGLTPQQVVAIASNGGGKQALETVQRLLPVLCQAHGLTPEQVVAIASNI

GGKQALETVQALLPVLCQAHGLTPQQVVAIASNGGGKQALETVQRLLPVLCQAHGLTPE

QVVAIASHDGGKQALETVQRLLPVLCQAHGLTPQQVVAIASNGGGRPALE

Repeat TRAC T01-R
                                                         (SEQ ID NO: 219)
LTPEQVVAIASHDGGKQALETVQRLLPVLCQAHGLTPQQVVAIASNGGGKQALETVQRLL

PVLCQAHGLTPEQVVAIASHDGGKQALETVQRLLPVLCQAHGLTPEQVVAIASNIGGKQA

LETVQALLPVLCQAHGLTPQQVVAIASNNGGKQALETVQRLLPVLCQAHGLTPEQVVAIA

SHDGGKQALETVQRLLPVLCQAHGLTPQQVVAIASNGGGKQALETVQRLLPVLCQAHGL

TPQQVVAIASNNGGKQALETVQRLLPVLCQAHGLTPQQVVAIASNNGGKQALETVQRLLP

VLCQAHGLTPQQVVAIASNGGGKQALETVQRLLPVLCQAHGLTPEQVVAIASNIGGKQAL

ETVQALLPVLCQAHGLTPEQVVAIASHDGGKQALETVQRLLPVLCQAHGLTPEQVVAIAS

NIGGKQALETVQALLPVLCQAHGLTPEQVVAIASHDGGKQALETVQRLLPVLCQAHGLTP

QQVVAIASNNGGKQALETVQRLLPVLCQAHGLTPQQVVAIASNGGGRPALE

Repeat TRBC T01-L
                                                         (SEQ ID NO: 220)
LTPQQVVAIASNNGGKQALETVQRLLPVLCQAHGLTPQQVVAIASNGGGKQALETVQRLL

PVLCQAHGLTPQQVVAIASNNGGKQALETVQRLLPVLCQAHGLTPQQVVAIASNGGGKQ

ALETVQRLLPVLCQAHGLTPQQVVAIASNGGGKQALETVQRLLPVLCQAHGLTPQQVVAI

ASNGGGKQALETVQRLLPVLCQAHGLTPQQVVAIASNNGGKQALETVQRLLPVLCQAHG

LTPEQVVAIASNIGGKQALETVQALLPVLCQAHGLTPQQVVAIASNNGGKQALETVQRLLP

VLCQAHGLTPEQVVAIASHDGGKQALETVQRLLPVLCQAHGLTPEQVVAIASHDGGKQAL

ETVQRLLPVLCQAHGLTPEQVVAIASNIGGKQALETVQALLPVLCQAHGLTPQQVVAIASN

GGGKQALETVQRLLPVLCQAHGLTPEQVVAIASHDGGKQALETVQRLLPVLCQAHGLTP

EQVVAIASNIGGKQALETVQALLPVLCQAHGLTPQQVVAIASNGGGRPALE

Repeat TRBC T01-R
                                                         (SEQ ID NO: 221)
NPQRSTVWYLTPQQVVAIASNNGGKQALETVQRLLPVLCQAHGLTPQQVVAIASNGGGK

QALETVQRLLPVLCQAHGLTPQQVVAIASNNGGKQALETVQRLLPVLCQAHGLTPQQVV
```

-continued

```
A1ASNNGGKQALETVQRLLPVLCQAHGLTPEQVVAIASHDGGKQALETVQRLLPVLCQAH

GLTPEQVVAIASHDGGKQALETVQRLLPVLCQAHGLTPQQVVAIASNGGGKQALETVQRL

LPVLCQAHGLTPQQVVAIASNGGGKQALETVQRLLPVLCQAHGLTPQQVVAIASNGGGK

QALETVQRLLPVLCQAHGLTPQQVVAIASNGGGKQALETVQRLLPVLCQAHGLTPQQVV

A1ASNNGGKQALETVQRLLPVLCQAHGLTPQQVVAIASNNGGKQALETVQRLLPVLCQAH

GLTPQQVVAIASNNGGKQALETVQRLLPVLCQAHGLTPQQVVAIASNGGGKQALETVQR

LLPVLCQAHGLTPQQVVAIASNNGGKQALETVQRLLPVLCQAHGLTPQQVVAIASNGGGR

PALE

Repeat TRBC T02-L
                                             (SEQ ID NO: 222)
LTPEQVVAIASHDGGKQALETVQRLLPVLCQAHGLTPEQVVAIASHDGGKQALETVQRLL

PVLCQAHGLTPEQVVAIASHDGGKQALETVQRLLPVLCQAHGLTPEQVVAIASNIGGKQA

LETVQALLPVLCQAHGLTPEQVVAIASHDGGKQALETVQRLLPVLCQAHGLTPEQVVAIAS

HDGGKQALETVQRLLPVLCQAHGLTPEQVVAIASHDGGKQALETVQRLLPVLCQAHGLT

PQQVVAIASNNGGKQALETVQRLLPVLCQAHGLTPEQVVAIASNIGGKQALETVQALLPVL

CQAHGLTPQQVVAIASNNGGKQALETVQRLLPVLCQAHGLTPQQVVAIASNNGGKQALE

TVQRLLPVLCQAHGLTPQQVVAIASNGGGKQALETVQRLLPVLCQAHGLTPEQVVAIASH

DGGKQALETVQRLLPVLCQAHGLTPQQVVAIASNNGGKQALETVQRLLPVLCQAHGLTP

EQVVAIASHDGGKQALETVQRLLPVLCQAHGLTPQQVVAIASNGGGRPALE

Repeat TRBC T02-R
                                             (SEQ ID NO: 223)
LTPQQVVAIASNNGGKQALETVQRLLPVLCQAHGLTPQQVVAIASNNGGKQALETVQRLL

PVLCQAHGLTPQQVVAIASNNGGKQALETVQRLLPVLCQAHGLTPEQVVAIASNIGGKQA

LETVQALLPVLCQAHGLTPQQVVAIASNNGGKQALETVQRLLPVLCQAHGLTPEQVVAIA

SNIGGKQALETVQALLPVLCQAHGLTPQQVVAIASNGGGKQALETVQRLLPVLCQAHGLT

PEQVVAIASHDGGKQALETVQRLLPVLCQAHGLTPQQVVAIASNGGGKQALETVQRLLPV

LCQAHGLTPEQVVAIASHDGGKQALETVQRLLPVLCQAHGLTPQQVVAIASNGGGKQAL

ETVQRLLPVLCQAHGLTPQQVVAIASNNGGKQALETVQRLLPVLCQAHGLTPEQVVAIAS

HDGGKQALETVQRLLPVLCQAHGLTPQQVVAIASNGGGKQALETVQRLLPVLCQAHGLT

PQQVVAIASNGGGKQALETVQRLLPVLCQAHGLTPQQVVAIASNGGGRPALE

Repeat CD52 T02-L
                                             (SEQ ID NO: 224)
LTPQQVVAIASNGGGKQALETVQRLLPVLCQAHGLTPEQVVAIASHDGGKQALETVQRLL

PVLCQAHGLTPEQVVAIASHDGGKQALETVQRLLPVLCQAHGLTPQQVVAIASNGGGKQ

ALETVQRLLPVLCQAHGLTPEQVVAIASHDGGKQALETVQRLLPVLCQAHGLTPEQVVAIA

SHDGGKQALETVQRLLPVLCQAHGLTPQQVVAIASNGGGKQALETVQRLLPVLCQAHGL

TPEQVVAIASNIGGKQALETVQALLPVLCQAHGLTPEQVVAIASHDGGKQALETVQRLLPV

LCQAHGLTPQQVVAIASNGGGKQALETVQRLLPVLCQAHGLTPEQVVAIASHDGGKQAL

ETVQRLLPVLCQAHGLTPEQVVAIASNIGGKQALETVQALLPVLCQAHGLTPEQVVAIASH

DGGKQALETVQRLLPVLCQAHGLTPEQVVAIASHDGGKQALETVQRLLPVLCQAHGLTPE

QVVAIASNIGGKQALETVQALLPVLCQAHGLTPQQVVAIASNGGGRPALE

Repeat CD52 T02-R
                                             (SEQ ID NO: 225)
LTPQQVVAIASNGGGKQALETVQRLLPVLCQAHGLTPQQVVAIASNNGGKQALETVQRLL

PVLCQAHGLTPEQVVAIASHDGGKQALETVQRLLPVLCQAHGLTPQQVVAIASNGGGKQ
```

-continued

```
ALETVQRLLPVLCQAHGLTPEQVVAIASHDGGKQALETVQRLLPVLCQAHGLTPQQVVAI

ASNGGGKQALETVQRLLPVLCQAHGLTPQQVVAIASNGGGKQALETVQRLLPVLCQAHG

LTPEQVVAIASNIGGKQALETVQALLPVLCQAHGLTPEQVVAIASHDGGKQALETVQRLLP

VLCQAHGLTPEQVVAIASHDGGKQALETVQRLLPVLCQAHGLTPQQVVAIASNGGGKQA

LETVQRLLPVLCQAHGLTPQQVVAIASNNGGKQALETVQRLLPVLCQAHGLTPQQVVAIA

SNGGGKQALETVQRLLPVLCQAHGLTPEQVVAIASNIGGKQALETVQALLPVLCQAHGLT

PEQVVAIASHDGGKQALETVQRLLPVLCQAHGLTPQQVVAIASNGGGRPALE
```

In another aspect, another step of genetically modifying a cell can be a method of expanding TCRα deficient T cells comprising introducing into the T cell pTα (also known as preTCRα) or a functional variant thereof and expanding the cells, optionally through stimulation of the CD3 complex. In some embodiments, the method comprises: a) transforming the cells with a nucleic acid encoding at least a fragment of pTα to support CD3 surface expression; b) expressing said pTα into the cells; and c) expanding the cells, optionally through stimulation of the CD3 complex.

Also provided are methods of preparing T cells for immunotherapy comprising steps of a method provided herein for expansion of T cells. In some embodiments, the pTα polynucleotide sequence can be introduced randomly or by homologous recombination. In some embodiments, the insertion can be associated with the inactivation of the TCRα gene.

Different functional variants of pTα can be used. A "functional variant" of the peptide refers to a molecule substantially similar to either the entire peptide or a fragment thereof. A "fragment" of the pTα or functional variant thereof refers to any subset of the molecule, that is, a shorter peptide than the full-length pTα. In some embodiments, pTα or functional variants can be, for example, full-length pTα or a C-terminal truncated pTα version. C-terminal truncated pTα lacks in C-terminal end one or more residues. As non limiting examples, C-terminal truncated pTα version lacks 18, 48, 62, 78, 92, 110 or 114 residues from the C-terminus of the protein. Amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In a preferred embodiment, at least one mutation is introduced in the different pTα versions as described above to affect dimerization. As a non limiting example, a mutated residue can be at least W46R, D22A, K24A, R102A or R117A of the human pTα protein or aligned positions using CLUSTALW method on pTα family or homologue member. Preferably pTα or a variant thereof as described above comprise the mutated residue W46R or the mutated residues D22A, K24A, R102A and R117A. In some embodiments, said pTα or variants are also fused to a signal-transducing domain such as CD28, OX40, ICOS, CD27, CD137 (4-1BB) and CD8 as non limiting examples. The extracellular domain of pTα or variants as described above can be fused to a fragment of the TCRα protein, particularly the transmembrane and intracellular domain of TCRα. pTα variants can also be fused to the intracellular domain of TCRα.

In some embodiments, pTα versions can be fused to an extracellular ligand-binding domain. In some embodiments, pTα or a functional variant thereof is fused to a single chain antibody fragment (scFv) comprising the light and the heavy variable fragment of a target antigen specific monoclonal antibody joined by a flexible linker.

The term "TCRα deficient T cell" refers to an isolated T cell that lacks expression of a functional TCRα chain. This may be accomplished by different means, as non limiting examples, by engineering a T cell such that it does not express any functional TCRα on its cell surface or by engineering a T cell such that it produces very little functional TCRα chain on its surface or by engineering a T cell to express mutated or truncated form of TCRα chain. TCRα deficient cells can no longer be expanded through CD3 complex. Thus, to overcome this problem and to allow proliferation of TCRα deficient cells, pTα or functional variant thereof is introduced into the cells, thus restoring a functional CD3 complex. In some embodiments, the method further comprises introducing into said T cells rare-cutting endonucleases able to selectively inactivate by DNA cleavage one gene encoding one component of the T cell receptor (TCR). In some embodiments, the rare-cutting endonuclease is a TALE-nuclease.

In another aspect, engineered T cells obtained by the methods described herein can be contacted with bispecific antibodies. For example, the T cells can be contacted with bispecific antibodies ex vivo prior to administration to a patient, or in vivo following administration to a patient. Bispecific antibodies comprise two variable regions with distinct antigen properties that facilitate bringing the engineered cells into proximity to a target antigen. As a non-limiting example, a bispecific antibody can be directed against a tumor marker and lymphocyte antigen, such as for example without limitation CD3, and has the potential to redirect and activate any circulating T cells against tumors.

In some embodiments, polynucleotides encoding polypeptides according to the present invention can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transforming T cells. In some embodiments, the method comprises: contacting a T cell with RNA and applying to the T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transforming T cell comprising contacting said T cell with RNA and applying to T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, as non limiting examples, an RNA encodes a rare-cutting endonuclease, one monomer of a rare-cutting endonuclease such as half-TALE-nuclease, a CAR, at least one component of a multi-chain chimeric antigen receptor, a pTα or functional variant thereof, an exogenous nucleic acid, and/or one additional catalytic domain.

Engineered Immune Cells

The invention also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be produced outside of cells, and then introduced into cells. Methods for introducing a polynucleotide construct into cells are known in the art. In some embodiments, stable transfection methods can be used to integrate the polynucleotide construct into the genome of the cell. In other embodiments, transient transfection methods can be used to transiently express the polynucleotide construct, and the polynucleotide construct is not integrated into the genome of the cell. In other embodiments, virus-mediated methods can be used. The polynucleotides may be introduced into a cell by any suitable means such as for example, recombinant viral vectors (e.g. retroviruses, adenoviruses), liposomes, and the like. Transient transfection methods include, for example without limitation, microinjection, electroporation or particle bombardment. Polynucleotides may be included in vectors, such as for example plasmid vectors or viral vectors.

Also provided herein are isolated cells and cell lines obtained by the above-described methods of engineering cells provided herein. In some embodiments, an isolated cell comprises at least one CAR as described above. In some embodiments, an isolated cell comprises a population of CARs, each CAR comprising different extracellular ligand-binding domains.

Also provided herein are isolated immune cells obtained according to any one of the methods described above. Any immune cell capable of expressing heterologous DNAs can be used for the purpose of expressing the CAR of interest. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes, memory T-lymphocytes, or helper T-lymphocytes. In some embodiments, the cell can be derived from the group consisting of CD4+ T-lymphocytes and CD8+T-lymphocytes.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer or from a patient diagnosed with an infection. In some embodiments, cells can be part of a mixed population of cells which present different phenotypic characteristics.

Also provided herein are cell lines obtained from a transfected T cell according to any of the above-described methods. Also provided herein are modified cells resistant to an immunosuppressive treatment. In some embodiments, an isolated cell according to the invention comprises a polynucleotide encoding a CAR.

The immune cells of the invention can be activated and expanded, either prior to or after genetic modification of the T cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-Vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFβ, and TNF, or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, AIM-V, DMEM, MEM, a-MEM, F-12, X-Vivo 10, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In some embodiments, the cells of the invention can be expanded by co-culturing with tissue or cells. The cells can also be expanded in vivo, for example in the subject's blood after administering the cell into the subject.

In some embodiments, an isolated cell according to the present invention comprises one inactivated gene selected from the group consisting of CD52, dCK, GR, PD-1, CTLA-4, LAG3, Tim3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present invention comprises two inactivated genes selected from the group consisting of: CD52 and GR, CD52 and TCRα, CDR52 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRp and/or expresses a CAR, a multi-chain CAR and a pTα transgene.

In some embodiments, TCR is rendered not functional in the cells according to the invention by inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, and which may be obtained by this method are encompassed in the scope of the present invention. Modified cells disclosed herein can be used for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCRα and/or TCRp genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are EGFRvIII specific CAR-T cells comprising an inactivated dCK gene. In some embodiments, the dCK knockout cells are made by transfection of T cells using polynucleotides encoding specific TAL-nuclease directed against dCK genes by, for example, electroporation of mRNA. The dCK knockout EGFRvIII specific CAR-T cells are resistant to PNAs, including for example clorofarabine and/or fludarabine, and maintain T cell cytotoxic activity toward EGFRvIII-expressing cells. In another example, the chemotherapy drug can be, for example, a CD52-targeting molecule, such as a monoclonal anti-CD52 antibody (e.g. alemtuzumab). CD52 is a protein present on the surface of lymphocytes, and anti-CD52 antibodies can induce apoptosis and lysis of immune cells through antibody- and complement-dependent cytotoxicity, leading to lymphodepletion. Provided herein are EGFRvIII specific CAR-T cells comprising an inactivated CD52 gene. In some embodiments, CD52 knockout cells are made by transfection of T cells using polynucleotides encoding a specific TAL-nuclease directed against the CD52 gene by, for example, electroporation of mRNA. The CD52 knockout EGFRvIII specific CAR-T cells are resistant to anti-CD52 molecules, including for example alemtuzumab, and maintain T cell cytotoxic activity toward EGFRvIII-expressing cells in the presence of anti-CD52 molecules.

In some embodiments, isolated cells or cell lines of the invention can comprise a pTα or a functional variant thereof. In some embodiments, an isolated cell or cell line can be further genetically modified by inactivating the TCRα gene.

In some embodiments, the CAR-T cell comprises a polynucleotide encoding a suicide polypeptide, such as for example RQR8. See, e.g., WO2013153391A, which is hereby incorporated by reference in its entirety. In CAR-T cells comprising the polynucleotide encoding a suicide polypeptide, the suicide polypeptide is expressed at the surface of a CAR-T cell. In some embodiments, the suicide polypeptide comprises the amino acid sequence shown in SEQ ID NO: 226.

(SEQ ID NO. 226)
CPYSNPSLCSGGGGSELPTQGTFSNVSTNVSPAKPTTTACPYSNPSLCSG
GGGSPAPRPPTPAPTIASQPLSLRPEACRPAAGGAVHTRGLDFACDIYIW
APLAGTCGVLLLSLVITLYCNHRNRRRVCKCPRPW.

In some embodiments, the suicide polypeptide may also comprise a signal peptide at the amino terminus. When the suicide polypeptide is expressed at the surface of a CAR-T cell, binding of rituximab to the R epitopes [i.e. the epitope recognized by rituximab—CPYSNPSLC (SEQ ID NO: 256)]) of the polypeptide causes lysis of the cell. More than one molecule of rituximab may bind per polypeptide expressed at the cell surface. Each R epitope of the polypeptide may bind a separate molecule of rituximab. Deletion of EGFRvIII specific CAR-T cells may occur in vivo, for example by administering rituximab to a patient. The decision to delete the transferred cells may arise from undesirable effects being detected in the patient which are attributable to the transferred cells, such as for example, when unacceptable levels of toxicity are detected.

In some embodiments, a suicide polypeptide may contain one, two, three or more epitopes recognized by an antibody (e.g. rituximab).

In some embodiments, a suicide polypeptide may be provided in an EGFRvIII specific CAR T cell in a polypeptide that is separate from the CAR-containing polypeptide. In some embodiments, a suicide polypeptide may be provided in an EGFRvIII specific CAR T cell in the same polypeptide chain as the CAR polypeptide. In CARs containing a suicide polypeptide, typically the suicide polypeptide is provided in the extracellular portion of the CAR.

In a CAR containing a suicide polypeptide, the suicide polypeptide may contain, for example, one or more copies of the amino acid sequence of the epitope recognized by rituximab [CPYSNPSLC (SEQ ID NO: 256)]. The suicide polypeptide may be located at different positions in the CAR. For example, the suicide polypeptide may be N-terminal to the scFv or it may be C-terminal to the scFv in the CAR. In some embodiments, the suicide peptide may be between the scFv and the hinge region of the CAR. In some embodiments, a CAR may contain more than one suicide polypeptide. For example, a CAR may contain a suicide polypeptide N-terminal to the scFv and a suicide polypeptide C-terminal to the scFv. Each of these polypeptides may contain one or more copies of the epitope recognized by rituximab. For example, a CAR may contain a first suicide polypeptide at a position N-terminal to the scFv, wherein the first suicide polypeptide contains one copy of the epitope recognized by rituximab, and a second suicide polypeptide at a position C-terminal to the scFv, wherein the second suicide polypeptide contains two copies of the epitope recognized by rituximab.

Also provided herein are nucleic acids encoding EGFRvIII-specific CARs that contain a suicide polypeptide sequence in the CAR.

In an example, a suicide polypeptide in the same polypeptide chain as an EGFRvIII specific CAR may have the sequence provided described herein as the "R2 suicide sequence". The R2 suicide sequence contains two copies of the epitope recognized by rituximab [CPYSNPSLC (SEQ ID NO: 256)]. Such EGFRvIII-specific CARs may be referred to herein as "EGFRvIII-R2 CARs". Table 5D provides amino acid sequences of exemplary EGFRvIII-R2 CARs of the present invention. In Table 5D, the signal/leader peptide sequence is in bold, the GS linker [(GGGGS)$_4$ (SEQ ID NO: 202)] is underlined, and the R2 suicide sequence is in bold and underlined. Table 5E provides exemplary nucleic acid sequences encoding exemplary EGFRvIII-R2 CARs of the present invention.

TABLE 5D

Amino acid sequences of exemplary EGFRvIII specific CARs with R2 suicide sequence

| CAR | CAR Amino Acid Sequence | Components (in order, N-terminus to C-terminus) |
|---|---|---|
| 14C11-R2 | MALPVTALLLPLALLLHAARPQVTLKESGPVLVKPTETL TLTCTVSGFSLNNARMGVSWIRQPPGKALEWFAHIFSTD EKSFRTSLRSRLTLSKDTSKSQVVLTMTNMDPVDTATYY CARDSSNYEGYFDYWGQGILVTVS<u>SGGGGSGGGGSGGGG SGGGGS</u>EIVMTQSPATLSVSPGERATLSCRASQSVSNNL AWYQQKPGQAPRLLIYGASTRATGVPARFSGSDSGTEFS LIISSLQSEDFAVYFCQQYKDWPFTFGPGTKVEIK<u>GSGG GGSCPYSNPSLCSGGGGSCPYSNPSLCSGGGGS</u>TTTPAP RPPTPAPTIASQPLSLRPEACRPAAGGAVHTRGLDFACD IYIWAPLAGTCGVLLLSLVITLYCKRGRKKLLYIFKQPF MRPVQTTQEEDGCSCRFPEEEEGGCELRVKFSRSADAPA YQQGQNQLYNELNLGRREEYDVLDKRRGRDPEMGGKPRR KNPQEGLYNELQKDKMAEAYSEIGMKGERRRGKGHDGLY QGLSTATKDTYDALHMQALPPR (SEQ ID NO: 248) | CD8α signal peptide; 14C11 VH (Table 1, SEQ ID NO: 15); GS linker; 14C11 VL (Table 1, SEQ ID NO: 16); R2 suicide sequence; CD8α hinge; CD8α TM; 4-1BB signaling domain; CD3zeta signaling domain |
| 32A10-R2 | MALPVTALLLPLALLLHAARPQVTLKESGPVLVKPTETL TLTCTVSGFSLSNARMGVSWIRQPPGKALEWLAHIFSTD EKSIRRSLRSRLTLSKDTSKSQVVLTMTNMDPVDTATYF CARDSSNYEGYFDYWGQGTLVTVS<u>SGGGGSGGGGSGGGG SGGGGS</u>EVVMTQSPATLSVSPGERVILSCRASQSVSSNF AWYQQRPGQAPRLLLYGATTRATGLPGRFSGSGSGTENI LTISSLQSEDFAIYFCQQYKDWPFTFGPGSKVDIK<u>GSGG GGSCPYSNPSLCSGGGGSCPYSNPSLCSGGGGS</u>TTTPAP RPPTPAPTIASQPLSLRPEACRPAAGGAVHTRGLDFACD IYIWAPLAGTCGVLLLSLVITLYCKRGRKKLLYIFKQPF MRPVQTTQEEDGCSCRFPEEEEGGCELRVKFSRSADAPA YQQGQNQLYNELNLGRREEYDVLDKRRGRDPEMGGKPRR KNPQEGLYNELQKDKMAEAYSEIGMKGERRRGKGHDGLY QGLS TATKDTYDALHMQALPPR (SEQ ID NO: 249) | CD8α signal peptide; 32A10 VH (Table 1 SEQ ID NO: 11); GS linker; 32A10 VL (Table 1 SEQ ID NO: 12); R2 suicide sequence; CD8α hinge; CD8α TM; 4-1BB signaling domain; CD3zeta signaling domain |
| 26B9-R2 | MALPVTALLLPLALLLHAARPEVQLVESWGVLVKPGGSL RLSCAASGFIFNNAWMSWVRQAPGKGLEWIGRIKSKSDG GTTDYAAPVKDRFTISRDDSKDTLYLQMNGLKTEDTAVY FCTTAPGGPFDYWGQGTLVTVS<u>SGGGGSGGGGSGGGGSG GGS</u>DIVLTQSPLSLPVTPGEPASISCRSSQSLLHRDGF NYLDWFLQKPGQSPQLLIYLASSRASGVPDRFSGSDSGT | CD8α signal peptide; 26B9 VH (Table 1, SEQ ID NO: 41); GS linker; 26B9 VL (Table 1, SEQ ID NO: 42); |

TABLE 5D-continued

Amino acid sequences of exemplary EGFRvIII specific CARs with R2 suicide sequence

| CAR | CAR Amino Acid Sequence | Components (in order, N-terminus to C-terminus) |
|---|---|---|
|  | DFTLKISRVEAEDVGVYYCMQALQTPITFGQGTRLEIK GSGGGGSCPYSNPSLCSGGGGSCPYSNPSLCSGGGGSTT TPAPRPPTPAPTIASQPLSLRPEACRPAAGGAVHTRGLD FACDIYIWAPLAGTCGVLLLSLVITLYCKRGRKKLLYIF KQPFMRPVQTTQEEDGCSCRFPEEEEGGCELRVKFSRSA DAPAYQQGQNQLYNELNLGRREEYDVLDKRRGRDPEMGG KPRRKNPQEGLYNELQKDKMAEAYSEIGMKGERRRGKGH DGLYQGLSTATKDTYDALHMQALPPR (SEQ ID NO: 250) | R2 suicide sequence; CD8α hinge; CD8α TM; 4-1BB signaling domain; CD3zeta signaling domain |
| 30D8-R2 | MALPVTALLLPLALLLHAARPEVQLVESGGGLVKPGGSL RLSCEASGFTFSDAWMSWVRQAPGKGLEWVGRIKSKTDG GTTDYVVPLNGRFIISRDDSRNTLYLQLNNLKTEDTAVY YCTTVPGSYGYWGQGTLVTVSS<u>GGGGSGGGGSGGGGSGG GGS</u>DIVMTQSPLSLPVTPGEPASISCRSSQSLLHKRNN YLDWFLQKPGQSPQLLIYLASNRASGVPDRFSGGGSGTD FTLKISRVEAEDVGVYYCMQAQQTPITFGQGTRLEIKGS GGGGSCPYSNPSLCSGGGGSCPYSNPSLCSGGGGSTTTP APRPPTPAPTIASQPLSLRPEACRPAAGGAVHTRGLDFA CDIYIWAPLAGTCGVLLLSLVITLYCKRGRKKLLYIFKQ PFMRPVQTTQEEDGCSCRFPEEEEGGCELRVKFSRSADA PAYQQGQNQLYNELNLGRREEYDVLDKRRGRDPEMGGKP RRKNPQEGLYNELQKDKMAEAYSEIGMKGERRRGKGHDG LYQGLSTATKDTYDALHMQALPPR (SEQ ID NO: 251) | CD8α signal peptide; 30D8 VH (Table 1, SEQ ID NO: 37); GS linker; 30D8 VL (Table 1, SEQ ID NO: 38); R2 suicide sequence; CD8α hinge; CD8α TM; 4-1BB signaling domain; CD3zeta signaling domain |

TABLE 5E

Nucleic acid sequences of exemplary EGFR VIII specific CARs with R2 suicide sequence

| CAR | CAR Nucleic Acid Sequence | Components |
|---|---|---|
| 14C11-R2 | ATGGCACTGCCAGTGACCGCCCTGCTGCTGCCTCTGGCCCTG CTGCTGCACGCAGCCAGACCCCAGGTGACACTGAAGGAGAG CCTGCACAGTGAGCGGCTTCTCCCTGAACAATGCAAGGATG GGCGTGTCCTGGATCAGGCAGCCACCTGGCAAGGCCCTGGA GTGGTTCGCCCACATCTTTAGCACCGACGAGAAGTCCTTTCG CACATCTCTGAGAAGCAGGCTGACCCTGAGCAAGGATACAA GCAAGTCCCAGGTGGTGCTGACCATGACAAACATGGACCCT GTGGATACCGCCACATACTATTGTGCCCGGGACAGCTCCAAT TACGAGGGCTATTTCGATTACTGGGGCCAGGGCATCCTGGT GACCGTGTCTAGCGGCGGCGGCGGCTCTGAGGAGGAGGA AGCGGAGGAGGAGGATCCGGCGGCGGCGGCTCTGAGATCG TGATGACCCAGTCCCCAGCCACACTGTCTGTGAGCCCAGGA GAGAGAGCCACCCTGTCTTGCAGGGCCTCCCAGTCTGTGAG CAACAATCTGGCCTGGTATCAGCAGAAGCCTGGCCAGGCCC CAAGGCTGCTGATCTACGGAGCAAGCACCAGAGCAACAGG AGTGCCTGCAAGGTTCTCCGGATCTGACAGCGGCACCGAGT TTTCTCTGACAATCTCCTCTCTGCAGAGCGAGGACTTCGCCG TGTATTTTGTCAGCAGTACAAGGATTGGCCATTCACCTTTG GCCCCGGCACAAAGGTGGAGATCAAGGGCTCCGGAGGAGG AGGATCCTGCCCCTATTCCAACCCTTCTCTGTGCAGCGGAGG AGGAGGAAGCTGTCCATACTCCAATCCCTCCCTGTGCTCCGG CGGCGGAGGATCCACCACAACCCCAGCACCTAGACCACCAA CCCCAGCACCAACAATCGCATCCCAGCCTCTGTCTCTGCGGC CCGAGGCATGCAGGCCAGCAGCAGGCGGCGCCGTGCACAC CAGGGGCCTGGACTTTGCCTGCGATATCTATATCTGGGCACC ACTGGCAGGAACCTGTGGCGTGCTGCTGCTGAGCCTGGTCA TCACCCTGTATTGCAAGCGCGGCCGGAAGAAGCTGCTGTAC ATCTTCAAGCAGCCTTTTATGCGCCCAGTGCAGACAACCCAG GAGGAGGACGGCTGCTCCTGTCGGTTCCCTGAAGAGGAGG AGGGAGGATGTGAGCTGCGCGTGAAGTTTTCCCGGTCTGCC GATGCCCCAGCCTATCAGCAGGGCCAGAACCAGCTGTACAA CGAGCTGAATCTGGGCCGGAGAGAGGAGTACGACGTGCTG GATAAGAGGAGGGGAAGAGATCCCGAGATGGGAGGCAAG CCTCGGAAAAAGAACCCACAGGAGGGCCTGTATAATGAGCT GCAGAAGGACAAGATGGCCGAGGCCTACTCTGAGATCGGC | CD8α signal peptide; 14C11 VH (Table 1, SEQ ID NO: 15); GS linker; 14C11 VL (Table 1, SEQ ID NO: 16); R2 suicide sequence; CD8α hinge; CD8α TM; 4-1BB signaling domain; CD3zeta signaling domain |

TABLE 5E-continued

Nucleic acid sequences of exemplary EGFR VIII specific CARs with R2 suicide sequence

| CAR | CAR Nucleic Acid Sequence | Components |
|---|---|---|
| | ATGAAGGGAGAGAGGCGCCGGGGCAAGGGACACGATGGC<br>CTGTATCAGGGCCTGTCCACCGCCACAAAGGACACCTACGAT<br>GCCCTGCACATGCAGGCCCTGCCTCCAAGGTGA<br>(SEQ ID NO: 252) | |
| 32A10-R2 | ATGGCACTGCCAGTGACCGCCCTGCTGCTGCCTCTGGCCCTG<br>CTGCTGCACGCAGCCAGACCCCAGGTGACACTGAAGGAGTC<br>CGGCCCCGTGCTGGTGAAGCCTACAGAGACACTGACCCTGA<br>CCTGCACAGTGAGCGGCTTCTCTCTGAGCAACGCAAGGATG<br>GGCGTGTCCTGGATCAGGCAGCCACCTGGCAAGGCCCTGGA<br>GTGGCTGGCCCACATCTTTTCCACCGACGAGAAGTCTATCCG<br>GAGAAGCCTGCGCTCCCGGCTGACCCTGAGCAAGGATACAT<br>CCAAGTCTCAGGTGGTGCTGACCATGACAAACATGGACCCT<br>GTGGATACCGCCACATACTTCTGTGCCCGGGACAGCTCCAAT<br>TACGAGGGCTATTTTGATTACTGGGGCCAGGGCACCCTGGT<br>GACAGTGTCTAGCGGAGGAGGAGGAAGCGGAGGAGGAGG<br>ATCAGGCGGCGGCGGCTCTGGCGGCGGCGGCAGCGAGGTG<br>GTCATGACCCAGTCTCCAGCCACACTGAGCGTGTCCCCAGGA<br>GAGCGCGTGACCCTGAGCTGCCGGGCCTCTCAGAGCGTGTC<br>CTCTAACTTCGCCTGGTATCAGCAGCGGCCCGGACAGGCAC<br>CAAGGCTGCTGCTGTACGGAGCAACCACAAGAGCAACAGGC<br>CTGCCTGGCAGGTTTTCCGGCTCTGGCAGCGGCACCGAGAA<br>TATCCTGACAATCAGCTCCCTGCAGAGCGAGGACTTCGCCAT<br>CTATTTTTGTCAGCAGTACAAGGATTGGCCATTCACCTTTGG<br>CCCCGGCTCCAAGGTGGACATCAAGGGATCCGGAGGAGGA<br>GGATCTTGCCCCTATTCTAACCCTAGCCTGTGCTCCGGAGGA<br>GGAGGATCCTGTCCATACTCTAATCCATCCCTGTGCAGCGGA<br>GGAGGAGGATCTACCACAACCCCAGCACCTAGACCACCAAC<br>CCCAGCACCCACAATCGCCTCTCAGCCTCTGAGCCTGCGCCC<br>AGAGGCATGCAGGCCAGCAGCAGGAGGAGCAGTGCACACC<br>AGGGGCCTGGACTTCGCCTGCGATATCTATATCTGGGCACCA<br>CTGGCAGGAACCTGTGGCGTGCTGCTGCTGTCCCTGGTCATC<br>ACCCTGTATTGCAAGAGAGGCAGGAAGAAGCTGCTGTACAT<br>CTTCAAGCAGCCTTTTATGCGCCCAGTGCAGACAACCCAGGA<br>GGAGGACGGCTGCAGCTGTCGGTTCCCTGAAGAGGAGGAG<br>GGCGGCTGTGAGCTGAGAGTGAAGTTTTCCAGGTCTGCCGA<br>TGCCCCAGCCTATCAGCAGGGCCAGAATCAGCTGTACAACG<br>AGCTGAATCTGGGCAGGCGCGAGGAGTACGACGTGCTGGA<br>TAAGAGGAGAGGACGCGATCCCGAGATGGGAGGCAAGCCT<br>AGGCGCAAGAACCCACAGGAGGGCCTGTATAATGAGCTGC<br>AGAAGGACAAGATGGCCGAGGCCTACTCTGAGATCGGCAT<br>GAAGGGAGAGCGGAGAAGGGGCAAGGGACACGATGGCCT<br>GTATCAGGGCCTGAGCACCGCCACAAAGGACACCTACGATG<br>CCCTGCACATGCAGGCCCTGCCTCCAAGGTGA<br>(SEQ ID NO: 253) | CD8α signal peptide;<br>32A10 VH (Table 1 SEQ ID NO: 11);<br>GS linker;<br>32A10 VL (Table 1 SEQ ID NO: 12);<br>R2 suicide sequence;<br>CD8α hinge;<br>CD8α TM;<br>4-1BB signaling domain;<br>CD3zeta signaling domain |
| 26B9-R2 | ATGGCCCTGCCAGTGACCGCCCTGCTGCTGCCACTGGCCCTG<br>CTGCTGCACGCCGCCAGACCTGAGGTGCAGCTGGTGGAGAG<br>CTGGGGCGTGCTGGTGAAGCCAGGAGGCTCTCTGAGGCTG<br>AGCTGCGCAGCATCCGGCTTCATCTTTAACAATGCCTGGATG<br>TCCTGGGTGAGACAGGCACCAGGCAAGGGCCTGGAGTGGA<br>TCGGCAGGATCAAGAGCAAGTCCGACGGAGGAACCACAGA<br>TTACGCAGCACCCGTGAAGGACCGCTTCACAATCTCTCGGGA<br>CGATAGCAAGGATACCCTGTATCTGCAGATGAACGGCCTGA<br>AGACAGAGGACACCGCCGTGTACTTCTGCACCACAGCCCCA<br>GGCGGCCCCTTTGATTATTGGGGCCAGGGCACACTGGTGAC<br>CGTGAGCTCCGGAGGAGGAGGAAGCGGCGAGGAGGCAG<br>CGGCGGCGGCGGCTCTGGCGGCGGCGGCAGCGACATCGTG<br>CTGACACAGAGCCCACTGTCCCTGCCTGTGACCCCAGGAGA<br>GCCCGCCTCTATCAGCTGTCGCTCTAGCCAGAGCCTGCTGCA<br>CCGGGACGGCTTCAATTACCTGGATTGGTTTCTGCAGAAGCC<br>TGGCCAGAGCCCACAGCTGCTGATCTATCTGGCCTCCTCTAG<br>AGCATCCGGAGTGCCTGACAGGTTCTCCGGATCTGACAGCG<br>GCACAGACTTCACCCTGAAGATCTCCCGCGTGGAGGCAGAG<br>GATGTGGGCGTGTACTATTGCATGCAGGCCCTGCAGACACC<br>AATCACCTTCGGCCAGGGCACACGGCTGGAGATCAAGGGAT<br>CCGGAGGAGGAGGATCTTGCCCCTACTCTAACCCTAGCCTGT<br>GCAGCGGCGAGGAGGATCTTGTCCATATTCTAATCCAAGC<br>CTGTGCAGCGGGGAGGAGGAAGCACCACAACCCCTGCAC<br>CAAGACCCCTACACCAGCACCTACCATCGCATCCCAGCCAC<br>TGTCTCTGCGGCCCGAGGCATGTAGGCCAGCAGCAGGAGG<br>AGCAGTGCACACCAGGGGCCTGGACTTTGCCTGCGATATCT<br>ACATCTGGGCACCACTGGCAGGAACATGTGGCGTGCTGCTG<br>CTGAGCCTGGTCATCACCCTGTACTGCAAGAGAGGCAGGAA<br>GAAGCTGCTGTATATCTTCAAGCAGCCTTTTATGCGCCCAGT | CD8α signal peptide;<br>26B9 VH (Table 1, SEQ ID NO: 41);<br>GS linker<br>26B9 VL (Table 1, SEQ ID NO: 42);<br>R2 suicide sequence;<br>CD8α hinge;<br>CD8α TM;<br>4-1BB signaling domain;<br>CD3zeta signaling domain |

TABLE 5E-continued

Nucleic acid sequences of exemplary EGFR VIII specific CARs with R2 suicide sequence

| CAR | CAR Nucleic Acid Sequence | Components |
|---|---|---|
| | GCAGACAACCCAGGAGGAGGACGGCTGCTCCTGTAGGTTCC<br>CAGAAGAGGAGGAGGGAGGATGTGAGCTGCGCGTGAAGTT<br>TTCCCGGTCTGCCGATGCACCTGCATACCAGCAGGGACAGA<br>ACCAGCTGTATAACGAGCTGAATCTGGGCCGGAGAGAGGA<br>GTACGACGTGCTGGATAAGAGGAGGGGACGCGATCCTGAG<br>ATGGGAGGCAAGCCCCGGAGAAAGAACCCTCAGGAGGGCC<br>TGTACAATGAGCTGCAGAAGGACAAGATGGCCGAGGCCTAT<br>TCCGAGATCGGCATGAAGGGAGAGAGGCGCCGGGGCAAG<br>GGACACGATGGCCTGTACCAGGGCCTGTCTACAGCCACCAA<br>GGACACCTATGATGCCCTGCACATGCAGGCCCTGCCACCAA<br>GGTGA<br>(SEQ ID NO: 254) | |
| 30D8-R2 | ATGGCACTGCCAGTGACAGCCCTGCTGCTGCCTCTGGCCCTG<br>CTGCTGCACGCAGCCAGACCAGAGGTGCAGCTGGTGGAGTC<br>CGGAGGAGGCCTGGTGAAGCCAGGAGGCTCCCTGAGGCTG<br>TCTTGCGAGGCCAGCGGCTTCACCTTTAGCGACGCCTGGAT<br>GTCCTGGGTGAGACAGGCACCAGGCAAGGGCCTGGAGTGG<br>GTGGGCAGGATCAAGAGCAAGACAGACGGCGGCACCCACAG<br>ATTACGTGGTGCCTCTGAACGGCCGGTTCATCATCTCCCGCG<br>ACGATTCTCGGAATACCCTGTATCTGCAGCTGAACAATCTGA<br>AGACAGAGGATACCGCCGTGTACTATTGCACCCACAGTGCCT<br>GGCTCCTACGGCTATTGGGGCCAGGGCACACTGGTGACCGT<br>GAGCTCCGGCGGCGGCGGCTCTGGAGGAGGAGGAAGCGG<br>AGGAGGAGGAAGCGGGGGCGGCGGCTCTGACATCGTGATG<br>ACACAGTCTCCACTGAGCCTGCCAGTGACCCCAGGAGAGCC<br>TGCCTCCATCTCTTGTCGCTCTAGCCAGTCCCTGCTGCACAAC<br>AAGCGGAACAATTACCTGGATTGGTTCCTGCAGAAGCCAGG<br>CCAGTCTCCCCAGCTGCTGATCTATCTGGCCAGCAATAGAGC<br>CTCCGGAGTGCCAGACAGGTTCTCTGGAGGAGGAAGCGGA<br>ACAGACTTCACCCTGAAGATCAGCCGCGTGGAGGCAGAGGA<br>CGTGGGCGTGTACTATTGCATGCAGGCCCAGCAGACACCCA<br>TCACCTTTGGCCAGGGAACCCGGCTGGAGATCAAGGGCTCC<br>GGAGGAGGAGGATCCTGCCCTTACTCCAACCCATCTCTGTGC<br>AGCGGAGGAGGAGGATCTTGTCCATATTCCAATCCTTCCCTG<br>TGCTCCGGAGGAGGAGGAAGCACCACAACCCCTGCACCAAG<br>ACCCCCTACACCAGCACCTACCATCGCATCCCAGCCTCTGTCT<br>CTGCGGCCCGAGGCATGTAGGCCAGCAGCAGGCGGCGCCG<br>TGCACACCAGGGGCCTGGACTTTGCCTGCGATATCTACATCT<br>GGGCACCACTGGCAGGAACATGTGGCGTGCTGCTGCTGTCT<br>CTGGTCATCACCCTGTACTGCAAGAGAGGCAGGAAGAAGCT<br>GCTGTATATCTTCAAGCAGCCCTTCATGCGGCCCGTGCAGAC<br>AACCCAGGAGGAGGACGGCTGCAGCTGTCGGTTCCCTGAAG<br>AGGAGGAGGGAGGATGTGAGCTGCGCGTGAAGTTTAGCCG<br>GTCCGCCGATGCACCAGCATACCAGCAGGGCCAGAACCAGC<br>TGTATAACGAGCTGAATCTGGGCCGGAGAGAGGAGTACGA<br>CGTGCTGGATAAGAGGAGGGGACGCGATCCTGAGATGGGA<br>GGCAAGCCTCGGAGAAAGAACCCACAGGAGGGCCTGTACA<br>ATGAGCTGCAGAAGGACAAGATGGCCGAGGCCTATAGCGA<br>GATCGGCATGAAGGGAGAGAGGCGCCGGGGCAAGGGACA<br>CGATGGCCTGTACCAGGGCCTGTCCACAGCCACCAAGGACA<br>CCTATGATGCCCTGCACATGCAGGCCCTGCCACCAAGGTGA<br>(SEQ ID NO: 255) | CD8α signal peptide;<br>30D8 VH (Table 1, SEQ ID NO: 37);<br>GS linker;<br>30D8 VL (Table 1, SEQ ID NO: 38);<br>R2 suicide sequence;<br>CD8α hinge;<br>CD8α TM;<br>4-1BB signaling domain;<br>CD3zeta signaling domain |

Therapeutic Applications

Isolated cells obtained by the methods described above, or cell lines derived from such isolated cells, can be used as a medicament. In some embodiments, such a medicament can be used for treating cancer, including solid tumors and liquid tumors. In some embodiments, the cancer is EGFRvIII related cancer (e.g., any EGFRvIII expressing cancer) including, but not limited to, glioblastoma (e.g., glioblastoma multiform), anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, mixed glioma, head and neck cancer, non-small cell lung cancer, breast cancer, ovarian cancer, prostate cancer, medulloblastoma, colorectal cancer, anal cancer, cervical cancer, renal cancer, skin cancer, pancreatic cancer, liver cancer, bladder cancer, gastric cancer, thyroid cancer, mesothelioma, uterine cancer, lymphoma, or leukemia.

In some embodiments, the medicament as described herein can be used for 1) inhibiting tumor growth or progression in a subject who has malignant cells expressing EGFRvIII; 2) inhibiting metastasis of malignant cells expressing EGFRvIII in a subject; and 3) inducing tumor regression in a subject who has malignant cells expressing EGFRvIII.

In some embodiments, an isolated cell according to the invention, or cell line derived from the isolated cells, can be used in the manufacture of a medicament for treatment of a cancer in a patient in need thereof.

Also provided herein are methods for treating patients. In some embodiments the method comprises providing an immune cell of the invention to a patient in need thereof. In some embodiments, the method comprises a step of administering transformed immune cells of the invention to a patient in need thereof.

In some embodiments, T cells of the invention can undergo robust in vivo T cell expansion and can persist for an extended amount of time.

Methods of treatment of the invention can be ameliorating, curative or prophylactic. The method of the invention may be either part of an autologous immunotherapy or part of an allogenic immunotherapy treatment. The invention is particularly suitable for allogeneic immunotherapy. T cells from donors can be transformed into non-alloreactive cells using standard protocols and reproduced as needed, thereby producing CAR-T cells which may be administered to one or several patients. Such CAR-T cell therapy can be made available as an "off the shelf" therapeutic product.

Cells that can be used with the disclosed methods are described, for example, in the previous section. Treatment can be used to treat patients diagnosed with, for example, cancer. Cancers that may be treated include, for example, cancers that are related to EGFRvIII, including any of the above-listed cancers. Types of cancers to be treated with the CARs and CAR-T cells of the invention include, but are not limited to certain liquid and solid tumors, such as glioblastoma multiforme, head and neck cancer, non-small cell lung cancer, breast cancer, ovarian cancer and prostate cancer. Adult tumors/cancers and pediatric tumors/cancers are also included.

In some embodiments, the treatment can be in combination with one or more therapies against cancer selected from the group of antibodies therapy, antibody-drug conjugate therapy, chemotherapy, targeted therapy, cytokines therapy, vaccine therapy, oncolytic virus therapy, dendritic cell therapy, gene therapy, nanoparticle therapy, hormone therapy, surgical resection, laser light therapy, tumor treating fields, and radiation therapy. For example, CARs and CAR-T cells of the invention can be administered to a patient in conjunction with (e.g., before, simultaneously, or following) 1) standard of care, including radiation, surgical resection, chemotherapy (e.g., temozolomide, procarbazine, carmustine, lomustine, vincristine etc.), antibody therapy such as bevacizumab, anti-angiogenic therapy, and/or tumor treating fields; 2) vaccine, including EGFRvIII vaccine; 3) antibody-drug conjugate therapy, including but not limited to drug conjugates that target the HER family of receptors such as EGFR, HER2, HER3, and HER4; 4) targeted therapy, such as kinase inhibitors (e.g., everolimus); and 5) immunotherapies, including but not limited to anti-PD-1, anti-PD-L1, anti-PD-L2, anti-41BB, anti-TIM3, anti-LAG3, anti-TIGIT, anti-OX40, anti-HVEM, anti-BTLA, anti-CD40, anti-CD47, anti-CSF1R, anti-CSF1, anti-MARCO, anti-IL8, anti-CXCR4, and anti-CTLA4 antibodies.

In some embodiments, treatment can be administered to patients undergoing an immunosuppressive treatment. Indeed, the invention preferably relies on cells or population of cells, which have been made resistant to at least one immunosuppressive agent (e.g., cyclosporin, azathioprine, methotrexate, mycophenolate, and FK506) due to the inactivation of a gene encoding a receptor for such immunosuppressive agent. In this aspect, the immunosuppressive treatment should help the selection and expansion of the T cells according to the invention within the patient. The administration of the cells or population of cells according to the invention may be carried out in any convenient manner, including by aerosol inhalation, injection, ingestion, transfusion, implantation or transplantation. The compositions described herein may be administered to a patient subcutaneously, intradermally, intratumorally, intracranially, intranodally, intramedullary, intramuscularly, by intravenous or intralymphatic injection, or intraperitoneally. In one embodiment, the cell compositions of the invention are preferably administered by intravenous injection.

In some embodiments, treatment can be administered to patients undergoing a lymphodepletion regimen. Depletion of the immune regulatory elements with cytotoxic agents or whole body irradiation can enhance the anti-tumor activity of the CARs and CAR-T cells of the present invention. For example, the cytotoxic agent in a lymphodepletion regimen includes, but is not limited to, fludarabine, cyclophosphamide, and/or alemtuzumab.

In some embodiments the administration of the cells or population of cells can comprise the administration of, for example, about $10^4$ to about $10^9$ cells per kg body weight including all integer values of cell numbers within those ranges. In some embodiments the administration of the cells or population of cells can comprise the administration of about $10^5$ to $10^6$ cells per kg body weight including all integer values of cell numbers within those ranges. The cells or population of cells can be administered in one or more doses. In some embodiments, said effective amount of cells can be administered as a single dose. In some embodiments, said effective amount of cells can be administered as more than one dose over a period time. Timing of administration is within the judgment of a managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

Kits

The invention also provides kits for use in the instant methods. Kits of the invention include one or more containers comprising a polynucleotide encoding an EGFRvIII specific CAR, or an engineered immune cell comprising a polynucleotide encoding EGFRvIII specific CAR as described herein, and instructions for use in accordance with any of the methods of the invention described herein. Generally, these instructions comprise a description of administration of the engineered immune cell for the above described therapeutic treatments.

The instructions relating to the use of the engineered immune cells as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, a nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an EGFRvIII antibody. The container may further comprise a second pharmaceutically active agent.

Kits may optionally provide additional components such as buffers and interpretive information. Normally, the kit comprises a container and a label or package insert(s) on or associated with the container.

Incorporated by reference herein for all purposes is the content of U.S. Provisional Patent Application Nos. 62/281, 533 (filed Jan. 21, 2016) and 62/431,758 (Filed Dec. 8, 2016).

The following examples are offered for illustrative purposes only, and are not intended to limit the scope of the invention in any way. Indeed, various modifications of the invention in addition to those shown and described herein will become apparent to those skilled in the art from the foregoing description and fall within the scope of the appended claims.

EXAMPLES

Example 1: Affinity Determination for Recombinant Anti-EGFRvII Murine-Human Chimeric Antibody and Humanized Antibodies This example determines the affinity of chimeric and humanized anti-EGFRvIII antibodies at 25° C. and 37° C.

Anti-EGFRvII mouse (m) antibody, m62G7, generated from hybridomas was sequenced and subcloned into suitable vectors for expression as murine-human chimeric antibodies. The CDRs of mouse antibody m62G7 were grafted onto human framework and expressed as human IgG1 recombinant antibody, h62G7. Affinity variants of h62G7 were made by introducing mutations in the CDRs of the heavy and light chains. The affinities of recombinant anti-EGFRvIII chimeric antibody m62G7 and humanized h62G7 antibodies were measured on a surface plasmon resonance Biacore™ T200 biosensor equipped with a research-grade anti-human Fc coupled CM4 sensor chip (GE Healthcare Inc., Piscataway, N.J.). Anti-EGFRvII antibodies were then captured by anti-human Fc. Monomeric 8-histidine tagged human EGFRvIII extracellular domain was then injected as the analyte at 10-fold dilution series with top concentration at 1000 nM. Affinity of anti-EGFRvIII antibodies towards human EGFRvIII was measured at both 25° C. and 37° C. (Table 6). None of these antibodies showed detectable binding to 1000 nM 8-histidine tagged recombinant wild-type protein EGFRwt under the same assay condition.

In Table 6, variants of h62G7 are described with reference to the heavy chain variation then the light chain variation. For example, antibody clone "h62G7-EQ/L6" refers to the h62G7 clone containing the "EQ" variation in the heavy chain (also referred to herein as "h62G7-EQ") and the "L6" variation in the light chain (also referred to herein as "h62G7-L6"). These heavy chain and light chain amino acid sequences are provided in Table 2. Also, in the present application, a h62G7 variant may be referred to with either the heavy chain or the light chain variant written first—so, for example, "h62G7-EQ/L6" and "h62G7-L6/EQ" both refer to an antibody which contains a h62G7-EQ heavy chain and a h62G7-L6 light chain.

TABLE 6

| Antibody | 25° C. | | | 37° C. | | |
| --- | --- | --- | --- | --- | --- | --- |
| | $k_a$(1/Ms) | $k_d$(1/s) | $K_D$(nM) | $k_a$(1/Ms) | $k_d$(1/s) | $K_D$(nM) |
| m62G7 | 7.30E+05 | 6.40E−02 | 88.7 | 8.00E+05 | 1.70E−01 | 207.0 |
| h62G7-EQ/L6 | 2.40E+05 | 1.00E−02 | 43.8 | 6.60E+05 | 7.40E−02 | 112.8 |
| h62G7-EQ/L1-DV | 2.00E+05 | 1.20E−05 | 59.9 | 3.70E+05 | 6.90E−02 | 185.8 |
| h62G7-H14/L1-DV | 1.80E+04 | 2.00E−02 | 1087.9 | 6.60E+04 | 1.00E−01 | 1539.6 |
| h62G7-H14/L6 | 1.30E+04 | 1.30E−02 | 992.2 | 4.30E+04 | 6.80E−02 | 1583.3 |

Example 2: Affinity Determination for Human Anti-EGFRvII Antibodies

This example determines the affinity of various human anti-EGFRvIII antibodies at 37° C.

To generate human antibodies against EGFRvIII, transgenic AlivaMab mice (Ablexis LLC, San Francisco, Calif.) were immunized with alternating schedule of paraformaldehyde-fixed rat glioblastoma cell line expressing EGFRvIII, F98-npEGFRvIII (American Type Culture Collection, Manassas, Va.) and peptides (SEQ ID NO: 227: CGSGSGLEEKKGNYVVTDH) directed to the junction region in EGFRvIII. Hybridomas were generated using standard techniques. To determine the binding affinity and specificity of these hybridomas to EGFRvIII, antibodies in culture supernatants were captured by anti-mouse Fc using Biacore™ T200 biosensor equipped with anti-mouse Fc coupled CM4 sensor chips (Biacore™ AB, Uppsala, Sweden—now GE Healthcare). Monomeric 8-histidine tagged human EGFRvIII extracellular domain was then injected as the analyte at 10-fold dilution series starting with top concentration 1000 nM. Affinity of anti-EGFRvIII antibodies towards human EGFRvIII was measured at 37° C. (Table 7). None of these hybridoma antibodies showed detectable binding to 1000 nM 8-histidine tagged recombinant wild-type protein EGFRwt under the same assay condition.

TABLE 7

| | EGFRvIII binding at 37° C. | | |
| --- | --- | --- | --- |
| Antibody | $k_a$ (1/Ms) | $k_d$ (1/s) | $K_D$ (nM) |
| 42G9 | 6.88E+04 | 5.63E−04 | 8.2 |
| 32A10 | 6.54E+04 | 6.26E−04 | 9.6 |

TABLE 7-continued

EGFRvIII binding at 37° C.

| Antibody | $k_a$ (1/Ms) | $k_d$ (1/s) | $K_D$ (nM) |
|---|---|---|---|
| 21E11 | 6.66E+04 | 6.32E-04 | 9.5 |
| 49B11 | 7.64E+04 | 6.95E-04 | 9.1 |
| 46E10 | 5.97E+04 | 7.16E-04 | 12.0 |
| 12H6 | 5.93E+04 | 7.33E-04 | 12.4 |
| 19A9 | 5.58E+04 | 1.04E-03 | 18.6 |
| 11B11 | 5.21E+04 | 1.13E-03 | 21.7 |
| 21E7 | 6.52E+04 | 1.30E-03 | 19.9 |
| 20B9 | 4.67E+04 | 1.50E-03 | 32.1 |
| 12B2 | 7.38E+04 | 1.79E-03 | 24.3 |
| 11F10 | 6.63E+04 | 2.81E-03 | 42.4 |
| 17G11 | 5.61E+04 | 3.00E-03 | 53.5 |
| 29D5 | 1.02E+05 | 4.24E-03 | 41.6 |
| 14C11 | 7.55E+04 | 5.93E-03 | 78.5 |
| 20E12 | 3.99E+04 | 1.41E-02 | 353.4 |
| 20G5 | 1.25E+05 | 2.89E-02 | 231.2 |
| 26B9 | 1.31E+05 | 3.20E-02 | 244.3 |
| 30D8 | 1.61E+05 | 2.77E-02 | 172.0 |
| 32G8 | 6.82E+03 | 1.22E-02 | 1788.9 |
| 34E7 | 3.77E+04 | 1.28E-02 | 339.5 |

Example 3: Binding Specificity of Anti-EGFRvIII Antibodies to EGFRvIII Expressing Cell Lines by Flow Cytometry This example demonstrates the cell binding specificity of anti-EGFRvIII antibodies to EGFRvIII expressing cells.

Figure 1A:
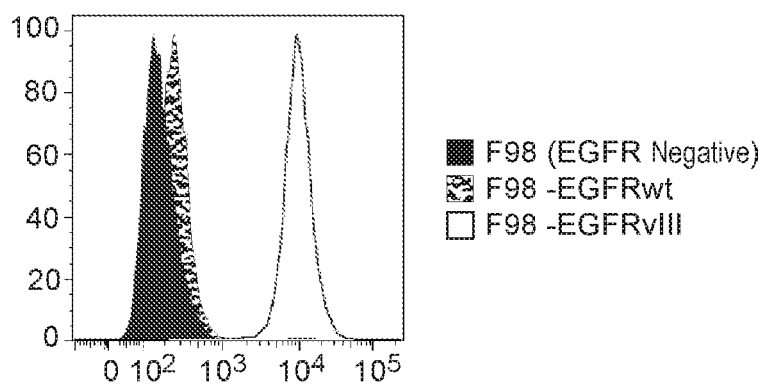
Figure 1B:
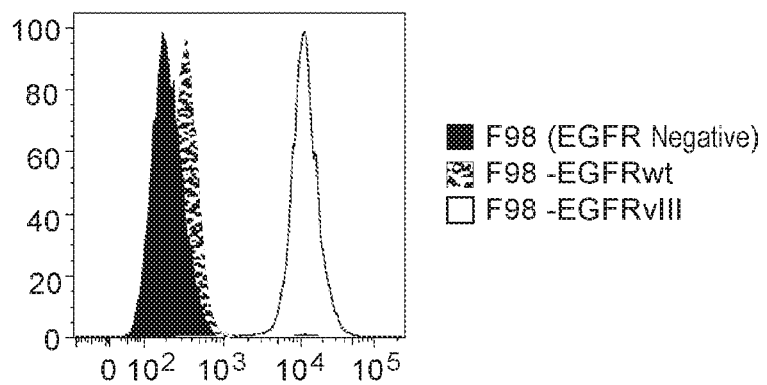
Figure 1C:
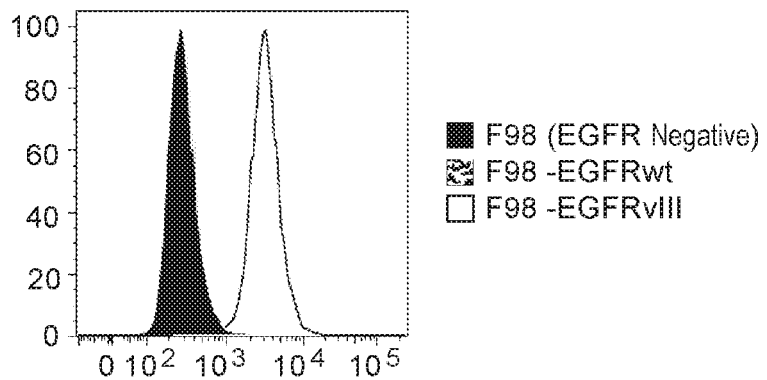

To assess the cell binding specificity of anti-EGFRvIII antibodies generated from the AlivaMab mice, three isogenic rat glioblastoma cell lines and a human cancer cell line were used: F98 (does not express any form of human EGFR), F98-EGFRwt (expresses wild-type EGFR), F98-npEGFRvII (expresses EGFRvIII) and A431 (an epidermoid carcinoma cell line with wild-type EGFR over-expression), all obtained from American Type Culture Collection (Manassas, Va.). For cell staining, 500,000 cells were incubated with 50 µl hybridoma supernatants for 45 min at 4° C., washed with binding buffer (PBS (Phosphate Buffered Saline)+0.5% BSA (Bovine Serum Albumin)), followed by incubation with FITC-conjugated goat anti-mouse Fc specific secondary antibody from Jackson ImmunoResearch Laboratories (West Grove, Pa.). Tables 8A and 8B show mean fluorescent intensities (MFI) of EGFRvIII antibodies (except clone 20G5) on EGFRvIII expressing cell line were at least 10-fold higher than on non-expressing cell lines. FIG. 1A, FIG. 1B, and FIG. 1C show examples of the FACS binding histograms of three EGFRvIII specific clones which had been cloned and expressed as recombinant human IgG1 antibodies, 42G9 (FIG. 1A), 32A10 (FIG. 1B) and 32G8 (FIG. 1C), to the three F98 cell lines.

TABLE 8A

| Antibody | F98 | | F98-EGFRwt | | F98-EGFRvIII | | A431 | |
|---|---|---|---|---|---|---|---|---|
| | MFI | % positive | MFI | % positive | MFI | % positive | MFI | % positive |
| 2nd Ab only | 170 | 0.6 | 202 | 1.7 | 258 | 2.3 | 592 | 0.4 |
| anti-EGFR(wt and vIII) | 163 | 0.5 | 9608 | 98.3 | 5329 | 99.4 | 55240 | 100.0 |
| 42G9 | 159 | 0.4 | 185 | 1.6 | 3247 | 98.5 | 538 | 0.3 |
| 32A10 | 159 | 0.5 | 185 | 1.4 | 3349 | 98.3 | 531 | 0.2 |
| 21E11 | 159 | 0.3 | 184 | 1.3 | 3105 | 98.5 | 555 | 0.5 |
| 49B11 | 156 | 0.6 | 185 | 1.3 | 2980 | 98.5 | 599 | 0.8 |
| 46E10 | 158 | 0.4 | 187 | 1.6 | 2986 | 98.7 | 560 | 0.5 |
| 12H6 | 157 | 0.5 | 188 | 1.9 | 3445 | 98.3 | 569 | 0.8 |
| 19A9 | 158 | 0.5 | 168 | 1.6 | 3100 | 98.1 | 578 | 1.0 |
| 11B11 | 161 | 0.6 | 187 | 1.7 | 3391 | 98.2 | 589 | 1.2 |
| 21E7 | 159 | 0.3 | 184 | 1.3 | 3105 | 98.5 | 603 | 1.1 |
| 20B9 | 157 | 0.3 | 189 | 1.8 | 3418 | 98.3 | 558 | 0.7 |
| 12B2 | 156 | 0.4 | 185 | 1.5 | 2749 | 97.9 | 571 | 0.8 |
| 11F10 | 155 | 0.5 | 187 | 1.6 | 3283 | 98.0 | 582 | 1.1 |
| 17G11 | 157 | 0.6 | 184 | 1.5 | 3357 | 98.1 | 556 | 0.7 |
| 29D5 | 155 | 0.3 | 185 | 1.3 | 2829 | 97.9 | 531 | 0.4 |
| 14C11 | 157 | 0.4 | 185 | 1.3 | 3213 | 98.2 | 580 | 0.8 |

TABLE 8B

| Antibody | F98 | | F98-EGFRwt | | F98-EGFRvIII | | A431 | |
|---|---|---|---|---|---|---|---|---|
| | MFI | % positive | MFI | % positive | MFI | % positive | MFI | % positive |
| 2nd Ab only | 235 | 0.2 | 252 | 0.2 | 322 | 1.3 | 185 | 0.7 |
| anti-EGFR(wt and vIII) | 245 | 0.3 | 6857 | 97.2 | 5827 | 99.4 | 44493 | 100.0 |
| 20E12 | 381 | 6.0 | 348 | 3.4 | 3976 | 97.9 | 302 | 2.6 |
| 20G5 | 1248 | 16.8 | 1070 | 12.6 | 4639 | 98.5 | 391 | 2.0 |
| 26B9 | 310 | 4.1 | 298 | 2.3 | 5405 | 98.6 | 276 | 1.7 |

TABLE 8B-continued

| Antibody | F98 MFI | F98 % positive | F98-EGFRwt MFI | F98-EGFRwt % positive | F98-EGFRvIII MFI | F98-EGFRvIII % positive | A431 MFI | A431 % positive |
|---|---|---|---|---|---|---|---|---|
| 30D8 | 296 | 4.0 | 280 | 1.7 | 5165 | 98.6 | 269 | 1.3 |
| 32G8 | 329 | 4.9 | 301 | 1.6 | 3734 | 98.6 | 271 | 1.2 |
| 34E7 | 485 | 6.9 | 371 | 4.0 | 4128 | 98.5 | 294 | 1.1 |

These results demonstrate the binding specificity of the anti-EGFRvIII antibodies to cells that express EGFRvIII.

Example 4: Affinity Determination for Fully Human Anti-EGFRvIII Antibodies from Phage Library This example determines the affinity of various human anti-EGFRvIII antibodies at 25° C.

Human anti-EGFRvIII antibodies were sequenced and subcloned into suitable vectors for expression as recombinant human IgG1 antibodies. The affinities of antibodies were measured at 25° C. (Table 9) on a surface plasmon resonance Biacore™ T200 biosensor equipped with an anti-human Fc coupled CM4 sensor chip (GE Healthcare Inc., Piscataway, N.J.). Anti-EGFRvII antibodies were captured by anti-human Fc. Monomeric 8-histidine tagged human EGFRvIII extracellular domain was then injected as the analyte at 10-fold dilution series starting at 1000 nM. Among the two antibodies, only C6 showed very weak but detectable binding to 1000 nM 8-histidine tagged recombinant wild-type protein EGFRwt at 25° C.

TABLE 9

| | EGFRvIII binding at 25° C. | | |
|---|---|---|---|
| Antibody | $k_a$ (1/Ms) | $k_d$ (1/s) | $K_D$ (nM) |
| B5 | 2.08E+04 | 1.41E−02 | 677.9 |
| C6 | 1.68E+04 | 8.94E−03 | 532.1 |

Example 5: Affinity Determination for Recombinant Single Chain Fv Formatted Anti-EGFRvIII Antibodies This example determines the affinity of various recombinant single chain Fv formatted anti-EGFRvIII antibodies at 37° C.

To convert conventional antibody into single chain Fv (scFv) fragment, the heavy chain variable domain and the light chain variable domain were joined together via a (GGGGS)$_4$ (SEQ ID NO: 202) linker. The scFv fragment was then fused to human IgG1 Fc moiety to facilitate recombinant expression and purification. Affinities of the scFv-Fc fusion proteins were measured at 37° C. on a surface plasmon resonance Biacore™ T200 biosensor equipped with an anti-human Fc coupled CM4 sensor chip (GE Healthcare Inc., Piscataway, N.J.) as described above. scFv-Fc proteins were captured by anti-human Fc. Monomeric 8-histidine tagged human EGFRvIII extracellular domain was then injected as the analyte at 10-fold dilution series starting at 1000 nM. Table 10 shows that scFv reformatted fusion proteins retain binding to EGFRvIII and that the affinities of the scFv-Fc proteins in both HL (with the heavy-chain variable domain at the N-terminus) and LH (with the light-chain variable domain at the N-terminus) orientations are comparable to their conventional antibody counterparts listed in Tables 6, 7 and 9. These scFv-Fc proteins were also tested for binding to 1000 nM 8-histidine tagged recombinant wild-type protein EGFRwt at 25° C., but none of them showed significant binding.

TABLE 10

| | EGFRvIII binding at 37° C. | | |
|---|---|---|---|
| scFv-Fc protein | ka (1/Ms) | kd (1/s) | KD (nM) |
| h62G7-L6/EQ | 7.5E+05 | 7.6E−02 | 100.9 |
| C6.HL | 1.9E+04 | 2.0E−02 | 1063.8 |
| 14C11.HL | 4.2E+04 | 4.3E−03 | 104.3 |
| 14C11.LH | 4.8E+04 | 6.5E−03 | 136.0 |
| 20B9.HL | 2.4E+04 | 1.8E−03 | 73.8 |
| 20B9.LH | 3.0E+04 | 2.5E−03 | 82.7 |
| 32A10.HL | 4.7E+04 | 1.2E−03 | 24.5 |
| 32A10.LH | 4.1E+04 | 1.2E−03 | 29.8 |
| 42G9.HL | 5.6E+04 | 1.1E−03 | 18.8 |
| 42G9.LH | 4.0E+04 | 8.8E−04 | 22.1 |
| 26B9.HL | 5.7E+04 | 4.0E−02 | 704.9 |
| 26B9.LH | 6.9E+04 | 3.4E−02 | 494.2 |
| 30D8.HL | 2.3E+05 | 5.3E−02 | 224.6 |
| 30D8.LH | 1.1E+05 | 3.8E−02 | 348.6 |
| 20E12.HL | 2.1E+04 | 1.9E−02 | 893.7 |
| 20E12.LH | 1.6E+04 | 1.5E−02 | 932.5 |
| 32G8.HL | 8.7E+03 | 1.3E−02 | 1490.0 |

Example 6: Production and Detection of EGFRvIII Specific Chimeric Antigen Receptor (CAR) T Cells This example determines the expression and antigen binding specificity of EGFRvIII specific CAR T cells.

Figure 2A:
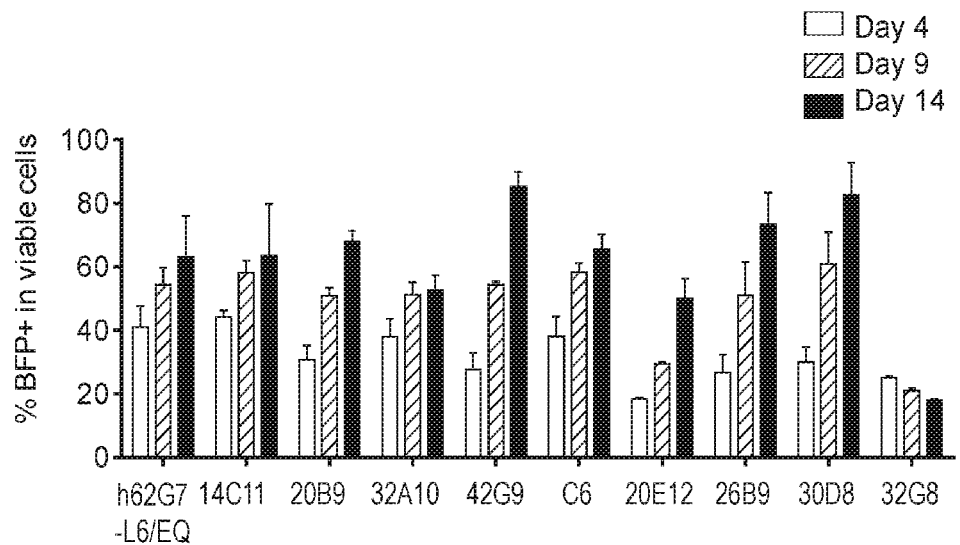
FIG. 2A shows a bar graph summarizing EGFRvIII specific CAR expression for CARs containing different EGFRvIII specific clones.

PBMC from healthy donors provided by AllCells (Alameda, Calif.) were thawed according to the provider's specification and cultured overnight in X-Vivo™-15 medium (Lonza, Walkersville, Md.) supplemented with 5% Human serum. T cells were activated for 3 days in X-Vivo™-15 medium (Lonza) supplemented with 20 ng/mL Human IL-2, 5% Human serum, and Dynabeads Human T activator CD3/CD28 at a bead:cell ratio 1:1 (Life Technologies, Carlsbad, Calif.). T cells were then transduced with a bicistronic lentiviral vector harboring a BFP-T2A-EGFRvIII specific CAR expression cassette under the control of the EF1α promoter at a multiplicity of infection (MOI) of 5. In this construct, the EGFRvIII specific CAR is co-expressed with BFP (blue fluorescent protein), to facilitate detection of the EGFRvIII specific CAR. The EGFRvIII specific CARs contained VH and VL sequences of different anti-EGRRvIII clones (h62G7-L6/EQ, 14C11, 20B9, 32A10, 42G9, C6, 20E12, 26B9, 30D8, and 32G8; described elsewhere herein). CAR T cells were maintained in culture for up to 14 days post-transduction. Percentage of cells expressing the EGFRvIII specific CAR was monitored over time (on Day 4, 9, and 14 post-lentivirus transduction of primary T cells)

by flow cytometry using BFP (blue fluorescent protein) for detection (FIG. 2A) (determined by percentage of BFP positive viable cells).

Figure 2B:
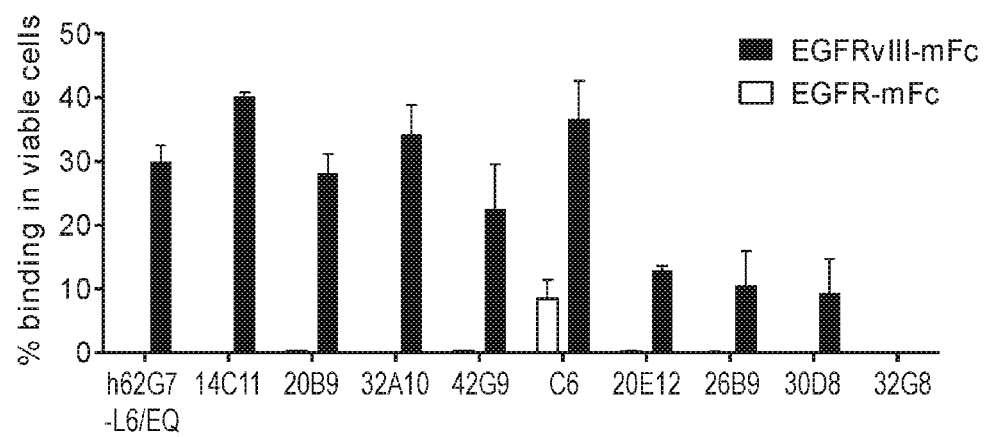
FIG. 2B shows a bar graph summarizing the percentage of EGFRvIII specific CAR T cells that bound to recombinant EGFR-mFc and EGFRvII-mFc.
Figure 2C:
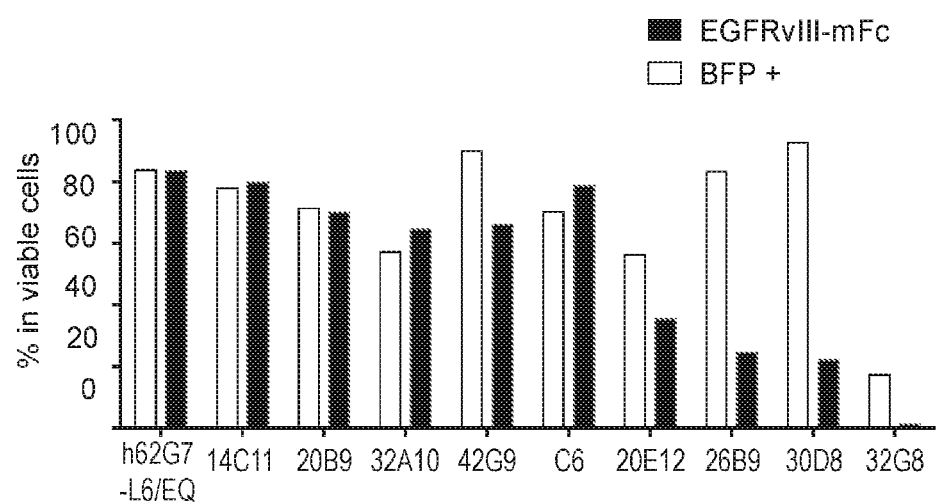
FIG. 2C shows a bar graph summarizing the expression of CARs containing 10 different EGFRvIII specific clones in CAR T cells.

To determine target binding specificity of the CARs, recombinant proteins EGFRvII-mFc and EGFR-mFc, which comprise of the extracellular domain of either human EGFRvIII or human wild-type EGFR, respectively, fused with mouse IgG1-Fc domain, were produced in HEK293 cells. The target binding specificity was determined by incubating the different EGFRvIII specific CAR T cells with either EGFRvII-mFc or EGFR-mFc protein followed by a PE-labeled goat anti-mouse Fc secondary antibody (Jackson ImmunoResearch) and analysed by flow cytometry on Day 4 post transduction of the T cells with vectors encoding CARs containing different EGFRvIII specific clones (h62G7-L6/EQ, 14C11, 20B9, 32A10, 42G9, C6, 20E12, 26B9, 30D8, and 32G8). As shown in FIG. 2B, CAR T cells comprising the VH and VL sequences of clones h62G7-L6/EQ, 14C11, 20B9, 32A10, 42G9, 20E12, 26B9, and 30D8 bind to EGFRvII-mFc but do not significantly bind to EGFR-mFc. On Day 14 post-transduction, the correlation of CAR expression as detected by BFP on the cells and recombinant EGFRvII-mFc binding by the cells was determined. A representative set of data is shown in FIG. 2C, which shows the expression of CARs containing ten different EGFRvIII specific clones (h62G7-L6/EQ, 14C11, 20B9, 32A10, 42G9, C6, 20E12, 26B9, 30D8, and 32G8) in CAR T cells on Day 14 post-transduction, as determined by BFP detection on the cells and recombinant EGFRvIII-mFc binding by the cells.

These results demonstrate that CAR T cells containing CARs comprising the VH and VL sequences of clones h62G7-L6/EQ, 14C11, 20B9, 32A10, 42G9, 20E12, 26B9, and 30D8 bind to EGFRvII-mFc but do not significantly bind to EGFR-mFc.

Example 7: Target Dependent and Independent Degranulation of EGFRvIII Specific CAR T Cells This example determines the degranulation activity of EGFRvIII specific CAR T cells in the presence and absence of target-expression cancer cell lines.

Five cell lines were used to evaluate the degranulation activity of CAR T cells. Human lung cancer cell line NCI-H522 and glioblastoma cell line U87MG were obtained from American Type Culture Collection (Manassas, Va.) and cultured in RPMI 1640 medium supplemented with 10% heat inactivated fetal bovine serum (Mediatech Inc., Manassas, Va.). Since most cancer cell lines do not express EGFRvIII, NCI-H522 (which does not express detectable level of wild-type EGFR or EGFRvIII) was tranduced with a lentivirus vector encoding the full length EGFRvIII gene (SEQ ID NO: 201) to generate "NCI-H522-EGFRvIII", which expresses low level of EGFRvIII. To generate isogenic human glioblastoma cell lines that express various EGFR proteins, the endogenous wild-type EGFR gene of U87MG was first knocked out to generate an EGFR-null cell line "U87-KO". U87-KO cell was then transduced with a lentivirus vector encoding the full length wild-type EGFR gene (accession number NP_005219) to obtain EGFR overexpressing cell line, "U87-KO-EGFRwt". Similarly, "U87-KO-EGFRvIII" (which over-expresses EGFRvIII), was generated from U87-KO by lentivirus traduction with a vector encoding the full length EGFRvIII gene (SEQ ID NO: 201).

For the degranulation assay, 100,000 T-cells expressing various EGFRvIII specific CARs (containing clones h62G7-L6/EQ, 14C11, 20B9, 32A10, 42G9, C6, 20E12, 26B9, 30D8, and 32G8) were incubated in 96-well plates with an equal number of cancer cells expressing various levels of the EGFRvIII protein or EGFRwt protein. Co-cultures were maintained in a final volume of 100 µl of X-Vivo™-15 medium (Lonza, Walkersville, Md.) for 6 hours at 37° C. with 5% $CO_2$. CD107a staining was done during cell stimulation, by the addition of a fluorescent anti-CD107a antibody (Miltenyi Biotec, San Diego, Calif.) at the beginning of the co-culture, together with a final concentration of 1 µg/ml of anti-CD49d (BD Pharmingen, San Diego, Calif.), 1 µg/ml of anti-CD28 (Miltenyi Biotec), and 1× Monensin (eBioscience, San Diego, Calif.) solution. After the 6h incubation period, cells were stained with a fixable viability dye and fluorochrome-conjugated anti-CD8 antibody (Miltenyi Biotec) and analyzed by flow cytometry. The degranulation activity was determined as the % of viable/CD8+/BFP+/CD107a+ cells, and by determining the mean fluorescence intensity signal (MFI) for CD107a staining among CD8+/BFP+ cells. Degranulation assays were carried out on Day 14 after CAR transduction. FIG. 3 shows the results from two PBMC donors for each EGFRvIII specific CAR. Except for CAR T cells containing clones C6 and 32G8, an increase in degranulation activity (over CAR-T alone) was only observed when EGFRvIII specific CAR T cells were cocultured with cell lines that express EGFRvIII, such as NCI-H522-EGFRvIII and U87-KO-EGFRvIII.

These results demonstrate that EGFRvIII specific CAR T cells exhibit degranulation activity in the presence of EGFRvIII-expressing tumor cells, but do not exhibit degranulation activity in the presence of tumor cells that do not express EGFRvIII.

Example 8: Interferon Gamma (IFNγ) Secretion of EGFRvIII Specific CAR T Cells

This example shows the level of IFNγ secretion of EGFRvIII specific CAR T cells upon co-culture of EGFRvIII specific CAR T cells with target protein expressing cell lines.

EGFRvIII specific CAR T-cells expressing CARs containing different EGFRvIII specific clones (h62G7-L6/EQ, 14C11, 20B9, 32A10, 42G9, C6, 20E12, 26B9, 30D8, and 32G8) were incubated in 96-well plates (100,000 cells/well), together with an equal number of cells expressing various levels of EGFRvIII or EGFRwt proteins (cells NCI-H522, NCI-H522-EGFRvII, U87-KO, U87-KO-EGFRwt, and U87-KO-EGFRvIII; each are described above in Example 7). Co-cultures were maintained in a final volume of 100 µl of X-Vivo™-15 medium (Lonza) for 18 hours at 37° C. with 5% $CO_2$. The supernatant was then collected and frozen. The IFNγ in the supernatant was measured with the Human IFN-gamma Quantikine ELISA Kit (R&D systems, Minneapolis, Minn.) according to the manufacturer's specifications. As shown in FIG. 4, for the majority of CAR T cells, the level of IFNγ secretion correlates with the amount of EGFRvIII expressed by the co-cultured cells: low expressor NCI-H522-EGFRvIII induced small amount of IFNγ, high expressor U87-KO-EGFRvIII induced large amount of IFNγ. T cells expressing EGFRvIII specific clone 32G8 CAR did not secrete significant levels of IFNγ under all conditions tested. EGFRvIII specific clone C6 CAR T cells, on the other hand, secreted high levels of IFNγ upon coculture with either U87-KO-EGFRwt or U87-KO-EGFRvIII cells.

These results demonstrate that for the majority of EGFRvIII specific CAR T cells, the level of IFNγ secretion correlates with the amount of EGFRvIII expressed by co-cultured cells

Example 9: Cytotoxicity of EGFRvIII Specific CAR T Cells

This example determines the cytotoxicity of EGFRvIII specific CAR T cells upon co-culture of EGFRvIII specific CAR T cells with target protein expressing cell lines.

EGFRvIII specific CAR T-cells expressing CARs containing different EGFRvIII specific clones (h62G7-L6/EQ, 14C11, 20B9, 32A10, 42G9, C6, 20E12, 26B9, 30D8, and 32G8) were seeded in 96-well plates (400,000 cells/well), together with 20,000 target cells expressing various levels of the EGFRvIII protein. The target cells were: U87-KO-EGFRwt, NCI-H522-EGFRvIII, and U87-KO-EGFRvIII, described above. Target (EGFRvIII positive: NCI-H522-EGFRvIII and U87-KO-EGFRvIII) and control (EGFRvIII negative: U87-KO-EGFRwt) cells were plated and labelled with the fluorescent intracellular dye CFSE before co-culturing them with the EGFRvIII specific CAR T-cells. The co-cultures were incubated for 4 hours at 37° C. with 5% $CO_2$. After this incubation period, cells were labelled with a fixable viability dye and analyzed by flow cytometry. Viability of each cellular population (EGFRvIII positive target cells or EGFRvIII negative control cells) was determined and the % of specific cell lysis was calculated. Cytotoxicity assays were carried out 14 days post CAR transduction of the T cells. All EGFRvIII specific CAR T cells, except 32G8, were able to lyse both low-level target expressing cells (NCI-H522-EGFRvIII) and high-level target expressing cells (U87-KO-EGFRvIII) to various degrees. In addition, EGFRvIII specific clone C6 CAR T cells lysed both wild-type EGFR and EGFRvIII expressing cells (FIG. 5).

These results demonstrate that EGFRvIII-specific CAR T cells effectively kill cells that express EGFRvIII.

Example 10: In Vivo Study of EGFRvIII Specific CAR T Cells in U87-KO-EGFRvIII Model This example shows the anti-tumor activity of EGFRvIII specific CAR T cells in a subcutaneous U87-KO-EGFRvIII GBM xenograph model.

Three million U87-KO-EGFRvIII GBM tumor cells (described above) were implanted subcutaneously into 5-6 week old NSG mice (Jackson Laboratory, Sacramento, Calif.). Tumor volume was measured once a week by a caliper device and calculated with the following formula: Tumor volume=(length×width$^2$)/2. On day 8 post tumor implantation, animals were randomized by tumor sizes into five animals per group and a single dose of 6 million CAR positive EGFRvIII specific CAR T cells (expressing the EGFRvIII specific clone 14C11, 32A10 or 26B9; the clones are described elsewhere herein) or the equivalent total number of non-transduced T cells were administered through bolus tail vein injection. FIG. 6 shows that the 14C11, 32A10 and 26B9 EGFRvIII specific CAR T cells, but not the non-transduced T cells, inhibited U87-KO-EGFRvIII xenograph tumor growth in vivo.

These results demonstrate that EGFRvIII-specific CAR T cells effectively inhibit tumor growth of EGFRvIII-expressing cells in vivo.

Example 11: Surface Expression of EGFRvIII Specific CARs Containing the R2 Suicide Sequence This example shows the expression of EGFRvIII specific CARs containing the R2 suicide sequence in T cells.

The R2 suicide sequence is a CD20 epitope based suicide sequence and contains two tandem copies of the rituximab recognition epitope. The R2 sequence was inserted between the scFv and the CD8α hinge sequences of various EGFRvIII specific CARs described elsewhere herein (14C11, 32A10, 30D8, and 26B9) to generate various EGFRvIII-R2 CARs (referred to herein as "14C11-R2", "32A10-R2", "30D8-R2", and "26B9-R2", respectively). T cells were transduced with a lentiviral vector harboring the various EGFRvIII-R2 CAR expression cassettes under the control of the EF1α promoter at a multiplicity of infection (MOI) of 5 or 25 (for clones 26B9-R2 and 30D8-R2). CAR T cells were maintained in culture for up to 14 or 15 days post-transduction. CAR expression was monitored over time (on Day 4, Day 9/10, and Day 14/15 post-T cell transduction) by flow cytometry using biotinylated recombinant proteins: EGFRvII-mFc or rituximab to the cells (conjugated with EZ-Link™ Sulfo-NHS—SS-Biotin; ThermoFisher, Waltham, Mass.), followed by PE conjugated streptavidin (BD Biosciences, San Diego, Calif.). The percentages of CAR positive cells as detected with biotinylated EGFRvII-mFc and biotinylated rituximab are shown in FIGS. 7 and 8, respectively. Binding to non-transduced T cells (NTD) is provided as a control.

These results demonstrate the expression in T cells of EGFRvIII-specific CARs containing the R2 suicide sequence.

Example 12: Cytotoxicity of EGFRvIII-Specific R2 CAR T Cells

This example shows the cytotoxicity of EGFRvIII-specific R2 CAR T cells upon co-culture with target expressing cell lines.

Cytotoxicity assays were carried out as described in Example 9, using the EGFRvIII-R2 CARs 14C11-R2, 32A10-R2, 30D8-R2, and 26B9-R2, which are described in Example 11. All EGFRvIII specific R2 CAR T cells tested were able to lyse both low-level target expressing cells (NCI-H522-EGFRvIII) and high-level target expressing cells (U87-KO-EGFRvIII) to various degrees (FIG. 9).

These results demonstrate that EGFRvIII-specific R2 CAR T cells effectively kill cells that express EGFRvIII.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated engineered immune cell comprising a polynucleotide encoding an Epidermal Growth Factor Receptor Variant III-specific (EGFRvIII-specific) chimeric antigen receptor (CAR), wherein the polynucleotide is under the transcriptional control of a promoter, wherein the EGFRvIII-specific CAR comprises an extracellular EGFRvIII-binding domain, a transmembrane domain, and a first intracellular signaling domain, and wherein the extracellular EGFRvIII-binding domain comprises:

a) a heavy chain variable (VH) region comprising three complementarity determining regions of VH complementary determining region 1 (VH CDR1), VH complementary determining region 2 (VH CDR2), and VH complementary determining region 3 (VH CDR3) of 42G9 arranged sequentially in the N terminus to C terminus direction of VH CDR1, VH CDR2, and VH CDR3, wherein VH CDR1 comprises the amino acid sequence of one of SEQ ID NOs: 74-76, VH CDR2 comprises the amino acid sequence of one of SEQ ID NOs: 77-78, and VH CDR3 comprises the amino acid sequence of SEQ ID NO: 79; and a light chain variable (VL) region comprising three complementarity determining regions of VL complementary determining region 1 (VL CDR1), VL complementary determining region 2 (VL CDR2), and VL complementarity determining region 3 (VL CDR3) of 42G9 arranged sequentially in the N terminus to C terminus direction of VL CDR1, VL CDR2, and VL CDR3, wherein VL CDR1 comprises the amino acid sequence of SEQ ID NO: 156, VL CDR2 comprises the amino acid sequence of SEQ ID NO: 157, and VL CDR3 comprises the amino acid sequence of SEQ ID NO: 158; or b) a VH region comprising three complementarity determining regions of VH CDR1, VH CDR2, and VH CDR3 of 32A10 arranged sequentially in the N terminus to C terminus direction of VH CDR1, VH CDR2, and VH CDR3, wherein VH CDR1 comprises the amino acid sequence of one of SEQ ID NOs: 80-82, VH CDR2 comprises the amino acid sequence of one of SEQ ID NOs: 83-84, and VH CDR3 comprises the amino acid sequence of SEQ ID NO: 85; and a VL region comprising three complementarity determining regions of VL CDR1, VL CDR2, and VL CDR3 of 32A10 arranged sequentially in the N terminus to C terminus direction of VL CDR1, VL CDR2, and VL CDR3, wherein VL CDR1 comprises the amino acid sequence of SEQ ID NO: 159, VL CDR2 comprises the amino acid sequence of SEQ ID NO: 160, and VL CDR3 comprises the amino acid sequence of SEQ ID NO: 161; or c) a VH region comprising three complementarity determining regions of VH CDR1, VH CDR2, and VH CDR3 of 20B9 arranged sequentially in the N terminus to C terminus direction of VH CDR1, VH CDR2, and VH CDR3, wherein VH CDR1 comprises the amino acid sequence of one of SEQ ID NOs: 80-82, VH CDR2 comprises the amino acid sequence of one of SEQ ID NOs: 86-87, and VH CDR3 comprises the amino acid sequence of SEQ ID NO: 79; and a VL region comprising three complementarity determining regions of VL CDR1, VL CDR2, and VL CDR3 of 20B9 arranged sequentially in the N terminus to C terminus direction of VL CDR1, VL CDR2, and VL CDR3, wherein VL CDR1 comprises the amino acid sequence of SEQ ID NO: 162, VL CDR2 comprises the amino acid sequence of SEQ ID NO: 163, and VL CDR3 comprises the amino acid sequence of SEQ ID NO: 164; or d) a VH region comprising three complementarity determining regions of VH CDR1, VH CDR2, and VH CDR3 of 14C11 arranged sequentially in the N terminus to C terminus direction of VH CDR1, VH CDR2, and VH CDR3, wherein VH CDR1 comprises the amino acid sequence of one of SEQ ID NOs: 88-90, VH CDR2 comprises the amino acid sequence of one of SEQ ID NOs: 91-92, and VH CDR3 comprises the amino acid sequence of SEQ ID NO: 85; and a VL region comprising three complementarity determining regions of VL CDR1, VL CDR2, and VL CDR3 of 14C11 arranged sequentially in the N terminus to C terminus direction of VL CDR1, VL CDR2, and VL CDR3, wherein VL CDR1 comprises the amino acid sequence of SEQ ID NO: 165, VL CDR2 comprises the amino acid sequence of SEQ ID NO: 163, and VL CDR3 comprises the amino acid sequence of SEQ ID NO: 161; or e) a VH region comprising three complementarity determining regions of VH CDR1, VH CDR2, and VH CDR3 of 30D8 arranged sequentially in the N terminus to C terminus direction of VH CDR1, VH CDR2, and VH CDR3, wherein VH CDR1 comprises the amino acid sequence of one of SEQ ID NOs: 109-111, VH CDR2 comprises the amino acid sequence of one of SEQ ID NOs: 112-113, and VH CDR3 comprises the amino acid sequence of SEQ ID NO: 114; and a VL region comprising three complementarity determining regions of VL CDR1, VL CDR2, and VL CDR3 of 30D8 arranged sequentially in the N terminus to C terminus direction of VL CDR1, VL CDR2, and VL CDR3, wherein VL CDR1 comprises the amino acid sequence of SEQ ID NO: 182, VL CDR2 comprises the amino acid sequence of SEQ ID NO: 183, and VL CDR3 comprises the amino acid sequence of SEQ ID NO: 184; or f) a VH region comprising three complementarity determining regions of VH CDR1, VH CDR2, and VH CDR3 of 20E12 arranged sequentially in the N terminus to C terminus direction of VH CDR1, VH CDR2, and VH CDR3, wherein VH CDR1 comprises the amino acid sequence of one of SEQ ID NOs: 115-117, VH CDR2 comprises the amino acid sequence of one of SEQ ID NOs: 118-119, and VH CDR3 comprises the amino acid sequence of SEQ ID NO: 120; and
  a VL region comprising three complementarity determining regions of VL CDR1, VL CDR2, and VL CDR3 of 20E12 arranged sequentially in the N terminus to C terminus direction of VL CDR1, VL CDR2, and VL CDR3, wherein VL CDR1 comprises the amino acid sequence of SEQ ID NO: 185, VL CDR2 comprises the amino acid sequence of SEQ ID NO: 186, and VL CDR3 comprises the amino acid sequence of SEQ ID NO: 184; or
g) a VH region comprising three complementarity determining regions of VH CDR1, VH CDR2, and VH CDR3 of 26B9 arranged sequentially in the N terminus to C terminus direction of VH CDR1, VH CDR2, and VH CDR3, wherein VH CDR1 comprises the amino acid sequence of one of SEQ ID NOs: 121-123, VH CDR2 comprises the amino acid sequence of one of SEQ ID NOs: 124-125, and VH CDR3 comprises the amino acid sequence of SEQ ID NO: 126; and
  a VL region comprising three complementarity determining regions of VL CDR1, VL CDR2, and VL CDR3 of 26B9 arranged sequentially in the N terminus to C terminus direction of VL CDR1, VL CDR2, and VL CDR3, wherein VL CDR1 comprises the amino acid sequence of SEQ ID NO: 187, VL CDR2 comprises the amino acid sequence of SEQ ID NO: 188, and VL CDR3 comprises the amino acid sequence of SEQ ID NO: 189; or
h) a VH region comprising three complementarity determining regions of VH CDR1, VH CDR2, and VH CDR3 of C6 arranged sequentially in the N terminus to C terminus direction of VH CDR1, VH CDR2, and VH CDR3, wherein VH CDR1 comprises the amino acid sequence of one of SEQ ID NOs: 137-139, VH CDR2 comprises the amino acid sequence of one of SEQ ID NOs: 140-141, and VH CDR3 comprises the amino acid sequence of SEQ ID NO: 142; and
  a VL region comprising three complementarity determining regions of VL CDR1, VL CDR2, and VL CDR3 of C6 arranged sequentially in the N terminus to C terminus direction of VL CDR1, VL CDR2, and VL CDR3, wherein VL CDR1 comprises the amino acid sequence of SEQ ID NO: 195, VL CDR2 comprises the amino acid sequence of SEQ ID NO: 196, and VL CDR3 comprises the amino acid sequence of SEQ ID NO: 197; or
i) a VH region comprising three complementarity determining regions of VH CDR1, VH CDR2, and VH CDR3 of 12B2 arranged sequentially in the N terminus to C terminus direction of VH CDR1, VH CDR2, and VH CDR3, wherein VH CDR1 comprises the amino acid sequence of one of SEQ ID NOs: 74-76, VH CDR2 comprises the amino acid sequence of one of SEQ ID NOs: 102-103, and VH CDR3 comprises the amino acid sequence of SEQ ID NO: 104; and
  a VL region comprising three complementarity determining regions of VL CDR1, VL CDR2, and VL CDR3 of 12B2 arranged sequentially in the N terminus to C terminus direction of VL CDR1, VL CDR2, and VL CDR3, wherein VL CDR1 comprises the amino acid sequence of SEQ ID NO: 176, VL CDR2 comprises the amino acid sequence of SEQ ID NO: 172, and VL CDR3 comprises the amino acid sequence of SEQ ID NO: 177,
thereby generating the engineered immune cell.

2. The engineered immune cell of claim 1, wherein the extracellular EGFRvIII-binding domain is a single-chain variable fragment (scFv).

3. The engineered immune cell of claim 2, wherein the scFv comprises a VH region and a VL region selected from the group consisting of:
  i) the VH region comprising the amino acid sequence of SEQ ID NO: 9 and the VL region comprising the amino acid sequence of SEQ ID NO: 10;
  ii) the VH region comprising the amino acid sequence of SEQ ID NO: 11 and the VL region comprising the amino acid sequence of SEQ ID NO: 12;
  iii) the VH region comprising the amino acid sequence of SEQ ID NO: 13 and the VL region comprising the amino acid sequence of SEQ ID NO: 14;
  iv) the VH region comprising the amino acid sequence of SEQ ID NO: 15 and the VL region comprising the amino acid sequence of SEQ ID NO: 16;
  v) the VH region comprising the amino acid sequence of SEQ ID NO: 37 and the VL region comprising the amino acid sequence of SEQ ID NO: 38;
  vi) the VH region comprising the amino acid sequence of SEQ ID NO: 39 and the VL region comprising the amino acid sequence of SEQ ID NO: 40;
  vii) the VH region comprising the amino acid sequence of SEQ ID NO: 41 and the VL region comprising the amino acid sequence of SEQ ID NO: 42;
  viii) the VH region comprising the amino acid sequence of SEQ ID NO: 48 and the VL region comprising the amino acid sequence of SEQ ID NO: 49; and
  ix) the VH region comprising the amino acid sequence of SEQ ID NO: 30 and the VL region comprising the amino acid sequence of SEQ ID NO: 31.

4. An isolated engineered immune cell comprising a polynucleotide encoding an Epidermal Growth Factor Receptor Variant III-specific (EGFRvIII-specific) chimeric antigen receptor (CAR),
  wherein the polynucleotide is under the transcriptional control of a promoter,
  wherein the EGFRvIII-specific CAR comprises an extracellular EGFRvIII-binding domain, a transmembrane domain, and a first intracellular signaling domain, and
  wherein the CAR comprises an amino acid sequence selected from the group consisting of SEQ ID NOs: 53-57 and 59-61.

5. The engineered immune cell of claim 4, wherein the CAR comprises the amino acid sequence of SEQ ID NO: 53.

6. The engineered immune cell of claim 4, wherein the CAR comprises the amino acid sequence of SEQ ID NO: 54.

7. The engineered immune cell of claim 4, wherein the CAR comprises the amino acid sequence of SEQ ID NO: 55.

8. The engineered immune cell of claim 4, wherein the CAR comprises the amino acid sequence of SEQ ID NO: 56.

9. The engineered immune cell of claim 4, wherein the CAR comprises the amino acid sequence of SEQ ID NO: 57.

10. The engineered immune cell of claim 4, wherein the CAR comprises the amino acid sequence of SEQ ID NO: 59.

11. The engineered immune cell of claim 4, wherein the CAR comprises the amino acid sequence of SEQ ID NO: 60.

12. The engineered immune cell of claim 4, wherein the CAR comprises the amino acid sequence of SEQ ID NO: 61.

13. The engineered immune cell of claim 1, wherein the engineered immune cell expresses at its cell surface membrane the EGFRvIII-specific CAR.

14. The engineered immune cell of claim 1, wherein the first intracellular signaling domain comprises a CD3zeta signaling domain.

15. The engineered immune cell of claim 1, wherein the EGFRvIII-specific CAR further comprises a second intracellular signaling domain.

16. The engineered immune cell of claim 15, wherein the first intracellular signaling domain comprises a CD3zeta signaling domain and the second intracellular signaling domain comprises a 4-1BB signaling domain.

17. The engineered immune cell of claim 1, wherein the engineered immune cell comprises a polynucleotide encoding a suicide polypeptide.

18. The engineered immune cell of claim 1, further comprising a polynucleotide that encodes a suicide polypeptide.

19. The engineered immune cell of claim 18, wherein the suicide polypeptide comprises an epitope that is recognized by rituximab.

20. The engineered immune cell of claim 19, wherein the suicide polypeptide comprises the amino acid sequence of SEQ ID NO: 226.

21. The engineered immune cell of claim 1, wherein the engineered immune cell comprises a disruption of one or more endogenous genes selected from the group consisting of genes encoding TCRα, TCRβ, CD52, glucocorticoid receptor (GR), deoxycytidine kinase (dCK), and programmed death-1 (PD-1).

22. The engineered immune cell of claim 1, wherein the engineered immune cell is prepared from a cell or cells obtained from a healthy donor.

23. The engineered immune cell of claim 1, wherein the engineered immune cell is prepared from a cell or cells obtained from a patient.

24. The engineered immune cell of claim 1, wherein the engineered immune cell is prepared from an inflammatory T-lymphocyte, a cytotoxic T-lymphocyte, a regulatory T-lymphocyte, a memory T-lymphocyte, a helper T-lymphocyte, a natural killer T-lymphocyte, or a natural killer cell.

25. A pharmaceutical composition comprising the engineered immune cell of claim 1, wherein the engineered immune cell expresses at its cell surface membrane the EGFRvIII specific CAR.

26. An isolated engineered immune cell comprising a polynucleotide encoding an Epidermal Growth Factor Receptor Variant III-specific (EGFRvIII-specific) chimeric antigen receptor (CAR),
  wherein the polynucleotide is under the transcriptional control of a promoter,
  wherein the EGFRvIII-specific CAR comprises an extracellular EGFRvIII-binding domain, a transmembrane domain, and a first intracellular signaling domain, and
  wherein the engineered immune cell expresses at its cell surface membrane the EGFRvIII-specific CAR,
  wherein the CAR comprises an amino acid sequence selected from the group consisting of SEQ ID NOs: 53-57 and 59-61.

27. The pharmaceutical composition of claim 25, wherein the extracellular EGFRvIII-binding domain is a single-chain variable fragment (scFv).

28. The pharmaceutical composition of claim 27, wherein the scFv comprises a VH region and a VL region selected from the group consisting of:
  i) the VH region comprising the amino acid sequence of SEQ ID NO: 9 and the VL region comprising the amino acid sequence of SEQ ID NO: 10;
  ii) the VH region comprising the amino acid sequence of SEQ ID NO: 11 and the VL region comprising the amino acid sequence of SEQ ID NO: 12;
  iii) the VH region comprising the amino acid sequence of SEQ ID NO: 13 and the VL region comprising the amino acid sequence of SEQ ID NO: 14;
  iv) the VH region comprising the amino acid sequence of SEQ ID NO: 15 and the VL region comprising the amino acid sequence of SEQ ID NO: 16;
  v) the VH region comprising the amino acid sequence of SEQ ID NO: 37 and the VL region comprising the amino acid sequence of SEQ ID NO: 38;
  vi) the VH region comprising the amino acid sequence of SEQ ID NO: 39 and the VL region comprising the amino acid sequence of SEQ ID NO: 40;
  vii) the VH region comprising the amino acid sequence of SEQ ID NO: 41 and the VL region comprising the amino acid sequence of SEQ ID NO: 42;
  viii) the VH region comprising the amino acid sequence of SEQ ID NO: 48 and the VL region comprising the amino acid sequence of SEQ ID NO: 49; and
  ix) the VH region comprising the amino acid sequence of SEQ ID NO: 30 and the VL region comprising the amino acid sequence of SEQ ID NO: 31.

29. The pharmaceutical composition of claim 25, wherein the polynucleotide encodes a CAR comprising the amino acid sequence of SEQ ID NO: 53.

30. The pharmaceutical composition of claim 25, wherein the polynucleotide encodes a CAR comprising the amino acid sequence of SEQ ID NO: 54.

31. The pharmaceutical composition of claim 25, wherein the polynucleotide encodes a CAR comprising the amino acid sequence of SEQ ID NO: 55.

32. The pharmaceutical composition of claim 25, wherein the polynucleotide encodes a CAR comprising the amino acid sequence of SEQ ID NO: 56.

33. The pharmaceutical composition of claim 25, wherein the polynucleotide encodes a CAR comprising the amino acid sequence of SEQ ID NO: 57.

34. The pharmaceutical composition of claim 25, wherein the polynucleotide encodes a CAR comprising the amino acid sequence of SEQ ID NO: 59.

35. The pharmaceutical composition of claim 25, wherein the polynucleotide encodes a CAR comprising the amino acid sequence of SEQ ID NO: 60.

36. The pharmaceutical composition of claim 25, wherein the polynucleotide encodes a CAR comprising the amino acid sequence of SEQ ID NO: 61.

37. The pharmaceutical composition of claim 25, wherein the first intracellular signaling domain comprises a CD3zeta signaling domain.

38. The pharmaceutical composition of claim 25, wherein the EGFR-specific CAR further comprises a second intracellular signaling domain.

39. The pharmaceutical composition of claim 38, wherein the first intracellular signaling domain comprises a CD3zeta signaling domain and the second intracellular signaling domain comprises a 4-1BB signaling domain.

40. The pharmaceutical composition of claim 25, wherein the engineered immune cell comprises a polynucleotide encoding a suicide polypeptide.

41. The pharmaceutical composition of claim 40, wherein the polynucleotide encoding the EGFRvIII-specific CAR comprises the polynucleotide encoding the suicide polypeptide.

42. The pharmaceutical composition of claim 41, wherein the suicide polypeptide comprises an epitope that is recognized by rituximab.

43. The pharmaceutical composition of claim 42, wherein the suicide polypeptide comprises the amino acid sequence of SEQ ID NO: 226.

44. The pharmaceutical composition of claim 25, wherein the engineered immune cell comprises a disruption of one or more endogenous genes selected from the group consisting of genes encoding TCRα, TCRβ, CD52, glucocorticoid receptor (GR), deoxycytidine kinase (dCK), and programmed death-1 (PD-1).

45. The pharmaceutical composition of claim 25, wherein the engineered immune cell is prepared from a cell or cells obtained from a healthy donor.

46. The pharmaceutical composition of claim 25, wherein the engineered immune cell is prepared from a cell or cells obtained from a patient.

47. The pharmaceutical composition of claim 25, wherein the engineered immune cell is prepared from an inflammatory T-lymphocyte, a cytotoxic T-lymphocyte, a regulatory T-lymphocyte, a memory T-lymphocyte, a helper T-lymphocyte, a natural killer T-lymphocyte, or a natural killer cell.

48. A pharmaceutical composition comprising the engineered immune cell of claim 26.

* * * * *

UNITED STATES PATENT AND TRADEMARK OFFICE
CERTIFICATE OF CORRECTION

| | | |
|---|---|---|
| PATENT NO. | : 11,267,892 B2 | Page 1 of 1 |
| APPLICATION NO. | : 16/255348 | |
| DATED | : March 8, 2022 | |
| INVENTOR(S) | : Oi Kwan Wong et al. | |

It is certified that error appears in the above-identified patent and that said Letters Patent is hereby corrected as shown below:

In the Claims

At the end of Claim 1 (Column 323, Lines 66-67), the phrase:
"acid sequence of SEQ ID NO: 177,
    thereby generating the engineered immune cell"
Should read:
--acid sequence of SEQ ID NO: 177.--

Signed and Sealed this
Twenty-eighth Day of June, 2022

Katherine Kelly Vidal
*Director of the United States Patent and Trademark Office*